(12) United States Patent
Dubensky, Jr. et al.

(10) Patent No.: US 9,044,420 B2
(45) Date of Patent: Jun. 2, 2015

(54) IMMUNOGENIC COMPOSITIONS AND METHODS OF USING THE COMPOSITIONS FOR INDUCING HUMORAL AND CELLULAR IMMUNE RESPONSES

(75) Inventors: Thomas W. Dubensky, Jr., Piedmont, CA (US); Scott H. Robbins, Lake Forest Park, WA (US)

(73) Assignee: IMMUNE DESIGN CORP., Seattle, WA (US)

( * ) Notice: Subject to any disclaimer, the term of this patent is extended or adjusted under 35 U.S.C. 154(b) by 0 days.

(21) Appl. No.: 13/441,502

(22) Filed: Apr. 6, 2012

(65) Prior Publication Data

US 2012/0328655 A1    Dec. 27, 2012

Related U.S. Application Data

(60) Provisional application No. 61/473,660, filed on Apr. 8, 2011.

(51) Int. Cl.
- *A61K 39/00* (2006.01)
- *A61K 39/12* (2006.01)
- *A61K 39/245* (2006.01)

(52) U.S. Cl.
CPC ......... *A61K 39/0011* (2013.01); *A61K 2039/53* (2013.01); *A61K 2039/545* (2013.01); *A61K 2039/55566* (2013.01); *A61K 2039/55572* (2013.01); *C12N 2710/16634* (2013.01); *C12N 2740/15034* (2013.01); *A61K 39/12* (2013.01); *C12N 2740/16043* (2013.01); *C12N 2810/609* (2013.01)

(58) Field of Classification Search
CPC ... A61K 39/00; A61K 39/0011; A61K 39/21; A61K 39/245; A61K 2039/5256; A61K 2039/53; A61K 2039/545; A61K 2039/55511; A61K 2039/55566; A61K 2039/55572; C12N 2320/31; C12N 2710/00043; C12N 2710/16634; C12N 2740/15034; C12N 2740/15043; C12N 2799/026

See application file for complete search history.

(56) References Cited

U.S. PATENT DOCUMENTS

| | | |
|---|---|---|
| 3,238,190 A | 3/1966 | Erbring et al. |
| 3,598,122 A | 8/1971 | Zaffaroni |
| 3,598,123 A | 8/1971 | Zaffaroni |
| 4,029,762 A | 6/1977 | Galanos et al. |
| 4,286,592 A | 9/1981 | Chandrasekaran |
| 4,314,557 A | 2/1982 | Chandrasekaran |
| 4,376,110 A | 3/1983 | David et al. |
| 4,379,454 A | 4/1983 | Campbell et al. |
| 4,411,993 A | 10/1983 | Gillis |
| 4,420,461 A | 12/1983 | Reckel et al. |
| 4,420,558 A | 12/1983 | De Mey et al. |
| 4,486,530 A | 12/1984 | David et al. |
| 4,543,439 A | 9/1985 | Frackelton, Jr. et al. |
| 4,568,343 A | 2/1986 | Leeper et al. |
| 4,569,794 A | 2/1986 | Smith et al. |
| 4,595,654 A | 6/1986 | Reckel et al. |
| 4,614,722 A | 9/1986 | Pasula |
| 4,629,722 A | 12/1986 | Ribi |
| 4,659,659 A | 4/1987 | Dwek et al. |
| 4,703,004 A | 10/1987 | Hopp et al. |
| 4,743,540 A | 5/1988 | Ralph et al. |
| 4,767,402 A | 8/1988 | Kost et al. |
| 4,769,330 A | 9/1988 | Paoletti et al. |
| 4,780,212 A | 10/1988 | Kost et al. |
| 4,844,894 A | 7/1989 | Ribi |
| 4,897,268 A | 1/1990 | Tice et al. |
| 4,902,614 A | 2/1990 | Wakabayashi et al. |
| 4,912,094 A | 3/1990 | Myers et al. |
| 4,937,190 A | 6/1990 | Palmenberg et al. |
| 4,948,587 A | 8/1990 | Kost et al. |
| 4,952,496 A | 8/1990 | Studier et al. |
| 4,981,684 A | 1/1991 | MacKenzie et al. |
| 4,987,237 A | 1/1991 | Myers et al. |
| 5,011,912 A | 4/1991 | Hopp et al. |
| 5,017,487 A | 5/1991 | Stunnenberg et al. |
| 5,057,540 A | 10/1991 | Kensil et al. |
| 5,075,109 A | 12/1991 | Tice et al. |

(Continued)

FOREIGN PATENT DOCUMENTS

| | | |
|---|---|---|
| DE | 3833319 A1 | 4/1989 |
| EP | 0198474 A1 | 10/1986 |

(Continued)

OTHER PUBLICATIONS

Beignon et al., Lentiviral vector-based prime/boost vaccination against AIDS: Pilot study shows protection against simian immunodeficiency virus SIVmac251 challenge in macaques, *J. Virol.*, 83(21):10963 (2009).

(Continued)

*Primary Examiner* — Louise Humphrey

(74) *Attorney, Agent, or Firm* — Marshall, Gerstein & Borun LLP

(57) ABSTRACT

Compositions and methods are provided herein for improved dual immunization strategies that induce in a subject an immune response that includes a humoral immune response and cellular immune response, both CD4 and CD8 T lymphocyte immune responses, thereby providing a complete adaptive immune response to one or more antigens. The methods described are therefore useful for treating and/or preventing (i.e., reducing the likelihood or risk of occurrence) different diseases, disorders, and conditions such as cancers and infectious diseases for which induction of both a humoral immune response and cellular immune response is desired and beneficial.

33 Claims, 13 Drawing Sheets

(56) References Cited

U.S. PATENT DOCUMENTS

| | | |
|---|---|---|
| 5,124,141 A | 6/1992 | Makler |
| 5,147,785 A | 9/1992 | Pasula |
| 5,162,990 A | 11/1992 | Odeyale et al. |
| 5,168,062 A | 12/1992 | Stinski |
| 5,231,168 A | 7/1993 | Dziegiel et al. |
| 5,273,965 A | 12/1993 | Kensil et al. |
| 5,278,302 A | 1/1994 | Caruthers et al. |
| 5,298,396 A | 3/1994 | Kotzin et al. |
| 5,352,449 A | 10/1994 | Beltz et al. |
| 5,385,839 A | 1/1995 | Stinski |
| 5,411,865 A | 5/1995 | Reed |
| 5,422,109 A | 6/1995 | Brancq et al. |
| 5,424,067 A | 6/1995 | Brancq et al. |
| 5,443,829 A | 8/1995 | Kensil et al. |
| 5,443,964 A | 8/1995 | Pickup et al. |
| 5,457,041 A | 10/1995 | Ginaven et al. |
| 5,464,387 A | 11/1995 | Haak et al. |
| 5,510,474 A | 4/1996 | Quail et al. |
| 5,530,113 A | 6/1996 | Christ et al. |
| 5,560,398 A | 10/1996 | Pfleger |
| 5,565,209 A | 10/1996 | Rijke |
| 5,591,139 A | 1/1997 | Lin et al. |
| 5,595,888 A | 1/1997 | Gray et al. |
| 5,612,041 A | 3/1997 | Burke et al. |
| 5,612,476 A | 3/1997 | Christ et al. |
| 5,618,275 A | 4/1997 | Bock |
| 5,650,155 A | 7/1997 | Cornelius et al. |
| 5,654,140 A | 8/1997 | Persico et al. |
| 5,656,016 A | 8/1997 | Ogden |
| 5,666,153 A | 9/1997 | Copeland |
| 5,667,784 A | 9/1997 | Cornelius et al. |
| 5,679,356 A | 10/1997 | Bonnem et al. |
| 5,693,531 A | 12/1997 | Chiorini et al. |
| 5,698,530 A | 12/1997 | Schlom et al. |
| 5,718,904 A | 2/1998 | Hjorth |
| 5,719,263 A | 2/1998 | Reed |
| 5,722,397 A | 3/1998 | Eppstein |
| 5,756,718 A | 5/1998 | Christ et al. |
| 5,776,468 A | 7/1998 | Hauser et al. |
| 5,786,148 A | 7/1998 | Bandman et al. |
| 5,795,577 A | 8/1998 | Kieny et al. |
| 5,840,871 A | 11/1998 | Hillman et al. |
| 5,843,464 A | 12/1998 | Bakaletz et al. |
| 5,843,918 A | 12/1998 | Christ et al. |
| 5,846,758 A | 12/1998 | Medenica |
| 5,885,211 A | 3/1999 | Eppstein et al. |
| 5,912,166 A | 6/1999 | Reed et al. |
| 5,952,309 A | 9/1999 | Rossignol et al. |
| 5,955,306 A | 9/1999 | Gimeno et al. |
| 5,961,970 A | 10/1999 | Lowell et al. |
| 5,976,538 A | 11/1999 | Hilgers et al. |
| 5,981,215 A | 11/1999 | Meissner et al. |
| 5,993,800 A | 11/1999 | Linsley et al. |
| 6,005,099 A | 12/1999 | Davies et al. |
| 6,018,678 A | 1/2000 | Mitragotri et al. |
| 6,027,730 A | 2/2000 | Francotte et al. |
| 6,027,732 A | 2/2000 | Morein et al. |
| 6,033,928 A | 3/2000 | Eriguchi et al. |
| 6,057,427 A | 5/2000 | Smith et al. |
| 6,106,824 A | 8/2000 | Kaplitt et al. |
| 6,120,769 A | 9/2000 | Gefter et al. |
| 6,143,290 A | 11/2000 | Zhang et al. |
| 6,146,632 A | 11/2000 | Momin et al. |
| 6,218,186 B1 | 4/2001 | Choi et al. |
| 6,231,861 B1 | 5/2001 | Barnwell |
| 6,235,724 B1 | 5/2001 | Asai et al. |
| 6,261,762 B1 | 7/2001 | Alizon et al. |
| 6,270,769 B1 | 8/2001 | Raychaudhuri et al. |
| 6,309,847 B1 | 10/2001 | Cohen et al. |
| 6,316,183 B1 | 11/2001 | Alizon et al. |
| 6,322,532 B1 | 11/2001 | D'Sa et al. |
| 6,375,944 B1 | 4/2002 | Trinchieri et al. |
| 6,395,713 B1 | 5/2002 | Beigelman et al. |
| 6,447,796 B1 | 9/2002 | Vook et al. |
| 6,472,515 B1 | 10/2002 | Climent-Johansson et al. |
| 6,488,936 B1 | 12/2002 | Mishkin et al. |
| 6,491,919 B2 | 12/2002 | Crane |
| 6,512,102 B1 | 1/2003 | Xu et al. |
| 6,544,518 B1 | 4/2003 | Friede et al. |
| 6,544,728 B1 | 4/2003 | Alizon et al. |
| 6,555,653 B2 | 4/2003 | Alderson et al. |
| 6,572,861 B1 | 6/2003 | Roberts et al. |
| 6,587,792 B1 | 7/2003 | Thomas |
| 6,596,501 B2 | 7/2003 | Roth |
| 6,596,535 B1 | 7/2003 | Carter |
| 6,613,892 B2 | 9/2003 | Preston et al. |
| 6,630,161 B1 | 10/2003 | Leesman |
| 6,654,462 B1 | 11/2003 | Hedberg |
| 6,660,487 B2 | 12/2003 | Faustman |
| 6,676,961 B1 | 1/2004 | Lichter |
| 6,682,901 B2 | 1/2004 | Blaschuk et al. |
| 6,683,063 B2 | 1/2004 | Rossignol et al. |
| 6,685,699 B1 | 2/2004 | Eppstein et al. |
| 6,692,752 B1 | 2/2004 | Slaoui et al. |
| 6,706,872 B1 | 3/2004 | Barnwell |
| 6,713,068 B1 | 3/2004 | Audonnet et al. |
| 6,733,763 B2 | 5/2004 | Raychaudhuri et al. |
| 6,734,172 B2 | 5/2004 | Scholler et al. |
| 6,749,856 B1 | 6/2004 | Berzofsky et al. |
| 6,752,995 B2 | 6/2004 | Johnston et al. |
| 6,770,445 B1 | 8/2004 | Scholler et al. |
| 6,783,981 B1 | 8/2004 | Uden et al. |
| 6,797,276 B1 | 9/2004 | Glenn et al. |
| 6,828,155 B1 | 12/2004 | Kaneko et al. |
| 6,844,192 B2 | 1/2005 | Orlando et al. |
| 6,846,489 B1 | 1/2005 | Garcon et al. |
| 6,846,648 B2 | 1/2005 | Maes |
| 6,855,317 B2 | 2/2005 | Koelle et al. |
| 6,855,322 B2 | 2/2005 | Lyon et al. |
| 6,869,607 B1 | 3/2005 | Buschle et al. |
| 6,871,477 B1 | 3/2005 | Tucker |
| 6,875,610 B2 | 4/2005 | Higginbotham et al. |
| 6,893,820 B1 | 5/2005 | Plass |
| 6,908,453 B2 | 6/2005 | Fleming et al. |
| 6,919,078 B2 | 7/2005 | Ni et al. |
| 6,919,210 B1 | 7/2005 | Okamoto |
| 6,929,796 B1 | 8/2005 | Conti-Fine |
| 6,932,972 B2 | 8/2005 | Stephenne et al. |
| 6,933,123 B2 | 8/2005 | Hu et al. |
| 6,936,255 B1 | 8/2005 | Wettendorff |
| 6,936,257 B1 | 8/2005 | Bennett |
| 6,949,246 B2 | 9/2005 | Reed et al. |
| 6,969,704 B1 | 11/2005 | Pinsky et al. |
| 6,970,739 B1 | 11/2005 | Inoue |
| 6,974,588 B1 | 12/2005 | Miranda et al. |
| 6,977,073 B1 | 12/2005 | Cezayirli et al. |
| 6,979,535 B2 | 12/2005 | Alizon et al. |
| 6,979,730 B2 | 12/2005 | Reiter et al. |
| 6,991,791 B2 | 1/2006 | Le et al. |
| 6,998,252 B1 | 2/2006 | Moss et al. |
| 7,001,770 B1 | 2/2006 | Atencio et al. |
| 7,008,774 B1 | 3/2006 | Ryan et al. |
| 7,012,134 B2 | 3/2006 | Ruben et al. |
| 7,018,345 B2 | 3/2006 | Mori et al. |
| 7,029,678 B2 | 4/2006 | Momin et al. |
| 7,029,685 B2 | 4/2006 | Lanar et al. |
| 7,030,232 B1 | 4/2006 | Reiter et al. |
| 7,033,598 B2 | 4/2006 | Lerner |
| 7,037,712 B2 | 5/2006 | Both et al. |
| 7,052,904 B2 | 5/2006 | Zheng et al. |
| 7,060,276 B2 | 6/2006 | Lanar et al. |
| 7,060,802 B1 | 6/2006 | Trakht et al. |
| 7,067,310 B2 | 6/2006 | Chartier et al. |
| 7,070,931 B2 | 7/2006 | Fujinaga et al. |
| 7,078,180 B2 | 7/2006 | Genetta |
| 7,084,256 B2 | 8/2006 | McCormick et al. |
| 7,087,231 B2 | 8/2006 | Guerin-Marchand et al. |
| 7,087,713 B2 | 8/2006 | Campos-Neto et al. |
| 7,125,717 B2 | 10/2006 | Carter |
| 7,247,615 B2 | 7/2007 | Schlom et al. |
| 7,357,936 B1 | 4/2008 | Garcon |
| 7,368,116 B2 | 5/2008 | Schlom et al. |
| 7,378,087 B2 | 5/2008 | Jefferies et al. |
| 7,402,572 B2 | 7/2008 | Krieg et al. |

(56) References Cited

U.S. PATENT DOCUMENTS

| | | | |
|---|---|---|---|
| 7,550,296 B2 | 6/2009 | Hermiston et al. | |
| 7,744,903 B2* | 6/2010 | Koelle et al. | 424/229.1 |
| 7,820,627 B2 | 10/2010 | Jiang et al. | |
| 8,187,872 B2 | 5/2012 | Allen et al. | |
| 8,273,345 B2 | 9/2012 | Wang et al. | |
| 8,273,361 B2 | 9/2012 | Reed et al. | |
| 8,323,662 B1 | 12/2012 | Nicolai et al. | |
| 8,329,162 B2 | 12/2012 | Wang et al. | |
| 8,343,512 B2 | 1/2013 | Reed et al. | |
| 2001/0007666 A1 | 7/2001 | Hoffman et al. | |
| 2002/0130430 A1 | 9/2002 | Castor | |
| 2002/0176867 A1 | 11/2002 | Andersen et al. | |
| 2003/0077829 A1 | 4/2003 | MacLachlan | |
| 2003/0165512 A1 | 9/2003 | Wheeler et al. | |
| 2003/0170249 A1 | 9/2003 | Hakomori et al. | |
| 2003/0215497 A1 | 11/2003 | Leesman | |
| 2004/0120924 A1 | 6/2004 | Hone et al. | |
| 2004/0161776 A1 | 8/2004 | Maddon et al. | |
| 2005/0208020 A1 | 9/2005 | Doolan et al. | |
| 2006/0257416 A1 | 11/2006 | Palmowski et al. | |
| 2007/0020238 A1 | 1/2007 | Baltimore et al. | |
| 2007/0072824 A1 | 3/2007 | Kawano et al. | |
| 2008/0131466 A1 | 6/2008 | Reed et al. | |
| 2009/0181078 A1 | 7/2009 | Reed et al. | |
| 2009/0208531 A1 | 8/2009 | Nabel et al. | |
| 2010/0047276 A1 | 2/2010 | Heeney et al. | |
| 2010/0120122 A1 | 5/2010 | Wang et al. | |
| 2010/0260807 A1 | 10/2010 | Berinstein et al. | |
| 2010/0297168 A1 | 11/2010 | Charneau et al. | |
| 2010/0310602 A1 | 12/2010 | Reed et al. | |
| 2010/0323403 A1 | 12/2010 | Kafri | |
| 2010/0330112 A1 | 12/2010 | Long et al. | |
| 2011/0014221 A1 | 1/2011 | Kang et al. | |
| 2011/0014274 A1 | 1/2011 | Reed et al. | |
| 2011/0064763 A1* | 3/2011 | Allen et al. | 424/199.1 |
| 2011/0070290 A1 | 3/2011 | Reed et al. | |
| 2011/0142880 A1 | 6/2011 | Lemiale et al. | |
| 2011/0212530 A1 | 9/2011 | Baltimore et al. | |
| 2011/0305748 A1 | 12/2011 | Clegg et al. | |
| 2011/0319480 A1 | 12/2011 | Berinstein et al. | |
| 2012/0039994 A1 | 2/2012 | Reed et al. | |
| 2012/0263754 A1 | 10/2012 | Dubensky et al. | |
| 2012/0288515 A1 | 11/2012 | Robbins et al. | |
| 2013/0084307 A1 | 4/2013 | Reed et al. | |
| 2013/0230554 A1 | 9/2013 | Wang et al. | |
| 2013/0302368 A1 | 11/2013 | Dropulic | |

FOREIGN PATENT DOCUMENTS

| | | |
|---|---|---|
| EP | 0224260 A2 | 6/1987 |
| EP | 0304578 A1 | 3/1989 |
| EP | 0324455 A2 | 7/1989 |
| EP | 0362279 A1 | 4/1990 |
| EP | 0366412 A2 | 5/1990 |
| EP | 0382271 A1 | 8/1990 |
| EP | 0414374 A2 | 2/1991 |
| EP | 0468520 A2 | 1/1992 |
| EP | 0761231 A1 | 3/1997 |
| EP | 772619 A1 | 5/1997 |
| EP | 1531158 A1 | 5/2005 |
| EP | 2272859 A2 | 1/2011 |
| GB | 2220211 A | 1/1990 |
| GB | 2232892 A | 1/1991 |
| JP | 05328975 B2 | 10/2013 |
| WO | WO-89/01973 A2 | 3/1989 |
| WO | WO-90/01496 A1 | 2/1990 |
| WO | WO-90/06951 A1 | 6/1990 |
| WO | WO-90/07936 A1 | 7/1990 |
| WO | WO-90/14837 A1 | 12/1990 |
| WO | WO-91/00106 A1 | 1/1991 |
| WO | WO-91/00107 A1 | 1/1991 |
| WO | WO-91/02805 A2 | 3/1991 |
| WO | WO-93/02184 A1 | 2/1993 |
| WO | WO-93/10152 A1 | 5/1993 |
| WO | WO-93/12778 A1 | 7/1993 |
| WO | WO-93/25234 A1 | 12/1993 |
| WO | WO-93/25698 A1 | 12/1993 |
| WO | WO-94/00152 A1 | 1/1994 |
| WO | WO-94/00153 A1 | 1/1994 |
| WO | WO-94/02595 A1 | 2/1994 |
| WO | WO-94/03622 A1 | 2/1994 |
| WO | WO-94/05792 A1 | 3/1994 |
| WO | WO-94/20137 A1 | 9/1994 |
| WO | WO-94/21292 A1 | 9/1994 |
| WO | WO-95/14026 A1 | 5/1995 |
| WO | WO-95/17209 A1 | 6/1995 |
| WO | WO-95/17210 A1 | 6/1995 |
| WO | WO-95/20600 A1 | 8/1995 |
| WO | WO-95/26204 A1 | 10/1995 |
| WO | WO-96/02555 A1 | 2/1996 |
| WO | WO-96/09310 A1 | 3/1996 |
| WO | WO-96/11272 A2 | 4/1996 |
| WO | WO-96/11711 A1 | 4/1996 |
| WO | WO-96/26277 A1 | 8/1996 |
| WO | WO-96/33739 A1 | 10/1996 |
| WO | WO-97/11708 A1 | 4/1997 |
| WO | WO-98/01139 A1 | 1/1998 |
| WO | WO-98/12302 A1 | 3/1998 |
| WO | WO-98/16247 A1 | 4/1998 |
| WO | WO-98/20117 A1 | 5/1998 |
| WO | WO-98/32869 A1 | 7/1998 |
| WO | WO-98/37418 A2 | 8/1998 |
| WO | WO-98/43670 A2 | 10/1998 |
| WO | WO-98/56414 A1 | 12/1998 |
| WO | WO-99/03884 A2 | 1/1999 |
| WO | WO-99/10375 A2 | 3/1999 |
| WO | WO-99/11241 A1 | 3/1999 |
| WO | WO-99/12565 A1 | 3/1999 |
| WO | WO-99/17741 A1 | 4/1999 |
| WO | WO-99/28475 A2 | 6/1999 |
| WO | WO-99/40188 A2 | 8/1999 |
| WO | WO-99/51748 A2 | 10/1999 |
| WO | WO-99/53061 A2 | 10/1999 |
| WO | WO-00/04149 A2 | 1/2000 |
| WO | WO-00/13029 A1 | 3/2000 |
| WO | WO-00/18929 A2 | 4/2000 |
| WO | WO-00/25815 A1 | 5/2000 |
| WO | WO-00/42994 A2 | 7/2000 |
| WO | WO-00/53722 A2 | 9/2000 |
| WO | WO-01/36433 A2 | 5/2001 |
| WO | WO-02/16560 A1 | 2/2002 |
| WO | WO-02/28424 A2 | 4/2002 |
| WO | WO-02/32450 A2 | 4/2002 |
| WO | WO 03020876 * | 3/2003 |
| WO | WO-03/046185 A1 | 6/2003 |
| WO | WO-03/047518 A2 | 6/2003 |
| WO | WO-2005/058357 A1 | 6/2005 |
| WO | WO-2006/040334 A1 | 4/2006 |
| WO | WO-2006/055729 A1 | 5/2006 |
| WO | WO 2008153541 * | 12/2008 |
| WO | WO-2009/035528 A2 | 3/2009 |
| WO | WO-2009/071613 A2 | 6/2009 |
| WO | WO-2009/076524 A2 | 6/2009 |
| WO | WO-2009143457 A2 | 11/2009 |
| WO | WO-2011/011584 A1 | 1/2011 |
| WO | WO-2012/038832 A2 | 3/2012 |
| WO | WO-2012/162428 A1 | 11/2012 |
| WO | WO-2013/091080 A1 | 6/2013 |

OTHER PUBLICATIONS

Brown et al., Heterologus prime-boost HIV-1 Vaccination Regimens in pre-clinical and clinical trials., *Viruses*, 2:435-67 (2010).

Casado et al., Lentivector immunization induces tumor antigen specific B and T cell responses in vivo, *European J. Immunol.*, 38:1867-76 (2008).

Cheevers et al., Prime-boost vaccination with plasmid DNA encoding caprine-arthritis encephalitis lentivirus env and viral SU suppressed challenge virus and development of arthritis, *Virology*, 306:116-25 (2003).

Dai et al., HIV-1 Gag-specific immunity induced by a lentivector-based vaccine directed to dendritic cells, 106(48):20382-7 (2009).

(56) References Cited

OTHER PUBLICATIONS

Dunachie et al., Review—Prime boost strategies for malaria vaccine development, *J. Exper. Biol.*, 206:3771-9 (2003).
Esslinger et al., In vivo administration of a lentiviral vaccine targets DCs and induces efficient CD8+ T cell responses, *J. Clin. Invest.*, 111:1673-81 (2003).
Goodman et al., A viral vectored prime-boost immunization regime targeting the Malaria Pfs25 antigen induces transmission-blocking activity, *PLoS One*, 6(12):e29428 (2011).
Lopes et al., Immunization with a lentivector that targets tumor antigen expression to dendritic cells induces potent $CD8^+$ and $CD4^+$ T-Cell Responses, *J. Virology*, 82(1):86 (2008).
Lu et al., Heterologous prime-boost vaccination, *Curr. Opin. Immunol.*, 21(3):346-51 (2009).
Nolz et al., Chapter 7: Strategies and implications for prime-boost vaccination to generate memory CD8 T cells, *Advances Exp. Medicine Biol.*, 69-83 (2011).
Tacken et al., Targeting antigen delivery and activation of dendritic cells in vivo: Steps towards cost effective vaccines, *Seminars Immunology*, 23:12-20 (2011).
Tacken et al., Targeting antigens to dendritic cells in vivo, *Immunobiology*, 211:599-608 (2006).
Xiao et al., Lentivector prime and vaccinia virus vector boost generate high-quality CD8 memory T cells and prevent autochthonous mouse melanoma, J. Immunol., 187:1788-96 (2011).
Alving et al., Lipid A and lipsomes containing lipid A as antigens and adjuvants, *Vaccine*, 26:3036-45 (2008).
Apolonia et al., Stable gene transfer to muscle using non-integrating lentiviral vectors, *Mol. Ther.*, 15(11):1947-54 (2007).
Apolonia, Thesis submitted to University College London, 82-97 (2009).
Avanti Polar Lipids, Inc., Product Data Sheet for Avanti Product No. 699200, Lipid A—Purified Detoxified Lipid A, http://www.avantilipds.com, <http://www.avantilipds.com/>download date Jan. 14, 2009.
Avanti Polar Lipids, Inc., Product Data Sheet for Avanti Product No. 699800, Lipid A (Synthetic)(PHAD™) Monophosphoryl Lipid A (Synthetic)(PHAD™), http://www.avantilipds.com, <http://www.avantilipds.com/>download date Jan. 14, 2009.
Avanti, Advertising: Synthetic adjuvant, *J. of Immunology*,178(10):1-5 (2007).
Avanti, Advertising: The new PHAD(tm) in vaccine technology Avanti's synthetic vaccine adjuvant, *J. Immunol.*, 179(12):1-6 (2007).
Baldridge et al., Monophosphoryl lipid A (MPL) formulations for the next generation of vaccines, *Methods*, 19:103-7 (1999).
Baldridge et al., Taking a toll on human disease: Toll-like receptor 4 agonists as vaccine adjuvants and monotherapeutic agents, *Exp. Opin. Biol. Ther.*, 4:1129-38 (2004).
Banchereau et al., Dendritic cells as therapeutic vaccines against cancer, *Nat. Rev. Immunol.*, 5:296-306 (2005).
Bayer, et al., A large U3 deletion causes increased in vivo expression from a nonintegrating lentiviral vector, *Mol. Ther.*, 16(12):1968-76 (2008).
Bayes et al., Gateways to clinical trials, *Methods Find Exp. Clin. Pharmacal.*, 27(3):193-219 (2005).
Beignon et al., Lentiviral vector-based prime/boost vaccination against AIDS: pilot study shows protection against Simian immunodeficiency virus SIVmac251 challenge in macaques, *J. Virol.*, 83(21):10963-74 (2009).
Bender et al., Improved methods for the generation of dendritic cells from nonproliferating progenitors in human blood, *J. Immunol. Methods*, 196(2):121 (1996).
Bennekov et al., Induction of immunity against human cytomegalovirus, *Mt. Sinai J. Med.*, 71 (2): 86-93 (2004).
Berkner, Development of adenovirus vectors for the expression of heterologous genes, *Biotechniques*, 6(7):616-27 (1988).
Bernard et al., Mutations in the E2 glycoprotein of Venezuelan equine encephalitis virus confer heparan sulfate interaction, low morbidity, and rapid clearance from blood of mice, *Virology*, 276:93-103 (2000).
Boehm et al., Cellular responses to interferon-gamma, *Ann. Rev. Immunol.*, 15:749-95 (1997).
Brazolot et al., CpG DNA can induce strong Thl humoral and cell mediated immune responses against hepatitis B surface antigen in young mice, *Proc. Natl. Acad. Sci. USA*, 95(26):15553-8 (1998).
Buchscher et al., Human immunodeficiency virus vectors for inducible expression of foreign genes, *J. Virol.*, 66:2731-9 (1992).
Burke, Development of a herpes simplex virus subunit glycoprotein vaccine for prophylactic and therapeutic use, *Rev. Infect. Dis.*, 13 Suppl. 11:S906-11 (1991).
Burmes et al., Binding of sindbis virus to cell surface heparin sulfate, *J. Virol.*, 72:7349-56 (1998).
Cattamanchi et al., Phase I study of a herpes simplex virus type 2 (HSV-2) DNA vaccine administered to healthy, HSV-2-seronegative adults by a needle-free injection system, *Clin. Vaccine Immunol.*, 15:1638-43 (2008).
Chang et al., Granulocyte-macrophage colony stimulating factor: an adjuvant for cancer vaccines, *Hematology*, 9(3):207-15 (2004).
Chen et al., Distinct responses of lung and spleen dendritic cells to the TLR9 against CpG oligodeoxynucleotide, *J Immunol.*, 177(4):2373-83 (2006).
Coler et al., Development and characterization of synthetic glucopyranosyl lipid adjuvant system as a vaccine adjuvant, *Plos One*, 6(1):E16333 (2011).
Coler et al., Immunization with a polyprotein vaccine consisting of the T-Cell antigensthiol-specific antioxidant, *Leishmania* major Stress-Inducible protein 1, and *Leishmania* elongation initiation factor protects against Leishmaniasis, *Infection and Immunity*, 70(8):4215-25 (2002).
Corey et al., Recombinant glycoprotein vaccine for the prevention of genital HSV-2 infection: two randomized controlled trials. Chiron HSV Vaccine Study Group, *JAMA*, 282(4):331-40 (1999).
Corey et al., Risk of recurrence after treatment of first-episode genital herpes with intravenous acyclovir, *Sex Transm. Dis.*, 12:215-8 (1985).
Cornetta et al., No. retroviremia or pathology in long-term follow-up of monkeys exposed to a murine amphotropic retrovirus, *Hum. Gene Ther.*, 2:215-9 (1991).
Dai et al., HIV-1 Gag-specific immunity induced by a lentivector-based vaccine directed to dendritic cells, *Proc. Natl. Acad. Sci.*, 106(48):20382-7 (2009).
Datta et al., A subset of toll-like receptor ligands induces cross-presentation by bone marrow-derived dendritic cells, *J Immunol.*, 170(8):4102-10 (2003).
Davis et al., CpG DNA is a potent enhancer of specific immunity in mice immunized with recombinant hepatitis B surface antigen, *J Immunol.*, 160(2):870-6 (1998).
Deavin et al., Statistical comparison of established T-cell epitope predictors against a large database of human and murine antigens, *Mol. Immunol.*, 33:145-55 (1996).
Deglon et al., Self-inactivating lentiviral vectors with enhanced transgene expression as potential gene transfer system in Parkinson's disease, *Hum. Gene Ther.*, 11:179-90 (2000).
DeGroot et al., From genome to vaccine: in silico predictions, ex vivo verification, *Vaccine*, 19:4385-95 (2001).
Deng et al., CpG oligodeoxynucleotides stimulate protective innate immunity against pulmonary *Klebsiella* infection, *J. Immunol.*, 173:5148-55 (2004).
Dhodapkar et al., Rapid generation of broad T-cell immunity in humans after a single injection of mature dendritic cells, *J. Clin. Invest.*, 104(2):173-80 (1999).
Douglas et al., Tailoring subunit vaccine immunogenicity: Maximizing antibody and T cell responses by using combinations of adenovirus, proxvirus and protein-adjuvant vaccines against *Plasmodium falciparum* MSP1, *Vaccine*, 28(44):7167-78 (2010).
Doytchinova et al., Quantitative approaches to computational vaccinology, *Immunol. Cell Biol.*, 80(3):270-9 (2002).
Dranoff, GM-CSF-based cancer vaccines, *Immunol. Rev.*, 188:147-54 (2002).

(56) References Cited

OTHER PUBLICATIONS

Edelman, The development and use of vaccine adjuvants, *Mol. Biotechnol.*, 21(2):129-48 (2002).
Edelman, Vaccine adjuvants, *Rev. Infect. Dis.*, 2(3):370-83 (1980).
Engelhard et al., Direct identification of human tumor-associated peptide antigens and a preclinical model to evaluate their use, *Cancer J.*, 3:S272-80 (2000).
Fearon et al., The instructive role oflnnate immunity in the acquired immune response, *Science*, 272(5258):50-4 (1996).
Figdor et al., Dendritic cell immunotherapy: mapping the way, *Nat. Med.*, 10:475-80 (2004).
Furth, Conditional control of gene expression in the mammary gland, *J. Mamm. Gland Biol. Neoplas.*, 2:373-83 (1997).
Gardner et al., Infection of human dendritic cells by a sindbis virus replicon vector is determined by a single amino acid substitution in the E2 glycoprotein, *J. Virol.*, 74:11849-57 (2000).
Geijtenbeek et al., Self- and nonself-recognition by C-type lectins on dendritic cells, *Annu. Rev. Immunol.*, 22:33-54 (2004).
Gibson et al., Plasmacytoid dendritic cells produce cytokines and mature in response to the TLR7 agonists, imiquimod and resiquimod, *Cell.Immunol.*, 218(1-2):74-86 (2002).
Hilgers et al., Synergistic effects of synthetic adjuvants on the humoral immuneresponse, *Int. Archs. Allergy Appl. Immunol.*, 79(4):392-6 (1986).
Hill et al., Prime-boost vectored malaria vaccines: progress and prospects, *Human Vaccines*, 6(1):78-83 (2010).
Hoffmeister et al., Mapping T cell epitopes by flow cytometry, *Methods*, 29:270-81 (2003).
Hofland et al., Novel therapeutics from modern biotechnology, *Handb. Exp. Pharmacol.*, 137:165-92 (1999).
Horsfall et al., Epitope mapping, *Immunol. Today*, 12:211-3 (1991).
Hu et al. Yaba-like disease virus: an alternative replicating poxvirus vector for cancer gene therapy, *J. Virol.*, 75:10300-8 (2001).
Hutchings et al., Combination of protein and viral vaccines induces potent cellular and humoral immune responses and enhanced protection from murine malaria challenge, *Infection & Immunology*, 75(12):5819-26 (2007).
Iwakuma et al., Self-inactivating lentiviral vectors with U3 and U5 modifications, *Virology*, 15:120-32 (1999).
Iwasaki et al., Toll-like receptor control of the adaptive immune responses, *Nat. Immunol.*, 5:987 (2004).
Johnson et al., Plasmid DNA vaccine encoding prostatic acid phosphatase is effective in eliciting autologous antigen-specific CD8+ T cells, *Cancer Immunology*, 56(6):885-95 (2006).
Johnson et al., TLR4 agonists as vaccine adjuvants, *Vaccine Adjuvants and Delivery Systems*, 131-56 (2007).
Kantoff et al., Overall survival analysis of a phase II randomized controlled trial of a Poxviral-based PSA-targeted immunotherapy in metastatic castration-resistant prostate cancer, *J. Clin. Oncol.*, 28(7):1099-105 (2010).
Kantoff et al., Sipuleucel-T immunotherapy for castration-resistant prostate cancer, *New Engl. J. Med.*, 363(5):411-22 (2010).
Kanzler et al., Therapeutic targeting of innate immunity with toll-like receptor agonists and antagonists, *Nature Medicine*, 13(5):552-9 (2007).
Klimstra et al., Adaptation of Sindbis virus to BHK cells selects for use of heparan sulfate as an attachment receptor, *J. Virol.*, 72(9):7357-66 (1998).
Klimstra et al., DC-SIGN and L-SIGN can act as attachment receptors for alphaviruses and distinguish between mosquito cell- and mammalian cell-derived viruses, *J. Virol.*, 7(22)12022-32 (2003).
Koelle et al., Clearance of HSV-2 from recurrent genital lesions correlates with infiltration of HSV-specific cytotoxic T lymphocytes, *J. Clin. Invest.*, 101:1500-8 (1998).
Koelle et al., Direct recovery of herpes simplex virus (HSV)-specific T lymphocyte clones from recurrent genital HSV-2 lesions, *J. Infect. Dis.*, 169:956 (1994).
Koelle et al., Expression of cutaneous lymphocyte-associated antigen by CD8(+) T cells specific for a skin-tropic virus, *J. Clin. Invest.*, 110:537-48 (2002).
Koelle et al., Recent progress in herpes simplex virus immunobiology and vaccine research, *Clin. MicrobioL Rev.*, 16: 96-113 (2003).
Koelle, et al., CD8 CTL from genital herpes simplex lesions: recognition of viral tegument and immediate early proteins and lysis of infected cutaneous cells, *J. Immunol.*, 166:4049-58 (2001).
Kung et al., A murine leukemia virus (MuLV) long terminal repeat derived from rhesus macaques in the context of a lentivirus vector and MuLV gag sequence results in high-level gene expression in human t lymphocytes, *J. Virol.*, 74:3668-81 (1999).
Kwok et al., Rapid epitope identification from complex class-II-restricted T-cell antigens, *Trends Immunol.*, 22:583-8 (2001).
Lamb et al., Identification of mycobacterial antigens recognized by T lymphocytes, *Rev. Infect. Dis.*, 2:S443-7 (1989).
Lieberman et al., Recognition of a small number of diverse epitopes dominates the cytotoxic T lymphocyte response to HIV type 1 in an infected individual, *AIDS Res Hum. Retroviruses*, 13(5):383-92 (1997).
Lin et al., Present status of the use of cytokines as adjuvants with vaccines to protect against infectious diseases, *Clin. Infect. Dis.*, 21(6):1439-49 (1995).
Liu et al., Immune control of an SIV challenge by a T-cell-based vaccine in rhesus monkeys, *Nature*, 457(7225):87-91 (2009).
Liu, Vaccine Developments, *Nature Medicine*, 4(5):515-9 (1998).
Loessner et al., Bacteria-mediated DNA transfer in gene therapy and vaccination, *Expert Opin. Biol. Ther.*, 4:157-68 (2004).
Loewendorf et al., Modulation of host innate and adaptive immune defenses by cytomegalovirus: timing is everything, *J. Intern. Med.*, 267(5):483-501 (2010).
Luster, The role of chemokines in linking innate and adaptive immunity, *Curr. Opin. Immunol.*, 14(1):129-35 (2002).
Maecker et al., Use of overlapping peptide mixtures as antigens for cytokine flow cytometry, *J. Immunol. Methods*, 255:27-40 (2001).
McWilliams et al., Mutations in the 5' end of the human immunodeficiency virus type 1 polypurine tract affect RNase H cleavage specificity and virus titer, *J. Virol.*, 77:11150-7 (2003).
Medzhitov et al., Innate immunity: Impact on the adaptive immune response, *Curr. Opin. Immunol.*, 9(1):4-9 (1997).
Medzhitov, Toll-like receptors and innate immunity, *Nat. Rev. Immunol.*, 1(2):135-45 (2001).
Menendez-Arias et al., Cytotoxic T-lymphocyte responses to HIV-1 reverse transcriptase (review), *Viral Immunol.*, 11(4):167-81 (1998).
Mettenleiter et al., Herpesvirus assembly: a tale of two membranes, *Curr. Opin. Microbiol.*, 9:423-9 (2006).
Miller et al., Construction and properties of retrovirus packaging cells based on gibbon ape leukemia virus, *J. Virol.*, 65:2220-4 (1991).
Miller et al., Gene transfer by retrovirus vectors occurs only in cells that are actively replicating at the time of infection, *Mol. Cell Biol.*, 10:4239 (1990).
Miyoshi et al., Development of a self-inactivating lentivirus vector, *J. Virol.*, 72:8150-7 (1998).
Navaratnarajah et al., Functional characterization of the sindbis virus E2 glycoprotein by transposon linker-insertion mutagenesis, *J. Virol.*, 363:134-47 (2007).
Nightingale et al., Transient gene expression by nonintegrating lentiviral vectors, *Mol. Therapy*, 13:1121-32 (2006).
O'Hagan et al., Novel approaches to vaccine delivery, *Pharm. Res.*, 21(9):1519-30 (2004).
Parr et al., Mucosal immunity to herpes simplex virus type 2 infection in the mouse vagina is impaired by in vivo depletion of T lymphocytes, *J. Virol.*, 72:2677 (1998).
Patel et al., A poxvirus-derived vector that directs high levels of expression of cloned genes in mammalian cells, *Proc. Natl. Acad. Sci.*, 85:9431 (1988).
Paterson, Listeria and Salmonella bacterial vectors of tumor-associated antigens for cancer immunotherapy, *Semin. Immunol.*, 22:183 (2010).
Persing et al., Taking toll: lipid A mimetics as adjuvants and immunomodulators, *Trends Microbiol.*, 10:S32-7 (2002).
Pfeifer et al., Gene therapy: promises and problems, *Annu. Rev. Genomics Hum. Genet.*, 2:177-211 (2001).
Philpott et al., Use of nonintegrating lentiviral vectors for gene therapy, *Human Gene Therapy*, 18:483 (2007).

(56) References Cited

OTHER PUBLICATIONS

Portielje et al., IL-12: A promising adjuvant for cancer vaccination, *Cancer Immunol. Immunother.*, 52(3):133-44 (2003).
Posavad et al., Tipping the scales of herpes simplex virus reactivation: the important responses are local, *Nat. Med.*, 4:381 (1998).
Powell et al., Sequence and structural determinants required for priming of plus-strand DNA synthesis by the human immunodeficiency virus type 1 polypurine tract, *J. Virol.*, 70:5288 (1996).
Radosevic et al., Heterologous prime-boost vaccinations for proverty-related diseases: advantages and future prospects, *Expert Review Vaccines*, 8(5):577-92 (2009).
Rajcani et al., Developments in herpes simplex virus vaccines: old problems and new challenges, *Folia Microbiol. (Praha)*, 51:67-85 (2006).
Reed et al., New horizons in adjuvants for vaccine development, *Trends in Immunology*, 30(1):23-32 (2009).
Renkvist et al., A listing of human tumor antigens recognized by T-cells, *Cancer Immunol. Immunother.*, 50:3-15 (2001).
Robbins et al., Human tumor antigens recognized by T-cells, *Curr. Opin. Immunol.*, 8(5):628-636 (1996).
Rodriguez et al., Impact of recombinant adenovirus serotype 35 priming versus boosting of a *Plasmodium falciparum* protein: Characterization of T- and B-cell responses to liver-stage antigen 1, *Infection and Immunity*, 76(4)1709-18 (2008).
Salem et al., The adjuvant effects of the toll-like receptor 3 ligand polyinosinic—cytidylic acid poly (I:C) on antigen-specific CDS+ T-cell responses are partially dependent on NK cells with the induction of a beneficial cytokine milieu, *Vaccine*, 24(24):5119-32 (2006).
Sallusto et al., Efficient presentation of soluble antigen by cultured human dendritic cells is maintained by granulocyte/macrophage colony-stimulating factor plus interleukin 4 and downregulated by tumor necrosis factor alpha, *J. Exp. Med.*, 179(4):1109-18 (1994).
Schuler et al., The use of dendritic cells in cancer immunotherapy, *Curr. Opin. Immunol.*, 15:138-47 (2003).
Schuler-Thurner et al., Mage-3 and influenza-matrix peptide-specific cytotoxic T cells are inducible in terminal stage HLA-A2.1+ melanoma patients by mature monocyte-derived dendritic cells, *J. Immunol.*, 165(6):3492 (2000).
Seder et al., T-cell quality in memory and protection: implications for vaccine design, *Nat. Rev. Immunol.*, 8:247 (2008).
Soboll et al., Expression of toll-like receptors (TLR) and responsiveness to TLR agonists by polarized mouse uterine epithelial cells in culture, *Biol. Reprod.*, 75(1):131-9 (2006).
Sommerfelt et al., Receptor interference groups of 20 retroviruses plating on human cells, *Virology*, 176:58-69 (1990).
Stanberry et al., Glycoprotein-D-adjuvant vaccine to prevent genital herpes, *N. Engl. J. Med.*, 347:1652 (2002).
Steers et al., Modulation of immunoprotease subunits by liposomal lipid A, *Vaccine*, 26:2849-59 (2008).
Stewart et al., Priming with an adenovirus 35-circumsporozoite protein (CS) vaccine followed by RTS,S/ASO1B boosting significantly improves immunogenicity to *Plasmodium falciparum* CD compared to that with either malaria vaccine alone, *Infection & Immunity*, 75(5):2283-90 (2007).
Szymczak et al. Correction of multi-gene deficiency in vivo using a single 'self-cleaving' 2A peptide-based retroviral vector, *Nat. Biotechnol.*, 22:589-594 (2004).
Takeda et al., Toll-like receptors, *Ann. Rev. Immunol.*, 21:335-76 (2003).
Takeda et al., Toll-like-receptors in innate immunity, *Int. Immunol.*, 17(1):1-14 (2005).
Tang et al., Vector prime/ protein boost vaccine that overcomes defects acquired during aging and cancer, *J. Immunol.*, 177:5697-707 (2006).
Taylor, Cytokines as adjuvants for vaccines: antigen-specific responses differ from polyclonal responses, *Infect. Immun.*,63(9):3241-4 (1995).
Theofilopoulos et al., Type I interferons (alpha/beta) in immunity and autoimmunity, *Ann. Rev. Immunol.*, 23:307-36 (2005).
Tomai et al., The adjuvant properties of a nontoxic monophosphoryl lipid A in hyporesponsive and aging mice, *J. Biol. Response Mod.*, 6:99-107 (1987).
Triozzi et al., Effects of a beta-human chorionic gonadotropin subunit immunogen administered in aqueous solution with a novel nonionic block copolymer adjuvant in patients with advanced cancer, *Clin. Cancer Res.*, 3(12 Pt 1):2355-62 (1997).
Ulmer et al., Heterologous protection against influenza by injection of DNA encoding a viral protein, *Science*, 259:1745-9 (1993).
Ulrich et al., Vaccine Design: The subunit and adjuvant approach Chapter 21 Monophosphoryl Lipid A as an adjuvant: past experiences and new directions, *Plenum Press*, (1995).
Van den Eynde et al., T cell defined tumor antigens, *Curr. Opin. Immunol.*, 9:684-93 (1997).
Van Regenmortel, Mapping Epitope Structure and Activity: From One-Dimensional Prediction to Four-Dimensional Description of Antigenic Specificity, *Methods*, 9:465-72 (1996).
Vollmer et al., Immunopharmacology of CpG oligodeoxynucleotides and ribavirin, *Antimicrob. Agents Chemother.*, 48(6):2314-7 (2004).
Vollmer, Progress in drug development of Immunostimulatory CpG oligodeoxynucleotide ligands for TLR9, *Exp. Opin. Biolog. Ther.*, 5(5):673-82 (2005).
Wang et al., High-affinity laminin receptor is a receptor for Sindbis virus in mammalian cells, *J. Virol.*, 66:4992 (1992).
Wang et al., pH-sensitive Immunoliposomes mediate target-cell-specific delivery and controlled expression of a foreign gene in mouse, *Proc. Natl. Acad. Sci. USA*, 84:7851-5 (1987).
Watkins, The hope for an HIV vaccine based on induction of CD8+ T lymphocytes—a review, *Mem. Inst. Oswaldo Cruz.*, 103(2):119-29 (2008).
Weeratna et al., TLR agonists as vaccine adjuvants: Comparison of CpG ODN and resiquimod (R-848), *Vaccine*, 23(45):5263-70 (2005).
Weihrauch et al., Phase I/II Combined chemoimmunotherapy with carcinoembryonic antigen-derived HLA-A2-restricted CAP-1 peptide and irinotecan, 5-Fluorouracil, and leucovorin in patients with primary metastatic colorectal cancer, *Clin. Cancer Res.*, 11(16):5993-6001 (2005).
Wheeler et al., Allergy vaccines—new approaches to an old concept, *Expert Opin. Biol. Ther.*, 4(9):1473-81 (2004).
Wu et al., Targeting genes: Delivery and persistent expression of a foreign gene driven by mammalian regulatory elements in vivo, *J. Biol. Chem.*, 264(29):16985-7 (1989).
Xiong et al., inhibition of Interleukin-12 p40 transcription and NF-kB activation by nitric oxide in murine macrophages and dendritic cells, *J. Biol. Chem.*, 279(11):10776-83 (2004).
Yang et al., Development of optimal bicistronic lentiviral vectors facilitates high-level TCR gene expression and robust tumor cell recognition, *Gene Ther.*, 15:1411 (2008).
Yang et al., The immunogenicity-enhancing effect of emulsion vaccine adjuvants is independent of thedispersion type and antigen release rate-a revisit of the role of the hydrophile-lipophile balance (HLB) value, *Vaccine*, 23:2665-75 (2005).
Yang, et al., Engineered lentivector targeting of dendritic cells for in vivo immunization, *Nat. Biotechnol.*, 26(3):326 (2008).
Yu et al., Self-inactivating retroviral vectors designed for transfer of whole genes into mammalian cells, *Proc. Natl. Acad. Sci. USA*, 83:3194-8 (1986).
Zhu et al., Virus-specific CD8+ T cells accumulate near sensory nerve endings in genital skin during subclinical HSV-2 reactivation, *J. Exp. Med.*, 204:595-603 (2007).
Zufferey et al., Self-inactivating lentivirus vector for safe and efficient in vivo gene delivery, *J. Virol.*, 72:9873-80 (1998).
International Search Report and Written Opinion of the International Searching Authority, European Patent Office, PCT/US2012/032550, dated Jun. 27, 2012.
Alencar et al., Cross-priming of long lived protective CD8+ T cells against *Trypanosoma cruzi* infection: Importance of a TLR9 agonist and CD4+ T cells, *Vaccine*, 25:6018-27 (2007).
Garcia-Hernandez et al., Prostate stem cell antigen vaccination induces a long-term protective immune response against prostate cancer in the absence of autoimmunity, *Cancer Res.*, 68(3):861-9 (2008).

(56) References Cited

OTHER PUBLICATIONS

Ishizaki et al., Heterologous prime/boost immunization with p53-based vaccines combined with toll-like receptor stimulation enhances tumor regression, *J. Immunother.*, 33(6):609-17 (2010).

Patterson et al., Replicating adenovirus vector prime/protein boost strategies for HIV vaccine development, *Exp. Opin. Biol. Ther.*, 8:1347-63 (2008).

Radosevic et al., the Th1 immune response to *Plasmodim falciparum* circumsporozoite protein is boosted by adenovirus vectors 35 and 26 with a homologous insert, *Clin. Vacc. Immunol.*, 17(11):1687-1694 (2010).

International Preliminary Report on Patentability and Written Opinion of the International Searching Authority, European Patent Office, PCT/US2012/032550, dated Oct. 8, 2013.

\* cited by examiner

| Prime | 1st Boost | 2nd Boost |
|---|---|---|
| Immunogen | Vector encoding immunogen | None |
| Immunogen | Vector encoding immunogen | Immunogen |
| Immunogen | Immunogen | Vector encoding immunogen |
| Immunogen | Immunogen and Vector encoding immunogen | None |
| Immunogen and Vector encoding immunogen | None | None |
| Immunogen and Vector encoding immunogen | Immunogen and Vector encoding immunogen | None |
| Vector encoding immunogen | Immunogen | None |
| Vector encoding immunogen | Immunogen | Vector encoding immunogen |
| Immunogen + adjuvant | Vector encoding immunogen | None |
| Immunogen + adjuvant | Vector encoding immunogen | Immunogen + adjuvant |
| Immunogen + adjuvant | Immunogen + adjuvant | Vector encoding immunogen |
| Immunogen + adjuvant | Immunogen + adjuvant and Vector encoding immunogen | None |
| Immunogen + adjuvant and Vector encoding immunogen | None | None |
| Immunogen + adjuvant and Vector encoding immunogen | Immunogen + adjuvant and Vector encoding immunogen | None |
| Vector encoding immunogen | Immunogen + adjuvant | None |
| Vector encoding immunogen | Immunogen + adjuvant | Vector encoding immunogen |

SEQUENCE LISTING

<160> NUMBER OF SEQ ID NOS: 45

<210> SEQ ID NO 1
<211> LENGTH: 423
<212> TYPE: PRT

-continued

<213> ORGANISM: Sindbis virus
<220> FEATURE:
<221> NAME/KEY: misc_feature
<222> LOCATION: (160)..(160)
<223> OTHER INFORMATION: Xaa can be any naturally occurring amino acid

<400> SEQUENCE: 1

```
Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asp Asn Thr Ile Arg Ile Gln Thr Ser
        35                  40                  45

Ala Gln Phe Gly Tyr Asp Gln Ser Gly Ala Ala Ser Ala Asn Lys Tyr
    50                  55                  60

Arg Tyr Met Ser Leu Lys Gln Asp His Thr Val Lys Glu Gly Thr Met
65                  70                  75                  80

Asp Asp Ile Lys Ile Ser Thr Ser Gly Pro Cys Arg Arg Leu Ser Tyr
                85                  90                  95

Lys Gly Tyr Phe Leu Leu Ala Lys Cys Pro Pro Gly Asp Ser Val Thr
            100                 105                 110

Val Ser Ile Val Ser Ser Asn Ser Ala Thr Ser Cys Thr Leu Ala Arg
        115                 120                 125

Lys Ile Lys Pro Lys Phe Val Gly Arg Glu Lys Tyr Asp Leu Pro Pro
    130                 135                 140

Val His Gly Lys Lys Ile Pro Cys Thr Val Tyr Asp Arg Leu Lys Xaa
145                 150                 155                 160

Thr Thr Ala Gly Tyr Ile Thr Met His Arg Pro Arg Pro His Ala Tyr
                165                 170                 175

Thr Ser Tyr Leu Glu Glu Ser Ser Gly Lys Val Tyr Ala Lys Pro Pro
            180                 185                 190

Ser Gly Lys Asn Ile Thr Tyr Glu Cys Lys Cys Gly Asp Tyr Lys Thr
        195                 200                 205

Gly Thr Val Ser Thr Arg Thr Glu Ile Thr Gly Cys Thr Ala Ile Lys
    210                 215                 220

Gln Cys Val Ala Tyr Lys Ser Asp Gln Thr Lys Trp Val Phe Asn Ser
225                 230                 235                 240

Pro Asp Leu Ile Arg His Asp Asp His Thr Ala Gln Gly Lys Leu His
                245                 250                 255

Leu Pro Phe Lys Leu Ile Pro Ser Thr Cys Met Val Pro Val Ala His
            260                 265                 270

Ala Pro Asn Val Ile His Gly Phe Lys His Ile Ser Leu Gln Leu Asp
        275                 280                 285

Thr Asp His Leu Thr Leu Leu Thr Thr Arg Arg Leu Gly Ala Asn Pro
    290                 295                 300

Glu Pro Thr Thr Glu Trp Ile Val Gly Lys Thr Val Arg Asn Phe Thr
305                 310                 315                 320

Val Asp Arg Asp Gly Leu Glu Tyr Ile Trp Gly Asn His Glu Pro Val
                325                 330                 335

Arg Val Tyr Ala Gln Glu Ser Ala Pro Gly Asp Pro His Gly Trp Pro
            340                 345                 350

His Glu Ile Val Gln His Tyr Tyr His Arg His Pro Val Tyr Thr Ile
        355                 360                 365

Leu Ala Val Ala Ser Ala Thr Val Ala Met Met Ile Gly Val Thr Val
    370                 375                 380

-continued

```
Ala Val Leu Cys Ala Cys Lys Ala Arg Arg Glu Cys Leu Thr Pro Tyr
385                 390                 395                 400

Ala Leu Ala Pro Asn Ala Val Ile Pro Thr Ser Leu Ala Leu Leu Cys
                405                 410                 415

Cys Val Arg Ser Ala Asn Ala
            420

<210> SEQ ID NO 2
<211> LENGTH: 986
<212> TYPE: PRT
<213> ORGANISM: Sindbis virus

<400> SEQUENCE: 2

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Ser Val Ile
50                  55                  60

Asp Asp Phe Thr Leu Thr Ser Pro Tyr Leu Gly Thr Cys Ser Tyr Cys
65                  70                  75                  80

His His Thr Val Pro Cys Phe Ser Pro Val Lys Ile Glu Gln Val Trp
                85                  90                  95

Asp Glu Ala Asp Asp Asn Thr Ile Arg Ile Gln Thr Ser Ala Gln Phe
            100                 105                 110

Gly Tyr Asp Gln Ser Gly Ala Ala Ser Ala Asn Lys Tyr Arg Tyr Met
            115                 120                 125

Ser Leu Lys Gln Met Tyr Pro Tyr Asp Val Pro Asp Tyr Ala Thr Val
130                 135                 140

Lys Glu Gly Thr Met Asp Asp Ile Lys Ile Ser Thr Ser Gly Pro Cys
145                 150                 155                 160

Arg Arg Leu Ser Tyr Lys Gly Tyr Phe Leu Leu Ala Lys Cys Pro Pro
                165                 170                 175

Gly Asp Ser Val Thr Val Ser Ile Val Ser Ser Asn Ser Ala Thr Ser
            180                 185                 190

Cys Thr Leu Ala Arg Lys Ile Lys Pro Lys Phe Val Gly Arg Glu Lys
            195                 200                 205

Tyr Asp Leu Pro Pro Val His Gly Lys Lys Ile Pro Cys Thr Val Tyr
210                 215                 220

Asp Arg Leu Ala Ala Thr Thr Ala Gly Tyr Ile Thr Met His Arg Pro
225                 230                 235                 240

Arg Pro His Ala Tyr Thr Ser Tyr Leu Glu Glu Ser Ser Gly Lys Val
                245                 250                 255

Tyr Ala Lys Pro Pro Ser Gly Lys Asn Ile Thr Tyr Glu Cys Lys Cys
            260                 265                 270

Gly Asp Tyr Lys Thr Gly Thr Val Ser Thr Arg Thr Glu Ile Thr Gly
            275                 280                 285

Cys Thr Ala Ile Lys Gln Cys Val Ala Tyr Lys Ser Asp Gln Thr Lys
290                 295                 300

Trp Val Phe Asn Ser Pro Asp Leu Ile Arg His Asp Asp His Thr Ala
305                 310                 315                 320

Gln Gly Lys Leu His Leu Pro Phe Lys Leu Ile Pro Ser Thr Cys Met
```

```
                    325                 330                 335
Val Pro Val Ala His Ala Pro Asn Val Ile His Gly Phe Lys His Ile
                340                 345                 350
Ser Leu Gln Leu Asp Thr Asp His Leu Thr Leu Leu Thr Thr Arg Arg
                355                 360                 365
Leu Gly Ala Asn Pro Glu Pro Thr Thr Glu Trp Ile Val Gly Lys Thr
                370                 375                 380
Val Arg Asn Phe Thr Val Asp Arg Asp Gly Leu Glu Tyr Ile Trp Gly
385                 390                 395                 400
Asn His Glu Pro Val Arg Val Tyr Ala Gln Glu Ser Ala Pro Gly Asp
                405                 410                 415
Pro His Gly Trp Pro His Glu Ile Val Gln His Tyr Tyr His Arg His
                420                 425                 430
Pro Val Tyr Thr Ile Leu Ala Val Ala Ser Ala Thr Val Ala Met Met
                435                 440                 445
Ile Gly Val Thr Val Ala Val Leu Cys Ala Cys Lys Ala Arg Arg Glu
                450                 455                 460
Cys Leu Thr Pro Tyr Ala Leu Ala Pro Asn Ala Val Ile Pro Thr Ser
465                 470                 475                 480
Leu Ala Leu Leu Cys Val Arg Ser Ala Asn Ala Glu Thr Phe Thr
                485                 490                 495
Glu Thr Met Ser Tyr Leu Trp Ser Asn Ser Gln Pro Phe Phe Trp Val
                500                 505                 510
Gln Leu Cys Ile Pro Leu Ala Ala Phe Ile Val Leu Met Arg Cys Cys
                515                 520                 525
Ser Cys Cys Leu Pro Phe Leu Val Val Ala Gly Ala Tyr Leu Ala Lys
                530                 535                 540
Val Asp Ala Tyr Glu His Ala Thr Thr Val Pro Asn Val Pro Gln Ile
545                 550                 555                 560
Pro Tyr Lys Ala Leu Val Glu Arg Ala Gly Tyr Ala Pro Leu Asn Leu
                565                 570                 575
Glu Ile Thr Val Met Ser Ser Glu Val Leu Pro Ser Thr Asn Gln Glu
                580                 585                 590
Tyr Ile Thr Cys Lys Phe Thr Thr Val Val Pro Ser Pro Lys Ile Lys
                595                 600                 605
Cys Cys Gly Ser Leu Glu Cys Gln Pro Ala Ala His Ala Gly Tyr Thr
                610                 615                 620
Cys Lys Val Phe Gly Gly Val Tyr Pro Phe Met Trp Gly Gly Ala Gln
625                 630                 635                 640
Cys Phe Cys Asp Ser Glu Asn Ser Gln Met Ser Glu Ala Tyr Val Glu
                645                 650                 655
Leu Ser Ala Asp Cys Ala Ser Asp His Ala Gln Ala Ile Lys Val His
                660                 665                 670
Thr Ala Ala Met Lys Val Gly Leu Arg Ile Val Tyr Gly Asn Thr Thr
                675                 680                 685
Ser Phe Leu Asp Val Tyr Val Asn Gly Val Thr Pro Gly Thr Ser Lys
                690                 695                 700
Asp Leu Lys Val Ile Ala Gly Pro Ile Ser Ala Ser Phe Thr Pro Phe
705                 710                 715                 720
Asp His Lys Val Val Ile His Arg Gly Leu Val Tyr Asn Tyr Asp Phe
                725                 730                 735
Pro Glu Tyr Gly Ala Met Lys Pro Gly Ala Phe Gly Asp Ile Gln Ala
                740                 745                 750
```

```
Thr Ser Leu Thr Ser Lys Asp Leu Ile Ala Ser Thr Asp Ile Arg Leu
            755                 760                 765

Leu Lys Pro Ser Ala Lys Asn Val His Val Pro Tyr Thr Gln Ala Ser
770                 775                 780

Ser Gly Phe Glu Met Trp Lys Asn Asn Ser Gly Arg Pro Leu Gln Glu
785                 790                 795                 800

Thr Ala Pro Phe Gly Cys Lys Ile Ala Val Asn Pro Leu Arg Ala Val
            805                 810                 815

Asp Cys Ser Tyr Gly Asn Ile Pro Ile Ser Ile Asp Ile Pro Asn Ala
            820                 825                 830

Ala Phe Ile Arg Thr Ser Asp Ala Pro Leu Val Ser Thr Val Lys Cys
            835                 840                 845

Glu Val Ser Glu Cys Thr Tyr Ser Ala Asp Phe Gly Gly Met Ala Thr
850                 855                 860

Leu Gln Tyr Val Ser Asp Arg Glu Gly Gln Cys Pro Val His Ser His
865                 870                 875                 880

Ser Ser Thr Ala Thr Leu Gln Glu Ser Thr Val His Val Leu Glu Lys
            885                 890                 895

Gly Ala Val Thr Val His Phe Ser Thr Ala Ser Pro Gln Ala Asn Phe
            900                 905                 910

Ile Val Ser Leu Cys Gly Lys Lys Thr Thr Cys Asn Ala Glu Cys Lys
            915                 920                 925

Pro Pro Ala Asp His Ile Val Ser Thr Pro His Lys Asn Asp Gln Glu
930                 935                 940

Phe Gln Ala Ala Ile Ser Lys Thr Ser Trp Ser Trp Leu Phe Ala Leu
945                 950                 955                 960

Phe Gly Gly Ala Ser Ser Leu Leu Ile Ile Gly Leu Met Ile Phe Ala
            965                 970                 975

Cys Ser Met Met Leu Thr Ser Thr Arg Arg
                980                 985

<210> SEQ ID NO 3
<211> LENGTH: 982
<212> TYPE: PRT
<213> ORGANISM: Sindbis virus

<400> SEQUENCE: 3

Met Ser Ala Ala Pro Leu Val Thr Ala Met Cys Leu Leu Gly Asn Val
1               5                   10                  15

Ser Phe Pro Cys Asp Arg Pro Thr Cys Tyr Thr Arg Glu Pro Ser
            20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
            115                 120                 125

Tyr Arg Tyr Met Ser Leu Glu Gln Asp His Thr Val Lys Glu Gly Thr
```

-continued

```
            130                 135                 140
Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Glu
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
    290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365

Pro Glu Pro Thr Thr Glu Trp Ile Val Gly Lys Thr Val Arg Asn Phe
    370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
        435                 440                 445

Val Ala Val Leu Cys Ala Cys Lys Ala Arg Arg Glu Cys Leu Thr Pro
    450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
        515                 520                 525

Pro Phe Leu Val Val Ala Gly Ala Tyr Leu Ala Lys Val Asp Ala Tyr
    530                 535                 540

Glu His Ala Thr Thr Val Pro Asn Val Pro Gln Ile Pro Tyr Lys Ala
545                 550                 555                 560
```

```
Leu Val Glu Arg Ala Gly Tyr Ala Pro Leu Asn Leu Glu Ile Thr Val
            565                 570                 575

Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
            595                 600                 605

Leu Glu Cys Gln Pro Ala Ala His Ala Asp Tyr Thr Cys Lys Val Phe
            610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
            645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
            675                 680                 685

Val Tyr Val Asn Gly Val Thr Pro Gly Thr Ser Lys Asp Leu Lys Val
            690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
            725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
            755                 760                 765

Ala Lys Asn Val His Val Pro Tyr Thr Gln Ala Ser Ser Gly Phe Glu
            770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
            805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
            835                 840                 845

Cys Thr Tyr Ser Ala Asp Phe Gly Gly Met Ala Thr Leu Gln Tyr Val
            850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
            885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
            915                 920                 925

His Ile Val Ser Thr Pro His Lys Asn Asp Gln Glu Phe Gln Ala Ala
            930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
            965                 970                 975
```

```
Leu Thr Ser Thr Arg Arg
            980

<210> SEQ ID NO 4
<211> LENGTH: 982
<212> TYPE: PRT
<213> ORGANISM: Sindbis virus

<400> SEQUENCE: 4

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
                35                  40                  45

Thr Leu Leu Asn Ala Ile Leu Arg Cys Gly Ser Ser Gly Arg Ser Lys
        50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Glu Gln Asp His Thr Val Glu Glu Gly Thr
130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Glu
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
    290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365
```

-continued

```
Pro Glu Pro Thr Thr Glu Trp Ile Val Gly Lys Thr Val Arg Asn Phe
    370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
        435                 440                 445

Val Ala Val Leu Cys Ala Cys Lys Ala Arg Arg Glu Cys Leu Thr Pro
    450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
        515                 520                 525

Pro Phe Leu Val Val Ala Gly Ala Tyr Leu Ala Lys Val Asp Ala Tyr
    530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
        595                 600                 605

Leu Glu Cys Gln Pro Ala Ala His Ala Asp Tyr Thr Cys Lys Val Phe
    610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
        675                 680                 685

Val Tyr Val Asn Gly Val Thr Pro Gly Thr Ser Lys Asp Leu Lys Val
    690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
        755                 760                 765

Ala Lys Asn Val His Val Pro Tyr Thr Gln Ala Ser Ser Gly Phe Glu
    770                 775                 780
```

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
            805                 810                 815

Gly Asn Ile Pro Ile Ser Ile Asp Ile Pro Asn Ala Ala Phe Ile Arg
        820                 825                 830

Thr Ser Asp Ala Pro Leu Val Ser Thr Val Lys Cys Glu Val Ser Glu
    835                 840                 845

Cys Thr Tyr Ser Ala Asp Phe Gly Gly Met Ala Thr Leu Gln Tyr Val
850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
        915                 920                 925

His Ile Val Ser Thr Pro His Lys Asn Asp Gln Glu Phe Gln Ala Ala
930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
            980

<210> SEQ ID NO 5
<211> LENGTH: 980
<212> TYPE: PRT
<213> ORGANISM: Sindbis virus

<400> SEQUENCE: 5

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Glu Gln Asp His Thr Val Lys Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

-continued

```
Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Thr
            210                 215                 220

Thr Ala Gly Tyr Ile Thr Met His Arg Pro Arg Pro His Ala Tyr Thr
225                 230                 235                 240

Ser Tyr Leu Glu Glu Ser Ser Gly Lys Val Tyr Ala Lys Pro Pro Ser
                245                 250                 255

Gly Lys Asn Ile Thr Tyr Glu Cys Lys Cys Gly Asp Tyr Lys Thr Gly
            260                 265                 270

Thr Val Ser Thr Arg Thr Glu Ile Thr Gly Cys Thr Ala Ile Lys Gln
            275                 280                 285

Cys Val Ala Tyr Lys Ser Asp Gln Thr Lys Trp Val Phe Asn Ser Pro
            290                 295                 300

Asp Leu Ile Arg His Asp Asp His Thr Ala Gln Gly Lys Leu His Leu
305                 310                 315                 320

Pro Phe Lys Leu Ile Pro Ser Thr Cys Met Val Pro Val Ala His Ala
                325                 330                 335

Pro Asn Val Ile His Gly Phe Lys His Ile Ser Leu Gln Leu Asp Thr
            340                 345                 350

Asp His Leu Thr Leu Leu Thr Thr Arg Arg Leu Gly Ala Asn Pro Glu
            355                 360                 365

Pro Thr Thr Glu Trp Ile Val Gly Lys Thr Val Arg Asn Phe Thr Val
            370                 375                 380

Asp Arg Asp Gly Leu Glu Tyr Ile Trp Gly Asn His Glu Pro Val Arg
385                 390                 395                 400

Val Tyr Ala Gln Glu Ser Ala Pro Gly Asp Pro His Gly Trp Pro His
                405                 410                 415

Glu Ile Val Gln His Tyr Tyr His Arg His Pro Val Tyr Thr Ile Leu
            420                 425                 430

Ala Val Ala Ser Ala Thr Val Ala Met Met Ile Gly Val Thr Val Ala
            435                 440                 445

Val Leu Cys Ala Cys Lys Ala Arg Arg Glu Cys Leu Thr Pro Tyr Ala
450                 455                 460

Leu Ala Pro Asn Ala Val Ile Pro Thr Ser Leu Ala Leu Leu Cys Cys
465                 470                 475                 480

Val Arg Ser Ala Asn Ala Glu Thr Phe Thr Glu Thr Met Ser Tyr Leu
                485                 490                 495

Trp Ser Asn Ser Gln Pro Phe Phe Trp Val Gln Leu Cys Ile Pro Leu
            500                 505                 510

Ala Ala Phe Ile Val Leu Met Arg Cys Cys Ser Cys Cys Leu Pro Phe
            515                 520                 525

Leu Val Val Ala Gly Ala Tyr Leu Ala Lys Val Asp Ala Tyr Glu His
            530                 535                 540

Ala Thr Thr Val Pro Asn Val Pro Gln Ile Pro Tyr Lys Ala Leu Val
545                 550                 555                 560

Glu Arg Ala Gly Tyr Ala Pro Leu Asn Leu Glu Ile Thr Val Met Ser
                565                 570                 575

Ser Glu Val Leu Pro Ser Thr Asn Gln Glu Tyr Ile Thr Cys Lys Phe
            580                 585                 590
```

```
Thr Thr Val Val Pro Ser Pro Lys Ile Lys Cys Cys Gly Ser Leu Glu
            595                 600                 605

Cys Gln Pro Ala Ala His Ala Asp Tyr Thr Cys Lys Val Phe Gly Gly
610                 615                 620

Val Tyr Pro Phe Met Trp Gly Gly Ala Gln Cys Phe Cys Asp Ser Glu
625                 630                 635                 640

Asn Ser Gln Met Ser Glu Ala Tyr Val Glu Leu Ser Ala Asp Cys Ala
                645                 650                 655

Ser Asp His Ala Gln Ala Ile Lys Val His Thr Ala Ala Met Lys Val
            660                 665                 670

Gly Leu Arg Ile Val Tyr Gly Asn Thr Thr Ser Phe Leu Asp Val Tyr
            675                 680                 685

Val Asn Gly Val Thr Pro Gly Thr Ser Lys Asp Leu Lys Val Ile Ala
690                 695                 700

Gly Pro Ile Ser Ala Ser Phe Thr Pro Phe Asp His Lys Val Val Ile
705                 710                 715                 720

His Arg Gly Leu Val Tyr Asn Tyr Asp Phe Pro Glu Tyr Gly Ala Met
                725                 730                 735

Lys Pro Gly Ala Phe Gly Asp Ile Gln Ala Thr Ser Leu Thr Ser Lys
            740                 745                 750

Asp Leu Ile Ala Ser Thr Asp Ile Arg Leu Leu Lys Pro Ser Ala Lys
            755                 760                 765

Asn Val His Val Pro Tyr Thr Gln Ala Ser Ser Gly Phe Glu Met Trp
770                 775                 780

Lys Asn Asn Ser Gly Arg Pro Leu Gln Glu Thr Ala Pro Phe Gly Cys
785                 790                 795                 800

Lys Ile Ala Val Asn Pro Leu Arg Ala Val Asp Cys Ser Tyr Gly Asn
                805                 810                 815

Ile Pro Ile Ser Ile Asp Ile Pro Asn Ala Ala Phe Ile Arg Thr Ser
            820                 825                 830

Asp Ala Pro Leu Val Ser Thr Val Lys Cys Glu Val Ser Glu Cys Thr
            835                 840                 845

Tyr Ser Ala Asp Phe Gly Gly Met Ala Thr Leu Gln Tyr Val Ser Asp
850                 855                 860

Arg Glu Gly Gln Cys Pro Val His Ser His Ser Ser Thr Ala Thr Leu
865                 870                 875                 880

Gln Glu Ser Thr Val His Val Leu Glu Lys Gly Ala Val Thr Val His
                885                 890                 895

Phe Ser Thr Ala Ser Pro Gln Ala Asn Phe Ile Val Ser Leu Cys Gly
            900                 905                 910

Lys Lys Thr Thr Cys Asn Ala Glu Cys Lys Pro Pro Ala Asp His Ile
            915                 920                 925

Val Ser Thr Pro His Lys Asn Asp Gln Glu Phe Gln Ala Ala Ile Ser
930                 935                 940

Lys Thr Ser Trp Ser Trp Leu Phe Ala Leu Phe Gly Gly Ala Ser Ser
945                 950                 955                 960

Leu Leu Ile Ile Gly Leu Met Ile Phe Ala Cys Ser Met Met Leu Thr
                965                 970                 975

Ser Thr Arg Arg
            980

<210> SEQ ID NO 6
<211> LENGTH: 981
<212> TYPE: PRT
```

<213> ORGANISM: Sindbis virus

<400> SEQUENCE: 6

Met Ser Ala Ala Pro Leu Val Thr Ala Met

```
Arg Val Tyr Ala Gln Glu Ser Ala Pro Gly Asp Pro His Gly Trp Pro
                405                 410                 415
His Glu Ile Val Gln His Tyr Tyr His Arg His Pro Val Tyr Thr Ile
            420                 425                 430
Leu Ala Val Ala Ser Ala Thr Val Ala Met Met Ile Gly Val Thr Val
        435                 440                 445
Ala Val Leu Cys Ala Cys Lys Ala Arg Arg Glu Cys Leu Thr Pro Tyr
    450                 455                 460
Ala Leu Ala Pro Asn Ala Val Ile Pro Thr Ser Leu Ala Leu Leu Cys
465                 470                 475                 480
Cys Val Arg Ser Ala Asn Ala Glu Thr Phe Thr Glu Thr Met Ser Tyr
                485                 490                 495
Leu Trp Ser Asn Ser Gln Pro Phe Phe Trp Val Gln Leu Cys Ile Pro
            500                 505                 510
Leu Ala Ala Phe Ile Val Leu Met Arg Cys Cys Ser Cys Cys Leu Pro
        515                 520                 525
Phe Leu Val Val Ala Gly Ala Tyr Leu Ala Lys Val Asp Ala Tyr Glu
    530                 535                 540
His Ala Thr Thr Val Pro Asn Val Pro Gln Ile Pro Tyr Lys Ala Leu
545                 550                 555                 560
Val Glu Arg Ala Gly Tyr Ala Pro Leu Asn Leu Glu Ile Thr Val Met
                565                 570                 575
Ser Ser Glu Val Leu Pro Ser Thr Asn Gln Glu Tyr Ile Thr Cys Lys
            580                 585                 590
Phe Thr Thr Val Pro Ser Pro Lys Ile Lys Cys Cys Gly Ser Leu
        595                 600                 605
Glu Cys Gln Pro Ala Ala His Ala Asp Tyr Thr Cys Lys Val Phe Gly
    610                 615                 620
Gly Val Tyr Pro Phe Met Trp Gly Gly Ala Gln Cys Phe Cys Asp Ser
625                 630                 635                 640
Glu Asn Ser Gln Met Ser Glu Ala Tyr Val Glu Leu Ser Ala Asp Cys
                645                 650                 655
Ala Ser Asp His Ala Gln Ala Ile Lys Val His Thr Ala Ala Met Lys
            660                 665                 670
Val Gly Leu Arg Ile Val Tyr Gly Asn Thr Thr Ser Phe Leu Asp Val
        675                 680                 685
Tyr Val Asn Gly Val Thr Pro Gly Thr Ser Lys Asp Leu Lys Val Ile
    690                 695                 700
Ala Gly Pro Ile Ser Ala Ser Phe Thr Pro Phe Asp His Lys Val Val
705                 710                 715                 720
Ile His Arg Gly Leu Val Tyr Asn Tyr Asp Phe Pro Glu Tyr Gly Ala
                725                 730                 735
Met Lys Pro Gly Ala Phe Gly Asp Ile Gln Ala Thr Ser Leu Thr Ser
            740                 745                 750
Lys Asp Leu Ile Ala Ser Thr Asp Ile Arg Leu Leu Lys Pro Ser Ala
        755                 760                 765
Lys Asn Val His Val Pro Tyr Thr Gln Ala Ser Ser Gly Phe Glu Met
    770                 775                 780
Trp Lys Asn Asn Ser Gly Arg Pro Leu Gln Glu Thr Ala Pro Phe Gly
785                 790                 795                 800
Cys Lys Ile Ala Val Asn Pro Leu Arg Ala Val Asp Cys Ser Tyr Gly
                805                 810                 815
Asn Ile Pro Ile Ser Ile Asp Ile Pro Asn Ala Ala Phe Ile Arg Thr
```

```
            820                 825                 830
Ser Asp Ala Pro Leu Val Ser Thr Val Lys Cys Glu Val Ser Glu Cys
            835                 840                 845

Thr Tyr Ser Ala Asp Phe Gly Gly Met Ala Thr Leu Gln Tyr Val Ser
            850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
                900                 905                 910

Gly Lys Lys Thr Thr Cys Asn Ala Glu Cys Lys Pro Pro Ala Asp His
            915                 920                 925

Ile Val Ser Thr Pro His Lys Asn Asp Gln Glu Phe Gln Ala Ala Ile
            930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975

Thr Ser Thr Arg Arg
            980

<210> SEQ ID NO 7
<211> LENGTH: 982
<212> TYPE: PRT
<213> ORGANISM: Sindbis virus

<400> SEQUENCE: 7

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Lys Gln Asp His Thr Val Lys Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205
```

```
Pro Val His Gly Lys Lys Ile Pro Cys Thr Val Tyr Asp Arg Leu Glu
    210                 215                 220
Gly Thr Thr Ala Gly Tyr Ile Thr Met His Arg Pro Arg Pro His Ala
225                 230                 235                 240
Tyr Thr Ser Tyr Leu Glu Glu Ser Ser Gly Lys Val Tyr Ala Lys Pro
                245                 250                 255
Pro Ser Gly Lys Asn Ile Thr Tyr Glu Cys Lys Cys Gly Asp Tyr Lys
            260                 265                 270
Thr Gly Thr Val Ser Thr Arg Thr Glu Ile Thr Gly Cys Thr Ala Ile
        275                 280                 285
Lys Gln Cys Val Ala Tyr Lys Ser Asp Gln Thr Lys Trp Val Phe Asn
    290                 295                 300
Ser Pro Asp Leu Ile Arg His Asp His Thr Ala Gln Gly Lys Leu
305                 310                 315                 320
His Leu Pro Phe Lys Leu Ile Pro Ser Thr Cys Met Val Pro Val Ala
                325                 330                 335
His Ala Pro Asn Val Ile His Gly Phe Lys His Ile Ser Leu Gln Leu
            340                 345                 350
Asp Thr Asp His Leu Thr Leu Leu Thr Thr Arg Arg Leu Gly Ala Asn
        355                 360                 365
Pro Glu Pro Thr Thr Glu Trp Ile Val Gly Lys Thr Val Arg Asn Phe
    370                 375                 380
Thr Val Asp Arg Asp Gly Leu Glu Tyr Ile Trp Gly Asn His Glu Pro
385                 390                 395                 400
Val Arg Val Tyr Ala Gln Glu Ser Ala Pro Gly Asp Pro His Gly Trp
                405                 410                 415
Pro His Glu Ile Val Gln His Tyr Tyr His Arg His Pro Val Tyr Thr
            420                 425                 430
Ile Leu Ala Val Ala Ser Ala Thr Val Ala Met Met Ile Gly Val Thr
        435                 440                 445
Val Ala Val Leu Cys Ala Cys Lys Ala Arg Arg Glu Cys Leu Thr Pro
    450                 455                 460
Tyr Ala Leu Ala Pro Asn Ala Val Ile Pro Thr Ser Leu Ala Leu Leu
465                 470                 475                 480
Cys Cys Val Arg Ser Ala Asn Ala Glu Thr Phe Thr Glu Thr Met Ser
                485                 490                 495
Tyr Leu Trp Ser Asn Ser Gln Pro Phe Phe Trp Val Gln Leu Cys Ile
            500                 505                 510
Pro Leu Ala Ala Phe Ile Val Leu Met Arg Cys Cys Ser Cys Cys Leu
        515                 520                 525
Pro Phe Leu Val Val Ala Gly Ala Tyr Leu Ala Lys Val Asp Ala Tyr
    530                 535                 540
Glu His Ala Thr Thr Val Pro Asn Val Pro Gln Ile Pro Tyr Lys Ala
545                 550                 555                 560
Leu Val Glu Arg Ala Gly Tyr Ala Pro Leu Asn Leu Glu Ile Thr Val
                565                 570                 575
Met Ser Ser Glu Val Leu Pro Ser Thr Asn Gln Glu Tyr Ile Thr Cys
            580                 585                 590
Lys Phe Thr Thr Val Val Pro Ser Pro Lys Ile Lys Cys Cys Gly Ser
        595                 600                 605
Leu Glu Cys Gln Pro Ala Ala His Ala Asp Tyr Thr Cys Lys Val Phe
    610                 615                 620
Gly Gly Val Tyr Pro Phe Met Trp Gly Gly Ala Gln Cys Phe Cys Asp
```

```
            625                 630                 635                 640
Ser Glu Asn Ser Gln Met Ser Glu Ala Tyr Val Glu Leu Ser Ala Asp
                    645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
                675                 680                 685

Val Tyr Val Asn Gly Val Thr Pro Gly Thr Ser Lys Asp Leu Lys Val
            690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
                755                 760                 765

Ala Lys Asn Val His Val Pro Tyr Thr Gln Ala Ser Ser Gly Phe Glu
            770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
835                 840                 845

Cys Thr Tyr Ser Ala Asp Phe Gly Gly Met Ala Thr Leu Gln Tyr Val
                850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
                915                 920                 925

His Ile Val Ser Thr Pro His Lys Asn Asp Gln Glu Phe Gln Ala Ala
            930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
            980

<210> SEQ ID NO 8
<211> LENGTH: 981
<212> TYPE: PRT
<213> ORGANISM: Sindbis virus

<400> SEQUENCE: 8

Met Ser Ala Ala Pro Leu Val Thr Ala Met Cys Leu Leu Gly Asn Val
1               5                   10                  15
```

```
Ser Phe Pro Cys Asp Arg Pro Pro Thr Cys Tyr Thr Arg Glu Pro Ser
             20                  25                  30

Arg Ala Leu Asp Ile Leu Glu Glu Asn Val Asn His Glu Ala Tyr Asp
         35                  40                  45

Thr Leu Leu Asn Ala Ile Leu Arg Cys Gly Ser Ser Gly Arg Ser Lys
 50                  55                  60

Arg Ser Val Ile Asp Asp Phe Thr Leu Thr Ser Pro Tyr Leu Gly Thr
 65                  70                  75                  80

Cys Ser Tyr Cys His His Thr Val Pro Cys Phe Ser Pro Val Lys Ile
             85                  90                  95

Glu Gln Val Trp Asp Glu Ala Asp Asn Thr Ile Arg Ile Gln Thr
            100                 105                 110

Ser Ala Gln Phe Gly Tyr Asp Gln Ser Gly Ala Ala Ser Ala Asn Lys
            115                 120                 125

Tyr Arg Tyr Met Ser Leu Lys Gln Asp His Thr Val Lys Glu Gly Thr
            130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Glu
            210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
            275                 280                 285

Gln Cys Val Ala Tyr Lys Ser Asp Gln Thr Lys Trp Val Phe Asn Ser
290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
            340                 345                 350

Thr Asp His Leu Thr Leu Leu Thr Thr Arg Arg Leu Gly Ala Asn Pro
            355                 360                 365

Glu Pro Thr Thr Glu Trp Ile Val Gly Lys Thr Val Arg Asn Phe Thr
            370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
```

-continued

```
                435                 440                 445
Ala Val Leu Cys Ala Cys Lys Ala Arg Arg Glu Cys Leu Thr Pro Tyr
450                 455                 460
Ala Leu Ala Pro Asn Ala Val Ile Pro Thr Ser Leu Ala Leu Leu Cys
465                 470                 475                 480
Cys Val Arg Ser Ala Asn Ala Glu Thr Phe Thr Glu Thr Met Ser Tyr
                485                 490                 495
Leu Trp Ser Asn Ser Gln Pro Phe Phe Trp Val Gln Leu Cys Ile Pro
                500                 505                 510
Leu Ala Ala Phe Ile Val Leu Met Arg Cys Cys Ser Cys Cys Leu Pro
                515                 520                 525
Phe Leu Val Val Ala Gly Ala Tyr Leu Ala Lys Val Asp Ala Tyr Glu
530                 535                 540
His Ala Thr Thr Val Pro Asn Val Pro Gln Ile Pro Tyr Lys Ala Leu
545                 550                 555                 560
Val Glu Arg Ala Gly Tyr Ala Pro Leu Asn Leu Glu Ile Thr Val Met
                565                 570                 575
Ser Ser Glu Val Leu Pro Ser Thr Asn Gln Glu Tyr Ile Thr Cys Lys
                580                 585                 590
Phe Thr Thr Val Val Pro Ser Pro Lys Ile Lys Cys Cys Gly Ser Leu
                595                 600                 605
Glu Cys Gln Pro Ala Ala His Ala Asp Tyr Thr Cys Lys Val Phe Gly
610                 615                 620
Gly Val Tyr Pro Phe Met Trp Gly Gly Ala Gln Cys Phe Cys Asp Ser
625                 630                 635                 640
Glu Asn Ser Gln Met Ser Glu Ala Tyr Val Glu Leu Ser Ala Asp Cys
                645                 650                 655
Ala Ser Asp His Ala Gln Ala Ile Lys Val His Thr Ala Ala Met Lys
                660                 665                 670
Val Gly Leu Arg Ile Val Tyr Gly Asn Thr Thr Ser Phe Leu Asp Val
                675                 680                 685
Tyr Val Asn Gly Val Thr Pro Gly Thr Ser Lys Asp Leu Lys Val Ile
690                 695                 700
Ala Gly Pro Ile Ser Ala Ser Phe Thr Pro Phe Asp His Lys Val Val
705                 710                 715                 720
Ile His Arg Gly Leu Val Tyr Asn Tyr Asp Phe Pro Glu Tyr Gly Ala
                725                 730                 735
Met Lys Pro Gly Ala Phe Gly Asp Ile Gln Ala Thr Ser Leu Thr Ser
                740                 745                 750
Lys Asp Leu Ile Ala Ser Thr Asp Ile Arg Leu Leu Lys Pro Ser Ala
                755                 760                 765
Lys Asn Val His Val Pro Tyr Thr Gln Ala Ser Ser Gly Phe Glu Met
                770                 775                 780
Trp Lys Asn Asn Ser Gly Arg Pro Leu Gln Glu Thr Ala Pro Phe Gly
785                 790                 795                 800
Cys Lys Ile Ala Val Asn Pro Leu Arg Ala Val Asp Cys Ser Tyr Gly
                805                 810                 815
Asn Ile Pro Ile Ser Ile Asp Ile Pro Asn Ala Ala Phe Ile Arg Thr
                820                 825                 830
Ser Asp Ala Pro Leu Val Ser Thr Val Lys Cys Glu Val Ser Glu Cys
                835                 840                 845
Thr Tyr Ser Ala Asp Phe Gly Gly Met Ala Thr Leu Gln Tyr Val Ser
850                 855                 860
```

-continued

```
Asp Arg Glu Gly Gln Cys Pro Val His Ser His Ser Thr Ala Thr
865                 870                 875                 880

Leu Gln Glu Ser Thr Val His Val Leu Glu Lys Gly Ala Val Thr Val
            885                 890                 895

His Phe Ser Thr Ala Ser Pro Gln Ala Asn Phe Ile Val Ser Leu Cys
        900                 905                 910

Gly Lys Lys Thr Thr Cys Asn Ala Glu Cys Lys Pro Pro Ala Asp His
            915                 920                 925

Ile Val Ser Thr Pro His Lys Asn Asp Gln Glu Phe Gln Ala Ala Ile
930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975

Thr Ser Thr Arg Arg
            980

<210> SEQ ID NO 9
<211> LENGTH: 982
<212> TYPE: PRT
<213> ORGANISM: Sindbis virus

<400> SEQUENCE: 9

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Lys Gln Asp His Thr Val Glu Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Glu
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
```

```
                   245                 250                 255
Pro Ser Gly Lys Asn Ile Thr Tyr Glu Cys Lys Cys Gly Asp Tyr Lys
                260                 265                 270

Thr Gly Thr Val Ser Thr Arg Thr Glu Ile Thr Gly Cys Thr Ala Ile
                275                 280                 285

Lys Gln Cys Val Ala Tyr Lys Ser Asp Gln Thr Lys Trp Val Phe Asn
                290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
                340                 345                 350

Asp Thr Asp His Leu Thr Leu Leu Thr Thr Arg Arg Leu Gly Ala Asn
                355                 360                 365

Pro Glu Pro Thr Thr Glu Trp Ile Val Gly Lys Thr Val Arg Asn Phe
                370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                    405                 410                 415

Pro His Glu Ile Val Gln His Tyr Tyr His Arg His Pro Val Tyr Thr
                420                 425                 430

Ile Leu Ala Val Ala Ser Ala Thr Val Ala Met Met Ile Gly Val Thr
                435                 440                 445

Val Ala Val Leu Cys Ala Cys Lys Ala Arg Arg Glu Cys Leu Thr Pro
450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
                500                 505                 510

Pro Leu Ala Ala Phe Ile Val Leu Met Arg Cys Cys Ser Cys Cys Leu
                515                 520                 525

Pro Phe Leu Val Val Ala Gly Ala Tyr Leu Ala Lys Val Asp Ala Tyr
                530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                    565                 570                 575

Met Ser Ser Glu Val Leu Pro Ser Thr Asn Gln Glu Tyr Ile Thr Cys
                580                 585                 590

Lys Phe Thr Thr Val Val Pro Ser Pro Lys Ile Lys Cys Cys Gly Ser
                595                 600                 605

Leu Glu Cys Gln Pro Ala Ala His Ala Asp Tyr Thr Cys Lys Val Phe
                610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
                660                 665                 670
```

-continued

Lys Val Gly Leu Arg Ile Val Tyr Gly Asn Thr Thr Ser Phe Leu Asp
            675                 680                 685

Val Tyr Val Asn Gly Val Thr Pro Gly Thr Ser Lys Asp Leu Lys Val
690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
            725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
            755                 760                 765

Ala Lys Asn Val His Val Pro Tyr Thr Gln Ala Ser Ser Gly Phe Glu
            770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
            835                 840                 845

Cys Thr Tyr Ser Ala Asp Phe Gly Gly Met Ala Thr Leu Gln Tyr Val
            850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
            915                 920                 925

His Ile Val Ser Thr Pro His Lys Asn Asp Gln Glu Phe Gln Ala Ala
            930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
            980

<210> SEQ ID NO 10
<211> LENGTH: 981
<212> TYPE: PRT
<213> ORGANISM: Sindbis virus

<400> SEQUENCE: 10

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys

```
                50              55                  60
Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                    85                  90                  95

Glu Gln Val Trp Asp Glu Ala Asp Asn Thr Ile Arg Ile Gln Thr
                100                 105                 110

Ser Ala Gln Phe Gly Tyr Asp Gln Ser Gly Ala Ala Ser Ala Asn Lys
                115                 120                 125

Tyr Arg Tyr Met Ser Leu Lys Gln Asp His Thr Val Glu Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
                180                 185                 190

Arg Lys Ile Lys Pro Lys Phe Val Gly Arg Glu Lys Tyr Asp Leu Pro
                195                 200                 205

Pro Val His Gly Lys Lys Ile Pro Cys Thr Val Tyr Asp Arg Leu Glu
    210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
                260                 265                 270

Gly Thr Val Ser Thr Arg Thr Glu Ile Thr Gly Cys Thr Ala Ile Lys
                275                 280                 285

Gln Cys Val Ala Tyr Lys Ser Asp Gln Thr Lys Trp Val Phe Asn Ser
    290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
                340                 345                 350

Thr Asp His Leu Thr Leu Leu Thr Thr Arg Arg Leu Gly Ala Asn Pro
                355                 360                 365

Glu Pro Thr Thr Glu Trp Ile Val Gly Lys Thr Val Arg Asn Phe Thr
    370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg His Pro Val Tyr Thr Ile
                420                 425                 430

Leu Ala Val Ala Ser Ala Thr Val Ala Met Met Ile Gly Val Thr Val
                435                 440                 445

Ala Val Leu Cys Ala Cys Lys Ala Arg Arg Glu Cys Leu Thr Pro Tyr
    450                 455                 460

Ala Leu Ala Pro Asn Ala Val Ile Pro Thr Ser Leu Ala Leu Leu Cys
465                 470                 475                 480
```

```
Cys Val Arg Ser Ala Asn Ala Glu Thr Phe Thr Glu Thr Met Ser Tyr
                485                 490                 495
Leu Trp Ser Asn Ser Gln Pro Phe Phe Trp Val Gln Leu Cys Ile Pro
            500                 505                 510
Leu Ala Ala Phe Ile Val Leu Met Arg Cys Cys Ser Cys Cys Leu Pro
        515                 520                 525
Phe Leu Val Val Ala Gly Ala Tyr Leu Ala Lys Val Asp Ala Tyr Glu
    530                 535                 540
His Ala Thr Thr Val Pro Asn Val Pro Gln Ile Pro Tyr Lys Ala Leu
545                 550                 555                 560
Val Glu Arg Ala Gly Tyr Ala Pro Leu Asn Leu Glu Ile Thr Val Met
            565                 570                 575
Ser Ser Glu Val Leu Pro Ser Thr Asn Gln Glu Tyr Ile Thr Cys Lys
        580                 585                 590
Phe Thr Thr Val Val Pro Ser Pro Lys Ile Lys Cys Cys Gly Ser Leu
    595                 600                 605
Glu Cys Gln Pro Ala Ala His Ala Asp Tyr Thr Cys Lys Val Phe Gly
610                 615                 620
Gly Val Tyr Pro Phe Met Trp Gly Gly Ala Gln Cys Phe Cys Asp Ser
625                 630                 635                 640
Glu Asn Ser Gln Met Ser Glu Ala Tyr Val Glu Leu Ser Ala Asp Cys
            645                 650                 655
Ala Ser Asp His Ala Gln Ala Ile Lys Val His Thr Ala Ala Met Lys
        660                 665                 670
Val Gly Leu Arg Ile Val Tyr Gly Asn Thr Thr Ser Phe Leu Asp Val
            675                 680                 685
Tyr Val Asn Gly Val Thr Pro Gly Thr Ser Lys Asp Leu Lys Val Ile
    690                 695                 700
Ala Gly Pro Ile Ser Ala Ser Phe Thr Pro Phe Asp His Lys Val Val
705                 710                 715                 720
Ile His Arg Gly Leu Val Tyr Asn Tyr Asp Phe Pro Glu Tyr Gly Ala
            725                 730                 735
Met Lys Pro Gly Ala Phe Gly Asp Ile Gln Ala Thr Ser Leu Thr Ser
            740                 745                 750
Lys Asp Leu Ile Ala Ser Thr Asp Ile Arg Leu Leu Lys Pro Ser Ala
        755                 760                 765
Lys Asn Val His Val Pro Tyr Thr Gln Ala Ser Ser Gly Phe Glu Met
    770                 775                 780
Trp Lys Asn Asn Ser Gly Arg Pro Leu Gln Glu Thr Ala Pro Phe Gly
785                 790                 795                 800
Cys Lys Ile Ala Val Asn Pro Leu Arg Ala Val Asp Cys Ser Tyr Gly
            805                 810                 815
Asn Ile Pro Ile Ser Ile Asp Ile Pro Asn Ala Ala Phe Ile Arg Thr
            820                 825                 830
Ser Asp Ala Pro Leu Val Ser Thr Val Lys Cys Glu Val Ser Glu Cys
        835                 840                 845
Thr Tyr Ser Ala Asp Phe Gly Gly Met Ala Thr Leu Gln Tyr Val Ser
    850                 855                 860
Asp Arg Glu Gly Gln Cys Pro Val His Ser His Ser Ser Thr Ala Thr
865                 870                 875                 880
Leu Gln Glu Ser Thr Val His Val Leu Glu Lys Gly Ala Val Thr Val
            885                 890                 895
```

-continued

His Phe Ser Thr Ala Ser Pro Gln Ala Asn Phe Ile Val Ser Leu Cys
                900                 905                 910

Gly Lys Lys Thr Thr Cys Asn Ala Glu Cys Lys Pro Pro Ala Asp His
        915                 920                 925

Ile Val Ser Thr Pro His Lys Asn Asp Gln Glu Phe Gln Ala Ala Ile
        930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975

Thr Ser Thr Arg Arg
                980

<210> SEQ ID NO 11
<211> LENGTH: 982
<212> TYPE: PRT
<213> ORGANISM: Sindbis virus

<400> SEQUENCE: 11

Met Ser Ala Ala Pro Leu Val Thr Ala Met Cys Leu Leu Gly Asn Val
1 5 10 15

Ser Phe Pro Cys Asp Arg Pro Pro Thr Cys Tyr Thr Arg Glu Pro Ser
20 25 30

Arg Ala Leu Asp Ile Leu Glu Glu Asn Val Asn His Glu Ala Tyr Asp
35 40 45

Thr Leu Leu Asn Ala Ile Leu Arg Cys Gly Ser Ser Gly Arg Ser Lys
50 55 60

Arg Ser Val Ile Asp Asp Phe Thr Leu Thr Ser Pro Tyr Leu Gly Thr
65 70 75 80

Cys Ser Tyr Cys His His Thr Val Pro Cys Phe Ser Pro Val Lys Ile
85 90 95

Glu Gln Val Trp Asp Glu Ala Asp Asp Asn Thr Ile Arg Ile Gln Thr
100 105 110

Ser Ala Gln Phe Gly Tyr Asp Gln Ser Gly Ala Ala Ser Ala Asn Lys
115 120 125

Tyr Arg Tyr Met Ser Leu Lys Gln Asp His Thr Val Glu Glu Gly Thr
130 135 140

Met Asp Asp Ile Lys Ile Ser Thr Ser Gly Pro Cys Arg Arg Leu Ser
145 150 155 160

Tyr Lys Gly Tyr Phe Leu Leu Ala Lys Cys Pro Pro Gly Asp Ser Val
165 170 175

Thr Val Ser Ile Val Ser Ser Asn Ser Ala Thr Ser Cys Thr Leu Ala
180 185 190

Arg Lys Ile Lys Pro Lys Phe Val Gly Arg Glu Lys Tyr Asp Leu Pro
195 200 205

Pro Val His Gly Lys Lys Ile Pro Cys Thr Val Tyr Asp Arg Leu Lys
210 215 220

Gly Thr Thr Ala Gly Tyr Ile Thr Met His Arg Pro Arg Pro His Ala
225 230 235 240

Tyr Thr Ser Tyr Leu Glu Glu Ser Ser Gly Lys Val Tyr Ala Lys Pro
245 250 255

Pro Ser Gly Lys Asn Ile Thr Tyr Glu Cys Lys Cys Gly Asp Tyr Lys
260 265 270

Thr Gly Thr Val Ser Thr Arg Thr Glu Ile Thr Gly Cys Thr Ala Ile
275 280 285

-continued

Lys Gln Cys Val Ala Tyr Lys Ser Asp Gln Thr Lys Trp Val Phe Asn
        290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Arg Arg Leu Gly Ala Asn
            355                 360                 365

Pro Glu Pro Thr Thr Glu Trp Ile Val Gly Lys Thr Val Arg Asn Phe
        370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
            435                 440                 445

Val Ala Val Leu Cys Ala Cys Lys Ala Arg Arg Glu Cys Leu Thr Pro
        450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
            515                 520                 525

Pro Phe Leu Val Val Ala Gly Ala Tyr Leu Ala Lys Val Asp Ala Tyr
        530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
            595                 600                 605

Leu Glu Cys Gln Pro Ala Ala His Ala Asp Tyr Thr Cys Lys Val Phe
        610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
            675                 680                 685

Val Tyr Val Asn Gly Val Thr Pro Gly Thr Ser Lys Asp Leu Lys Val
        690                 695                 700

```
Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
            725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
            755                 760                 765

Ala Lys Asn Val His Val Pro Tyr Thr Gln Ala Ser Ser Gly Phe Glu
            770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
            805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
            835                 840                 845

Cys Thr Tyr Ser Ala Asp Phe Gly Gly Met Ala Thr Leu Gln Tyr Val
850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
            885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
            915                 920                 925

His Ile Val Ser Thr Pro His Lys Asn Asp Gln Glu Phe Gln Ala Ala
            930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
            965                 970                 975

Leu Thr Ser Thr Arg Arg
            980

<210> SEQ ID NO 12
<211> LENGTH: 981
<212> TYPE: PRT
<213> ORGANISM: Sindbis virus

<400> SEQUENCE: 12

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
            50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
            85                  90                  95
```

```
Glu Gln Val Trp Asp Glu Ala Asp Asp Asn Thr Ile Arg Ile Gln Thr
                100                 105                 110
Ser Ala Gln Phe Gly Tyr Asp Gln Ser Gly Ala Ala Ser Ala Asn Lys
                115                 120                 125
Tyr Arg Tyr Met Ser Leu Lys Gln Asp His Thr Val Glu Glu Gly Thr
            130                 135                 140
Met Asp Asp Ile Lys Ile Ser Thr Ser Gly Pro Cys Arg Arg Leu Ser
145                 150                 155                 160
Tyr Lys Gly Tyr Phe Leu Leu Ala Lys Cys Pro Pro Gly Asp Ser Val
                    165                 170                 175
Thr Val Ser Ile Val Ser Ser Asn Ser Ala Thr Ser Cys Thr Leu Ala
                180                 185                 190
Arg Lys Ile Lys Pro Lys Phe Val Gly Arg Glu Lys Tyr Asp Leu Pro
            195                 200                 205
Pro Val His Gly Lys Lys Ile Pro Cys Thr Val Tyr Asp Arg Leu Lys
            210                 215                 220
Thr Thr Ala Gly Tyr Ile Thr Met His Arg Pro Arg Pro His Ala Tyr
225                 230                 235                 240
Thr Ser Tyr Leu Glu Glu Ser Ser Gly Lys Val Tyr Ala Lys Pro Pro
                245                 250                 255
Ser Gly Lys Asn Ile Thr Tyr Glu Cys Lys Cys Gly Asp Tyr Lys Thr
                260                 265                 270
Gly Thr Val Ser Thr Arg Thr Glu Ile Thr Gly Cys Thr Ala Ile Lys
            275                 280                 285
Gln Cys Val Ala Tyr Lys Ser Asp Gln Thr Lys Trp Val Phe Asn Ser
290                 295                 300
Pro Asp Leu Ile Arg His Asp Asp His Thr Ala Gln Gly Lys Leu His
305                 310                 315                 320
Leu Pro Phe Lys Leu Ile Pro Ser Thr Cys Met Val Pro Val Ala His
                325                 330                 335
Ala Pro Asn Val Ile His Gly Phe Lys His Ile Ser Leu Gln Leu Asp
                340                 345                 350
Thr Asp His Leu Thr Leu Leu Thr Thr Arg Arg Leu Gly Ala Asn Pro
            355                 360                 365
Glu Pro Thr Thr Glu Trp Ile Val Gly Lys Thr Val Arg Asn Phe Thr
            370                 375                 380
Val Asp Arg Asp Gly Leu Glu Tyr Ile Trp Gly Asn His Glu Pro Val
385                 390                 395                 400
Arg Val Tyr Ala Gln Glu Ser Ala Pro Gly Asp Pro His Gly Trp Pro
                    405                 410                 415
His Glu Ile Val Gln His Tyr Tyr His Arg His Pro Val Tyr Thr Ile
                420                 425                 430
Leu Ala Val Ala Ser Ala Thr Val Ala Met Met Ile Gly Val Thr Val
            435                 440                 445
Ala Val Leu Cys Ala Cys Lys Ala Arg Arg Glu Cys Leu Thr Pro Tyr
            450                 455                 460
Ala Leu Ala Pro Asn Ala Val Ile Pro Thr Ser Leu Ala Leu Leu Cys
465                 470                 475                 480
Cys Val Arg Ser Ala Asn Ala Glu Thr Phe Thr Glu Thr Met Ser Tyr
                485                 490                 495
Leu Trp Ser Asn Ser Gln Pro Phe Phe Trp Val Gln Leu Cys Ile Pro
                500                 505                 510
```

-continued

Leu Ala Ala Phe Ile Val Leu Met Arg Cys Cys Ser Cys Cys Leu Pro
515                 520                 525

Phe Leu Val Val Ala Gly Ala Tyr Leu Ala Lys Val Asp Ala Tyr Glu
530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
            580                 585                 590

Phe Thr Thr Val Pro Ser Pro Lys Ile Lys Cys Cys Gly Ser Leu
        595                 600                 605

Glu Cys Gln Pro Ala Ala His Ala Asp Tyr Thr Cys Lys Val Phe Gly
    610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
        675                 680                 685

Tyr Val Asn Gly Val Thr Pro Gly Thr Ser Lys Asp Leu Lys Val Ile
    690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
                725                 730                 735

Met Lys Pro Gly Ala Phe Gly Asp Ile Gln Ala Thr Ser Leu Thr Ser
            740                 745                 750

Lys Asp Leu Ile Ala Ser Thr Asp Ile Arg Leu Leu Lys Pro Ser Ala
        755                 760                 765

Lys Asn Val His Val Pro Tyr Thr Gln Ala Ser Ser Gly Phe Glu Met
    770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
            820                 825                 830

Ser Asp Ala Pro Leu Val Ser Thr Val Lys Cys Glu Val Ser Glu Cys
        835                 840                 845

Thr Tyr Ser Ala Asp Phe Gly Gly Met Ala Thr Leu Gln Tyr Val Ser
    850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
            900                 905                 910

Gly Lys Lys Thr Thr Cys Asn Ala Glu Cys Lys Pro Pro Ala Asp His
        915                 920                 925

Ile Val Ser Thr Pro His Lys Asn Asp Gln Glu Phe Gln Ala Ala Ile

```
                930              935              940
Ser Lys Thr Ser Trp Ser Trp Leu Phe Ala Leu Phe Gly Gly Ala Ser
945                  950                 955                 960

Ser Leu Leu Ile Ile Gly Leu Met Ile Phe Ala Cys Ser Met Met Leu
                965                 970                 975

Thr Ser Thr Arg Arg
            980

<210> SEQ ID NO 13
<211> LENGTH: 982
<212> TYPE: PRT
<213> ORGANISM: Sindbis virus

<400> SEQUENCE: 13

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
                100                 105                 110

Ser Ala Gln Phe Gly Tyr Asp Gln Ser Gly Ala Ala Ser Ala Asn Lys
            115                 120                 125

Tyr Arg Tyr Met Ser Leu Glu Gln Asp His Thr Val Lys Glu Gly Thr
130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Lys
210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
        290                 295                 300

Ser Pro Asp Leu Ile Arg His Asp Asp His Thr Ala Gln Gly Lys Leu
305                 310                 315                 320
```

```
His Leu Pro Phe Lys Leu Ile Pro Ser Thr Cys Met Val Pro Val Ala
            325                 330                 335
His Ala Pro Asn Val Ile His Gly Phe Lys His Ile Ser Leu Gln Leu
        340                 345                 350
Asp Thr Asp His Leu Thr Leu Leu Thr Thr Arg Arg Leu Gly Ala Asn
            355                 360                 365
Pro Glu Pro Thr Thr Glu Trp Ile Val Gly Lys Thr Val Arg Asn Phe
370                 375                 380
Thr Val Asp Arg Asp Gly Leu Glu Tyr Ile Trp Gly Asn His Glu Pro
385                 390                 395                 400
Val Arg Val Tyr Ala Gln Glu Ser Ala Pro Gly Asp Pro His Gly Trp
                405                 410                 415
Pro His Glu Ile Val Gln His Tyr Tyr His Arg His Pro Val Tyr Thr
                420                 425                 430
Ile Leu Ala Val Ala Ser Ala Thr Val Ala Met Met Ile Gly Val Thr
            435                 440                 445
Val Ala Val Leu Cys Ala Cys Lys Ala Arg Arg Glu Cys Leu Thr Pro
        450                 455                 460
Tyr Ala Leu Ala Pro Asn Ala Val Ile Pro Thr Ser Leu Ala Leu Leu
465                 470                 475                 480
Cys Cys Val Arg Ser Ala Asn Ala Glu Thr Phe Thr Glu Thr Met Ser
                485                 490                 495
Tyr Leu Trp Ser Asn Ser Gln Pro Phe Phe Trp Val Gln Leu Cys Ile
            500                 505                 510
Pro Leu Ala Ala Phe Ile Val Leu Met Arg Cys Cys Ser Cys Cys Leu
        515                 520                 525
Pro Phe Leu Val Val Ala Gly Ala Tyr Leu Ala Lys Val Asp Ala Tyr
    530                 535                 540
Glu His Ala Thr Thr Val Pro Asn Val Pro Gln Ile Pro Tyr Lys Ala
545                 550                 555                 560
Leu Val Glu Arg Ala Gly Tyr Ala Pro Leu Asn Leu Glu Ile Thr Val
                565                 570                 575
Met Ser Ser Glu Val Leu Pro Ser Thr Asn Gln Glu Tyr Ile Thr Cys
            580                 585                 590
Lys Phe Thr Thr Val Val Pro Ser Pro Lys Ile Lys Cys Cys Gly Ser
        595                 600                 605
Leu Glu Cys Gln Pro Ala Ala His Ala Asp Tyr Thr Cys Lys Val Phe
    610                 615                 620
Gly Gly Val Tyr Pro Phe Met Trp Gly Gly Ala Gln Cys Phe Cys Asp
625                 630                 635                 640
Ser Glu Asn Ser Gln Met Ser Glu Ala Tyr Val Glu Leu Ser Ala Asp
                645                 650                 655
Cys Ala Ser Asp His Ala Gln Ala Ile Lys Val His Thr Ala Ala Met
            660                 665                 670
Lys Val Gly Leu Arg Ile Val Tyr Gly Asn Thr Thr Ser Phe Leu Asp
        675                 680                 685
Val Tyr Val Asn Gly Val Thr Pro Gly Thr Ser Lys Asp Leu Lys Val
    690                 695                 700
Ile Ala Gly Pro Ile Ser Ala Ser Phe Thr Pro Phe Asp His Lys Val
705                 710                 715                 720
Val Ile His Arg Gly Leu Val Tyr Asn Tyr Asp Phe Pro Glu Tyr Gly
                725                 730                 735
Ala Met Lys Pro Gly Ala Phe Gly Asp Ile Gln Ala Thr Ser Leu Thr
```

```
                        740                 745                 750
Ser Lys Asp Leu Ile Ala Ser Thr Asp Ile Arg Leu Leu Lys Pro Ser
            755                 760                 765

Ala Lys Asn Val His Val Pro Tyr Thr Gln Ala Ser Ser Gly Phe Glu
        770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
        835                 840                 845

Cys Thr Tyr Ser Ala Asp Phe Gly Gly Met Ala Thr Leu Gln Tyr Val
    850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
        915                 920                 925

His Ile Val Ser Thr Pro His Lys Asn Asp Gln Glu Phe Gln Ala Ala
    930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
            980

<210> SEQ ID NO 14
<211> LENGTH: 981
<212> TYPE: PRT
<213> ORGANISM: Sindbis virus

<400> SEQUENCE: 14

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125
```

```
Tyr Arg Tyr Met Ser Leu Glu Gln Asp His Thr Val Lys Glu Gly Thr
            130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
        275                 280                 285

Gln Cys Val Ala Tyr Lys Ser Asp Gln Thr Lys Trp Val Phe Asn Ser
    290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
            340                 345                 350

Thr Asp His Leu Thr Leu Leu Thr Thr Arg Arg Leu Gly Ala Asn Pro
        355                 360                 365

Glu Pro Thr Thr Glu Trp Ile Val Gly Lys Thr Val Arg Asn Phe Thr
370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
        435                 440                 445

Ala Val Leu Cys Ala Cys Lys Ala Arg Arg Glu Cys Leu Thr Pro Tyr
    450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
        515                 520                 525

Phe Leu Val Val Ala Gly Ala Tyr Leu Ala Lys Val Asp Ala Tyr Glu
530                 535                 540

His Ala Thr Thr Val Pro Asn Val Pro Gln Ile Pro Tyr Lys Ala Leu
```

```
545                 550                 555                 560
Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
                580                 585                 590

Phe Thr Thr Val Val Pro Ser Pro Lys Ile Lys Cys Cys Gly Ser Leu
                595                 600                 605

Glu Cys Gln Pro Ala Ala His Ala Asp Tyr Thr Cys Lys Val Phe Gly
                610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
                660                 665                 670

Val Gly Leu Arg Ile Val Tyr Gly Asn Thr Thr Ser Phe Leu Asp Val
                675                 680                 685

Tyr Val Asn Gly Val Thr Pro Gly Thr Ser Lys Asp Leu Lys Val Ile
                690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
                725                 730                 735

Met Lys Pro Gly Ala Phe Gly Asp Ile Gln Ala Thr Ser Leu Thr Ser
                740                 745                 750

Lys Asp Leu Ile Ala Ser Thr Asp Ile Arg Leu Leu Lys Pro Ser Ala
                755                 760                 765

Lys Asn Val His Val Pro Tyr Thr Gln Ala Ser Ser Gly Phe Glu Met
                770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
                820                 825                 830

Ser Asp Ala Pro Leu Val Ser Thr Val Lys Cys Glu Val Ser Glu Cys
                835                 840                 845

Thr Tyr Ser Ala Asp Phe Gly Gly Met Ala Thr Leu Gln Tyr Val Ser
                850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
                900                 905                 910

Gly Lys Lys Thr Thr Cys Asn Ala Glu Cys Lys Pro Pro Ala Asp His
                915                 920                 925

Ile Val Ser Thr Pro His Lys Asn Asp Gln Glu Phe Gln Ala Ala Ile
                930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975
```

Thr Ser Thr Arg Arg
            980

<210> SEQ ID NO 15
<211> LENGTH: 982
<212> TYPE: PRT
<213> ORGANISM: Sindbis virus

<400> SEQUENCE: 15

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Glu Gln Asp His Thr Val Glu Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
    290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn

```
                355                 360                 365
Pro Glu Pro Thr Thr Glu Trp Ile Val Gly Lys Thr Val Arg Asn Phe
370                     375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                    405                 410                 415

Pro His Glu Ile Val Gln His Tyr Tyr His Arg His Pro Val Tyr Thr
                420                 425                 430

Ile Leu Ala Val Ala Ser Ala Thr Val Ala Met Met Ile Gly Val Thr
            435                 440                 445

Val Ala Val Leu Cys Ala Cys Lys Ala Arg Arg Glu Cys Leu Thr Pro
        450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
                500                 505                 510

Pro Leu Ala Ala Phe Ile Val Leu Met Arg Cys Cys Ser Cys Cys Leu
            515                 520                 525

Pro Phe Leu Val Val Ala Gly Ala Tyr Leu Ala Lys Val Asp Ala Tyr
        530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
                580                 585                 590

Lys Phe Thr Thr Val Val Pro Ser Pro Lys Ile Lys Cys Cys Gly Ser
            595                 600                 605

Leu Glu Cys Gln Pro Ala Ala His Ala Asp Tyr Thr Cys Lys Val Phe
        610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
                660                 665                 670

Lys Val Gly Leu Arg Ile Val Tyr Gly Asn Thr Thr Ser Phe Leu Asp
            675                 680                 685

Val Tyr Val Asn Gly Val Thr Pro Gly Thr Ser Lys Asp Leu Lys Val
        690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
                740                 745                 750

Ser Lys Asp Leu Ile Ala Ser Thr Asp Ile Arg Leu Leu Lys Pro Ser
            755                 760                 765

Ala Lys Asn Val His Val Pro Tyr Thr Gln Ala Ser Ser Gly Phe Glu
        770                 775                 780
```

-continued

```
Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
            805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
            835                 840                 845

Cys Thr Tyr Ser Ala Asp Phe Gly Gly Met Ala Thr Leu Gln Tyr Val
    850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
            885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
            915                 920                 925

His Ile Val Ser Thr Pro His Lys Asn Asp Gln Glu Phe Gln Ala Ala
    930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
            965                 970                 975

Leu Thr Ser Thr Arg Arg
            980

<210> SEQ ID NO 16
<211> LENGTH: 981
<212> TYPE: PRT
<213> ORGANISM: Sindbis virus

<400> SEQUENCE: 16

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
            85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
            115                 120                 125

Tyr Arg Tyr Met Ser Leu Glu Gln Asp His Thr Val Glu Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
```

```
            165                 170                 175
Thr Val Ser Ile Val Ser Ser Asn Ser Ala Thr Ser Cys Thr Leu Ala
            180                 185                 190
Arg Lys Ile Lys Pro Lys Phe Val Gly Arg Glu Lys Tyr Asp Leu Pro
            195                 200                 205
Pro Val His Gly Lys Lys Ile Pro Cys Thr Val Tyr Asp Arg Leu Lys
            210                 215                 220
Thr Thr Ala Gly Tyr Ile Thr Met His Arg Pro Arg Pro His Ala Tyr
225                 230                 235                 240
Thr Ser Tyr Leu Glu Glu Ser Ser Gly Lys Val Tyr Ala Lys Pro Pro
                245                 250                 255
Ser Gly Lys Asn Ile Thr Tyr Glu Cys Lys Cys Gly Asp Tyr Lys Thr
                260                 265                 270
Gly Thr Val Ser Thr Arg Thr Glu Ile Thr Gly Cys Thr Ala Ile Lys
                275                 280                 285
Gln Cys Val Ala Tyr Lys Ser Asp Gln Thr Lys Trp Val Phe Asn Ser
        290                 295                 300
Pro Asp Leu Ile Arg His Asp Asp His Thr Ala Gln Gly Lys Leu His
305                 310                 315                 320
Leu Pro Phe Lys Leu Ile Pro Ser Thr Cys Met Val Pro Val Ala His
                325                 330                 335
Ala Pro Asn Val Ile His Gly Phe Lys His Ile Ser Leu Gln Leu Asp
                340                 345                 350
Thr Asp His Leu Thr Leu Leu Thr Thr Arg Arg Leu Gly Ala Asn Pro
                355                 360                 365
Glu Pro Thr Thr Glu Trp Ile Val Gly Lys Thr Val Arg Asn Phe Thr
        370                 375                 380
Val Asp Arg Asp Gly Leu Glu Tyr Ile Trp Gly Asn His Glu Pro Val
385                 390                 395                 400
Arg Val Tyr Ala Gln Glu Ser Ala Pro Gly Asp Pro His Gly Trp Pro
                405                 410                 415
His Glu Ile Val Gln His Tyr Tyr His Arg His Pro Val Tyr Thr Ile
                420                 425                 430
Leu Ala Val Ala Ser Ala Thr Val Ala Met Met Ile Gly Val Thr Val
                435                 440                 445
Ala Val Leu Cys Ala Cys Lys Ala Arg Arg Glu Cys Leu Thr Pro Tyr
        450                 455                 460
Ala Leu Ala Pro Asn Ala Val Ile Pro Thr Ser Leu Ala Leu Leu Cys
465                 470                 475                 480
Cys Val Arg Ser Ala Asn Ala Glu Thr Phe Thr Glu Thr Met Ser Tyr
                485                 490                 495
Leu Trp Ser Asn Ser Gln Pro Phe Phe Trp Val Gln Leu Cys Ile Pro
                500                 505                 510
Leu Ala Ala Phe Ile Val Leu Met Arg Cys Cys Ser Cys Cys Leu Pro
                515                 520                 525
Phe Leu Val Val Ala Gly Ala Tyr Leu Ala Lys Val Asp Ala Tyr Glu
        530                 535                 540
His Ala Thr Thr Val Pro Asn Val Pro Gln Ile Pro Tyr Lys Ala Leu
545                 550                 555                 560
Val Glu Arg Ala Gly Tyr Ala Pro Leu Asn Leu Glu Ile Thr Val Met
                565                 570                 575
Ser Ser Glu Val Leu Pro Ser Thr Asn Gln Glu Tyr Ile Thr Cys Lys
                580                 585                 590
```

```
Phe Thr Thr Val Val Pro Ser Pro Lys Ile Lys Cys Cys Gly Ser Leu
            595                 600                 605

Glu Cys Gln Pro Ala Ala His Ala Asp Tyr Thr Cys Lys Val Phe Gly
    610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
                660                 665                 670

Val Gly Leu Arg Ile Val Tyr Gly Asn Thr Thr Ser Phe Leu Asp Val
            675                 680                 685

Tyr Val Asn Gly Val Thr Pro Gly Thr Ser Lys Asp Leu Lys Val Ile
        690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
                725                 730                 735

Met Lys Pro Gly Ala Phe Gly Asp Ile Gln Ala Thr Ser Leu Thr Ser
            740                 745                 750

Lys Asp Leu Ile Ala Ser Thr Asp Ile Arg Leu Leu Lys Pro Ser Ala
        755                 760                 765

Lys Asn Val His Val Pro Tyr Thr Gln Ala Ser Ser Gly Phe Glu Met
    770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
            820                 825                 830

Ser Asp Ala Pro Leu Val Ser Thr Val Lys Cys Glu Val Ser Glu Cys
        835                 840                 845

Thr Tyr Ser Ala Asp Phe Gly Gly Met Ala Thr Leu Gln Tyr Val Ser
    850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
            900                 905                 910

Gly Lys Lys Thr Thr Cys Asn Ala Glu Cys Lys Pro Pro Ala Asp His
        915                 920                 925

Ile Val Ser Thr Pro His Lys Asn Asp Gln Glu Phe Gln Ala Ala Ile
        930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975

Thr Ser Thr Arg Arg
            980

<210> SEQ ID NO 17
<211> LENGTH: 982
```

<212> TYPE: PRT
<213> ORGANISM: Sindbis virus

<400> SEQUENCE: 17

```
Met Ser Ala Ala

-continued

```
Val Arg Val Tyr Ala Gln Glu Ser Ala Pro Gly Asp Pro His Gly Trp
            405                 410                 415
Pro His Glu Ile Val Gln His Tyr Tyr His Arg His Pro Val Tyr Thr
            420                 425                 430
Ile Leu Ala Val Ala Ser Ala Thr Val Ala Met Met Ile Gly Val Thr
            435                 440                 445
Val Ala Val Leu Cys Ala Cys Lys Ala Arg Arg Glu Cys Leu Thr Pro
450                 455                 460
Tyr Ala Leu Ala Pro Asn Ala Val Ile Pro Thr Ser Leu Ala Leu Leu
465                 470                 475                 480
Cys Cys Val Arg Ser Ala Asn Ala Glu Thr Phe Thr Glu Thr Met Ser
                485                 490                 495
Tyr Leu Trp Ser Asn Ser Gln Pro Phe Phe Trp Val Gln Leu Cys Ile
                500                 505                 510
Pro Leu Ala Ala Phe Ile Val Leu Met Arg Cys Cys Ser Cys Cys Leu
                515                 520                 525
Pro Phe Leu Val Val Ala Gly Ala Tyr Leu Ala Lys Val Asp Ala Tyr
            530                 535                 540
Glu His Ala Thr Thr Val Pro Asn Val Pro Gln Ile Pro Tyr Lys Ala
545                 550                 555                 560
Leu Val Glu Arg Ala Gly Tyr Ala Pro Leu Asn Leu Glu Ile Thr Val
                565                 570                 575
Met Ser Ser Glu Val Leu Pro Ser Thr Asn Gln Glu Tyr Ile Thr Cys
                580                 585                 590
Lys Phe Thr Thr Val Val Pro Ser Pro Lys Ile Lys Cys Cys Gly Ser
                595                 600                 605
Leu Glu Cys Gln Pro Ala Ala His Ala Asp Tyr Thr Cys Lys Val Phe
            610                 615                 620
Gly Gly Val Tyr Pro Phe Met Trp Gly Gly Ala Gln Cys Phe Cys Asp
625                 630                 635                 640
Ser Glu Asn Ser Gln Met Ser Glu Ala Tyr Val Glu Leu Ser Ala Asp
                645                 650                 655
Cys Ala Ser Asp His Ala Gln Ala Ile Lys Val His Thr Ala Ala Met
                660                 665                 670
Lys Val Gly Leu Arg Ile Val Tyr Gly Asn Thr Thr Ser Phe Leu Asp
            675                 680                 685
Val Tyr Val Asn Gly Val Thr Pro Gly Thr Ser Lys Asp Leu Lys Val
            690                 695                 700
Ile Ala Gly Pro Ile Ser Ala Ser Phe Thr Pro Phe Asp His Lys Val
705                 710                 715                 720
Val Ile His Arg Gly Leu Val Tyr Asn Tyr Asp Phe Pro Glu Tyr Gly
                725                 730                 735
Ala Met Lys Pro Gly Ala Phe Gly Asp Ile Gln Ala Thr Ser Leu Thr
                740                 745                 750
Ser Lys Asp Leu Ile Ala Ser Thr Asp Ile Arg Leu Leu Lys Pro Ser
                755                 760                 765
Ala Lys Asn Val His Val Pro Tyr Thr Gln Ala Ser Ser Gly Phe Glu
            770                 775                 780
Met Trp Lys Asn Asn Ser Gly Arg Pro Leu Gln Glu Thr Ala Pro Phe
785                 790                 795                 800
Gly Cys Lys Ile Ala Val Asn Pro Leu Arg Ala Val Asp Cys Ser Tyr
                805                 810                 815
```

-continued

```
Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
835                 840                 845

Cys Thr Tyr Ser Ala Asp Phe Gly Gly Met Ala Thr Leu Gln Tyr Val
    850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Gly Lys Gly Ala Val Thr
            885                 890                 895

Val His Phe Ser Thr Ala Ser Pro Gln Ala Asn Phe Ile Val Ser Leu
        900                 905                 910

Cys Gly Lys Lys Thr Thr Cys Asn Ala Glu Cys Lys Pro Pro Ala Asp
    915                 920                 925

His Ile Val Ser Thr Pro His Lys Asn Asp Gln Glu Phe Gln Ala Ala
930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
            965                 970                 975

Leu Thr Ser Thr Arg Arg
            980
```

<210> SEQ ID NO 18

<400> SEQUENCE: 18

000

<210> SEQ ID NO 19

<400> SEQUENCE: 19

000

<210> SEQ ID NO 20
<211> LENGTH: 488
<212> TYPE: PRT
<213> ORGANISM: Sindbis virus

<400> SEQUENCE: 20

```
Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125
```

```
Tyr Arg Tyr Met Ser Leu Lys Gln Asp His Thr Val Lys Glu Gly Thr
            130                 135                 140
Met Asp Asp Ile Lys Ile Ser Thr Ser Gly Pro Cys Arg Arg Leu Ser
145                 150                 155                 160
Tyr Lys Gly Tyr Phe Leu Leu Ala Lys Cys Pro Pro Gly Asp Ser Val
                165                 170                 175
Thr Val Ser Ile Val Ser Ser Asn Ser Ala Thr Ser Cys Thr Leu Ala
            180                 185                 190
Arg Lys Ile Lys Pro Lys Phe Val Gly Arg Glu Lys Tyr Asp Leu Pro
            195                 200                 205
Pro Val His Gly Lys Lys Ile Pro Cys Thr Val Tyr Asp Arg Leu Lys
210                 215                 220
Glu Thr Thr Ala Gly Tyr Ile Thr Met His Arg Pro Arg Pro His Ala
225                 230                 235                 240
Tyr Thr Ser Tyr Leu Glu Glu Ser Ser Gly Lys Val Tyr Ala Lys Pro
                245                 250                 255
Pro Ser Gly Lys Asn Ile Thr Tyr Glu Cys Lys Cys Gly Asp Tyr Lys
            260                 265                 270
Thr Gly Thr Val Ser Thr Arg Thr Glu Ile Thr Gly Cys Thr Ala Ile
            275                 280                 285
Lys Gln Cys Val Ala Tyr Lys Ser Asp Gln Thr Lys Trp Val Phe Asn
290                 295                 300
Ser Pro Asp Leu Ile Arg His Asp Asp His Thr Ala Gln Gly Lys Leu
305                 310                 315                 320
His Leu Pro Phe Lys Leu Ile Pro Ser Thr Cys Met Val Pro Val Ala
                325                 330                 335
His Ala Pro Asn Val Ile His Gly Phe Lys His Ile Ser Leu Gln Leu
            340                 345                 350
Asp Thr Asp His Leu Thr Leu Leu Thr Thr Arg Arg Leu Gly Ala Asn
            355                 360                 365
Pro Glu Pro Thr Thr Glu Trp Ile Val Gly Lys Thr Val Arg Asn Phe
370                 375                 380
Thr Val Asp Arg Asp Gly Leu Glu Tyr Ile Trp Gly Asn His Glu Pro
385                 390                 395                 400
Val Arg Val Tyr Ala Gln Glu Ser Ala Pro Gly Asp Pro His Gly Trp
                405                 410                 415
Pro His Glu Ile Val Gln His Tyr Tyr His Arg His Pro Val Tyr Thr
            420                 425                 430
Ile Leu Ala Val Ala Ser Ala Thr Val Ala Met Met Ile Gly Val Thr
            435                 440                 445
Val Ala Val Leu Cys Ala Cys Lys Ala Arg Arg Glu Cys Leu Thr Pro
450                 455                 460
Tyr Ala Leu Ala Pro Asn Ala Val Ile Pro Thr Ser Leu Ala Leu Leu
465                 470                 475                 480
Cys Cys Val Arg Ser Ala Asn Ala
                485
```

<210> SEQ ID NO 21
<211> LENGTH: 683
<212> TYPE: DNA
<213> ORGANISM: Human immunodeficiency virus type 1

<400> SEQUENCE: 21

```
cctagaaaaa catggagcaa tcacaagtag caatacagca gctaccaatg ctgattgtgc    60
```

```
ctggctagaa gcacaagagg aggaggaggt gggttttcca gtcacacctc aggtaccttt      120
aagaccaatg acttacaagg cagctgtaga tcttagccac ttttaaaag aaaaggggg       180 actggaaggg ctaattcact cccaacgaag acaagatatc cttgatctgt ggatctacca      240
cacacaaggc tacttccctg attggcagaa ctacacacca gggccaggga tcagatatcc      300 actgacctt  ggatggtgct acaagctagt accagttgag caagagaagg tagaagaagc      360
caatgaagga gagaacaccc gcttgttaca ccctgtgagc ctgcatggga tggatgaccc      420
ggagagagaa gtattagagt ggaggtttga cagccgccta gcatttcatc acatggcccg      480
agagctgcat ccggactgta ctgggtctct ctggttagac cagatctgag cctgggagct      540
ctctggctaa ctagggaacc cactgcttaa gcctcaataa agcttgcctt gagtgcttca      600
agtagtgtgt gcccgtctgt tgtgtgactc tggtaactag agatccctca gaccctttta      660
gtcagtgtgg aaaatctcta gca                                             683

<210> SEQ ID NO 22
<211> LENGTH: 416
<212> TYPE: DNA
<213> ORGANISM: Human immunodeficiency virus type 1

<400> SEQUENCE: 22
cctagaaaaa catggagcaa tcacaagtag caatacagca gctaccaatg ctgattgtgc       60
ctggctagaa gcacaagagg aggaggaggt gggttttcca gtcacacctc aggtaccttt      120
aagaccaatg acttacaagg cagctgtaga tcttagccac ttttaaaag aaaaggggg       180 actggaaggg ctaattcact cccaacgaag acaagatctg cttttttgcct gtactgggtc      240 tctctggtta gaccagatct gagcctggga gctctctggc taactaggga acccactgct      300
taagcctcaa taaagcttgc cttgagtgct tcaagtagtg tgtgcccgtc tgttgtgtga      360
ctctggtaac tagagatccc tcagaccctt ttagtcagtg tggaaaatct ctagca         416

<210> SEQ ID NO 23
<211> LENGTH: 401
<212> TYPE: DNA
<213> ORGANISM: Human immunodeficiency virus type 1

<400> SEQUENCE: 23
cctagaaaaa catggagcaa tcacaagtag caatacagca gctaccaatg ctgattgtgc       60
ctggctagaa gcacaagagg aggaggaggt gggttttcca gtcacacctc aggtaccttt      120
aagaccaatg acttacaagg cagctgtaga tcttagccac tttttactgg aagggctaat      180
tcactcccaa cgaagacaag atctgctttt tgcctgtact gggtctctct ggttagacca      240
gatctgagcc tgggagctct ctggctaact agggaaccca ctgcttaagc ctcaataaag      300
cttgccttga gtgcttcaag tagtgtgtgc ccgtctgttg tgtgactctg gtaactagag      360
atccctcaga cccttttagt cagtgtggaa aatctctagc a                         401

<210> SEQ ID NO 24

<400> SEQUENCE: 24

000

<210> SEQ ID NO 25

<400> SEQUENCE: 25

000
```

<210> SEQ ID NO 26
<211> LENGTH: 5
<212> TYPE: PRT
<213> ORGANISM: Sindbis virus

<400> SEQUENCE: 26

Arg Ser Lys Arg Ser
1               5

<210> SEQ ID NO 27
<211> LENGTH: 4
<212> TYPE: PRT
<213> ORGANISM: Sindbis virus

<400> SEQUENCE: 27

Arg Ser Lys Arg
1

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35
<211> LENGTH: 8
<212> TYPE: PRT
<213> ORGANISM: Artificial Sequence
<220> FEATURE:
<223> OTHER INFORMATION: a tag peptide sequence

<400> SEQUENCE: 35

Asp Tyr Lys Asp Asp Asp Lys
1               5

<210> SEQ ID NO 36
<211> LENGTH: 1374
<212> TYPE: PRT
<213> ORGANISM: Human herpesvirus 2

<400> SEQUENCE: 36

Met Ala Ala Pro Ala Arg Asp Pro Pro Gly Tyr Arg Tyr Ala Ala
1               5                   10                  15

Ile Leu Pro Thr Gly Ser Ile Leu Ser Thr Ile Glu Val Ala Ser His
                20                  25                  30

Arg Arg Leu Phe Asp Phe Phe Ala Ala Val Arg Ser Asp Glu Asn Ser
                35                  40                  45

Leu Tyr Asp Val Glu Phe Asp Ala Leu Leu Gly Ser Tyr Cys Asn Thr
    50                  55                  60

Leu Ser Leu Val Arg Phe Leu Glu Leu Gly Leu Ser Val Ala Cys Val
65                  70                  75                  80

Cys Thr Lys Phe Pro Glu Leu Ala Tyr Met Asn Glu Gly Arg Val Gln
                85                  90                  95

Phe Glu Val His Gln Pro Leu Ile Ala Arg Asp Gly Pro His Pro Val
                100                 105                 110

Glu Gln Pro Val His Asn Tyr Met Thr Lys Val Ile Asp Arg Arg Ala
                115                 120                 125

Leu Asn Ala Ala Phe Ser Leu Ala Thr Glu Ala Ile Ala Leu Leu Thr
    130                 135                 140

Gly Glu Ala Leu Asp Gly Thr Gly Ile Ser Leu His Arg Gln Leu Arg
145                 150                 155                 160

Ala Ile Gln Gln Leu Ala Arg Asn Val Gln Ala Val Leu Gly Ala Phe
                165                 170                 175

Glu Arg Gly Thr Ala Asp Gln Met Leu His Val Leu Leu Glu Lys Ala
                180                 185                 190

Pro Pro Leu Ala Leu Leu Pro Met Gln Arg Tyr Leu Asp Asn Gly
                195                 200                 205

Arg Leu Ala Thr Arg Val Ala Arg Ala Thr Leu Val Ala Glu Leu Lys
    210                 215                 220

Arg Ser Phe Cys Asp Thr Ser Phe Phe Leu Gly Lys Ala Gly His Arg
225                 230                 235                 240

Arg Glu Ala Ile Glu Ala Trp Leu Val Asp Leu Thr Thr Ala Thr Gln
                245                 250                 255

Pro Ser Val Ala Val Pro Arg Leu Thr His Ala Asp Thr Arg Gly Arg
                260                 265                 270

Pro Val Asp Gly Val Leu Val Thr Thr Ala Ala Ile Lys Gln Arg Leu
                275                 280                 285

Leu Gln Ser Phe Leu Lys Val Glu Asp Thr Glu Ala Asp Val Pro Val
    290                 295                 300

Thr Tyr Gly Glu Met Val Leu Asn Gly Ala Asn Leu Val Thr Ala Leu
305                 310                 315                 320

Val Met Gly Lys Ala Val Arg Ser Leu Asp Asp Val Gly Arg His Leu
                325                 330                 335

Leu Asp Met Gln Glu Glu Gln Leu Glu Ala Asn Arg Glu Thr Leu Asp
                340                 345                 350

-continued

```
Glu Leu Glu Ser Ala Pro Gln Thr Thr Arg Val Arg Ala Asp Leu Val
            355                 360                 365

Ala Ile Gly Asp Arg Leu Val Phe Leu Glu Ala Leu Glu Arg Arg Ile
370                 375                 380

Tyr Ala Ala Thr Asn Val Pro Tyr Pro Leu Val Gly Ala Met Asp Leu
385                 390                 395                 400

Thr Phe Val Leu Pro Leu Gly Leu Phe Asn Pro Ala Met Glu Arg Phe
                405                 410                 415

Ala Ala His Ala Gly Asp Leu Val Pro Ala Pro Gly His Pro Glu Pro
                420                 425                 430

Arg Ala Phe Pro Pro Arg Gln Leu Phe Phe Trp Gly Lys Asp His Gln
            435                 440                 445

Val Leu Arg Leu Ser Met Glu Asn Ala Val Gly Thr Val Cys His Pro
            450                 455                 460

Ser Leu Met Asn Ile Asp Ala Ala Val Gly Gly Val Asn His Asp Pro
465                 470                 475                 480

Val Glu Ala Ala Asn Pro Tyr Gly Ala Tyr Val Ala Ala Pro Ala Gly
                485                 490                 495

Pro Gly Ala Asp Met Gln Gln Arg Phe Leu Asn Ala Trp Arg Gln Arg
                500                 505                 510

Leu Ala His Gly Arg Val Arg Trp Val Ala Glu Cys Gln Met Thr Ala
            515                 520                 525

Glu Gln Phe Met Gln Pro Asp Asn Ala Asn Leu Ala Leu Glu Leu His
            530                 535                 540

Pro Ala Phe Asp Phe Phe Ala Gly Val Ala Asp Val Glu Leu Pro Gly
545                 550                 555                 560

Gly Glu Val Pro Pro Ala Gly Pro Gly Ala Ile Gln Ala Thr Trp Arg
                565                 570                 575

Val Val Asn Gly Asn Leu Pro Leu Ala Leu Cys Pro Val Ala Phe Arg
            580                 585                 590

Asp Ala Arg Gly Leu Glu Leu Gly Val Gly Arg His Ala Met Ala Pro
            595                 600                 605

Ala Thr Ile Ala Ala Val Arg Gly Ala Phe Glu Asp Arg Ser Tyr Pro
            610                 615                 620

Ala Val Phe Tyr Leu Leu Gln Ala Ala Ile His Gly Asn Glu His Val
625                 630                 635                 640

Phe Cys Ala Leu Ala Arg Leu Val Thr Gln Cys Ile Thr Ser Tyr Trp
                645                 650                 655

Asn Asn Thr Arg Cys Ala Ala Phe Val Asn Asp Tyr Ser Leu Val Ser
            660                 665                 670

Tyr Ile Val Thr Tyr Leu Gly Gly Asp Leu Pro Glu Glu Cys Met Ala
            675                 680                 685

Val Tyr Arg Asp Leu Val Ala His Val Glu Ala Leu Ala Gln Leu Val
            690                 695                 700

Asp Asp Phe Thr Leu Pro Gly Pro Glu Leu Gly Gln Ala Gln Ala
705                 710                 715                 720

Glu Leu Asn His Leu Met Arg Asp Pro Ala Leu Leu Pro Pro Leu Val
                725                 730                 735

Trp Asp Cys Asp Gly Leu Met Arg His Ala Ala Leu Asp Arg His Arg
                740                 745                 750

Asp Cys Arg Ile Asp Ala Gly Gly His Glu Pro Val Tyr Ala Ala Ala
            755                 760                 765
```

```
Cys Asn Val Ala Thr Ala Asp Phe Asn Arg Asn Asp Gly Arg Leu Leu
770                 775                 780

His Asn Thr Gln Ala Arg Ala Ala Asp Ala Ala Asp Asp Arg Pro His
785                 790                 795                 800

Arg Pro Ala Asp Trp Thr Val His His Lys Ile Tyr Tyr Tyr Val Leu
                805                 810                 815

Val Pro Ala Phe Ser Arg Gly Arg Cys Cys Thr Ala Gly Val Arg Phe
                820                 825                 830

Asp Arg Val Tyr Ala Thr Leu Gln Asn Met Val Val Pro Glu Ile Ala
                835                 840                 845

Pro Gly Glu Glu Cys Pro Ser Asp Pro Val Thr Asp Pro Ala His Pro
850                 855                 860

Leu His Pro Ala Asn Leu Val Ala Asn Thr Val Lys Arg Met Phe His
865                 870                 875                 880

Asn Gly Arg Val Val Asp Gly Pro Ala Met Leu Thr Leu Gln Val
                885                 890                 895

Leu Ala His Asn Met Ala Glu Arg Thr Thr Ala Leu Leu Cys Ser Ala
                900                 905                 910

Ala Pro Asp Ala Gly Ala Asn Thr Ala Ser Thr Ala Asn Met Arg Ile
                915                 920                 925

Phe Asp Gly Ala Leu His Ala Gly Val Leu Leu Met Ala Pro Gln His
930                 935                 940

Leu Asp His Thr Ile Gln Asn Gly Glu Tyr Phe Tyr Val Leu Pro Val
945                 950                 955                 960

His Ala Leu Phe Ala Gly Ala Asp His Val Ala Asn Ala Pro Asn Phe
                965                 970                 975

Pro Pro Ala Leu Arg Asp Leu Ala Arg Asp Val Pro Leu Val Pro Pro
                980                 985                 990

Ala Leu Gly Ala Asn Tyr Phe Ser Ser Ile Arg Gln Pro Val Val Gln
                995                 1000                1005

His Ala Arg Glu Ser Ala Ala Gly Glu Asn Ala Leu Thr Tyr Ala
                1010                1015                1020

Leu Met Ala Gly Tyr Phe Lys Met Ser Pro Val Ala Leu Tyr His
                1025                1030                1035

Gln Leu Lys Thr Gly Leu His Pro Gly Phe Gly Phe Thr Val Val
                1040                1045                1050

Arg Gln Asp Arg Phe Val Thr Glu Asn Val Leu Phe Ser Glu Arg
                1055                1060                1065

Ala Ser Glu Ala Tyr Phe Leu Gly Gln Leu Gln Val Ala Arg His
                1070                1075                1080

Glu Thr Gly Gly Gly Val Asn Phe Thr Leu Thr Gln Pro Arg Gly
                1085                1090                1095

Asn Val Asp Leu Gly Val Gly Tyr Thr Ala Val Ala Ala Thr Gly
                1100                1105                1110

Thr Val Arg Asn Pro Val Thr Asp Met Gly Asn Leu Pro Gln Asn
                1115                1120                1125

Phe Tyr Leu Gly Arg Gly Ala Pro Pro Leu Leu Asp Asn Ala Ala
                1130                1135                1140

Ala Val Tyr Leu Arg Asn Ala Val Val Ala Gly Asn Arg Leu Gly
                1145                1150                1155

Pro Ala Gln Pro Leu Pro Val Phe Gly Cys Ala Gln Val Pro Arg
                1160                1165                1170

Arg Ala Gly Met Asp His Gly Gln Asp Ala Val Cys Glu Phe Ile
```

-continued

```
            1175                1180                1185

Ala Thr Pro Val Ala Thr Asp Ile Asn Tyr Phe Arg Arg Pro Cys
    1190                1195                1200

Asn Pro Arg Gly Arg Ala Ala Gly Gly Val Tyr Ala Gly Asp Lys
    1205                1210                1215

Glu Gly Asp Val Ile Ala Leu Met Tyr Asp His Gly Gln Ser Asp
    1220                1225                1230

Pro Ala Arg Pro Phe Ala Ala Thr Ala Asn Pro Trp Ala Ser Gln
    1235                1240                1245

Arg Phe Ser Tyr Gly Asp Leu Leu Tyr Asn Gly Ala Tyr His Leu
    1250                1255                1260

Asn Gly Ala Ser Pro Val Leu Ser Pro Cys Phe Lys Phe Phe Thr
    1265                1270                1275

Ala Ala Asp Ile Thr Ala Lys His Arg Cys Leu Glu Arg Leu Ile
    1280                1285                1290

Val Glu Thr Gly Ser Ala Val Ser Thr Ala Thr Ala Ala Ser Asp
    1295                1300                1305

Val Gln Phe Lys Arg Pro Pro Gly Cys Arg Glu Leu Val Glu Asp
    1310                1315                1320

Pro Cys Gly Leu Phe Gln Glu Ala Tyr Pro Ile Thr Cys Ala Ser
    1325                1330                1335

Asp Pro Ala Leu Leu Arg Ser Ala Arg Asp Gly Glu Ala His Ala
    1340                1345                1350

Arg Glu Thr His Phe Thr Gln Tyr Leu Ile Tyr Asp Ala Ser Pro
    1355                1360                1365

Leu Lys Gly Leu Ser Leu
    1370

<210> SEQ ID NO 37
<211> LENGTH: 15
<212> TYPE: PRT
<213> ORGANISM: Human herpesvirus 2

<400> SEQUENCE: 37

Asn Tyr Phe Ser Ser Ile Arg Gln Pro Val Val Gln His Ala Arg
1               5                   10                  15

<210> SEQ ID NO 38
<211> LENGTH: 15
<212> TYPE: PRT
<213> ORGANISM: Human herpesvirus 2

<400> SEQUENCE: 38

Cys Glu Phe Ile Ala Thr Pro Val Ala Thr Asp Ile Asn Tyr Phe
1               5                   10                  15

<210> SEQ ID NO 39
<211> LENGTH: 15
<212> TYPE: PRT
<213> ORGANISM: Human herpesvirus 2

<400> SEQUENCE: 39

Glu Asn Ala Leu Thr Tyr Ala Leu Met Ala Gly Tyr Phe Lys Met
1               5                   10                  15

<210> SEQ ID NO 40
<211> LENGTH: 15
<212> TYPE: PRT
<213> ORGANISM: Human herpesvirus 2
```

-continued

```
<400> SEQUENCE: 40

His Pro Gly Phe Gly Phe Thr Val Val Arg Gln Asp Arg Phe Val
1               5                   10                  15

<210> SEQ ID NO 41
<211> LENGTH: 8
<212> TYPE: PRT
<213> ORGANISM: Artificial Sequence
<220> FEATURE:
<223> OTHER INFORMATION: a tag peptide sequence

<400> SEQUENCE: 41

Asp Leu Tyr Asp Asp Asp Asp Lys
1               5

<210> SEQ ID NO 42
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 42

Gly Pro Lys Glu Pro Phe Gln Ser Tyr Val Asp Arg Phe Tyr Lys Ser
1               5                   10                  15

Leu Arg Ala Glu Gln Thr Asp Ala Ala Val Lys Asn Trp Met Thr Gln
            20                  25                  30

Thr Leu Leu Ile Gln Asn Ala Asn Pro Asp Cys Lys Leu
        35                  40                  45

<210> SEQ ID NO 43
<211> LENGTH: 11
<212> TYPE: PRT
<213> ORGANISM: Artificial Sequence
<220> FEATURE:
<223> OTHER INFORMATION: Synthetic peptide

<400> SEQUENCE: 43

Ala Ala Val Lys Asn Trp Met Thr Gln Thr Leu
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide

<400> SEQUENCE: 44

Lys Ser Leu Tyr Asn Thr Val Cys Val
1               5

<210> SEQ ID NO 45
<211> LENGTH: 13
<212> TYPE: PRT
<213> ORGANISM: Artificial Sequence
<220> FEATURE:
<223> OTHER INFORMATION: Synthetic peptide

<400> SEQUENCE: 45

Asp Arg Phe Tyr Lys Ser Leu Arg Ala Glu Gln Thr Asp
1               5                   10
```

IMMUNOGENIC COMPOSITIONS AND METHODS OF USING THE COMPOSITIONS FOR INDUCING HUMORAL AND CELLULAR IMMUNE RESPONSES

CROSS-REFERENCE TO RELATED APPLICATION

This patent application claims priority to U.S. Provisional Application No. 61/473,660, filed Apr. 8, 2011, which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 46441A_SeqListing.txt. The text file is 163,840 bytes, was created on Apr. 6, 2012, and is being submitted electronically via EFS-Web.

GOVERNMENT SUPPORT

This invention was made with U.S. government support under grant number 5-R43-AI087444-02 awarded by the National Institutes of Health and National Institute of Allergy and Infectious Disease. The government has certain rights in the invention.

BACKGROUND

1. Technical Field

The present disclosure relates generally to methods for enhancing the specific immune response to an immunogen by immunizing a subject with at least two compositions to induce humoral and cellular immune responses to the immunogen.

2. Description of the Related Art

The immune system of a host provides the means for quickly and specifically mounting a protective response to pathogenic microorganisms and also for contributing to rejection of malignant tumors. Immune responses have been generally described as including humoral responses, in which antibodies specific for antigens are produced by differentiated B lymphocytes, and cell mediated responses, in which various types of T lymphocytes eliminate antigens by a variety of mechanisms. For example, CD4 (also called CD4+) helper T cells that are capable of recognizing specific antigens may respond by releasing soluble mediators such as cytokines to recruit additional cells of the immune system to participate in an immune response. CD8 (also called CD8+) cytotoxic T cells are also capable of recognizing specific antigens and may bind to and destroy or damage an antigen-bearing cell or particle. In particular, cell mediated immune responses that include a cytotoxic T lymphocyte (CTL) response can be important for elimination of tumor cells and cells infected by a microorganism, such as virus, bacteria, or parasite.

Cancer includes a broad range of diseases and affects approximately one in four individuals worldwide. A CTL response is a key feature of effective cancer vaccines; effective CD4 T cell help is also likely to play a critical role in productive CD8 T cell activation and thus provide clinical benefit. The autologous dendritic cell (DC)-based vaccine Sipuleucel-T (PROVENGE®) was recently approved by the U.S. Food and Drug Administration (FDA) for the treatment of metastatic, castrate-resistant prostate cancer though the survival benefit associated with this treatment is a modest 4.1 months, leaving significant need for improvement (see, e.g., Kantoff, et al., New Engl. J. Med. 363(5):411 (2010)). The poxvirus-vector based vaccine ProstVac® VF also shows a significant survival benefit in Phase II (see, e.g., Kantoff, et al., J. Clin. Oncol. 28(7):1099 (2010)). Active immune therapies such as Sipuleucel-T and ProstVac® VF have generally been better tolerated than the chemotherapeutic regimens that comprise the current standard of care for castrate-resistant disease (see, e.g., Petrylak, et al., N. Engl. J. Med. 351(15): 1513 (2004); Sylwester, et al., J. Exp. Med. 202(5):673 (2005)). These clinical successes demonstrate that the immune response can be harnessed in a cancer setting to provide improved patient outcomes and extended survival.

With respect to microbial infections, malaria, tuberculosis, HIV-AIDS and other viral infections such as Herpes Simplex Virus (HSV) infections (the leading cause of genital ulcers worldwide) continue to contribute to global health concerns. HSV-2 prevalence is increasing at an alarming rate across the globe (see, e.g., Corey et al., J. Acquir. Immune Defic. Syndr. 35:435 (2004)). In the United States, the overall HSV-2 seroprevalence rate exceeds 20%, and in developing nations HSV-2 prevalence is estimated between 30% and 50%. In addition to the profound burden of HSV-2 infection in adults, the incidence of neonatal HSV-2 infection is increasing. Even when treated, neonatal encephalitis from HSV-2 infection has a mortality >15%, and the neurological morbidity among HSV-2 infected infants is an additional 30 to 50% of surviving cases. Concomitant with the HSV-2 epidemic is a stark realization that HSV-2 infection substantially increases the risk for HIV-1 acquisition and transmission. Data from Africa show that HSV-2 infection can increase the risk for HIV transmission by as much as 7-fold and that as many as half of newly acquired HIV cases are directly attributed to HSV-2 infection (see, e.g., Abu-Raddad et al., PLoS ONE 3(5):e2230 (2008)). Overall, the relative risk of HIV acquisition increases more than 2-fold in HSV-2-infected individuals.

The increasing prevalence of HSV-2 in the adult and pediatric populations persists despite the widespread use of pharmacological intervention. Antiviral medication given at high doses early in infection can reduce HSV transmission, but this does not prevent latent infection (see, e.g., Corey et al., Sex Transm. Dis. 12:215 (1985)). In a recent study, continuous suppressive administration with Valacyclovir reduced HSV transmission by less than 50% despite early intervention (see, e.g., Corey et al., N. Engl. J. Med. 350:11 (2004)). Alternatives to antiviral drugs, such as topical microbicides are unproven clinically. For these reasons, many leading authorities believe that vaccination is essential for diminishing the health impact of HSV-2 disease.

A need exists for vaccines, including improved vaccines, against infectious disease microorganisms, such as Human Immunodeficiency Virus (HIV) and Herpes Simplex Virus, malaria, antibiotic resistant bacteria, for which inducing a robust humoral and/or cell-mediated response is important for successful prevention and treatment of infection. In addition, considerable potential and need exists for improved cancer vaccine potency.

BRIEF SUMMARY

Provided herein are immunogenic compositions, preparations of these immunogenic compositions and, methods for using the preparations and compositions for inducing an immune response specific for one or more immunogens and related antigens. In one embodiment, a method is provided for inducing an immune response in a subject, the method comprising (a) administering to the subject at least one dose of a first immunogenic composition comprising at least a first immunogen, wherein the at least one immunogen is capable of inducing an immune response specific for a first designated antigen; and (b) administering to the subject at least one dose second immunogenic composition comprising a recombinant expression vector comprising a nucleotide sequence that encodes the first immunogen, thereby inducing an immune response specific for the first designated antigen. In a particular embodiment, (i) the first immunogenic composition further comprises an adjuvant; (ii) the second composition further comprises an adjuvant; or (iii) each of the first composition and the second composition further comprises an adjuvant. In certain embodiments, the second immunogenic composition is administered subsequent to administration of the first immunogenic composition. In other certain embodiments, the second immunogenic composition is administered prior to administration of the first immunogenic composition. In still another certain embodiment, the first immunogenic composition and the second immunogenic composition are administered concurrently. In specific embodiments, at least two doses of the first immunogenic composition are administered or at least two doses of the second immunogenic composition are administered. In still other embodiments, (a) two doses; (b) three doses; (c) four doses; or (d) five doses of the first immunogenic composition are administered. In another embodiment, when two or more doses are administered, (a) each dose of the first immunogenic composition is administered prior to administration of the second immunogenic composition; (b) at least one dose of the first immunogenic composition is administered subsequent to administration of the second immunogenic composition; (c) at least one dose of the first immunogenic composition is administered concurrently with administration of the second immunogenic composition; (d) at least one dose of the first immunogenic composition is administered prior to administration of the second immunogenic composition and each of any remaining doses of the first immunogenic composition is administered subsequent to administration of the second immunogenic composition; or (e) each dose of the first composition is administered concurrently with the second composition. With respect to each of these methods and embodiments, the immune response induced by the first immunogen comprises a CD4 T cell immune response specific for the first designated antigen, and in certain embodiments the immune response induced by the first immunogen comprises a CD8 T cell immune response specific for the first designated antigen; and in other certain embodiments, the immune response induced by the first immunogen comprises a CD4 T cell immune response and a CD8 T cell immune response specific for the first designated antigen.

In certain embodiments of the methods described above and herein, the first immunogenic composition further comprises a second immunogen, and the recombinant expression vector further comprises a nucleotide sequence that encodes the second immunogen, wherein the second immunogen induces an immune response specific for a second designated antigen. In certain particular embodiments, the first designated antigen and the second designated antigen are the same. In other certain particular embodiments, the first designated antigen and the second designated antigen are different. In certain other embodiments of the methods described above and herein, the recombinant expression vector further comprises a nucleotide sequence that encodes a second immunogen capable of inducing an immune response specific for a second designated antigen. In certain particular embodiments, the first designated antigen and the second designated antigen are the same. In other certain particular embodiments, the first designated antigen and the second designated antigen are different. In particular embodiments with respect to such methods, the immune response induced by the first immunogen comprises a CD4 T cell response specific for the first designated antigen. In particular embodiments with respect to such methods, the immune response induced by the second immunogen comprises a CD8 T cell response specific for the second designated antigen.

In particular embodiments of the methods described above and herein and when one or more of the immunogenic compositions comprises an adjuvant, the adjuvant is a non-toxic lipid A-related adjuvant. In certain particular embodiments, the non-toxic lipid A-related adjuvant is glucopyranosyl lipid A (GLA); in more particular embodiments, GLA is formulated in a stable oil-in-water emulsion.

In other particular embodiments of the methods described above and herein, the first designated antigen is (a) a tumor-associated antigen or (b) from an infectious microorganism selected from a virus, a bacterium, a fungus, and a parasite. In a more specific embodiment, the first designated antigen is a tumor-associated antigen selected from a renal cell carcinoma antigen, a prostate cancer antigen, a mesothelioma antigen, a pancreatic cancer antigen, a melanoma antigen, a breast cancer antigen, a lung cancer antigen, and an ovarian cancer antigen. In still more specific embodiments, the prostate cancer antigen is prostatic acid phosphatase, prostate specific antigen, NKX3.1, or prostate specific membrane antigen. In other particular embodiments, the first designated antigen is from a virus. In a more specific embodiment, the virus is Herpes Simplex Virus-2 (HSV-2). In certain particular embodiments, the first designated antigen is HSV-2 UL19 polypeptide or HSV-2 gD polypeptide.

In other specific embodiments of the methods described above and herein when an immune response is induced specific for a first designated and a second designated antigen, each of the first designated antigen and the second designated antigen is a tumor-associated antigen. In more specific embodiments, each of the first designated antigen and the second designated antigen is selected from a renal cell carcinoma antigen, a prostate cancer antigen, a mesothelioma antigen, a pancreatic cancer antigen, a melanoma antigen, a breast cancer antigen, a lung cancer antigen, and an ovarian cancer antigen. In still more specific embodiments, each of the first designated antigen and the second designated antigen is a prostate cancer antigen selected from prostatic acid phosphatase, prostate specific antigen, NKX3.1, or prostate specific membrane antigen. In other particular embodiments, each of the first designated antigen and the second designated antigen is an antigen from an infectious microorganism selected from a virus, a bacterium, a fungus, and a parasite. In a more specific embodiment, the infectious disease organism is a virus, which in more particular embodiments is Herpes Simplex Virus-2 (HSV-2). In certain embodiments, at least one of the first designated antigen and the second designated antigen is HSV-2 UL19 polypeptide and the other of the first designated antigen and the second designated antigen is HSV-2 gD polypeptide.

In other specific embodiments of the methods described above and herein, the recombinant expression vector is selected from a lentiviral vector genome, poxvirus vector genome, vaccinia virus vector genome, adenovirus vector genome, adenovirus-associated virus vector genome, herpes virus vector genome, and an alpha virus vector genome. In a particular embodiment, the recombinant expression vector is incorporated into a vector particle, which in certain specific embodiments delivers the recombinant expression vector to an antigen-presenting cell. In a specific embodiment, the antigen-presenting cell is a dendritic cell. In particular embodiments, the vector particle is a lentiviral vector particle that comprises the lentiviral vector genome; a poxvirus vector particle that comprises the poxvirus vector genome; a vaccinia virus vector particle that comprises the vaccinia virus vector genome; an adenovirus vector particle that comprises the adenovirus vector genome; an adenovirus-associated virus vector particle that comprises the adenovirus-associated virus vector genome; a herpes virus vector particle that comprises the herpes virus vector genome; or an alpha virus vector particle that comprises the alpha virus vector genome. In a more specific embodiment, the vector particle is a lentiviral vector particle that comprises the lentiviral vector genome. In still more specific embodiments, the lentiviral vector particle further comprises an envelope comprising a Sindbis virus E2 glycoprotein comprising an amino acid sequence having at least one amino acid change compared to SEQ ID NO:1, wherein residue 160 of SEQ ID NO:1 is either absent or an amino acid other than glutamic acid, and wherein the E2 glycoprotein is not a moiety of a fusion protein that comprises Sindbis virus E3 protein. In further particular embodiments, the E2 glycoprotein binds to dendritic cell-specific intercellular adhesion molecule-3-grabbing non-integrin (DC-SIGN).

Also provided herein in one embodiment are preparations, which in one embodiment, the preparation comprises (a) a first immunogenic composition that comprises at least a first immunogen capable of inducing an immune response specific for a first designated antigen; and (b) a second immunogenic composition that comprises a recombinant expression vector that comprises a nucleotide sequence encoding the first immunogen. In a specific embodiment, the specific immune response induced by the first immunogen comprises a CD4 T cell response specific for the first designated antigen. In another specific embodiment, the specific immune response induced by the first immunogen comprises a CD8 T cell response specific for the first designated antigen. In other specific embodiments, the immune response induced by the first immunogen comprises a CD4 T cell immune response and a CD8 T cell immune response specific for the first designated antigen. In another embodiment of the preparations described above and herein, these preparations are provided for use in inducing a cytotoxic T lymphocyte response against a tumor cell bearing (a) the first designated antigen. In other particular embodiments, preparations described above and herein are provided for use in inducing a cytotoxic T lymphocyte response against an infectious disease microorganism bearing the first designated antigen. In other particular embodiments, the preparations described above and herein are provided for use in reducing the likelihood of occurrence or recurrence of a tumor comprising a plurality of tumor cells that bear the tumor-associated antigen. In another embodiment, these preparations are provided for use in preventing or treating an infection caused by an infectious microorganism.

Additional embodiments of the preparations are provided wherein the first immunogenic composition further comprises a second immunogen, and wherein the recombinant expression vector further comprises a nucleotide sequence that encodes the second immunogen, wherein the second immunogen induces an immune response specific for a second designated antigen. In one specific embodiment, the first designated antigen and the second designated antigen are the same. In another specific embodiment, the first designated antigen and the second designated antigen are different. In still other specific embodiments of the preparations described above and herein, the recombinant expression vector further comprises a nucleotide sequence that encodes a second immunogen capable of inducing an immune response specific for a second designated antigen. In certain specific embodiments, the first designated antigen and the second designated antigen are the same, and in other specific embodiments, the first designated antigen and the second designated antigen are different. In these embodiments, the immune response induced by the first immunogen comprises a CD4 T cell response specific for the first designated antigen. Also, with respect to these embodiments, of the preparations, the immune response induced by the second immunogen comprises a CD8 T cell response specific for the second designated antigen.

With respect to embodiments of the preparations provided above and herein, (a) the first immunogenic composition further comprises an adjuvant (b) the second immunogenic composition further comprises an adjuvant; or (c) the first immunogenic composition and the second immunogenic composition each further comprises an adjuvant. In more specific embodiments, the adjuvant is a non-toxic lipid A-related adjuvant. In still a more specific embodiment, the non-toxic lipid A-related adjuvant is glucopyranosyl lipid A (GLA), which in specific embodiments, is formulated in a stable oil-in-water emulsion.

With respect to embodiments of the preparations provided above and herein, the first designated antigen is (a) a tumor-associated antigen or (b) from an infectious microorganism selected from a virus, a bacterium, a fungus, and a parasite. In specific embodiments, the first designated antigen is a tumor-associated antigen selected from a renal cell carcinoma antigen, a prostate cancer antigen, a mesothelioma antigen, a pancreatic cancer antigen, a melanoma antigen, a breast cancer antigen, a lung cancer antigen, and an ovarian cancer antigen. In more specific embodiments, the prostate cancer antigen is prostatic acid phosphatase, prostate specific antigen, NKX3.1, or prostate specific membrane antigen. In other specific embodiments, the first designated antigen is from a virus. In a more specific embodiment, the virus is Herpes Simplex Virus-2 (HSV-2). In yet another specific embodiment, the first designated antigen is HSV-2 UL19 polypeptide or HSV-2 gD polypeptide.

In other embodiments of the preparations described above and herein, when the immune response induced by the preparations comprises an immune response specific for a first designated antigen and a second designated antigen, each of the first designated antigen and the second designated antigen is a tumor-associated antigen. In a more specific embodiment, each of the first designated antigen and the second designated antigen is selected from a renal cell carcinoma antigen, a prostate cancer antigen, a mesothelioma antigen, a pancreatic cancer antigen, a melanoma antigen, a breast cancer antigen, a lung cancer antigen, and an ovarian cancer antigen. In yet another more particular embodiment, each of the first designated antigen and the second designated antigen is a prostate cancer antigen selected from prostatic acid phosphatase, prostate specific antigen, NKX3.1, and prostate specific membrane antigen. In other specific embodiments, each of the first designated antigen and the second designated antigen is an antigen from an infectious microorganism selected from a virus, a bacterium, a fungus, and a parasite. In one particular embodiment, the infectious disease organism is a virus. In a particular embodiment, the virus is Herpes Simplex Virus-2 (HSV-2). In still another specific embodiment, at least one of the first designated antigen and the second designated antigen is HSV-2 UL19 polypeptide and the other of the first designated antigen and the second designated antigen is HSV-2 gD polypeptide.

In other embodiments of the preparations described above and herein, the recombinant expression vector is selected from a lentiviral vector genome, poxvirus vector genome, vaccinia virus vector genome, adenovirus vector genome, adenovirus-associated virus vector genome, herpes virus vector genome, and alpha virus vector genome. In one specific embodiment, the recombinant expression vector is incorporated into a vector particle. In still another specific embodiment, the vector particle is capable of delivering the recombinant expression vector to an antigen-presenting cell. In more specific embodiments, the antigen-presenting cell is a dendritic cell. In other specific embodiments, the vector particle is a lentiviral vector particle that comprises the lentiviral vector genome; a poxvirus vector particle that comprises the poxvirus vector genome; a vaccinia virus vector particle that comprises the vaccinia virus vector genome; an adenovirus vector particle that comprises the adenovirus vector genome; an adenovirus-associated virus vector particle that comprises the adenovirus-associated virus vector genome; a herpes virus vector particle that comprises the herpes virus vector genome; or an alpha virus vector particle that comprises the alpha virus vector genome. In a more particular embodiment, the vector particle is a lentiviral vector particle that comprises the lentiviral vector genome. In yet more specific embodiments, the lentiviral vector particle further comprises an envelope comprising a Sindbis virus E2 glycoprotein comprising an amino acid sequence having at least one amino acid change compared to SEQ ID NO:1, wherein residue 160 of SEQ ID NO:1 is either absent or an amino acid other than glutamic acid, and wherein the E2 glycoprotein is not a moiety of a fusion protein that comprises Sindbis virus E3 protein. In a more particular embodiment, the E2 glycoprotein binds to dendritic cell-specific intercellular adhesion molecule-3-grabbing non-integrin (DC-SIGN).

In another embodiment of the preparations described above and herein, these preparations are provided for use in inducing a cytotoxic T lymphocyte response against a tumor cell bearing (a) the first designated antigen; (b) the second designated antigen; or (c) the first designated antigen and the second designated antigen. In other particular embodiments, preparations described above and herein are provided for use in inducing a cytotoxic T lymphocyte response against an infectious disease microorganism bearing (a) the first designated antigen; (b) the second designated antigen; or (c) the first designated antigen and the second designated antigen. In other particular embodiments, the preparations described above and herein are provided for use in reducing the likelihood of occurrence or recurrence of a tumor comprising a plurality of tumor cells that bear the tumor-associated antigen. In another embodiment, these preparations are provided for use in preventing or treating an infection caused by the infectious microorganism.

As used herein, the term "isolated" means that a material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such a nucleic acid could be part of a vector. A nucleic acid, which may be part of a vector, may still be isolated in that the nucleic acid is not part of the natural environment for the nucleic acid. An isolated polypeptide or protein, or fragment thereof, could be a component of a composition, and still be isolated in that the composition is not part of the natural environment for the polypeptide. The term "gene" means the segment of DNA involved in producing a polypeptide chain; a gene includes regions preceding and following the coding region "leader and trailer" as well as intervening sequences (introns) between individual coding segments (exons). Amino acids may be referred to herein according to the single letter and three letter codes, which are common textbook knowledge in the art, and therefore with which a person skilled in the art is familiar. The term "fusion polypeptide" used herein may also be used interchangeably with "fusion protein," and unless specifically indicated otherwise, the two terms are not meant to indicate molecules that have distinguishable properties or characteristics.

As used herein and in the appended claims, the singular forms "a," "and," and "the" include plural referents unless the context clearly dictates otherwise. Thus, for example, reference to "an antigen" includes a plurality of such antigens, and reference to "a cell" or "the cell" includes reference to one or more cells and equivalents thereof (e.g., plurality of cells) known to those skilled in the art, and so forth. Similarly, reference to "a compound" or "a composition" includes a plurality of such compounds or compositions, and refers to one or more compounds or compositions, respectively, unless the context clearly dictates otherwise. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

BRIEF DESCRIPTION OF THE DRAWINGS

FIG. 4A (left) depicts cytokine production for one representative mouse per group. The right side of FIG. 4A illustrates the percent cytokine positive CD8 T cells that were stimulated by each of two different CD8 UL19 epitopes. FIG. 4B presents the total IgG measured in animals from each immunized group. GLA-SE-adjuvanted rUL19 protein is represented by "rP" in FIG. 4B. BLD: Below Level of Detection FIG. 5A (left) depicts cytokine production for one representative mouse per group. The right side of FIG. 5A illustrates the percent cytokine positive CD4 T cells that were stimulated by each of two different CD4 UL19 epitopes and the percent cytokine positive CD8 T cells that were stimulated by each of two different CD8 UL19 epitopes.

Sera were obtained from animals in each group five days post-boost and ten days post boost, and specific IgG antibodies were detected. FIG. 5B presents the total IgG measured in animals from each immunized group. GLA-SE-adjuvanated rUL19 protein is represented by "rP" in FIG. 5B. From left to right, the four data sets represent the IgG titer in animals that received (1) PBS (priming composition, 1°) followed by immunization with GLA-SE-adjuvanated rUL19 protein and DC-NILV encoding UL19 (rP+LV) (boosting composition, 2°) (sera obtained five days after boosting; (2) PBS (priming composition, 1°) followed by immunization with rP+LV (boosting composition, 2°) (sera obtained ten days after boosting; (3) GLA-SE-adjuvanated rUL19 protein (rP) (priming composition, 1°), followed by immunization with rP+LV (boosting composition, 2°) (sera obtained five days after boosting; (4) rP (priming composition, 1°), followed by immunization with rP+LV (boosting composition, 2°) (sera obtained ten days after boosting).

FIG. 6 illustrates several exemplary immunization regimens that may be employed using the immunogenic compositions described herein for inducing a specific CD4 T cell response, specific CD8 T cell response, and specific antibody response. Immunogen: a recombinant or isolated polypeptide(s) of interest; Vector encoding immunogen: a recombinant expression vector containing a polynucleotide that encodes the polypeptide(s) of interest.

DETAILED DESCRIPTION

Figure 1:
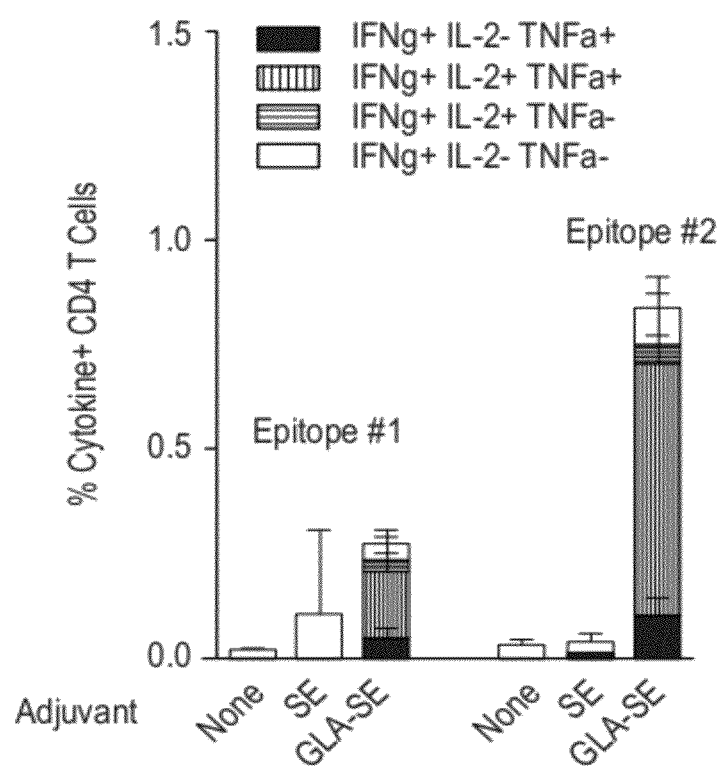
FIG. 1 depicts the CD4 immune response specific for HSV-2 UL19 protein. Groups of five mice were immunized via a prime/boost immunization regimen (d0 prime/d21 boost) with 5 ug of recombinant HSV-2 UL19 in combination with 5 μg of glucopyranosyl Lipid A (GLA) formulated in a stable oil-in water emulsion (GLA-SE), stable oil-in water emulsion (SE), or PBS (None). Splenic CD4 T cell responses were measured after ex vivo re-stimulation with UL19 T cell epitope containing peptides. The level of IFN-γ, TNF-α, and IL-2 was determined by intracellular cytokine staining (ICS) followed by fluorescence activated cell sorting (FACS). Percent cytokine positive CD4 T cells are depicted for each group.

Vaccination against diseases and conditions, such as, infectious diseases, has included strategies in which subjects are immunized with one composition (the priming composition) and subsequently immunized with a different composition (boosting composition). However, the dual vaccination strategies to date have not adequately induced both CD4 and CD8 T cell responses as well as humoral immunity that provide sufficient protection against many diseasse and conditions.

Provided herein are compositions and methods for improved dual immunization strategies that induce in a subject an immune response that includes a humoral immune response and cellular immune response, both CD4 and CD8 T lymphocyte immune responses, providing a complete adaptive immune response to one or more antigens. Accordingly, the compositions described herein may be developed and formulated as vaccines. The methods described are therefore useful for treating and preventing (i.e., reducing the likelihood or risk of occurrence or recurrence in a biologically, clinically, and/or statistically significant manner) different diseases, disorders, and conditions such as cancers and infectious diseases for which induction of both a humoral immune response and cellular immune response improves the clinical outcome or is necessary for optimal benefit.

Provided herein are two different immunogenic compositions that are administered concurrently or sequentially in either order to a subject in need thereof. At least one of the immunogenic compositions induces a specific humoral (i.e., antibody response) and/or a specific CD4 T cell response (which may include a memory CD4 T cell response) to an immunogen, and at least one of the immunogenic compositions induces a specific CD8 T cell response, which may include a cytotoxic T cell (CTL) response, specific for the immunogen. In certain embodiments, one of the two immunogenic compositions may be more effective for inducing a specific humoral and/or specific CD4 T cell response and the other of the two immunogenic compositions may be more effective for inducing a specific CD8 T cell response.

One immunogenic composition comprises at least one immunogen that is capable of inducing an immune response specific for a designated antigen of interest. This immunogenic composition may further comprise an adjuvant that enhances, or that may be required, for inducing an immune response specific for the immunogen and the designated antigen. A second immunogenic composition comprises a recombinant expression vector comprising a nucleotide sequence that encodes the immunogen. The recombinant expression vector further comprises at least one regulatory sequence operatively linked to the nucleotide sequence that encodes the immunogen and, thus, the recombinant expression vector is capable of directing expression of the immunogen. In certain specific embodiments, the recombinant expression vector is incorporated into a vector particle (e.g., a virus vector particle). As described further herein, the immunogen may be an immunogenic fragment of the designated antigen or may be the full-length designated antigen (or an immunogenic variant thereof), or a fusion protein that comprises one or more immunogenic fragments or that comprises the full-length designated antigen (or immunogenic variant thereof).

Thus, any use of the term "immunogen" herein refers to the entire group of polypeptides that are: (a) full length antigen, (2) immunogenic fragments of the antigen, (3) immunogenic variants of the full length antigen or immunogenic fragment, (4) chimeric fusions thereof comprising portions of a different polypeptide, and (5) conjugates thereof. Thus, an "immunogen" represents a polypeptide comprising any of (i) the first designated antigen, (ii) an immunogenic fragment thereof, or (iii) a variant thereof capable of inducing an immune response specific for the first designated antigen.

For example, such immunogenic variants retain at least 90% amino acid identity over at least 10 contiguous amino acids of the antigen, or at least 85% amino acid identity over at least 15 contiguous amino acids of the antigen (e.g. an envelope protein or a tumor-associated antigen). As another example, such immunogenic fragments comprise at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 contiguous amino acids of the antigen. Other examples include at least 70%, 75%, 80%, 85%, 90%, 91%, 92%, 93%, 94%, 95%, 96%, 97%. 98%, or 99% identity over at least 50 contiguous amino acids of the antigen, or over at least 100 contiguous amino acids of the antigen.

It is understood that, in the methods herein, when reference is made to a first immunogenic composition comprising an immunogen and a second immunogenic composition comprising a nucleotide sequence that encodes "the immunogen", the encoded immunogen polypeptide of the second immunogenic composition need not have the same amino acid sequence as the polypeptide immunogen of the first immunogenic composition. Thus, the methods and compositions described herein contemplate that the first immunogenic composition comprise at least one, two, three or more small fragments of an antigen (e.g. an envelope protein or a tumor-associated antigen) and the second immunogenic composition comprises a nucleotide sequence encoding the full length antigen or a larger fragment thereof, or vice versa. For example, the first polypeptide is a small immunogenic fragment of the antigen, of about 50 amino acids or less in length, and the second polypeptide is full-length antigen or a larger fragment thereof, of about 50 amino acids or more in length, optionally having at least 80%, 85%, 90% or 95% identity to the full length antigen.

In other specific embodiments provided herein, a second immunogen is included in either immunogenic composition. The second immunogen is capable of inducing an immune response to a designated antigen, which may be the same or different from the designated antigen for which the first immunogen induces a specific immune response. In another specific embodiment, the first immunogen induces a specific CD4 T cell immune response and may also induce a specific antibody response, and the second immunogen induces at least a CD8 T cell immune response. In certain particular embodiments, the subject to be immunized is intended to be immunized with the second immunogen only via expression of the second immunogen by the recombinant expression vector. Accordingly, the immunogenic composition comprising the first immunogen (and which may further comprise an adjuvant) lacks the second immunogen, and the recombinant expression vector comprises a nucleotide sequence that encodes the first immunogen and that encodes a second immunogen.

The immunogenic compositions and methods described herein may be useful for preventing or treating an infectious disease, particularly infectious diseases for which no satisfactory vaccine or post-infection treatment is available (for example, viral infections such as HIV and HSV-2, and parasitic infections such as malaria). In other embodiments, the immunogenic compositions and methods described herein may be used for treating and/or reducing the likelihood of occurrence of a cancer and malignancy.

The various embodiments of the immunogenic compositions, preparations comprising the immunogenic compositions, and methods of using the preparations and compositions are described in detail below.

Immunogenic Compositions

Different immunogenic compositions are described herein that when used in a coordinated immunization strategy are useful for inducing specific, adaptive immune responses. One immunogenic composition comprises at least one immunogen and may further comprise a physiologically suitable (i.e., pharmaceutically acceptable or suitable) adjuvant. The immunogen included in this first immunogenic composition is typically an isolated immunogen, which may be isolated from its natural environment or may be recombinantly produced. For ease of reference the immunogen present in the first immunogenic composition is called herein an isolated/recombinant immunogen. A second, different composition comprises a recombinant expression vector that comprises a nucleotide sequence encoding the immunogen. The second immunogenic composition may also further comprise an adjuvant. If both the first composition and second compostion comprise an adjuvant, the adjuvant included in each composition may be the same or different.

Administration of the two different compositions to a subject induces a specific immune response to the at least one immunogen and to a respective antigen of interest (also called herein a designated antigen). The specific immune response includes a specific humoral immune response (i.e., specific antibody response) and a specific cellular immune response (including a CD4 T cell response and a CD8 T cell response), each response specific for the immunogen and thereby specific for the designated antigen of interest. An immunogenic preparation referred to herein, comprises these two immunogenic compositions, which may be referred to herein for convenience as a first immunogenic composition and a second immunogenic composition. Accordingly, in one embodiment, an immunogenic preparation comprises (a) at least one immunogenic composition that comprises at least one isolated/recombinant immunogen capable of eliciting an immune response specific for a designated antigen; and (b) at least one second immunogenic composition that comprises a recombinant expression vector comprising a nucleotide sequence encoding the at least one immunogen. The immunogenic compositions of the preparations may be administered concurrently or sequentially in either order to a subject to induce an immune response specific for the immunogen and for the respective designated antigen. Each of the immunogenic compositions and uses for the compositions are described in greater detail herein.

Each immunogenic composition may further comprise at least one physiologically (or pharmaceutically) acceptable or suitable excipient. Any physiologically or pharmaceutically suitable excipient or carrier (i.e., a non-toxic material that does not interfere with the activity of the active ingredient) known to those of ordinary skill in the art for use in pharmaceutical compositions may be employed in the immunogenic compositions described herein. Exemplary excipients include diluents and carriers that maintain stability and integrity of proteins. Excipients for therapeutic use are well known, and are described, for example, in Remington: The Science and Practice of Pharmacy (Gennaro, 21st Ed. Mack Pub. Co., Easton, Pa. (2005)), and are described in greater detail herein.

The immunogen may be identical to the designated antigen, that is, the immunogen comprises an exemplary full-length amino acid sequence of the designated antigen, or may comprise a variant thereof that shares a high percent identity with the exemplary full-length designated antigen and that retains a functional characteristic of the designated antigen, for example, the capability to induce a specific immune response. Alternatively, an immunogen may be an immunogenic fragment of the designated antigen. Immunogens that are variants or fragments of a designated antigen exhibit the capability to induce an immune response (e.g., a humoral response (i.e., B cell response) or a cell-mediated response (i.e., T cell response (including a cytotoxic T lymphocyte response)) or both a humoral and cell-mediated response in a subject in a statistically, clinically, and/or biologically significant manner. Designated antigens of interest and immunogenic fragments and immunogenic variants of designated antigens thereof are described in greater detail herein.

With respect to the immunogenic composition that comprises at least one isolated/recombinant immunogen, the immunogen may be a polypeptide or peptide that has been recombinantly produced in a host cell and then isolated from the host cell or isolated from the host cell culture (i.e., removed from its original host cell environment) according to methods routinely practiced in the molecular biology and protein isolation arts. When the immunogen is recombinantly produced according to methods described herein and in the art and with which a skilled person is familiar, the immunogen may be called a recombinant immunogen. Alternatively, the immunogen may be isolated or removed from a natural source, such as, for example, a virus, bacteria, parasite, fungus, or tumor cell. Methods for isolating one or more immunogens and antigens from natural sources are described in the art and also may be readily empirically determined by a skilled person using methods and techniques routinely practiced in the art.

As described herein, the recombinant expression vector included in the second immunogenic composition comprises a nucleotide sequence (also called herein a polynucleotide sequence) that encodes the at least one immunogen. The recombinant expression vector further comprises at least one regulatory sequence that is operatively linked to the encoding nucleotide sequence such that the vector is capable of directing expression of the immunogen. The immunogen that is encoded and expressed by the recombinant expression vector may be identical to the designated antigen, that is, the immunogen comprises an exemplary full-length amino acid sequence of the designated antigen, or may comprise a variant thereof that shares a high percent identity with the exemplary full-length designated antigen and that retains a functional characteristic of the designated antigen, for example, the capability to induce a specific immune response. Alternatively, the encoded immunogen may be an immunogenic fragment of the designated antigen. Immunogens that are variants or fragments of a designated antigen exhibit the capability to induce an immune response (e.g., a humoral response (i.e., B cell response) or a cell-mediated response (i.e., T cell response (including a cytotoxic T lymphocyte response)) or both a humoral and cell-mediated response in a subject in a statistically, clinically, and/or biologically significant manner. Designated antigens of interest and immunogenic fragments and immunogenic variants of designated antigens thereof are described in greater detail herein.

In certain embodiments, the recombinant expression vector is incorporated into a vector particle (e.g., a virus vector particle or a cell particle). The recombinant expression vector or vector particle comprising the vector is constructed in a manner that enables the particle to be introduced into (i.e., delivered to) a target cell. In certain embodiments, the target cell is an antigen-presenting cell. In more specific embodiments, the target cell is a professional antigen-presenting cell such as a dendritic cell. The immunogen is then expressed in the target cell, and the immunogen or a fragment thereof is presented on the surface of the antigen-presenting cell and induces an immune response specific for the immunogen and thereby for the respective designated antigen.

In other embodiments, the immunogenic composition that comprises at least one isolated/recombinant immunogen (and which may further comprise an adjuvant) further comprises at least one additional immunogen (i.e., at least two, three, four, five, or more immunogens which may be restated as two, three, four, five, or more immunogens)). In certain embodiments, an immunogenic composition may comprise two or more isolated/recombinant immunogens (i.e., at least two immunogens), forming a multivalent immunogenic composition. In instances when the two or more immunogens are combined with an adjuvant, the immunogenic composition may comprise each immunogen formulated separately with an adjuvant and then the adjuvanated immunogens are combined to form the immunogenic composition. Alternatively, the two or more immunogens may be formulated together with an adjuvant. In certain specific embodiments, each of the additional immunogens (e.g., the second, third, etc. immunogen) may induce an immune response to the same designated antigen as the first immunogen. In other specific embodiments, each of the additional immunogens (e.g., the second, third, etc. immunogen) may induce an immune response specific for a different (e.g., a second, third, etc.) designated antigen, respectively.

In certain alternative embodiments, a multivalent immunogenic composition may comprise a cell lysate, cell organelle, or cell supernatant that includes at least two immunogens. For example, immunogens removed from their original environment, such as immunogens obtained from microorganisms may be partially isolated from the microorganism so that two or more immunogens are present in the immunogenic composition. Similarly, immunogens obtained from a tumor cell may be partially isolated from the tumor cell so that two or more tumor associated antigens are present in the immunogenic composition.

With respect to immunogenic compositions comprising a recombinant expression vector, the nucleotide sequence may encode more than one immunogen, for example, at least two, three, four, five, or more immunogens (i.e., two, three, four, five, or more immunogens). In certain specific embodiments, each of the additional immunogens (e.g., second, third, etc. immunogen) may induce an immune response to the same designated antigen as the first immunogen. In other specific embodiments, each of the additional immunogens (e.g., second, third, etc. immunogen) may induce an immune response specific for a different (e.g., a second, third, etc.) designated antigen, respectively.

In particular embodiments, one immunogenic composition (also called a first immunogenic composition) that comprises the at least one isolated/recombinant immunogen (and which composition may further comprise an adjuvant) is capable of inducing a CD4 T cell response that is specific for the immunogen and thereby specific for the designated antigen and may also induce a humoral response (i.e., specific antibody response or antigen-specific antibody response) to the immunogen and the designated antigen. The other immunogenic composition (or second immunogenic composition) comprising the recombinant expression vector that comprises a nucleotide sequence encoding the immunogen is capable of inducing a CD8 T cell response specific for the immunogen and thus capable of inducing a CD8 T cell response specific for the designated antigen. As described in greater detail herein, the immunogen has one or more immunogenic regions that comprise epitope(s) that are capable of inducing a CD4 T cell response and a CD8 T cell response specific for the immunogen.

In other particular embodiments, immunogenic preparations are provided wherein the first immunogenic composition comprising at least one isolated/recombinant immunogen (called for convenience a first immunogen) may further comprise at least one additional isolated/recombinant immunogen. In other embodiments, the recombinant expression vector included in the second, different immunogenic composition may encode the first immunogen and encode at least one additional immunogen. In still other alternative embodiments, the first immunogenic composition comprises at least two isolated/recombinant immunogens and the second immunogenic composition comprises an expression vector that contains a nucleotide sequence that encodes the first immunogen and at least one additional immunogen.

In certain embodiments when induction of an immune response specific for two or more immunogens is desired, at least one immunogen is capable of inducing an immune response that comprises at least a specific humoral and/or CD4 T cell response and at least one additional immunogen is capable of inducing an immune response that comprises at least a specific CD8 T cell immune repsonse. Accordingly, provided herein in one embodiment is an immunogenic preparation comprising (a) an immunogenic composition (which may be called a first immunogenic composition) that comprises a first isolated/recombinant immunogen (which composition may further comprise an adjuvant) and (b) a second immunogenic composition that comprises a recombinant expression vector that encodes and directs expression of the first immunogen and a second immunogen, wherein at least the second immunogen is capable of inducing a specific CD8 T cell response. In certain embodiments, each of the at least two immunogens has the capability to induce an immune response to the same designated antigen. Alternatively, each of the at least two immunogens has the capability to induce an immune response specific for a different designated antigen (for convenience, also called the first and second designated antigens, etc. respectively).

Immunogens and Designated Antigens

An immunogen, which may be an isolated and/or recombinant immunogen included in one immunogenic composition and/or which is encoded by a recombinant expression vector contained within the second immunogenic composition, used in the methods and for the uses described herein includes any immunogen for which induction of a specific immune response is desired. In certain embodiments, the immunogen comprises an exemplary full-length amino acid sequence of a designated antigen of interest, or the immunogen may be an immunogenic fragment of the respective designated antigen. In other certain embodiments, an immunogen may comprise a variant of the designated antigen, which variant shares a high percent identity with an exemplary full-length designated antigen and exhibits substantially the same level of immunogenicity as the designated antigen comprising the exemplary amino acid sequence (i.e., the variant retains a level of immunogenicity to a statistically, clinically, and/or biologically significant degree compared with the immunogenicity of the exemplary or wild-type antigen). In particular, immunogens that immunogenic fragments or are variants of a designated antigen retain, in a statistically, clinically, or biologically significant manner, the capability to induce a humoral immune response (i.e., a B cell response resulting in expression of specific antibodies) or cell-mediated response (i.e., a CD4 T cell response and/or CD8 T cell response and including a cytotoxic T lymphocyte response)) or both a humoral and cell-mediated response in a subject. Designated antigens of interest and immunogenic fragments and immunogenic variants thereof are described in greater detail herein.

As described in greater detail herein, an immunogen comprises at least one immunogenic region or immunogenic epitope capable of inducing in a subject an immune response specific for a designated antigen. In one specific embodiment, the immunogen comprises one or more immunogenic regions such that the immunogen is capable of inducing any one or more of an antibody response, a CD4 T cell response, and a CD8 T cell response, wherein each response is specific for the immunogen and thus specific for the respective designated antigen. Accordingly, the immunogenic region comprises at least one epitope (i.e., one or more epitopes) that induces one or more of an antibody response, a CD4 T cell response, and a CD8 T cell response.

A cell-mediated immune response includes a cytotoxic T lymphocyte response, which response may destroy or damage a cell (e.g., a tumor cell, bacterial cell, virus, parasite, or fungal cell) or infectious particle (e.g., a virus particle) that produces or expresses the immunogen or the respective designated antigen. Any antigen that is associated with a disease or disorder for which a humoral response or cell-mediated immune response or both is beneficial to the immunized subject can be used as an immunogen.

Antigens associated with many diseases and disorders are well known in the art. An antigen of interest (i.e., a designated antigen) may be previously known to be associated with the disease or disorder, or may be identified as an antigen associated with a disease or disorder by any method known and practiced in the art. For example, an antigen associated with a type of cancer from which a patient is suffering may be known, such as a tumor-associated antigen, or may be identified from the tumor itself by any of a variety of methods practiced in the art. In certain embodiments, the designated antigen is a tumor-associated antigen (also called herein a tumor antigen) derived from a cancer cell (i.e., tumor cell), and one or more such tumor antigens may be useful for the immunotherapeutic treatment of cancers. By way of non-limiting example, tumor-associated antigens may be derived from prostate, breast, colorectal, lung, pancreatic, renal, mesothelioma, ovarian, or melanoma cancers. These and additional tumor-associated antigens are described herein and in the art.

In certain embodiments, immunogens include full-length proteins that are the designated antigens and are derived from a tumor or malignancy. In other certain embodiments, an immunogen comprises one or more immunogenic fragments that contain one or more epitopes from such proteins. In still other embodiments, an immunogen comprises a fusion polypeptide that comprises the full-length designated antigen or that comprises one, two, three, or more immunogenic fragments of the designated antigen derived from a tumor cell. In other embodiments, when an immunogenic composition is prepared for use in inducing an immune response against two or more designated antigens, a fusion polypeptide may comprise any combination of full-length antigen or one or more immunogenic fragments thereof for each of the two or more designated antigens. By way of example, a fusion polypeptide may comprise one or more immunogenic fragments obtained from one tumor associated antigen and may further comprise one or more immunogenic fragments obtained a second, different tumor associated antigen. Fusion proteins may comprise, in additional to the immunogenic polypeptide or peptide, at least one polypeptide or peptide, which is sometimes referred to as a carrier protein in the immunology art, that enhances the immune response to the immunogen of interest.

Exemplary tumor associated) antigens or tumor cell-derived antigens include MAGE 1, 3, and MAGE 4 (or other MAGE antigens such as those disclosed in International Patent Application Publication No. WO99/40188); PRAME; BAGE; RAGE, Lage (also known as NY ESO 1); SAGE; and HAGE (see, e.g., International Patent Application Publication No. WO 99/53061) or GAGE (Robbins et al., Curr. Opin. Immunol. 8:628-36 (1996); Van den Eynde et al., Int. J. Clin. Lab. Res. 27:81-86 (1997); Van den Eynde et al., Curr. Opin. Immunol. 9:648-93 (1997); Correale et al., J. Natl. Cancer Inst. 89: 293 (1997)). These non-limiting examples of tumor antigens are expressed in a wide range of tumor types such as melanoma, lung carcinoma, sarcoma, and bladder carcinoma. See, e.g., U.S. Pat. No. 6,544,518. Prostate cancer tumor-associated antigens include, for example, prostate specific membrane antigen (PSMA), prostate-specific antigen (PSA), prostatic acid phosphates, NKX3.1, and six-transmembrane epithelial antigen of the prostate (STEAP) (Hubert et al., Proc. Natl. Acad. Sci. USA 96 14523-28, 1999); see also, e.g., Reiter et al., Proc. Nat. Acad. Sci. USA 95:1735-40, 1998; Nelson, et al., Proc. Natl. Acad. Sci. USA 96:3114-19 (1999); WO 98/12302; U.S. Pat. Nos. 5,955,306; 5,840,871 and 5,786,148; Intl Patent Appl. Publication Nos. WO 98/20117; WO 00/04149; WO 98/137418).

Other tumor associated antigens include Plu-1 (J. Biol. Chem. 274:15633-45, 1999), HASH -1, HasH-2, Cripto (Salomon et al., Bioessays 199, 21:61-70; U.S. Pat. No. 5,654,140) and Criptin (U.S. Pat. No. 5,981,215). Additionally, a tumor antigen may be a self peptide hormone, such as whole length gonadotrophin hormone releasing hormone (GnRH, Int'l Patent Appl. Publication No. WO 95/20600), a short 10 amino acid long peptide, useful in the treatment of many cancers.

Tumor antigens include tumor antigens derived from cancers that are characterized by tumor associated antigen expression, such as HER-2/neu expression. Tumor associated antigens of interest include lineage-specific tumor antigens such as the melanocyte-melanoma lineage antigens MART-1/Melan-A, gp100, gp75, mda-7, tyrosinase and tyrosinase-related protein. Illustrative tumor-associated antigens include, but are not limited to, tumor antigens derived from or comprising any one or more of, p53, Ras, c-Myc, cytoplasmic serine/threonine kinases (e.g., A-Raf, B-Raf, and C-Raf, cyclin-dependent kinases), MAGE-A1, MAGE-A2, MAGE-A3, MAGE-A4, MAGE-A6, MAGE-A10, MAGE-A12, MART-1, BAGE, DAM-6, -10, GAGE-1, -2, -8, GAGE-3, -4, -5, -6, -7B, NA88-A, MART-1, MC1R, Gp100, PSA, PSM, Tyrosinase, TRP-1, TRP-2, ART-4, CAMEL, CEA, Cyp-B, hTERT, hTRT, iCE, MUC1, MUC2, Phosphoinositide 3-kinases (PI3Ks), TRK receptors, PRAME, P15, RU1, RU2, SART-1, SART-3, Wilms' tumor antigen (WT1), AFP, -catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TAC-STD1) TACSTD2, receptor tyrosine kinases (e.g., Epidermal Growth Factor receptor (EGFR) (in particular, EGFRvIII), platelet derived growth factor receptor (PDGFR), vascular endothelial growth factor receptor (VEGFR)), cytoplasmic tyrosine kinases (e.g., src-family, syk-ZAP70 family), integrin-linked kinase (ILK), signal transducers and activators of transcription STAT3, STATS, and STATE, hypoxia inducible factors (e.g., HIF-1 and HIF-2), Nuclear Factor-Kappa B (NF-κB), Notch receptors (e.g., Notch1-4), c-Met, mammalian targets of rapamycin (mTOR), WNT, extracellular signal-regulated kinases (ERKs), and their regulatory subunits, PMSA, PR-3, MDM2, Mesothelin, renal cell carcinoma—5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGsS, SART3, STn, PAX5, OY-TES1, sperm protein 17, LCK, HMWMAA, AKAP-4, SSX2, XAGE 1, B7H3, legumain, TIE2, Page4, MAD-CT-1, FAP, MAD-CT-2, fos related antigen 1, and idiotype.

Immunogens also include tumor antigens that comprise epitopic regions or epitopic peptides derived from genes mutated in tumor cells or from genes transcribed at different levels in tumor cells compared to normal cells, such as telomerase enzyme, survivin, mesothelin, mutated ras, bcr/abl rearrangement, Her2/neu, mutated or wild-type p53, cytochrome P450 1B1, and abnormally expressed intron sequences such as N-acetylglucosaminyltransferase-V; clonal rearrangements of immunoglobulin genes generating unique idiotypes in myeloma and B-cell lymphomas; tumor antigens that comprise epitopic regions or epitopic peptides derived from oncoviral processes, such as human papilloma virus proteins E6 and E7; Epstein bar virus protein LMP2; nonmutated oncofetal proteins with a tumor-selective expression, such as carcinoembryonic antigen and alpha-fetoprotein. See also Boon et al., Ann. Rev. Immunol. 12:337-65 (1994); Renkvist et al., Cancer Immunol. Immunother. 50:3-15 (2001).

In other embodiments, an immunogen is obtained or derived from a pathogenic microorganism or from an opportunistic pathogenic microorganism (also called herein an infectious disease microorganism), such as a virus, fungus, parasite, and bacterium. In certain embodiments, immunogens derived from such a microorganism include full-length proteins that are the selected designated antigens. In other certain embodiments, an immunogen comprises one or more immunogenic fragments that contain one or more epitopes from such proteins. In still other embodiments, an immunogen comprises a fusion polypeptide that comprises one, two, or more immunogenic fragments of a protein derived from a microorganism. In still other embodiments, an immunogen comprises a fusion polypeptide that comprises the full-length designated antigen or that comprises one, two, three, or more immunogenic fragments of the designated antigen derived from a microorganism. In other embodiments, when an immunogenic composition is prepared for use in inducing an immune response against two or more designated antigens of an infectious disease microorganism, a fusion polypeptide may comprise any combination of full-length antigen or one or more immunogenic fragments thereof for each of the two or more designated antigens. By way of example, a fusion polypeptide may comprise one or more immunogenic fragments obtained from one microbial antigen (i.e., a viral, bacterial, parasitic, or fungal antigen) and may further comprise one or more immunogenic fragments obtained a second, different microbial antigen (i.e., a second, different viral, bacterial, parasitic, or fungal antigen). Fusion proteins may comprise, in additional to the immunogenic polypeptide or peptide, at least one polypeptide or peptide, which is sometimes referred to as a carrier protein in the immunology art, that enhances the immune response to the immunogen of interest.

Illustrative pathogenic organisms whose antigens are contemplated as designated antigens and immunogens for use in the immunogenic compositions described herein and that are encoded by the vectors and vector particles described herein include human immunodeficiency virus (HIV), herpes simplex virus (HSV), respiratory syncytial virus (RSV), cytomegalovirus (CMV), Epstein-Barr virus (EBV), Influenza A, B, and C, vesicular stomatitis virus (VSV), vesicular stomatitis virus (VSV), *Staphylococcus* species including Methicillin-resistant *Staphylococcus aureus* (MRSA), and *Streptococcus* species including *Streptococcus pneumoniae*. As would be understood by the skilled person, proteins derived from these and other pathogenic microorganisms for use as immunogens as described herein are known in the art and the amino acid sequences of such proteins (and species thereof) and nucleotide sequences encoding the proteins may be identified in publications and in public databases such as GENBANK, Swiss-Prot, and TrEMBL.

Antigens derived from human immunodeficiency virus (HIV) that may be immunogens and used as described herein include any of the HIV virion structural proteins (e.g., gp120, gp41, p17, p24), protease, reverse transcriptase, or HIV proteins encoded by tat, rev, nef, vif, vpr and vpu. HIV proteins and immunogenic fragments thereof are well known to the skilled person and may be found in any of a number of public databases (see, e.g., Vider-Shalit et al., AIDS 23(11):1311-18 (2009); Watkins, Mem. Inst. Oswaldo Cruz. 103(2):119-29 (2008); Gao et al., Expert Rev. Vaccines (4 Suppl):S161-68 (2004)). (See also, e.g., Klimstra et al., 2003. J. Virol. 77:12022-32; Bernard et al., Virology 276:93-103 (2000); Byrnes et al., J. Virol. 72: 7349-56 (1998); Lieberman et al., AIDS Res Hum. Retroviruses 13(5): 383-92 (1997); Menendez-Arias et al., Viral Immunol. 11(4): 167-181 (1998).

Antigens derived from herpes simplex virus (e.g., HSV 1 and HSV2) that are contemplated for use as immunogens in the compositions described herein and encoded by vectors and vector particles described herein include, but are not limited to, proteins expressed from HSV late genes. The late group of genes predominantly encodes proteins that form the virion particle. Such proteins include the five proteins from (UL) which form the viral capsid: UL6, UL18, UL35, UL38 and the major capsid protein UL19, UL45, and UL27, each of which may be used as an immunogens as described herein (see, e.g., McGeoch et al., Virus Res. 117:90-104 (2006); Mettenleiter et al., Curr. Opin. Microbiol. 9: 423-29 (2006)). Other illustrative HSV proteins contemplated for use as immunogens herein include the ICP27 (H1, H2), glycoprotein B (gB) and glycoprotein D (gD) proteins. The HSV genome comprises at least 74 genes, each encoding a protein that could potentially be used as an immunogen to induce a T cell response (including a CTL response), B cell response, or both a CTL response and a B cell response.

Protective immune responses against HSV-2 in humans (see, e.g., Corey et al., "Genital Herpes," in Sexually Transmitted Diseases, Holmes et al., eds. (McGraw-Hill, New York, 1999) 285-312) and in animal models (see, e.g., Parr et al., J. Virol. 72:2677 (1998)) suggest that an appropriate HSV-2 vaccine formulation is a desirable and obtainable objective. Over the past four decades, a series of HSV vaccine human trials using inactivated, whole HSV preparations and subunit HSV proteins formulated with adjuvants have been conducted in the United States and in Europe. Although moderate therapeutic efficacy with these vaccines was observed in some short-term studies, results from appropriately controlled trials with longer follow-up windows have been largely disappointing (see, e.g., Rajcani et al., Folia Microbiol. (Praha) 51:67 (2006)).

In Europe in the 1960's and 1970's, large clinical trials were conducted with formaldehyde-inactivated HSV (Eli Lilly trial) or heat-inactivated HSV (Lupidon H trial). Although improvements in the severity and frequency of HSV recurrences were reported, only a small subset of these trials was placebo-controlled and double-blinded. Furthermore, these vaccines did not confer long-term therapeutic efficacy. Maternal-fetal HSV-2 transmission studies in the 1980's demonstrated that infants of HSV-2 seropositive women possessed a lower risk of transmission versus women who acquired HSV-2 near term, suggesting that neutralizing antibodies (nAb) against the HSV-2 glycoproteins gD and gB may confer protection (see, e.g., Koelle et al., Clin. Microbiol. Rev. 16: 96 (2003)). Designed to generate nAb against these HSV-2 glycoprotein, trials by Glaxo-SmithKline and Chiron in the United States in the 1990's tested recombinant subunit vaccines with gD alone or with gB formulated with three different adjuvants: alum, MF-59 (oil-in-water), and monophosphoryl lipid A (MPL). These vaccines elicited or boosted HSV-2 specific nAb in seronegative individuals and cross-reactive nAb in HSV-1 seropositive individuals (see, e.g., Burke, Rev. Infect. Dis. 13 Suppl 11:S906-S911 (1991)). However, despite reaching target levels of humoral immunogenicity, these vaccines showed no therapeutic efficacy in men and only transient efficacy in women, suggesting that anti-HSV nAb are insufficient and that a successful HSV vaccine will likely need to generate potent T cell immunity (see, e.g., Corey et al., JAMA 282: 331 (1999); Stanberry, et al., N. Engl. J. Med. 347:1652 (2002)).

Previously conducted HSV vaccine trials indicates that nAb may not be sufficient to protect humans against HSV-2 infection, and data suggested that HSV-2-specific T cells play a critical role in reducing viral acquisition, transmission, and reactivation (see, e.g., Corey et al., JAMA (1999) supra). For example, individuals with deficiencies in T cell function have prolonged, more severe episodes of HSV-2 infection, and in longitudinal biopsy studies of HSV-2 lesions, viral clearance correlated with the infiltration of CD8 T cells (see, e.g., Koelle et al., J. Clin. Invest. 101:1500 (1998)). Additional HSV studies have shown that: type 1 helper T cell (Th1) responses were protective in animal models (see, e.g., Koelle, et al., J. Immunol. 166:4049 (2001); Zhu, et al., J. Exp. Med. 204:595 (2007)), the severity and frequency of HSV-2 reactivation was inversely correlated to the frequency of HSV-specific T cells, and infiltration of HSV-2 specific CTL into genital lesions correlated with viral clearance (see, e.g., Koelle et al., J. Infect. Dis. 169:956 (1994); Koelle et al., J. Clin. Invest. 110:537 (2002); Koelle et al., J. Clin. Invest. (1998) supra). These findings are consistent with data from subunit vaccine studies that implicated CD8 and Th1 CD4 T cell responses in mucosal HSV-2 clearance (see, e.g., Posavad et al., Nat. Med. 4:381 (1998)). Furthermore, HSV-2-specific CD8 T cells have been detected for long periods at the dermal-epidermal junction after resolution of genital herpes (see, e.g., Cattamanchi et al., Clin. Vaccine Immunol. 15:1638 (2008)).

Antigens derived from cytomegalovirus (CMV) that are contemplated for use in certain embodiments of the present immunogenic compositions and methods described herein include CMV structural proteins, viral antigens expressed during the immediate early and early phases of virus replication, glycoproteins I and III, capsid protein, coat protein, lower matrix protein pp65 (ppUL83), p52 (ppUL44), IE1 and IE2 (UL123 and UL122), protein products from the cluster of genes from UL128-UL150 (Rykman, et al., J. Virol. January 2006; 80(2):710-22), envelope glycoprotein B (gB), gH, gN, and pp150. As would be understood by the skilled person, CMV proteins for use as immunogens described herein may be identified in public databases such as GenBank, Swiss-Prot, and TrEMBL (see e.g., Bennekov et al., Mt. Sinai J. Med. 71 (2): 86-93 (2004); Loewendorf et al., J. Intern. Med. 267(5):483-501 (2010); Marschall et al., Future Microbiol. 4:731-42 (2009)).

Antigens derived from Epstein-Ban virus (EBV) that are contemplated for use in certain embodiments include EBV lytic proteins gp350 and gp110, EBV proteins produced during latent cycle infection including Epstein-Barr nuclear antigen (EBNA)-1, EBNA-2, EBNA-3A, EBNA-3B, EBNA-3C, EBNA-leader protein (EBNA-LP) and latent membrane proteins (LMP)-1, LMP-2A and LMP-2B (see, e.g., Lockey et al., Front. Biosci. 13:5916-27 (2008)).

Antigens derived from respiratory syncytial virus (RSV) that are contemplated for use as immunogens as described herein include any of the eleven proteins encoded by the RSV genome, or immunogenic fragments thereof: NS1, NS2, N (nucleocapsid protein), M (Matrix protein) SH, G and F (viral coat proteins), M2 (second matrix protein), M2-1 (elongation factor), M2-2 (transcription regulation), RNA polymerase, and phosphoprotein P.

Antigens derived from Vesicular stomatitis virus (VSV) that are contemplated for use as immunogens include any one of the five major proteins encoded by the VSV genome, and immunogenic fragments thereof: large protein (L), glycoprotein (G), nucleoprotein (N), phosphoprotein (P), and matrix protein (M) (see, e.g., Rieder et al., J. Interferon Cytokine Res. (2009) (9):499-509; Roberts et al., Adv. Virus Res. (1999) 53:301-19).

Antigens derived from an influenza virus that are contemplated for use in certain embodiments include hemagglutinin (HA), neuraminidase (NA), nucleoprotein (NP), matrix proteins M1 and M2, NS1, NS2 (NEP), PA, PB1, PB1-F2, and PB2. See e.g., Nature 437 (7062): 1162-66.

Examples of immunogens that are viral antigens also include, but are not limited to, adenovirus polypeptides, alphavirus polypeptides, calicivirus polypeptides (e.g., a calicivirus capsid antigen), coronavirus polypeptides, distemper virus polypeptides, Ebola virus polypeptides, enterovirus polypeptides, flavivirus polypeptides, hepatitis virus (AE) polypeptides (a hepatitis B core or surface antigen, a hepatitis C virus E1 or E2 glycoproteins, core, or non-structural proteins), herpesvirus polypeptides (as discussed herein and including a herpes simplex virus or varicella zoster virus glycoprotein), infectious peritonitis virus polypeptides, leukemia virus polypeptides, Marburg virus polypeptides, orthomyxovirus polypeptides, papilloma virus polypeptides, parainfluenza virus polypeptides (e.g., the hemagglutinin and neuraminidase polypeptides), paramyxovirus polypeptides, parvovirus polypeptides, pestivirus polypeptides, picorna virus polypeptides (e.g., a poliovirus capsid polypeptide), pox virus polypeptides (e.g., a vaccinia virus polypeptide), rabies virus polypeptides (e.g., a rabies virus glycoprotein G), reovirus polypeptides, retrovirus polypeptides, and rotavirus polypeptides.

In certain embodiments, bacterial antigens may be selected as designated antigens, and a bacterial antigen, or an immunogenic fragment or variant thereof, may be used as an immunogen. In certain embodiments, a bacterial antigen of interest may be a secreted polypeptide. In other certain embodiments, bacterial antigens that may be useful as immunogens for inducing an immune response include antigens that have a portion or portions of the polypeptide exposed on the outer cell surface of the bacteria. The portions of the polypeptide immunogens exposed on the cell surface are accessible to immune cells and/or antibodies in the host and thus may be useful immunogens encoded by the recombinant expression vectors and included in the immunogenic compositions comprising an immunogen (which may further comprise an adjuvant) described herein.

Antigens derived from *Staphylococcus* species including Methicillin-resistant *Staphylococcus aureus* (MRSA) that are contemplated for use as immunogens include virulence regulators, such as the Agr system, Sar and Sae, the Arl system, Sar homologues (Rot, MgrA, SarS, SarR, SarT, SarU, SarV, SarX, SarZ and TcaR), the Srr system and TRAP. Other Staphylococcus proteins that may serve as immunogens include Clp proteins, HtrA, MsrR, aconitase, CcpA, SvrA, Msa, CfvA and CfvB (see, e.g., *Staphylococcus*: Molecular Genetics, 2008 Caister Academic Press, Ed. Jodi Lindsay). The genomes for two species of *Staphylococcus aureus* (N315 and Mu50) have been sequenced and are publicly available, for example at PATRIC (PATRIC: The VBI Patho-Systems Resource Integration Center, Snyder et al., Nucleic Acids Res. (2007) 35: 401-406). As would be understood by the skilled person, *Staphylococcus* proteins for use as immunogens may also be identified in other public databases such as GenBank, Swiss-Prot, and TrEMBL.

Antigens derived from *Streptococcus pneumoniae* that are contemplated for use as immunogens in certain embodiments described herein include pneumolysin, PspA, choline-binding protein A (CbpA), NanA, NanB, SpnHL, PavA, LytA, Pht, and pilin proteins (RrgA; RrgB; RrgC). Immunogenic proteins of Streptococcus pneumoniae are also known in the art and are contemplated for use as immunogens (see, e.g., Zysk et al., Infect. Immun. 2000 68(6):3740-43). The complete genome sequence of a virulent strain of *Streptococcus pneumoniae* has been sequenced (see, e.g., Tettelin H, et al., Science (2001) 293(5529):498-506) and, as would be understood by the skilled person, *S. pneumoniae* proteins for use in the compositions described herein may also be identified in other public databases such as GenBank, Swiss-Prot, and TrEMBL. Proteins of particular interest for immunogens according to the present disclosure include virulence factors and proteins predicted to be exposed at the surface of the pneumococci (see, e.g., Tettelin et al., supra; Frolet et al., BMC Microbiol. (2010) July 12; 10:190; Rigden, et al., Crit. Rev. Biochem. Mol. Biol. (2003) 38(2):143-68; Jedrzejas, Microbiol. Mol. Biol. Rev. (2001) 65(2):187-207).

Examples of bacterial antigens that may be used as immunogens include, but are not limited to, *Actinomyces* polypeptides, *Bacillus* polypeptides, *Bacteroides* polypeptides, *Bordetella* polypeptides, *Bartonella* polypeptides, *Borrelia* polypeptides (e.g., *B. burgdorferi* OspA), *Brucella* polypeptides, *Campylobacter* polypeptides, *Capnocytophaga* polypeptides, *Chlamydia* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides (e.g., *H. influenzae* type b outer membrane protein), *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides (i.e., *S. pneumoniae* polypeptides) (see description herein), *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, group A *streptococcus* polypeptides (e.g., *S. pyogenes* M proteins), group B *streptococcus* (*S. agalactiae*) polypeptides, *Treponema* polypeptides, and *Yersinia* polypeptides (e.g., *Y. pestis* F1 and V antigens).

Examples of fungal antigens that may be immunogens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides. Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides. (e.g., *P. falciparum* circumsporozoite (PfCSP)), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of ectoparasite antigens include, but are not limited to, polypeptides (including protective antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

Induction of an immune response, including either a humoral response (i.e., a B cell response) or a cell-mediated response (including a cytotoxic T lymphocyte (CTL) response) or both may also contribute to phagocytosis or killing of additional organisms such as *Pseudomonas aeruginosa, Mycobacterium tuberculosis, M. leprae,* and *Listeria innocula*. A CTL immune response contributes to killing of *P. aeruginosa, M. tuberculosis, M. leprae,* and *L. innocula* (see, e.g., Oykhman et al., J. Biomed. Biotechnol. (2010: 249482); published on-line Jun. 23, 2010). Accordingly, immunogens useful for the immunogenic compositions described herein and that may be encoded by the recombinant expression vectors and vector particles comprising the vectors may also be derived from these bacteria. The amino acid sequences of numerous polypeptides encoded by the bacterial genome of any one of the bacteria species and expressed by the bacteria can be readily identified in the art and in publicly available protein sequence data bases. (See also, e.g., Stover et al., Nature 406:959 (2000)).

Immunogens as described herein may be obtained or derived from fungi or parasites. Exemplary parasites that induce an immune response, including a CTL immune response, include *Schistosoma mansoni, Entameoba histolytica, Toxoplasma gondii,* and *Plasmodium falciparum* (see, e.g., Oykhman, supra). Accordingly, protein antigens derived or obtained from these parasites may be useful as immunogens to induce an immune response against the respective parasite. Immunogens may also be obtained or derived from species of fungus, including without limitation, *Cryptococcus neoformans* and *Candida albicans* (see, e.g., Oykhman, supra).

Polypeptides that comprise at least one immunogenic fragment of an immunogenic polypeptide (e.g., any of the tumor associated antigens or microbial antigens described herein and/or in the art) may be used as immunogens and encoded by the recombinant expression vectors described herein. An immunogenic fragment comprises at least one T cell epitope or at least one B cell epitope. The immunogenic fragment may consist of at least 6, 10, 15, 20, 30, 40, 50, 60, 70, 80, 90, 100, or more contiguous amino acids of an immunogenic polypeptide. The immunogenic fragment may comprise any number of contiguous amino acids between the aforementioned such that, for example, an immunogenic fragment is between about 6-10, 10-15, 15-20, 20-30, 30-40, 40-50, 50-60, 60-70, 70-80, 80-90, 90-100, or more contiguous amino acids of an immunogenic polypeptide. The immunogenic fragments may comprise a sufficient number of contiguous amino acids that form a linear epitope and/or may comprise a sufficient number of contiguous amino acids that permit the fragment to fold in the same (or sufficiently similar) three-dimensional conformation as the full-length polypeptide from which the fragment is derived to present a non-linear epitope or epitopes (also referred to in the art as conformational epitopes). Assays for assessing whether the immunogenic fragment folds into a conformation comparable to the full-length polypeptide include, for example, the ability of the protein to react with mono- or polyclonal antibodies that are specific for native or unfolded epitopes, the retention of other ligand-binding functions, and the sensitivity or resistance of the polypeptide fragment to digestion with proteases (see, e.g., Sambrook et al., Molecular Cloning: A Laboratory Manual, 3d ed., Cold Spring Harbor Laboratory Press, NY (2001)). Accordingly, by way of example, the three-dimensional conformation of a polypeptide fragment is sufficiently similar to the full-length polypeptide when the capability to bind and the level of binding of an antibody that specifically binds to the full-length polypeptide is substantially the same for the fragment as for the full-length polypeptide (i.e., the level of binding has been retained to a statistically, clinically, and/or biologically sufficient degree compared with the immunogenicity of the exemplary or wild-type full-length antigen).

Determination of the three-dimensional structures of a polypeptide, or immunogenic fragment thereof, of interest may be performed by routine methodologies to determine whether the immunogenic fragment retains the spatial positioning of the amino acids as found in the full-length polypeptide. See, for instance, Bradley et al., Science 309:1868-71 (2005); Schueler-Furman et al., Science 310:638 (2005); Dietz et al., Proc. Nat. Acad. Sci. USA 103:1244 (2006); Dodson et al., Nature 450:176 (2007); Qian et al., Nature 450:259 (2007). Also available in the art are software tools, for example, PSORT or PSORT II, and Spscan (Wisconsin Sequence Analysis Package, Genetics Computer Group) that are useful for predicting transmembrane segments and membrane topology of polypeptides that are known or believed to traverse a cellular membrane (see, for example, Nakai et al., Trends Biochem. Sci. 24:34-36 (1999)).

Separately, or in combination with the above-described techniques, and given an exemplary amino acid sequence of a designated antigen of interest, a person skilled in the art can identify potential epitopes of the polypeptide antigen (see, e.g., Jameson and Wolf, Comput. Appl. Biosci. 4:181-86 (1988)). By way of another example, Hopp and Woods describe the hydrophilicity method, which is based on empirical demonstrations of the close correlation between the hydrophilicity of polypeptide regions and their antigenicity (see, e.g., Hopp, Pept. Res. 6:183-90 (1993); Hofmann et al., Biomed. Biochim. Acta 46:855-66 (1987)). Computer programs are also available for identifying B cell or T cell epitopes. A BASIC program called EPIPLOT predicts B-cell antigenic sites in proteins from their primary structures by calculating and plotting flexibility, hydrophilicity, and antigenicity profiles using 13 different scales (see, for example, Menendez et al., Comput. Appl. Biosci. 6:101-105 (1990)). See also, such as, Van Regenmortel, Methods: a companion to Methods in Enzymology, 9: 465-472 (1996); Pellequer et al., "Epitope predictions from the primary structure of proteins," In Peptide antigens: a practical approach (ed. G.B. Wisdom), pp. 7-25; Oxford University Press, Oxford (1994); Van Regenmortel, "Molecular dissection of protein antigens" In Structure of antigens (ed. M. H. V. Van Regenmortel), Vol. 1, pp. 1-27. CRC Press, Boca Raton (1992).

T cell epitopes of a designated antigen that may be used as an immunogen may also be identified using a peptide motif searching program based on algorithms developed by Rammensee, et al. (Immunogenetics 50: 213-219 (1999)); by Parker, et al. (supra), or by using methods such as those described by Doytchinova and Flower in Immunol. Cell Biol. 80(3):270-9 (2002); Blythe et al., Bioinformatics 18:434-439 (2002); Guan et al., Applied Bioinformatics 2:63-66 (2003); Flower et al., Applied Bioinformatics 1:167-176 (2002); Mallios, Bioinformatics 17: 942-48 (2001); Schirle et al., J. Immunol. Meth. 257:1-16 (2001).

Epitopic regions of designated microbial antigens or designated tumor antigens that may be used as immunogens in the compositions and methods described herein are also described in the art. See by way of example, Lamb et al., Rev. Infect. Dis. Mar-Apr: Suppl 2:s443-447 (1989); Lamb et al., EMBO J. 6:1245-49 (1987); Lamb et al., Lepr. Rev. Suppl 2:131-37 (1986); Mehra et al., Proc. Natl. Acad. Sci. USA 83:7013-27 (1986); Horsfall et al., Immunol. Today 12:211-13 (1991); Rothbard et al., Curr. Top. Microbiol. Immunol. 155:143-52 (1990); Singh et al., Bioinformatics 17:1236-37 (2001); DeGroot et al., Vaccine 19:4385-95 (2001); DeLalla et al., J. Immunol. 163:1725-29 (1999); Cochlovius et al., J. Immunol. 165:4731-41 (2000); Consogno et al., Blood 101:1039-44 (2003); Roberts et al., AIDS Res. Hum. Retrovir. 12:593-610 (1996); Kwok et al., Trends Immunol. 22:583-88 (2001); Novak et al., J. Immunol. 166:6665-70 (2001).

Additional methods for identifying epitopic regions include methods described in Hoffmeister et al., Methods 29:270-281 (2003); Maecker et al., J. Immunol. Methods 255:27-40 (2001). Assays for identifying epitopes are described herein and known to the skilled artisan and include, for example, those described in Current Protocols in Immunology, Coligan et al. (Eds), John Wiley & Sons, New York, N.Y. (1991).

Identifying an immunogenic region and/or epitope of a designated antigen of interest can also be readily determined empirically by a person skilled in the art and/or by computer analysis and computer modeling, using methods and techniques that are routinely practiced by persons skilled in the art. Empirical methods include, by way of example, synthesizing polypeptide fragments comprising a particular length of contiguous amino acids of a protein, or generating fragments by use of one or more proteases and then determining the immunogenicity of the fragments using any one of numerous binding assays or immunoassay methods routinely practiced in the art. Exemplary methods for determining the capability of an antibody (polyclonal, monoclonal, or antigen-binding fragment thereof) to specifically bind to a fragment include, but are not limited to, ELISA, radioimmunoassay, immunoblot, competitive binding assays, fluorescence activated cell sorter analysis (FACS), and surface plasmon resonance.

Sequences of T cell and B cell epitopes can be obtained from publically available databases. For example, a peptide database that includes T-cell defined tumor antigens can be found on the Internet in a peptide database sponsored by Cancer Immunity (see cancerimmunity(dot)org/peptidedatabase/Tcellepitopes.htm), which is updated periodically. Another available database supported by the National Institute of Allergy and Infectious Diseases, which provides tools for searching for B cell and T cell epitopes and provides epitope analysis tools (see Immune Epitope Database and Analysis Resource at immunoepitope(dot)org).

In certain instances when antigen-specific T cell lines or clones are available, for example tumor-infiltrating lymphocytes (TIL), virus-specific or bacteria-specific cytotoxic T lymphocytes (CTL), these cells may be used to screen for the presence of relevant epitopes using target cells prepared with specific antigens. Such targets can be prepared using random, or selected, synthetic peptide libraries, which would be used to sensitize the target cells for lysis by the CTL. Another approach to identify a relevant epitope when T cell lines or clones are available is to use recombinant DNA methodologies. Gene or cDNA libraries from CTL-susceptible targets are first prepared and transfected into non-susceptible target cells. This allows the identification and cloning of the gene encoding the protein precursor of the peptide containing the CTL epitope. The second step in this process is to prepare truncated genes from the relevant cloned gene, in order to narrow down the region that encodes for the at least one CTL epitope. This step is optional if the gene is not too large. The third step is to prepare synthetic peptides of, for example, approximately 10-20 amino acids in length, overlapping by 5-10 residues, which are used to sensitize targets for the CTL. When a peptide, or peptides, is shown to contain the relevant epitope, and if desired, smaller peptides can be prepared to establish the peptide of minimal size that contains the epitope. These epitopes are typically, but not necessarily, contained within 9-10 residues for CTL epitopes and up to 20 or 30 residues for helper T lymphocyte (HTL) epitopes.

Alternatively, epitopes may be defined by direct elution of peptides that are non-covalently bound by particular major histocompatibility complex (MHC) molecules followed by amino acid sequencing of the eluted peptides (see, for example, Engelhard et al., Cancer J. 2000 May; 6 Suppl 3:S272-80). Briefly, the eluted peptides are separated using a purification method such as HPLC, and individual fractions are tested for their capacity to sensitize targets for CTL lysis or to induce proliferation of cytokine secretion in HTL. When a fraction has been identified as containing the peptide, it is further purified and submitted to sequence analysis. The peptide sequence can also be determined using tandem mass spectrometry. A synthetic peptide is then prepared and tested with the CTL or HTL to corroborate that the correct sequence and peptide have been identified.

Epitopes may also be identified using computer analysis, such as the Tsites program (see, e.g., Rothbard and Taylor, EMBO J. 7:93-100, 1988; Deavin et al., Mol. Immunol. 33:145-155, 1996), which searches for peptide motifs that have the potential to elicit Th responses. CTL peptides with motifs appropriate for binding to murine and human class I or class II MHC may be identified according to BIMAS (Parker et al., J. Immunol. 152:163, 1994) and other HLA peptide binding prediction analyses. Briefly, the protein sequences, for example from microbial components or antigens, or tumor cell components or tumor antigens, are examined for the presence of MHC-binding motifs. These binding motifs, which exist for each MHC allele, are conserved amino acid residues, usually at positions 2 (or 3) and 9 (or 10) for MHC class I binding peptides that are typically 9-10 residues long. Synthetic peptides are then prepared that comprise those sequences bearing the MHC binding motifs, and subsequently such peptides are tested for their ability to bind to MHC molecules. The MHC binding assay can be carried out either using cells which express high numbers of empty (unoccupied) MHC molecules (cellular binding assay), or using purified MHC molecules. Lastly, the MHC binding peptides are then tested for their capacity to induce a CTL response in naive individuals, either in vitro using human lymphocytes, or in vivo using HLA-transgenic animals. These CTL are tested using peptide-sensitized target cells, and targets that naturally process the antigen, such as viral infected cells or tumor cells. To further confirm immunogenicity, a peptide may be tested using an HLA A2 transgenic mouse model and/or any of a variety of in vitro stimulation assays.

In certain embodiments, an immunogen includes polypeptide species of the designated antigen that have one or more amino acid substitutions, insertions, or deletions in an amino acid sequence that is known and available in the art for the respective immunogen. Conservative substitutions of amino acids are well known and may occur naturally in the polypeptide or may be introduced when the polypeptide is recombinantly produced. Amino acid substitutions, deletions, and additions may be introduced into a polypeptide using well-known and routinely practiced mutagenesis methods (see, e.g., Sambrook et al. Molecular Cloning: A Laboratory Manual, 3d ed., Cold Spring Harbor Laboratory Press, NY 2001)). Oligonucleotide-directed site-specific (or segment specific) mutagenesis procedures may be employed to provide an altered polynucleotide that has particular codons altered according to the substitution, deletion, or insertion desired. Deletion or truncation variants of designated antigens that may be used as immunogens may also be constructed by using convenient restriction endonuclease sites adjacent to the desired deletion. Subsequent to restriction, overhangs may be filled in and the DNA re-ligated. Alternatively, random mutagenesis techniques, such as alanine scanning mutagenesis, error prone polymerase chain reaction mutagenesis, and oligonucleotide-directed mutagenesis may be used to prepare immunogen polypeptide variants (see, e.g., Sambrook et al., supra). Species (or variants) of a particular designated antigen (or polypeptide fragment thereof) include a polypeptide immunogen that has at least 85%, 90%, 95%, or 99% amino acid sequence identity to any of the exemplary amino acid sequences known in the art.

These polypeptide immunogen variants retain one or more biological activities or functions of the respective designated antigen. In particular, immunogens that are variants of a designated antigen retain, in a statistically, clinically, or biologically significant manner, the capability to induce an immune response (e.g., a humoral response (i.e., B cell response), cell-mediated response (i.e., T cell response (including a cytotoxic T lymphocyte response)) or both a humoral and cell-mediated response in a subject. Given the many molecular biology, protein expression, and protein isolation techniques and methods routinely practiced in the art for introducing mutations in a polypeptide, preparing polypeptide fragments, isolating the fragments and variants, and analyzing same, immunogen polypeptide variants and fragments having the desired biological activities can be made readily and without undue experimentation.

A variety of criteria known to persons skilled in the art indicate whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the polypeptide to the sequence of a second polypeptide (e.g., using GENEWORKS, Align, the BLAST algorithm, or other algorithms described herein and practiced in the art).

As described herein for immunogenic fragments, assays for assessing whether a respective variant folds into a conformation comparable to the non-variant polypeptide or fragment include, for example, the ability of the protein to react with mono- or polyclonal antibodies that are specific for native or unfolded epitopes, the retention of ligand-binding functions, and the sensitivity or resistance of the mutant protein to digestion with proteases (see Sambrook et al., supra). Such variants can be identified, characterized, and/or made according to methods described herein or other methods known in the art, which are routinely practiced by persons skilled in the art.

Isolated/recombinant immunogens included in the immunogenic compositions described herein may be produced and prepared according to various methods and techniques routinely practiced in the molecular biology and/or polypeptide purification arts. Construction of an expression vector that is used for recombinantly producing an immunogen of interest can be accomplished using any of numerous suitable molecular biology engineering techniques known in the art, including, without limitation, the standard techniques of restriction endonuclease digestion, ligation, transformation, plasmid purification, and DNA sequencing, for example as described in Sambrook et al. (1989 and 2001 editions; Molecular Cloning: A Laboratory Manual, Cold Spring Harbor Laboratory Press, NY) and Ausubel et al. (Current Protocols in Molecular Biology (2003)). To obtain efficient transcription and translation, the polynucleotide sequence in each recombinant expression construct includes at least one appropriate expression control sequence (also called a regulatory sequence), such as a leader sequence and particularly a promoter operatively linked to the nucleotide sequence encoding the immunogen.

Host cells are genetically engineered with the recombinant expression vector to produce the immunogen(s), or fragments or variants thereof, by recombinant techniques. Each of the polypeptides and fusion polypeptides described herein can be expressed in mammalian cells, yeast, bacteria, insect, or other cells under the control of appropriate promoters. Cell-free translation systems can also be employed to produce such proteins using RNAs derived from DNA constructs. Appropriate cloning and expression vectors for use with prokaryotic and eukaryotic hosts are described, for example, by Sambrook, et al., Molecular Cloning: A Laboratory Manual, Third Edition, Cold Spring Harbor, New York, (2001).

Generally, recombinant expression vectors useful for producing an immunogen of interest include origins of replication, selectable markers permitting transformation of the host cell, for example, the ampicillin resistance gene of *E. coli* and *S. cerevisiae* TRP1 gene, and a promoter derived from a highly expressed gene to direct transcription of a downstream structural sequence. Promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences.

Optionally, a heterologous sequence can be inserted in frame with the nucleotide sequence that encodes the immunogen to provide a peptide or polypeptide that imparts desired characteristics, e.g., that simplifies purification of the expressed recombinant product. Such identification peptides include a polyhistidine tag (his tag) or FLAG® epitope tag (DYKDDDDK, SEQ ID NO:35), beta-galactosidase, alkaline phosphatase, GST, or the XPRESS™ epitope tag (DLYDDDDK, SEQ ID NO:41; Invitrogen Life Technologies, Carlsbad, Calif.) and the like (see, e.g., U.S. Pat. No. 5,011,912; Hopp et al., (Bio/Technology 6:1204 (1988)). The affinity sequence may be supplied by a vector, such as, for example, a hexa-histidine tag that is provided in pBAD/His (Invitrogen). Alternatively, the affinity sequence may be added either synthetically or engineered into the primers used to recombinantly generate the nucleic acid coding sequence (e.g., using the polymerase chain reaction).

Host cells containing described recombinant expression constructs may be genetically engineered (transduced, transformed, or transfected) with the expression constructs (for example, a cloning vector, a shuttle vector, or an expression construct). The vector or construct may be in the form of a plasmid, a viral particle, a phage, etc. The engineered host cells can be cultured in conventional nutrient media modified as appropriate for activating promoters, selecting transformants, or amplifying encoding-nucleotide sequences. Selection and maintenance of culture conditions for particular host cells, such as temperature, pH and the like, will be readily apparent to the ordinarily skilled artisan. Preferably the host cell can be adapted to sustained propagation in culture to yield a cell line according to art-established methodologies for production of polypeptides. In certain embodiments, the cell line is an immortal cell line, which refers to a cell line that can be repeatedly (at least ten times while remaining viable) passaged in culture following log-phase growth.

Useful bacterial expression constructs are constructed by inserting into an expression vector a structural DNA sequence encoding a desired immunogen together with suitable translation initiation and termination signals in operable reading phase with a functional promoter. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice. Any other plasmid or vector may be used as long as they are replicable and viable in the host. Thus, for example, the nucleotide sequence that encodes an immunogen or designated antigen of interest may be included in any one of a variety of recombinant expression constructs for expressing a polypeptide. Such vectors and constructs include chromosomal, nonchromosomal, and synthetic DNA sequences, e.g., bacterial plasmids; phage DNA; baculovirus; yeast plasmids; vectors derived from combinations of plasmids and phage DNA; viral DNA, such as vaccinia, adenovirus, fowl pox virus, and pseudorabies. However, any other vector may be used for preparation of a recombinant expression construct as long as it is replicable and viable in the host.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. Numerous standard techniques are described, for example, in Ausubel et al. (Current Protocols in Molecular Biology (Greene Publ. Assoc. Inc. & John Wiley & Sons, Inc., 2003)); Sambrook et al. (Molecular Cloning: A Laboratory Manual, 3rd Ed., (Cold Spring Harbor Laboratory 2001)); Maniatis et al. (Molecular Cloning, (Cold Spring Harbor Laboratory 1982)), and elsewhere.

The DNA sequence encoding a polypeptide immunogen in the expression vector is operatively linked to at least one appropriate expression control sequences (e.g., a promoter or a regulated promoter) to direct mRNA synthesis. Representative examples of such expression control sequences include LTR or SV40 promoter, the E. coli lac or trp, the phage lambda PL promoter, and other promoters known to control expression of genes in prokaryotic or eukaryotic cells or their viruses. Promoter regions can be selected from any desired gene using CAT (chloramphenicol transferase) vectors or other vectors with selectable markers. Particular bacterial promoters include lacI, lacZ, T3, T5, T7, gpt, lambda PR, PL, and trp. Eukaryotic promoters include CMV immediate early, HSV thymidine kinase, early and late SV40, LTRs from retroviruses, and mouse metallothionein-I. Selection of the appropriate vector and promoter and preparation of certain recombinant expression constructs comprising at least one promoter or regulated promoter operatively linked to a nucleotide sequence that encodes an at least one immunogen is well within the level of ordinary skill in the art.

Design and selection of inducible, regulated promoters and/or tightly regulated promoters are known in the art and will depend on the particular host cell and expression system (see, e.g., E. coli arabinose operon (Pbad or Para) as described in Guzman et al., J. Bacteriology 177:4121-30 (1995); Smith et al., J. Biol. Chem. 253:6931-33 (1978); Hirsh et al., Cell 11:545-50 (1977); PET Expression Systems (see U.S. Pat. No. 4,952,496) available from Stratagene (La Jolla, Calif.); tet-regulated expression systems (Gossen et al., Proc. Natl. Acad. Sci. USA 89:5547-51 (1992); Gossen et al., Science 268:1766-69 (1995)); pLP-TRE2 Acceptor Vector (BD Biosciences Clontech, Palo Alto, Calif.) is designed for use with CLONTECH's Creator™ Cloning Kits); see also, e.g., Sauer, Methods 14:381-92 (1998); Furth, J. Mamm. Gland Biol. Neoplas. 2:373 (1997)); see, e.g., Cascio, Artif. Organs 25:529 (2001)).

The immunogen-encoding nucleic acid sequences may be cloned into a baculovirus shuttle vector, which is then recombined with a baculovirus to generate a recombinant baculovirus expression construct that is used to infect, for example, Sf9 host cells (see, e.g., Baculovirus Expression Protocols, Methods in Molecular Biology Vol. 39, Richardson, Ed. (Human Press 1995); Piwnica-Worms, "Expression of Proteins in Insect Cells Using Baculoviral Vectors," Section II, Chapter 16 in Short Protocols in Molecular Biology, 2nd Ed., Ausubel et al., eds., (John Wiley & Sons 1992)).

Methods that may be used for isolated and purifying a recombinant immunogen, by way of example, may include obtaining supernatants from suitable host/vector systems that secrete the recombinant immunogen into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen or designated antigen from its natural environment.

Methods for large scale production of one or more of the isolated/recombinant immunogens described herein include batch cell culture, which is monitored and controlled to maintain appropriate culture conditions. Purification of the immunogen may be performed according to methods described herein and known in the art and that comport with laws and guidelines of domestic and foreign regulatory agencies.

Adjuvants and Adjuvant Compositions

As described herein, immunogenic compositions may further comprise at least one adjuvant that is intended to enhance (or improve, augment) the immune response to the immunogen and to its respective designated antigen (i.e., increase the level of the specific immune response to the immunogen and designated antigen in a statistically, biologically, or clinically significant manner compared with the level of the specific immune response in the absence of administering the adjuvant). In certain embodiments, an immunogenic composition comprises at least one immunogen, which may be isolated and/or recombinant, and at least one adjuvant.

In other certain embodiments, an immunogenic composition comprising a recombinant expression vector that encodes the at least one immunogen and is capable of directing expression of the immunogen further comprises an adjuvant. In other certain embodiments, both the immunogenic composition that comprises the at least one immunogen and the immunogenic composition comprising the recombinant expression vector further comprise an adjuvant. In still other embodiments, instead of combining an adjuvant with the immunogenic composition comprising the recombination expression vector or administering the adjuvant concurrently with this immunogenic composition, the adjuvant is administered at a later time and may be administered by a different route and/or a different site than the immunogenic composition comprising the vector. When the adjuvant is administered after administration of the immunogenic composition comprising the recombinant expression vector, the adjuvant is administered at 18 hours, 24 hours, 36 hours, 72 hours or 1 day, 2 days, 3 days, 4, days, 5 days, 6 days, or seven days (1 week) after administration of the immunogenic composition. Methods and techniques for determining the level of an immune response are discussed in greater detail herein and are routinely practiced in the art.

Exemplary adjuvants that may be included in the immunogenic compositions and used in the methods described herein include, but are not necessarily limited to, the following. Adjuvants that may be used in these methods include adjuvants useful for enhancing the humoral response, the cellular response, or both the humoral and cellular responses specific for the immunogen(s) and respective designated antigen(s). The cellular immune response comprises a CD4 T cell response (which may include a memory CD4 T cell response) and a CD8 T cell response specific for the immunogen and its respective designated antigen. The cellular response may also include a cytotoxic T cell response (CTL response) to the immunogen (or to a cell or particle bearing or expressing the immunogen(s)). Desired adjuvants augment the response to the immunogen without causing conformational changes in the immunogen that might adversely affect the qualitative form of the response. Suitable adjuvants include aluminum salts, such as alum (potassium aluminum sulfate), or other aluminum containing adjuvants; nontoxic lipid A-related adjuvants such as, by way of non-limiting example, nontoxic monophosphoryl lipid A (see, e.g., Tomai et al., J. Biol. Response Mod. 6:99-107 (1987); Persing et al., Trends Microbiol. 10:s32-s37 (2002)); GLA described herein; 3 De-O-acylated monophosphoryl lipid A (MPL) (see, e.g., United Kingdom Patent Application No. GB 2220211); adjuvants such as QS21 and QuilA that comprise a triterpene glycoside or saponin isolated from the bark of the *Quillaja saponaria* Molina tree found in South America (see, e.g., Kensil et al., in Vaccine Design: The Subunit and Adjuvant Approach (eds. Powell and Newman, Plenum Press, NY, 1995); U.S. Pat. No. 5,057,540). Other suitable adjuvants include oil in water emulsions (such as squalene or peanut oil), optionally in combination with immune stimulants, such as monophosphoryl lipid A (see, e.g., Stoute et al., N. Engl. J. Med. 336, 86-91 (1997)). Another suitable adjuvant is CpG (see, e.g., Klinman, Int. Rev. Immunol. 25(3-4):135-54 (2006); U.S. Pat. No. 7,402,572; European Patent No. 772 619).

As described herein, a suitable adjuvant is an aluminum salt, such as aluminum hydroxide, aluminum phosphate, or aluminum sulfate. Such adjuvants can be used with or without other specific immunostimulating agents such as MPL or 3-DMP, QS21, polymeric or monomeric amino acids such as polyglutamic acid or polylysine. Another class of suitable adjuvants is oil-in-water emulsion formulations (also called herein stable oil in water emulsions). Such adjuvants can be optionally used with other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide™), or other bacterial cell wall components. Oil-in-water emulsions include (1) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.); (2) SAF, containing 10% Squalane, 0.4% Tween 80, 5% pluronic-blocked polymer L121, and thr-MDP, either microfluidized into a submicron emulsion or vortexed to generate a larger particle size emulsion, and (3) Ribi adjuvant system (RAS), (Ribi Immunochem, Hamilton, Mont.) containing 2% squalene, 0.2% Tween 80, and one or more bacterial cell wall components from the group consisting of monophosphoryl lipid A (MPL), trehalose dimycolate (TDM), and cell wall skeleton (CWS), preferably MPL+CWS (Detox™). Also as described above, suitable adjuvants include saponin adjuvants, such as Stimulon™ (QS21, Aquila, Worcester, Mass.) or particles generated therefrom such as ISCOMs (immunostimulating complexes) and ISCOMATRIX. Other adjuvants include Complete Freund's Adjuvant (CFA) (which is suitable for non-human use but is unsuitable for human use) and Incomplete Freund's Adjuvant (IFA). Other adjuvants include cytokines, such as interleukins (IL-1, IL-2, and IL-12), macrophage colony stimulating factor (M-CSF), and tumor necrosis factor (TNF).

As described herein, an adjuvant may be a non-toxic lipid A-related (or lipid A derivative) adjuvant. In a particular embodiment, an adjuvant is selected on the basis of its capability to act as a Toll-like receptor (TLR) agonist. By way of example, a non-toxic lipid A-related adjuvant that acts as a TLR4 agonist and that may be used in the compositions described herein is identified as DSLP. DSLP compounds share the features that they contain a disaccharide (DS) group formed by the joining together of two monosaccharide groups selected from glucose and amino substituted glucose, where the disaccharide is chemically bound to both a phosphate (P) group and to a plurality of lipid (L) groups. More specifically, the disaccharide may be visualized as being formed from two monosaccharide units, each having six carbons. In the disaccharide, one of the monosaccharides will form a reducing end, and the other monosaccharide will form a non-reducing end. For convenience, the carbons of the monosaccharide forming the reducing terminus will be denoted as located at positions 1, 2, 3, 4, 5 and 6, while the corresponding carbons of the monosaccharide forming the non-reducing terminus will be denoted as being located at positions 1', 2', 3', 4', 5' and 6', following conventional carbohydrate numbering nomenclature. In the DSLP, the carbon at the 1 position of the non-reducing terminus is linked, through either an ether (—O—) or amino (—NH—) group, to the carbon at the 6' position of the reducing terminus. The phosphate group will be linked to the disaccharide, preferably through the 4' carbon of the non-reducing terminus. Each of the lipid groups will be joined, through either amide (—NH—C(O)—) or ester (—O—C(O)—) linkages to the disaccharide, where the carbonyl group joins to the lipid group. The disaccharide has 7 positions that may be linked to an amide or ester group, namely, positions 2', 3', and 6' of the non-reducing terminus, and positions 1, 2, 3 and 4 of the reducing terminus.

A lipid group has at least six carbons, preferably at least 8 carbons, and more preferably at least 10 carbons, where in each case the lipid group has no more than 24 carbons, no more than 22 carbons, or no more than 20 carbons. In one embodiment, the lipid groups taken together provide 60-100 carbons, preferably 70 to 90 carbons. A lipid group may consist solely of carbon and hydrogen atoms, i.e., it may be a hydrocarbyl lipid group, or it may contain one hydroxyl group, i.e., it may be a hydroxyl-substituted lipid group, or it may contain an ester group which is, in turn, joined to a hydrocarbyl lipid or a hydroxyl-substituted lipid group through the carbonyl (—C(O)—) of the ester group, i.e., a ester substituted lipid. A hydrocarbyl lipid group may be saturated or unsaturated, where an unsaturated hydrocarbyl lipid group will have one double bond between adjacent carbon atoms.

The DSLP comprises 3, or 4, or 5, or 6 or 7 lipid groups. In one aspect, the DSLP comprises 3 to 7 lipid groups, while in another aspect the DSLP comprises 4-6 lipids. In one aspect, the lipid group is independently selected from hydrocarbyl lipid, hydroxyl-substituted lipid, and ester substituted lipid. In one aspect, the 1, 4' and 6' positions are substituted with hydroxyl. In one aspect, the monosaccharide units are each glucosamine. The DSLP may be in the free acid form, or in the salt form, e.g., an ammonium salt.

In certain embodiments, the lipid on the DSLP is described by the following: the 3' position is substituted with —O—(CO)—CH2-CH(Ra)(—O—C(O)—Rb); the 2' position is substituted with —NH—(CO)—CH2-CH(Ra)(—O—C(O)—Rb); the 3 position is substituted with —O—(CO)—CH2-CH(OH)(Ra); the 2 position is substituted with —NH—(CO)—CH2-CH(OH)(Ra); where each of Ra and Rb is selected from decyl, undecyl, dodecyl, tridecyl, tetradecyl, wherein each of these terms refer to saturated hydrocarbyl groups. In one embodiment, Ra is undecyl and Rb is tridecyl, where this adjuvant is described in, for example, U.S. Patent Application Publication 2008/0131466 as "GLA." The compound wherein Ra is undecyl and Rb is tridecyl may be used in a stereochemically defined form, as available from, for example, Avanti Polar Lipid as PHAD™ adjuvant.

In one aspect, the DSLP is a mixture of naturally-derived compounds known as 3D-MPL. 3D-MPL adjuvant is produced commercially in a pharmaceutical grade form by GlaxoSmithKline Company as their MPL™ adjuvant. 3D-MPL has been extensively described in the scientific and patent literature, see, e.g., Vaccine Design: the subunit and adjuvant approach, Powell M. F. and Newman, M. J. eds., Chapter 21 Monophosphoryl Lipid A as an adjuvant: past experiences and new directions by Ulrich, J. T. and Myers, K. R., Plenum Press, New York (1995) and U.S. Pat. No. 4,912,094.

In another aspect, the DSLP adjuvant may be described as comprising (i) a diglucosamine backbone having a reducing terminus glucosamine linked to a non-reducing terminus glucosamine through an ether linkage between hexosamine position 1 of the non-reducing terminus glucosamine and hexosamine position 6 of the reducing terminus glucosamine; (ii) an O-phosphoryl group attached to hexosamine position 4 of the non-reducing terminus glucosamine; and (iii) up to six fatty acyl chains; wherein one of the fatty acyl chains is attached to 3-hydroxy of the reducing terminus glucosamine through an ester linkage, wherein one of the fatty acyl chains is attached to a 2-amino of the non-reducing terminus glucosamine through an amide linkage and comprises a tetradecanoyl chain linked to an alkanoyl chain of greater than 12 carbon atoms through an ester linkage, and wherein one of the fatty acyl chains is attached to 3-hydroxy of the non-reducing terminus glucosamine through an ester linkage and comprises a tetradecanoyl chain linked to an alkanoyl chain of greater than 12 carbon atoms through an ester linkage. See, e.g., U.S. Patent Application Publication No. 2008/0131466.

In another aspect, the adjuvant may be a synthetic disaccharide having six lipid groups as described in U.S. patent application publication 2010/0310602.

In another aspect, a DSLP adjuvant is described by chemical formula (I) and is referred to as glucopyranosyl lipid A (GLA):

(I)

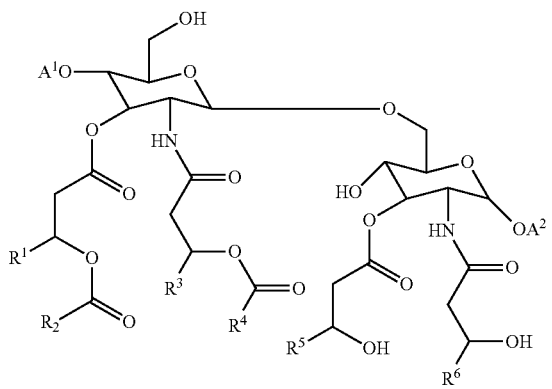

wherein the moieties A1 and A2 are independently selected from the group of hydrogen, phosphate, and phosphate salts. Sodium and potassium are exemplary counterions for the phosphate salts. The moieties R1, R2, R3, R4, R5, and R6 are independently selected from the group of hydrocarbyl having 3 to 23 carbons, represented by C3-C23. For added clarity it will be explained that when a moiety is "independently selected from" a specified group having multiple members, it should be understood that the member chosen for the first moiety does not in any way impact or limit the choice of the member selected for the second moiety. The carbon atoms to which R1, R3, R5 and R6 are joined are asymmetric, and thus may exist in either the R or S stereochemistry. In one embodiment all of those carbon atoms are in the R stereochemistry, while in another embodiment all of those carbon atoms are in the S stereochemistry. "Hydrocarbyl" refers to a chemical moiety formed entirely from hydrogen and carbon, where the arrangement of the carbon atoms may be straight chain or branched, noncyclic or cyclic, and the bonding between adjacent carbon atoms maybe entirely single bonds, that is, to provide a saturated hydrocarbyl, or there may be double or triple bonds present between any two adjacent carbon atoms, i.e., to provide an unsaturated hydrocarbyl, and the number of carbon atoms in the hydrocarbyl group is between 3 and 24 carbon atoms. The hydrocarbyl may be an alkyl, where representative straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while branched alkyls include isopropyl, sec-butyl, isobutyl, tert-butyl, isopentyl, and the like. Representative saturated cyclic hydrocarbyls include cyclopropyl, cyclobutyl, cyclopentyl, cyclohexyl, and the like; while unsaturated cyclic hydrocarbyls include cyclopentenyl and cyclohexenyl, and the like. Unsaturated hydrocarbyls contain at least one double or triple bond between adjacent carbon atoms (referred to as an "alkenyl" or "alkynyl," respectively, if the hydrocarbyl is non-cyclic, and cycloalkeny and cycloalkynyl, respectively, if the hydrocarbyl is at least partially cyclic). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl- 1-butynyl, and the like. The adjuvant of formula (I) may be obtained by synthetic methods known in the art, for example, the synthetic methodology disclosed in PCT International Publication No. WO 2009/035528, which is incorporated herein by reference, as well as the publications identified in WO 2009/035528, each of which publications is also incorporated herein by reference. Certain of the adjuvants may also be obtained commercially.

The DSLP adjuvant may be obtained by synthetic methods known in the art, for example, the synthetic methodology disclosed in PCT International Publication No. WO 2009/035528, which is incorporated herein by reference, as well as the publications identified in WO 2009/035528, where each of those publications is also incorporated herein by reference. A chemically synthesized DSLP adjuvant, e.g., the adjuvant of formula (I), can be prepared in substantially homogeneous form, which refers to a preparation that is at least 80%, at least 85%, at least 90%, at least 95% or at least 96%, 97%, 98% or 99% pure with respect to the DSLP molecules present, e.g., the compounds of formula (I). Determination of the degree of purity of a given adjuvant preparation can be readily made by those familiar with the appropriate analytical chemistry methodologies, such as by gas chromatography, liquid chromatography, mass spectroscopy and/or nuclear magnetic resonance analysis. DSLP adjuvants obtained from natural sources are typically not easily made in a chemically pure form, and thus synthetically prepared adjuvants are preferred adjuvants for use in the compositions and methods described herein. As discussed previously, certain of the adjuvants may be obtained commercially. One such DSLP adjuvant is Product No. 699800 as identified in the catalog of Avanti Polar Lipids, Alabaster A L, see E1 in combination with E10, below.

In various embodiments, the adjuvant has the chemical structure of formula (I) but the moieties A1, A2, R1, R2, R3, R4, R5, and R6 are selected from subsets of the options previously provided for these moieties, wherein these subsets are identified below by E1, E2, etc.

E1: A1 is phosphate or phosphate salt and A2 is hydrogen.
E2: R1, R3, R5 and R6 are C3-C21 alkyl; and R2 and R4 are C5-C23 hydrocarbyl.
E3: R1, R3, R5 and R6 are C5-C17 alkyl; and R2 and R4 are C7-C19 hydrocarbyl.
E4: R1, R3, R5 and R6 are C7-C15 alkyl; and R2 and R4 are C9-C17 hydrocarbyl.
E5: R1, R3, R5 and R6 are C9-C13 alkyl; and R2 and R4 are C11-C15 hydrocarbyl.
E6: R1, R3, R5 and R6 are C9-C15 alkyl; and R2 and R4 are C11-C17 hydrocarbyl.
E7: R1, R3, R5 and R6 are C7-C13 alkyl; and R2 and R4 are C9-C15 hydrocarbyl.
E8: R1, R3, R5 and R6 are C11-C20 alkyl; and R2 and R4 are C12-C20 hydrocarbyl.
E9: R1, R3, R5 and R6 are C11 alkyl; and R2 and R4 are C13 hydrocarbyl.
E10: R1, R3, R5 and R6 are undecyl and R2 and R4 are tridecyl.

In certain embodiments, each of E2 through E10 is combined with embodiment E1, and/or the hydrocarbyl groups of E2 through E9 are alkyl groups, preferably straight chain alkyl groups. The DSLP adjuvant, e.g., the adjuvant of formula (I) may be formulated into a pharmaceutical composition, optionally with a co-adjuvant, each as discussed below. In this regard reference is made to U.S. Patent Publication No. 2008/0131466 that provides formulations, such as aqueous formulation (AF) and stable emulsion formulations (SE) for GLA adjuvant, wherein these formulations may be used for any of the adjuvants of formula (I). In certain specific embodiments, an immunogenic composition comprises GLA wherein the GLA adjuvant (see formula I) is formulated in a stable oil-in water emulsion (SE) (GLA/SE or GLA-SE) and then combined with at least one immunogen.

Optionally, as described in greater detail below and herein, two or more different adjuvants can be used simultaneously, such as by way of non-limiting example, an aluminum salt with a DSLP adjuvant, an aluminum salt with QS21, a DSLP adjuvant with QS21, and alumna aluminum salt, QS21, and MPL or GLA together. Also, Incomplete Freund's adjuvant can be used (see, e.g., Chang et al., Advanced Drug Delivery Reviews 32, 173-186 (1998)), optionally in combination with any of an aluminum salt, QS21, and MPL and all combinations thereof.

In certain embodiments, the DSLP adjuvant, e.g., the adjuvant of formula (I), may be formulated into a pharmaceutical (or adjuvant composition), optionally with a co-adjuvant, each as discussed below or any other adjuvant described herein or available in the art. In this regard reference is made to U.S. Patent Publication No. 2008/0131466 that provides formulations, such as aqueous formulation (AF) and stable emulsion formulations (SE) for GLA adjuvant, which formulations may be used with respect to any of the adjuvants of formula (I).

As provided herein the DSLP adjuvant, such as the adjuvant of formula I, may be used in combination with a second adjuvant, referred to herein as a co-adjuvant. In three exemplary embodiments, the co-adjuvant may be a delivery system, or it may be an immunopotentiator, or it may be a composition that functions as both a delivery system and an immunopotentiator (see, e.g., O'Hagan et al., Pharm. Res. 21(9):1519-30 (2004)). The co-adjuvant may be an immunopotentiator that operates via a member of the Toll-like receptor family biomolecules. For example, the co-adjuvant may be selected for its primary mode of action, as either a TLR4 agonist, or a TLR8 agonist, or a TLR9 agonist. Alternatively, or in supplement, the co-adjuvant may be selected for its carrier properties; for example, the co-adjuvant may be an emulsion, a liposome, a microparticle, or alum.

In one embodiment, the co-adjuvant is alum, where this term refers to aluminum salts, such as aluminum phosphate (AlPO4) and aluminum hydroxide (Al(OH)3). When alum is used as the co-adjuvant, the alum may be present in a dose of an immunogenic composition (or preparation comprising the immunogenic composition) in an amount of about 100 to 1,000 µg, or 200 to 800 µg, or 300 to 700 µg or 400 to 600 µg. The adjuvant of formula (1) is typically present in an amount less than the amount of alum, and in various specific embodiments the adjuvant of formula (1), on a weight basis, is present at 0.1-1%, or 1-5%, or 1-10%, or 1-100% relative to the weight of alum.

In one particular embodiment, the adjuvant is an emulsion having adjuvanating properties sufficient for use in a vaccine or immunogenic composition. Such emulsions include oil-in-water emulsions. Freund's incomplete adjuvant (IFA) is one such adjuvant. Another suitable oil-in-water emulsion is MF-59™ adjuvant, which contains squalene, polyoxyethylene sorbitan monooleate (also known as Tween™ 80 surfactant), and sorbitan trioleate. Squalene is a natural organic compound originally obtained from shark liver oil, although also available from plant sources (primarily vegetable oils), including amaranth seed, rice bran, wheat germ, and olives. Other suitable adjuvants are Montanide™ adjuvants (Seppic Inc., Fairfield N.J.) including Montanide™ ISA 50V, which is a mineral oil-based adjuvant; Montanide™ ISA 206; and Montanide™ IMS 1312. While mineral oil may be present in the co-adjuvant, in one embodiment the oil component(s) of the immunogenic compositions described herein are all metabolizable oils.

Examples of immunopotentiators that may be used in the practice of the methods described herein as co-adjuvants include: MPL™; MDP and derivatives; oligonucleotides; double-stranded RNA; alternative pathogen-associated molecular patterns (PAMPS); saponins; small-molecule immune potentiators (SMIPs); cytokines; and chemokines.

In one embodiment, the co-adjuvant is MPL™ adjuvant, which is commercially available from GlaxoSmithKline (originally developed by Ribi ImmunoChem Research, Inc. Hamilton, Mont.). See, e.g., Ulrich and Myers, Chapter 21 from Vaccine Design: The Subunit and Adjuvant Approach, Powell and Newman, eds. Plenum Press, New York (1995). Related to MPL™ adjuvant, and also suitable as co-adjuvants for use in the compositions and methods described herein, are AS02™ adjuvant and AS04™ adjuvant. AS02™ adjuvant is an oil-in-water emulsion that contains both MPL™ adjuvant and QS-21™ adjuvant (a saponin adjuvant discussed elsewhere herein). AS04™ adjuvant contains MPL™ adjuvant and alum MPL™ adjuvant is prepared from lipopolysaccharide (LPS) of *Salmonella* minnesota R595 by treating LPS with mild acid and base hydrolysis followed by purification of the modified LPS.

In another embodiment, the co-adjuvant is a saponin such as those derived from the bark of the *Quillaja saponaria* tree species, or a modified saponin (see, e.g., U.S. Pat. Nos. 5,057,540; 5,273,965; 5,352,449; 5,443,829; and 5,560,398). The product QS-21™ adjuvant sold by Antigenics, Inc. Lexington, Mass. is an exemplary saponin-containing co-adjuvant that may be used with the adjuvant of formula (I). An alternative co-adjuvant, related to the saponins, is the ISCOM™ family of adjuvants, originally developed by Iscotec (Sweden) and typically formed from saponins derived from *Quillaja saponaria* or synthetic analogs, cholesterol, and phospholipid, all formed into a honeycomb-like structure.

In yet another embodiment, the co-adjuvant is a cytokine that functions as a co-adjuvant (see, e.g., Lin et al., Clin. Infect. Dis. 21(6):1439-49 (1995); Taylor, Infect. Immun. 63(9):3241-44 (1995); and Egilmez, Chap. 14 in Vaccine Adjuvants and Delivery Systems, John Wiley & Sons, Inc. (2007)). In various embodiments, the cytokine may be, for example, granulocyte-macrophage colony-stimulating factor (GM-CSF) (see, e.g., Change et al., Hematology 9(3):207-15 (2004); Dranoff, Immunol. Rev. 188:147-54 (2002); and U.S. Pat. No. 5,679,356); or an interferon, such as a type I interferon (e.g., interferon-α (IFN-α) or interferon-β (IFN-β), or a type II interferon (e.g., interferon-γ (IFN-γ) (see, e.g., Boehm et al., Ann. Rev. Immunol. 15:749-95 (1997); and Theofilopoulos et al., Ann. Rev. Immunol. 23:307-36 (2005)); an interleukin, specifically including interleukin-1α (IL-1α), interleukin-1β (IL-1β), interleukin-2 (IL-2) (see, e.g., Nelson, J. Immunol. 172(7):3983-88 (2004); interleukin-4 (IL-4), interleukin-7 (IL-7), interleukin-12 (IL-12) (see, e.g., Portielje et al., Cancer Immunol. Immunother. 52(3):133-44 (2003); and Trinchieri, Nat. Rev. Immunol. 3(2):133-46 (2003)); interleukin-15 (Il-15), interleukin-18 (IL-18); fetal liver tyrosine kinase 3 ligand (Flt3L), or tumor necrosis factor α (TNFα). The DSLP adjuvant, such as the adjuvant of formula (I), may be co-formulated with the cytokine prior to combination with the vaccine antigen, or the antigen, DSLP adjuvant (e.g., adjuvant of formula (I)), and cytokine co-adjuvant may be formulated separately and then combined.

In certain embodiments, an immunogenic composition that comprises an immunogen (which may be isolated and/or recombinant) and an adjuvant are formulated together. In other certain embodiments, when the immunogenic composition comprises two or more immunogens, an adjuvant may be formulated with each immunogen separately or the two or more immunogens may be formulated together with an adjuvant to form a single immunogenic composition. When two or more immunogens are intended to be administered to a subject and when each immunogen is separately formulated with an adjuvant, each composition may then be combined to form a single immunogenic composition.

In other certain embodiments, an immunogenic composition comprising the immunogen or a composition comprising a recombinant expression vector that encodes the immunogen or a vector particle comprising the vector are packaged and supplied in separate vials than those containing the adjuvant. Each of the immunogenic compositions and adjuvant may be combined with a pharmaceutically acceptable (i.e., physiologically suitable or acceptable) excipient(s), which are described in greater detail herein. Appropriate labels are typically packaged with each composition indicating the intended therapeutic application. The choice of an adjuvant and/or the excipient depends on the stability of the immunogen, recombinant expression vector, and/or vector particle; the route of administration; the dosing schedule; and the efficacy of the adjuvant for the species being vaccinated. For administration in humans, a pharmaceutically acceptable adjuvant is one that has been approved or is approvable for human administration by pertinent regulatory bodies. For example, as discussed herein and known in the art, Complete Freund's adjuvant is not suitable for human administration.

Adjuvants useful for use in the immunological compositions and methods described herein are physiologically or pharmaceutically suitable adjuvants for the subject to whom the adjuvant is administered. Adjuvant compositions comprise at least one adjuvant (i.e., one or more adjuvants) and, optionally, at least one physiologically or pharmaceutically suitable (or acceptable) excipient. Any physiological or pharmaceutically suitable excipient or carrier (i.e., a non-toxic material that does not interfere with the activity of the active ingredient) known to those of ordinary skill in the art for use in pharmaceutical compositions may be employed in the adjuvant compositions described herein. Exemplary excipients include diluents and carriers that maintain stability and integrity of the component(s) of the adjuvant. Excipients for therapeutic use are well known, and are described, for example, in Remington: The Science and Practice of Pharmacy (Gennaro, 21st Ed. Mack Pub. Co., Easton, Pa. (2005)), and are described in greater detail herein.

Recombinant Expression Vectors

In one embodiment, recombinant expression vectors are provided that comprise a polynucleotide sequence encoding at least one immunogen that induces an immune response to the immunogen and to its respective designated antigen. To obtain efficient transcription and translation of the immunogen, the encoding polynucleotide sequences in each vector include at least one appropriate expression control sequence (also called a regulatory expression sequence or feature) (e.g., promoter, enhancer, leader), which are described in greater detail herein, that is operatively linked to the encoding polynucleotide sequence(s). These recombinant expression vectors are thus provided for directing expression of the immunogen or for directing co-expression of at least two immunogens in any appropriate host cell that has been transformed, transduced, or transfected with the recombinant expression vector or vector particle containing the recombinant expression vector.

The recombinant expression vectors described herein may encode one or more immunogens (i.e., at least one, at least two, at least three immunogens, etc.), which immunogens are described in greater detail herein. In particular embodiments, at least one, two, or three, or more immunogens from an infectious microorganism (e.g., a virus, bacteria, fungus, or parasite) may be encoded by a recombinant expression vector Immunogens and designated antigens obtained from infectious disease microorganisms are described in greater detail herein. By way of example, an immunogen may be an HSV-2 protein, such as UL19 or gD, (or an immunogenic variant thereof) or may be an immunogenic fragment or region of the HSV-2 protein. In another specific embodiment, a recombinant expression vector described herein may encode at least one, two, three, or more tumor-associated antigens, or immunogenic variants or fragments thereof. These tumor associated antigens are described in greater detail herein and may be, for example, a tumor-associated antigen from a renal cell carcinoma antigen, a prostate cancer antigen (e.g., prostatic acid phosphatase, prostate specific antigen, NKX3.1, and prostate specific membrane antigen), a mesothelioma antigen, a pancreatic cancer antigen, a melanoma antigen, a breast cancer antigen, a colorectal cancer antigen, a lung cancer antigen, an ovarian cancer antigen, or any cancer or tumor-associate antigen described herein and in the art.

Recombinant expression vectors may be used for expression of any one or more of the immunogens described herein. In particular embodiments, the recombinant expression vector is delivered to an appropriate cell (for example, an antigen-presenting cell i.e., a cell that displays a peptide/MHC complex on its cell surface, such as a dendritic cell) or tissue (e.g., lymphoid tissue) that will induce the desired immune response (i.e., a specific humoral response (i.e., B cell response) and/or induction of a specific cell-medicated immune response, which may include an immunogen-specific CD4 and/or CD8 T cell response, which CD8 T cell response may include a cytotoxic T cell (CTL) response). The recombinant expression vectors may therefore also include, for example, lymphoid tissue-specific transcriptional regulatory elements (TRE) such as a B lymphocyte, T lymphocyte, or dendritic cell specific TRE. Lymphoid tissue specific TRE are known in the art (see, e.g., Thompson et al., Mol. Cell. Biol. 12, 1043-53 (1992); Todd et al., J. Exp. Med. 177, 1663-74 (1993); Penix et al., J. Exp. Med. 178:1483-96 (1993)).

In a particular embodiment, the recombinant expression vector is plasmid DNA or cosmid DNA. Plasmid DNA or cosmid DNA containing one or more polynucleotides encoding an immunogen as described herein is readily constructed using standard techniques well known in the art. The vector genome may be typically constructed in a plasmid form that can then be transfected into a packaging or producer cell line. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance. Typical bacterial drug resistance products are those that confer resistance to ampicillin or tetracycline. For analysis to confirm that the correct nucleotide sequences are incorporated in plasmids, the plasmid may be replicated in E. coli, purified, and analyzed by restriction endonuclease digestion and/or its nucleotide sequence determined by conventional methods.

In other particular embodiments, the recombinant expression vector is a viral vector. Exemplary recombinant expression viral vectors include a lentiviral vector genome, poxvirus vector genome, vaccinia virus vector genome, adenovirus vector genome, adenovirus-associated virus vector genome, herpes virus vector genome, and alpha virus vector genome. Viral vectors may be live, attenuated, replication conditional or replication deficient, and typically is a non-pathogenic (defective), replication competent viral vector.

By way of example, in a specific embodiment, when the viral vector is a vaccinia virus vector genome, the polynucleotide encoding an immunogen of interest may be inserted into a non-essential site of a vaccinia viral vector. Such non-essential sites are described, for example, in Perkus et al., Virology 152:285 (1986); Hruby et al., Proc. Natl. Acad. Sci. USA 80:3411 (1983); Weir et al., J. Virol. 46:530 (1983). Suitable promoters for use with vaccinia viruses include but are not limited to P7.5 (see, e.g., Cochran et al., J. Virol. 54:30 (1985); P11 (see, e.g., Bertholet, et al., Proc. Natl. Acad. Sci. USA 82:2096 (1985)); and CAE-1 (see, e.g., Patel et al., Proc. Natl. Acad. Sci. USA 85:9431 (1988)). Highly attenuated strains of vaccinia are more acceptable for use in humans and include Lister, NYVAC, which contains specific genome deletions (see, e.g., Guerra et al., J. Virol. 80:985-98 (2006); Tartaglia et al., AIDS Research and Human Retroviruses 8:1445-47 (1992)), or MVA (see, e.g., Gheradi et al., J. Gen. Virol. 86:2925-36 (2005); Mayr et al., Infection 3:6-14 (1975)). See also Hu et al. (J. Virol. 75:10300-308 (2001), describing use of a Yaba-Like disease virus as a vector for cancer therapy); U.S. Pat. Nos. 5,698,530 and 6,998,252. See also, e.g., U.S. Pat. No. 5,443,964. See also U.S. Pat. Nos. 7,247,615 and 7,368,116.

In certain embodiments, an adenovirus vector or adenovirus-associated virus vector may be used for expressing an immunogen of interest. Several adenovirus vector systems and methods for administering the vectors have been described (see, e.g., Molin et al., J. Virol. 72:8358-61 (1998); Narumi et al., Am J. Respir. Cell Mol. Biol. 19:936-41 (1998); Mercier et al., Proc. Natl. Acad. Sci. USA 101:6188-93 (2004); U.S. Pat. Nos. 6,143,290; 6,596,535; 6,855,317; 6,936,257; 7,125,717; 7,378,087; 7,550,296).

Retroviral vector genomes may include those based upon murine leukemia virus (MuLV), gibbon ape leukemia virus (GaLV), ecotropic retroviruses, simian immunodeficiency virus (SIV), human immunodeficiency virus (HIV), and combinations (see, e.g., Buchscher et al., J. Virol. 66:2731-39 (1992); Johann et al., J. Virol. 66:1635-40 (1992); Sommerfelt et al., Virology 176:58-59 (1990); Wilson et al., J. Virol. 63:2374-78 (1989); Miller et al., J. Virol. 65:2220-24 (1991); Miller et al., Mol. Cell Biol. 10:4239 (1990); Kolberg, NIH Res. 4:43 1992; Cornetta et al., Hum Gene Ther. 2:215 (1991)).

In a more specific embodiment, the recombinant expression viral vector is a lentiviral vector genome. The genome can be derived from any of a large number of suitable, available lentiviral genome based vectors, including those identified for human gene therapy applications (see, e.g., Pfeifer et al., Annu. Rev. Genomics Hum Genet. 2:177-211 (2001)). Suitable lentiviral vector genomes include those based on Human Immunodeficiency Virus (HIV-1), HIV-2, feline immunodeficiency virus (FIV), equine infectious anemia virus, Simian Immunodeficiency Virus (SIV), and maedi/visna virus. A desirable characteristic of lentiviruses is that they are able to infect both dividing and non-dividing cells, although target cells need not be dividing cells or be stimulated to divide. Generally, the genome and envelope glycoproteins will be based on different viruses, such that the resulting viral vector particle is pseudotyped. Safety features of the vector genome are desirably incorporated. Safety features include self-inactivating LTR and a non-integrating genome. Exemplary vectors contain a packaging signal (psi), a Rev-responsive element (RRE), splice donor, splice acceptor, central poly-purine tract (cPPT), and WPRE element. In certain exemplary embodiments, the viral vector genome comprises sequences from a lentivirus genome, such as the HIV-1 genome or the SIV genome. The viral genome construct may comprise sequences from the 5' and 3' LTRs of a lentivirus, and in particular may comprise the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or HIV. Typically, the LTR sequences are HIV LTR sequences.

The vector genome may comprise an inactivated or self-inactivating 3' LTR (see, e.g., Zufferey et al., J. Virol. 72:9873, 1998; Miyoshi et al., J. Virol. 72:8150, 1998; both of which are incorporated in their entirety). A self-inactivating vector generally has a deletion of the enhancer and promoter sequences from the 3' long terminal repeat (LTR), which is copied over into the 5' LTR during vector integration. In one instance, the U3 element of the 3' LTR contains a deletion of its enhancer sequence, the TATA box, Sp1 and NF-kappa B sites. As a result of the self-inactivating 3' LTR, the provirus that is generated following entry and reverse transcription will comprise an inactivated 5' LTR. The rationale is to improve safety by reducing the risk of mobilization of the vector genome and the influence of the LTR on nearby cellular promoters. The self-inactivating 3' LTR may be constructed by any method known in the art.

Optionally, the U3 sequence from the lentiviral 5' LTR may be replaced with a promoter sequence in the viral construct, such as a heterologous promoter sequence. This can increase the titer of virus recovered from the packaging cell line. An enhancer sequence may also be included. Any enhancer/promoter combination that increases expression of the viral RNA genome in the packaging cell line may be used. In one example, the CMV enhancer/promoter sequence is used (see, e.g., U.S. Pat. Nos. 5,385,839 and 5,168,062).

In certain embodiments, the risk of insertional mutagenesis is minimized by constructing the lentiviral vector genome to be integration defective. A variety of approaches can be pursued to produce a non-integrating vector genome. These approaches entail engineering a mutation(s) into the integrase enzyme component of the pol gene, such that it encodes a protein with an inactive integrase. The vector genome itself can be modified to prevent integration by, for example, mutating or deleting one or both attachment sites, or making the 3' LTR-proximal polypurine tract (PPT) non-functional through deletion or modification. In addition, non-genetic approaches are available; these include pharmacological agents that inhibit one or more functions of integrase. The approaches are not mutually exclusive, that is, more than one of them can be used at a time. For example, both the integrase and attachment sites can be non-functional, or the integrase and PPT site can be non-functional, or the attachment sites and PPT site can be non-functional, or all of them can be non-functional.

Integrase is involved in cleavage of viral double-stranded blunt-ended DNA and joining the ends to 5'-phosphates in the two strands of a chromosomal target site. Integrase has three functional domains: N-terminal domain, which contains a zinc-binding motif (HHCC); the central domain core, which contains the catalytic core and a conserved DD35E motif (D64, D116, E152 in HIV-1); and a C-terminal domain, which has DNA binding properties. Point mutations introduced into integrase are sufficient to disrupt normal function. Many integrase mutations have been constructed and characterized (see, e.g., Philpott and Thrasher, Human Gene Therapy 18:483, 2007; Apolonia, Thesis submitted to University College London, April 2009, pp, 82-97; Engelman et al., J. Virol. 69: 2729, 1995; Nightingale et al., Mol. Therapy, 13: 1121, 2006). The sequence encoding the integrase protein can be deleted or mutated to render the protein inactive, preferably without significantly impairing reverse transcriptase activity or nuclear targeting, thereby only preventing integration of the provirus into the target cell genome. Acceptable mutations can reduce integrase catalysis, strand transfer, binding to att sites, binding to host chromosomal DNA, and other functions. For example, a single aspartic acid to asparagine substitution at residue 35 of HIV or SIV integrase completely abolishes viral DNA integration. Deletions of integrase will generally be confined to the C-terminal domain. Deletion of coding sequence for residues 235-288 result in a useful non-functional integrase (see, e.g., Engelman et al., J. Virol. 69:2729, 1995). As further examples, mutations can be generated, for example, Asp64 (residue numbers are given for HIV-1, corresponding residue numbers for integrase from other lentiviruses or retroviruses can be readily determined by one of ordinary skill) (e.g., D64E, D64V), Asp116 (e.g., D116N), Asn120 (e.g., N120K), Glu152, Gln148 (e.g., Q148A), Lys156, Lys159, Trp235 (e.g., W235E), Lys264 (e.g., K264R), Lys266 (e.g., K266R), Lys273 (e.g., K273R). Other mutations can be constructed and tested for integration, transgene expression, and any other desirable parameter. Assays for these functions are well known. Mutations can be generated by any of a variety of techniques, including site-directed mutagenesis and chemical synthesis of nucleic acid sequence. One mutation may be made or more than one of these mutations can be present in integrase. For example, an integrase may have mutations at two amino acids, three amino acids, four amino acids, and so on.

Alternatively or in combination with the use of integrase mutant(s), the attachment sites (att) in U3 and U5 can also be mutated. Integrase binds to these sites and the 3'-terminal dinucleotide is cleaved at both ends of the vector genome. A CA dinucleotide is located at the recessed 3' end; the CA is required for processing, mutation of the nucleotides blocks integration into the host chromosome. The A of the CA dinucleotide is the most critical nucleotide for integration, and mutations at both ends of the genome will give the best results (see, e.g., Brown et al., J. Virol. 73:9011 (1999)). In one exemplification, the CA at each end is changed to TG. In other exemplifications, the CA at each end is changed to TG at one end and GT at the other end. In other exemplifications, the CA at each end is deleted; in other exemplifications, the A of the CA is deleted at each end.

Integration can also be inhibited by mutation or deletion of polypurine tract (PPT) (see, e.g., WO 2009/076524), located proximally to the 3' LTR. The PPT is a polypurine sequence of about 15 nucleotides that can serve as a primer binding site for plus-strand DNA synthesis. In this instance, mutations or deletions of PPT targets the reverse transcription process. Without wishing to be held to a particular mechanism, by mutating or deleting PPT, production of linear DNA is radically reduced, and essentially only 1-LTR DNA circles are produced. Integration requires a linear double-stranded DNA vector genome, and integration is essentially eliminated without it. As stated herein, a PPT can be made non-functional by mutation or by deletion. Typically, the entire about 15 nt PPT is deleted, although in some embodiments, shorter deletions of 14 nt, 13 nt, 12 nt, 11 nt, 10 nt, 9 nt, 8 nt, 7 nt, 6 nt, 5 nt, 4 nt, 3 nt and 2 nt may be made. When mutations are made, typically multiple mutations are made, especially in the 5' half of the PPT (see, e.g., McWilliams et al., J. Virol. 77:11150, 2003), although single and double mutations in the first four bases still reduce transcription. Mutations made at the 3' end of PPT generally have a more dramatic effect (see, e.g., Powell et al., J. Virol. 70:5288, 1996).

These different approaches to make a vector genome non-integrating can be used individually or in combination. Using more than one approach may be used to build a fail-safe vector through redundant mechanisms. Thus, PPT mutations or deletions can be combined with att site mutations or deletions or with Integrase mutations or PPT mutations or deletions can be combined with both att site mutations or deletions and Integrase mutations. Similarly, att site mutations or deletions and Integrase mutations may be combined with each other or with PPT mutations or deletions.

As described herein, lentiviral vector constructs contain a promoter for expression in mammalian cells. Promoters, which are discussed in greater detail herein, include, for example, the human ubiquitin C promoter (UbiC), the cytomegalovirus immediate early promoter (CMV), and the Rous sarcoma virus (RSV) promoter. The U3 region may comprise a PPT (polypurine tract) sequence immediately upstream. In certain specific embodiments, any one of at least three different U3 regions (at the 3' end) may be included in the lentiviral vector (see SEQ ID NOS:21-23). The constructs contain deletions in the U3 regions. The SIN construct has a deletion of about 130 nucleotides in the U3 (see, e.g., Miyoshi, et al. J. Virol. 72: 8150, 1998; Yu et al., Proc. Natl. Acad. Sci. USA 83: 3194, 1986), which removes the TATA box, thereby abolishing LTR promoter activity. The deletions in constructs 703 and 704 increase expression from lentivirus vectors (see, e.g., Bayer et al., Mol. Therapy 16: 1968, 2008). In addition, construct 704 contains a deletion of the 3' PPT, which decreases integration of the vector (see, e.g., WO 2009/076524). See also U.S. patent application Ser. No. 12/842,609 and International Patent Application Publication No. WO 2011/011584 (International Patent Application No. PCT/US10/042870), which are each incorporated by reference in their entirety.

Regulatory Expression Sequences

As described herein, the recombinant expression vector comprises at least one regulatory expression sequence. In certain embodiments, when the recombinant expression vector comprises a viral vector genome, expression of the at least one immunogen is desired in particular target cells. Typically, for example, in a lentiviral vector the polynucleotide sequence encoding the immunogen is located between the 5' LTR and 3' LTR sequences. Further, the encoding nucleotide sequence(s) is preferably operatively linked in a functional relationship with other genetic or regulatory sequences or features, for example transcription regulatory sequences including promoters or enhancers, that regulate expression of the immunogen in a particular manner In certain instances, the useful transcriptional regulatory sequences are those that are highly regulated with respect to activity, both temporally and spatially. Expression control elements that may be used for regulating the expression of the encoded polypeptides are known in the art and include, but are not limited to, inducible promoters, constitutive promoters, secretion signals, enhancers, and other regulatory sequences.

The polynucleotide encoding the immunogen and any other expressible sequence is typically in a functional relationship with internal promoter/enhancer regulatory sequences. With respect to lentiviral vector constructs, an "internal" promoter/enhancer is one that is located between the 5' LTR and the 3' LTR sequences in the viral vector and is operatively linked to the encoding polynucleotide sequence of interest. The internal promoter/enhancer may be any promoter, enhancer or promoter/enhancer combination known to increase expression of a gene with which it is in a functional relationship. A "functional relationship" and "operatively linked" mean, without limitation, that the sequence is in the correct location and orientation with respect to the promoter and/or enhancer such that the sequence of interest will be expressed when the promoter and/or enhancer is contacted with the appropriate molecules.

The choice of an internal promoter/enhancer is based on the desired expression pattern of the immunogen and the specific properties of known promoters/enhancers. Thus, the internal promoter may be constitutively active. Non-limiting examples of constitutive promoters that may be used include the promoter for ubiquitin (see, e.g., U.S. Pat. No. 5,510,474; WO 98/32869); CMV (see, e.g., Thomsen et al., Proc. Natl. Acad. Sci. USA 81:659, 1984; U.S. Pat. No. 5,168,062); beta-actin (Gunning et al. 1989 Proc. Natl. Acad. Sci. USA 84:4831-4835); and pgk (see, for example, Adra et al. 1987 Gene 60:65-74; Singer-Sam et al. 1984 Gene 32:409-417; and Dobson et al. 1982 Nucleic Acids Res. 10:2635-2637).

Alternatively, the promoter may be a tissue specific promoter. In some embodiments, the promoter is a target cell-specific promoter. For example, the promoter can be from any product expressed by dendritic cells, including CD11c, CD103, TLRs, DC-SIGN, BDCA-3, DEC-205, DCIR2, mannose receptor, Dectin-1, Clec9A, MHC class II. In addition, promoters may be selected to allow for inducible expression of the immunogen. A number of systems for inducible expression are known in the art, including the tetracycline responsive system, the lac operator-repressor system, as well as promoters responsive to a variety of environmental or physiological changes, including heat shock, metal ions, such as metallothionein promoter, interferons, hypoxia, steroids, such as progesterone or glucocorticoid receptor promoter, radiation, such as VEGF promoter. A combination of promoters may also be used to obtain the desired expression of each of the immunogen-encoding polynucleotide sequences. The artisan of ordinary skill will be able to select a promoter based on the desired expression pattern of the polynucleotide sequence in the organism or the target cell of interest.

A recombinant expression vector, including a viral vector genome, may comprise at least one RNA Polymerase II or III responsive promoter. This promoter can be operatively linked to the polynucleotide sequence of interest and can also be linked to a termination sequence. In addition, more than one RNA Polymerase II or III promoter may be incorporated. RNA polymerase II and III promoters are well known to persons of skill in the art. A suitable range of RNA polymerase III promoters can be found, for example, in Paule and White, Nucleic Acids Res., Vol. 28, pp 1283-1298 (2000). RNA polymerase II or III promoters also include any synthetic or engineered DNA fragment that can direct RNA polymerase II or III to transcribe downstream RNA coding sequences. Further, the RNA polymerase II or III (Pol II or III) promoter or promoters used as part of the viral vector genome can be inducible. Any suitable inducible Pol II or III promoter can be used with the methods described herein. Particularly suited Pol II or III promoters include the tetracycline responsive promoters provided in Ohkawa and Taira, Human Gene Therapy, 11:577-585 (2000) and in Meissner et al., Nucleic Acids Res., 29:1672-1682 (2001).

An internal enhancer may also be present in the recombinant expression vector, including a viral vector genome, to increase expression of the polynucleotide sequence of interest. For example, the CMV enhancer (see, e.g., Boshart et al., Cell 41:521, 1985) may be used. Many enhancers in viral genomes, such as HIV, CMV, and in mammalian genomes have been identified and characterized (see, e.g., publically available databases such as GenBank). An enhancer can be used in combination with a heterologous promoter. One of ordinary skill in the art will be able to select the appropriate enhancer based on the desired expression pattern.

When targeting delivery of a recombinant expression vector, including a viral vector genome, to a particular target cell, the vector genome will usually contain a promoter that is recognized by the target cell and that is operatively linked to the sequence of interest, viral components (when the vector is a viral vector), and other sequences discussed herein. A promoter is an expression control element formed by a nucleic acid sequence that permits binding of RNA polymerase and transcription to occur. Promoters may be inducible, constitutive, temporally active or tissue specific. The activity of inducible promoters is induced by the presence or absence of biotic or abiotic factors. Inducible promoters can be a useful tool in genetic engineering because the expression of genes to which they are operatively linked can be turned on or off at certain stages of development of an organism, its manufacture, or in a particular tissue. Inducible promoters can be grouped as chemically-regulated promoters, and physically-regulated promoters. Typical chemically-regulated promoters include, not are not limited to, alcohol-regulated promoters (e.g., alcohol dehydrogenase I (alcA) gene promoter), tetracycline-regulated promoters (e.g., tetracycline-responsive promoter), steroid-regulated promoter (e.g., rat glucocorticoid receptor (GR)-based promoter, human estrogen receptor (ER)-based promoter, moth ecdysone receptor-based promoter, and the promoters based on the steroid/retinoid/thyroid receptor superfamily), metal-regulated promoters (e.g., metallothionein gene-based promoters), and pathogenesis-related promoters (e.g., *Arabidopsis* and maize pathogen-related (PR) protein-based promoters). Typical physically-regulated promoters include, but are not limited to, temperature-regulated promoters (e.g., heat shock promoters), and light-regulated promoters (e.g., soybean SSU promoter). Other exemplary promoters are described elsewhere, for example, in patents and published patent applications that can be identified by searching the U.S. Patent and Trademark Office databases.

One of skill in the art will be able to select an appropriate promoter based on the specific circumstances. Many different promoters are well known in the art, as are methods for operatively linking the promoter to the polynucleotide sequence to be expressed. Both native promoter sequences and many heterologous promoters may be used to direct expression in the packaging cell and target cell. Heterologous promoters are typically used because they generally permit greater transcription and higher yields of the desired protein as compared to the native promoter.

The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus, and Simian Virus 40 (SV40). The promoter may also be, for example, a heterologous mammalian promoter, for example, the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system. In some embodiments, the promoter is a dendritic cell-specific promoter. The dendritic cell-specific promoter can be, for example, CD11c promoter.

Transcription may be increased by inserting an enhancer sequence into the vector(s). Enhancers are typically cis-acting elements of DNA, usually about 10 to 300 base pairs in length, that act on a promoter to increase its transcription. Many enhancer sequences are now known from mammalian genes (globin, elastase, albumin, alpha-fetoprotein, and insulin) and from eukaryotic cell viruses. Examples include the SV40 enhancer on the late side of the replication origin (base pair 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence, but is preferably located at a site 5' from the promoter.

Expression vectors may also contain sequences necessary for the termination of transcription and for stabilizing the mRNA. These sequences are often found in the 5' and, occasionally 3', untranslated regions of eukaryotic or viral DNAs or cDNAs and are well known in the art.

A recombinant expression construction, including a viral vector genome, may also contain additional genetic elements. The types of elements that may be included in the construct are not limited in any way and may be chosen to achieve a particular result. For example, a signal that facilitates nuclear entry of the recombinant expression vector or viral genome in the target cell may be included. An example of such a signal is the HIV-1 flap signal. Additional regulatory sequences may be included that facilitate the characterization of the provirus integration site in the target cell. For example, a tRNA amber suppressor sequence may be included in the construct. An insulator sequence, for example from chicken β-globin, may also be included in the viral genome construct. This element reduces the chance of silencing an integrated provirus in the target cell due to methylation and heterochromatinization effects. In addition, the insulator may shield the internal enhancer, promoter and exogenous polynucleotide sequences from positive or negative positional effects from surrounding DNA at the integration site on the chromosome. In addition, the recombinant construct, including the vector genome, may contain one or more genetic elements designed to enhance expression of the gene of interest. For example, a woodchuck hepatitis virus responsive element (WRE) may be placed into the construct (see, e.g., Zufferey et al. 1999. J. Virol. 74:3668-81; Deglon et al., 2000. Hum Gene Ther. 11:179-90).

When the recombinant expression vector is a viral vector genome, the viral vector genome is typically constructed in a plasmid form that may be transfected into a packaging or producer cell line for production of the viral vector genome construct. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance. Typical bacterial drug resistance products are those that confer resistance to ampicillin or tetracycline.

In certain configurations, recombinant expression vectors contain polynucleotide sequences that encode dendritic cell (DC) maturation/stimulatory factors. Exemplary stimulatory molecules include GM-CSF, IL-2, IL-4, IL-6, IL-7, IL-15, IL-21, IL-23, TNFα, B7.1, B7.2, 4-1BB, CD40 ligand (CD40L), drug-inducible CD40 (iCD40), and the like. These polynucleotides are typically under the control of one or more regulatory elements that direct the expression of the coding sequences in dendritic cells. In certain other particular embodiments, a recombinant expression vector is excluded that directs expression of and includes a nucleotide sequence that encodes both an immunogen and GM-CSF. Maturation of dendritic cells contributes to successful vaccination (see, e.g., Banchereau et al., Nat. Rev. Immunol. 5:296-306 (2005); Schuler et al., Curr. Opin. Immunol. 15:138-147 (2003); Figdor et al., Nat. Med. 10:475-480 (2004)). Maturation can transform DCs from cells actively involved in antigen capture into cells specialized for T cell priming For example, engagement of CD40 by CD40L on CD4-helper T cells is a critical signal for DC maturation, resulting in potent activation of CD8+ T cells. Such stimulatory molecules are also referred to as maturation factors or maturation stimulatory factors Immune checkpoints represent significant barriers to activation of functional cellular immunity in cancer, and antagonistic antibodies specific for inhibitory ligands on T cells including CTLA4 and programmed death-1 (PD-1) are examples of targeted agents being evaluated in the clinics A significant tolerance mechanism in chronic infections and cancer is the functional exhaustion of antigen-specific T cells that express high levels of PD-1. As the potency of therapeutic immunization has been shown to be significantly enhanced by combination with immune checkpoint control, as a non-limiting example, it can be appreciated by those of ordinary skill in the art that an alternative approach to inhibiting immune checkpoint is to inhibit the expression of programmed death (PD)

ligands one and two (PD-L1/L2). One way to accomplish inhibition is by the expression of RNA molecules such as those described herein, which repress the expression of PD-L1/L2 in the DCs transduced with a viral vector genome, such as the lentivirus vector genome, encoding one or more of the relevant molecules. Maturation of DCs or expression of particular elements such as immune checkpoints, for example PD-1 ligands, can be characterized by flow cytometry analysis of up-regulation of surface marker such as MHC II, and by profiling expressed chemokines and cytokines, for example, by performing techniques and methods described herein.

A sequence encoding a detectable product, usually a protein, can be included to allow for identification of cells that are expressing the desired immunogen. For example, a fluorescent marker protein, such as green fluorescent protein (GFP), is incorporated into the recombinant expression construct along with a polynucleotide sequence of interest (i.e., encoding an at least one immunogen). In other instances, the protein may be detectable by an antibody, or the protein may be an enzyme that acts on a substrate to yield a detectable product, or may be a protein product that allows selection of a transfected or transduced target cell, for example confers drug resistance, such as hygromycin resistance. Typical selection genes encode proteins that confer resistance to antibiotics or other toxins suitable for use in eukaryotic cells, for example, neomycin, methotrexate, blasticidine, among others known in the art, or complement auxotrophic deficiencies, or supply critical nutrients withheld from the media. The selectable marker can optionally be present on a separate plasmid and introduced by co-transfection.

With respect to vector particles described herein, one or more multicistronic expression units may be used that include two or more of a polynucleotide sequence encoding an immunogen, and a sequence encoding an envelope molecule as described herein or one or more DC maturation factors necessary for production of the desired vector particle in packaging cells. The use of multicistronic vectors reduces the total number of nucleic acid molecules required and thus may avoid the possible difficulties associated with coordinating expression from multiple vector genomes. In a multicistronic vector the various elements to be expressed are operatively linked to one or more promoters (and other expression control elements as necessary). In some configurations, a multicistronic vector comprises a sequence encoding an at least one immunogen (i.e., one or more) of interest, a sequence encoding a reporter product, and a sequence encoding one or more vector particle components. In certain embodiments in which the recombinant construct comprises a polynucleotide that encodes an immunogen, the construct optionally encodes a DC maturation factor. In certain other embodiments, a multicistronic vector comprises a polynucleotide sequences that encode each of an immunogen, a DC maturation factor, and optionally viral components when the expression vector is a viral expression vector. In still other embodiments, multicistronic vectors direct expression and encode at least two or more immunogens.

Each component to be expressed in a multicistronic expression vector may be separated, for example, by an internal ribosome entry site (IRES) element or a viral 2A element, to allow for separate expression of the various proteins from the same promoter. IRES elements and 2A elements are known in the art (see, e.g., U.S. Pat. No. 4,937,190; de Felipe et al. 2004. Traffic 5: 616-626). In one embodiment, oligonucleotides such as furin cleavage site sequences (RAKR) (see, e.g., Fang et al. 2005 Nat. Biotech. 23: 584-590) linked with 2A-like sequences from foot-and-mouth diseases virus (FMDV); equine rhinitis A virus (ERAV); and thosea asigna virus (TaV) (see, e.g., Szymczak et al. 2004 Nat. Biotechnol. 22: 589-594) are used to separate genetic elements in a multicistronic vector. The efficacy of a particular multicistronic vector can readily be tested by detecting expression of each of the genes using standard protocols.

In a specific exemplification, a viral vector genome comprises: a cytomegalovirus (CMV) enhancer/promoter sequence; the R and U5 sequences from the HIV 5' LTR; a packaging sequence (ψ); the HIV-1 flap signal; an internal enhancer; an internal promoter; a gene of interest; the woodchuck hepatitis virus responsive element; a tRNA amber suppressor sequence; a U3 element with a deletion of its enhancer sequence; the chicken β-globin insulator; and the R and U5 sequences of the 3' HIV LTR. In some exemplifications, the vector genome comprises an intact lentiviral 5' LTR and a self-inactivating 3' LTR (see, e.g., Iwakuma et al. Virology 15:120, 1999).

Construction of the vector genome can be accomplished using any suitable genetic engineering techniques known in the art, including, without limitation, the standard techniques of restriction endonuclease digestion, ligation, transformation, plasmid purification, and DNA sequencing, for example as described in Sambrook et al. (1989 and 2001 editions; Molecular Cloning: A Laboratory Manual, Cold Spring Harbor Laboratory Press, NY); Coffin et al. (Retroviruses. Cold Spring Harbor Laboratory Press, N.Y. (1997)); and "RNA Viruses: A Practical Approach" (Alan J. Cann, Ed., Oxford University Press, (2000), each of the foregoing which is incorporated herein by reference in its entirety.

Vectors constructed for transient expression in mammalian cells may also be used. Transient expression involves the use of an expression vector that is able to replicate efficiently in a host cell, such that the host cell accumulates many copies of the expression vector and, in turn, synthesizes high levels of a the polypeptide encoded by the immunogen-specific polynucleotide in the expression vector. See Sambrook et al., supra, pp. 16.17-16.22, 1989. Other vectors and methods suitable for adaptation to the expression of polypeptides are well known in the art and are readily adapted to the specific circumstances.

By using the teachings provided herein and the knowledge in the art, a person skilled in the art will recognize that the efficacy of a particular expression system can be tested by transfecting packaging cells with a vector comprising a polynucleotide sequence encoding a reporter protein and measuring the expression using a suitable technique, for example, measuring fluorescence from a green fluorescent protein conjugate. Other suitable reporter genes are well known in the art.

A recombinant expression vector that comprises a polynucleotide sequence that encodes an immunogen may be used for production of the immunogen. Recombinant expression vectors include at least one regulatory expression sequence, such as a promoter or enhancer, that is operatively linked to the polynucleotide encoding the immunogen. Each of the expression vectors may be used to transform, transducer, or transfect an appropriate host cell for recombinant production of a respective immunogen. Suitable host cells for production of the immunogen include prokaryotes, yeast and higher eukaryotic cells (e.g., CHO and COS). The immunogen may each be isolated from the respective host cell or host cell culture using any one of a variety of isolation methods (e.g., filtration, diafiltration, chromatography (including affinity chromatography, high pressure liquid chromatography), and preparative electrophoresis) known and routinely practiced in the protein art. In certain embodiments, as described herein, the isolated immunogen may then be formulated with a pharmaceutically suitable excipient to provide an immunogenic composition.

Particular methods for producing polypeptides recombinantly are generally well known and routinely used. For example, molecular biology procedures are described by Sambrook et al. (Molecular Cloning, A Laboratory Manual, 2nd ed., Cold Spring Harbor Laboratory, New York, 1989; see also Sambrook et al., 3rd ed., Cold Spring Harbor Laboratory, New York, (2001)). DNA sequencing can be performed as described in Sanger et al. (Proc. Natl. Acad. Sci. USA 74:5463 (1977)) and the Amersham International plc sequencing handbook and including improvements thereto.

Vector Particles

In another embodiment, vector particles are provided. A vector particle comprises any one of the recombinant expression vectors described herein that comprise a polynucleotide sequence encoding at least one immunogen. In certain other embodiments, a vector particle comprises a recombinant expression system that comprises one recombinant expression vector (also called a first recombinant expression vector) comprising a polynucleotide sequence encoding at least one immunogen that induces a specific immune response. Also provided herein are methods for delivering a polynucleotide encoding at least one immunogen (as described herein) to a target cell. In particular embodiments, the target cell is an immune cell that is an antigen-presenting cell; in more specific embodiments and as described herein, the target cell is a dendritic cell. Such methods comprise contacting (i.e., permitting interaction) of the target cell with a vehicle that delivers the polynucleotide. As described herein, the recombinant expression vector may be multicistronic, encoding and directing expression of at least two immunogens. In particular embodiments, described in detail herein, methods for delivering the polynucleotide comprise contacting the cell by administering to a subject a vector particle that comprises a recombinant expression vector that contains a polynucleotide sequence that encodes the immunogen. The vector particles, recombinant expression vectors, polynucleotides, and immunogens are discussed in greater detail herein.

In certain embodiments, the vector particle is a viral vector particle and in other certain embodiments, the vector particle is a particle derived from a bacteria such as, for example, *Listeria monocytogenes, Salmonella* spp., *Mycobacterium bovis, Escherichia coli, Shigella* spp., and *Yersinia* spp. (see, e.g., Paterson, Semin Immunol (2010) 22:183; Loessner, Expert Opin. Biol. Ther. (2004) 4:157; Daudel, Expert Rev. Vaccines (2007) 6:97). Exemplary viral vector particles include a lentiviral vector particle that comprises a lentiviral vector genome; a poxvirus vector particle that comprises a poxvirus vector genome; a vaccinia virus vector particle that comprises a vaccinia virus vector genome; an adenovirus vector particle that comprises a adenovirus vector genome; an adenovirus-associated virus vector particle that comprises a adenovirus-associated virus vector genome; a herpes virus vector particle that comprises a herpes virus vector genome (e.g., Herpes simplex virus I or II); or an alpha virus vector particle that comprises an alpha virus vector genome.

In a more particular embodiment, the vector particle is a lentiviral vector particle that comprises a lentiviral vector genome (which is described in detail above). Methods and compositions are provided herein for targeting cells and targeting dendritic cells (DCs) in particular by using a lentiviral vector particle (which may also be called a virion, a lentivirus particle) for delivering a sequence that encodes at least one immunogen to DCs. The lentiviral vector particle comprises an envelope glycoprotein variant derived from Sindbis virus E2, and a recombinant expression construct that comprises the genome that includes the sequences of interest, and optionally other components. The glycoprotein variant exhibits reduced binding to heparan sulfate compared to the glycoprotein from HR, a reference Sindbis virus strain. The envelope glycoprotein facilitates infection of dendritic cells by the lentiviral vector particles. "Facilitates" infection, as used herein, is the same as facilitates transduction and refers to the role of the envelope glycoprotein, acting alone or in concert with other molecules, in promoting or enhancing receptor-mediated entry of a pseudotyped retrovirus or lentivirus particle into a target cell.

In general, the lentiviral vector particles are produced by a cell line that contains one or more plasmid vectors and/or integrated elements that together encode the components necessary to generate functional vector particles. These lentiviral vector particles are typically not replication-competent, i.e., they are only capable of a single round of infection. Most often, multiple plasmid vectors or individual expression cassettes integrated stably into the producer cell chromosome are utilized to separate the various genetic components that generate the lentiviral vector particles; however, a single plasmid vector having all of the lentiviral components can be used. In one exemplification, the packaging cell line is transfected with one or more plasmids containing the viral vector genome, including LTRs, a cis-acting packaging sequence, and the sequences of interest (i.e., at least a nucleotide sequence encoding one immunogen), at least one plasmid encoding the virus enzymatic and structural components (e.g., gag and pol), and at least one plasmid encoding an Arbovirus envelope glycoprotein. Viral particles bud through the cell membrane and comprise a core that includes typically two RNA genomes containing the sequences of interest and an Arbovirus envelope glycoprotein that targets dendritic cells. In certain embodiments, the Arbovirus glycoprotein is a Sindbis virus E2 glycoprotein, and the glycoprotein is engineered to have reduced binding to heparan sulfate compared to E2 from the reference strain HR. This usually involves at least one amino acid change compared to the HR E2 glycoprotein sequence. As well, the E2 glycoprotein may be engineered to increase targeting specificity to dendritic cells.

Without wishing to be bound by theory, binding of the viral particle to a cell surface is believed to induce endocytosis, bringing the virus into an endosome, triggering membrane fusion, and allowing the virus core to enter the cytosol. For certain embodiments, which utilize integrating lentiviral vector particles, following reverse transcription and migration of the product to the nucleus, the genome of the virus integrates into the target cell genome, incorporating the sequences of interest into the genome of the target cell. To reduce the chance of insertional mutagenesis and to promote transient expression of a designated immunogen(s), however, other embodiments utilize non-integrating lentiviral vector particles (i.e., those which do not integrate into the target cell genome), but instead express the sequences of interest from an episome. In either instance, the infected DC then expresses the sequences of interest (e.g., an immunogen and optionally a stimulatory molecule). The immunogen can then be processed by dendritic cells and presented to T and B cells, generating an antigen-specific immune response. The specific pathway described above is not required so long as the dendritic cell is able to stimulate an antigen-specific immune response.

The viral particles can be administered to a subject in the immunogenic composition described herein to provide a prophylactic or therapeutic effect. Following infection of dendritic cells and expression of the immunogen product, an immune response is generated to the products.

Dendritic cells (DCs) are essential antigen presenting cells for the initiation and control of immune responses. DCs can develop along two pathways: one pathway is independent of monocytes and the second pathway is derived from monocytes (Mo-DCs). Blood monocytes, upon culture with GM-CSF and IL-4 acquire a dendritic morphology and strong capacities to initiate adaptive immunity (see, e.g., Bender et al., J. Immunol. Methods 196(2):121 (1996); Sallusto et al., J. Exp. Med. 179(4), 1109 (1994), including in vivo in humans (see, e.g., Dhodapkar, et al., J. Clin. Invest 104(2), 173 (1999); Schuler-Thurner, et al., J. Immunol. 165(6):3492 (2000)). A more effective immunogen-specific T cell responses may be achieved by using a vector particle vaccine, in particular a lentiviral vector particle system that efficiently delivers immunogens directly to Mo-DCs in vivo, without the need for ex vivo cellular manipulation. Human Mo-DCs express high levels of two C-type lectin receptors, mannose receptor (MMR) and DC-specific intercellular adhesion molecule-3-grabbing non-integrin (DC-SIGN). As described in greater detail herein, expression of immunogens may be targeted to Mo-DCs using a recombinant lentiviral vector engineered to target DC-SIGN.

A DC-SIGN-targeting envelope, SVGmu, consisting of an engineered Sindbis virus (SIN) glycoprotein that selectively binds DC-SIGN has been modified as described (see description herein and U.S. patent application Ser. No. 12/842,609; International Patent Application Publication No. WO 2011/011584). The lentiviral vector induced highly functional CD8 T cell immune responses after a single immunization in mice (see, e.g., Dai, et al., Proc. Natl. Acad. Sci. U.S.A (2009); Yang, et al., Nat. Biotechnol. 26(3), 326 (2008)). This prototype has been significantly advanced by two major modifications. The lentiviral vector described herein comprises a glycoprotein envelope (termed SINvar1) based on native SIN, an arbovirus known to infect dermal DCs via the DC-SIGN receptor (see, e.g., Gardner, et al., J. Virol. 74(24), 11849 (2000); Klimstra, et al., J. Virol. 77(22), 12022 (2003)) that is modified to prevent binding to ubiquitous heparan sulfate receptors (see, e.g., Klimstra et al., J. Virol. 72(9), 7357 (1998)). The SINvar1 envelope confers both increased productivity and in vivo function compared with the parental SVGmu envelope. The vector is also redundantly integration incompetent through the combination of a mutant Integrase (polD64V), rendering it non-functional (see, e.g., Apolonia, et al., Mol. Ther. 15(11), 1947 (2007)), and a vector backbone deleted of the U3 region of the LTR (up to att) and the 3' LTR poly-purine tract (PPT). Thus, in addition to a disabled Integrase, the composition of the vector backbone prevents transcription of the full-length vector genome (self-inactivating mutation) resulting in single-LTR reverse transcribed episomal dsDNA circles in the infected DC, which are not a template for chromosomal integration (see, e.g., Bayer, et al., Mol. Ther. 16(12):1968 (2008); Breckpot et al., J. Virol. (2010); Ma et al., Mol. Ther. 10(1):139 (2004)). Approximately 75% of the parental HIV genome has been removed from DC-NILV, including all of the regulatory and accessory proteins except for Rev. After a single injection, DC-NILV induces highly robust tumor antigen-specific CD8 T cell response. The potency of lentivector vaccination is dependent at least in part on engagement of TLR3 and TLR7 pattern recognition receptors (see, e.g., Beignon et al., J. Virol. (2009); Breckpot et al., supra).

Viral Vector Envelope

Arthropod-borne viruses (Arboviruses) are viruses that are transmitted to a host, such as humans, horses, or birds by an infected arthropod vector such as a mosquito. Arboviruses are further divided into sub-families of viruses including alphaviruses and flaviviruses, which have a single-stranded RNA genome of positive polarity and a glycoprotein-containing envelope. For example, dengue fever virus, yellow fever virus and West Nile virus belong to the flavivirus family, and Sindbis virus, Semliki Forest virus and Venezuelan Equine Encephalitis virus, are members of the alphavirus family (see, e.g., Wang et al., J. Virol. 66, 4992 (1992)). The envelope of Sindbis virus includes two transmembrane glycoproteins (see, e.g., Mukhopadhyay et al. Nature Rev. Microbiol. 3, 13 (2005)): E1, believed to be responsible for fusion, and E2, believed to be responsible for cell binding. Sindbis virus envelope glycoproteins are known to pseudotype other retroviruses, including oncoretroviruses and lentiviruses.

As discussed herein, an arbovirus envelope glycoprotein can be used to pseudotype a lentiviral-based vector genome. A "pseudotyped" lentivirus is a lentiviral particle having one or more envelope glycoproteins that are encoded by a virus that is distinct from the lentiviral genome. The envelope glycoprotein may be modified, mutated or engineered as described herein.

The envelope of Sindbis virus and other alphaviruses incorporates into the lipid bilayer of the viral particle membrane, and typically includes multiple copies of two glycoproteins, E1 and E2. Each glycoprotein has membrane-spanning regions; E2 has an about 33 residue cytoplasmic domain whereas the cytoplasmic tail of E1 is very short (about 2 residues). Both E1 and E2 have palmitic acids attached in or near the membrane-spanning regions. E2 is initially synthesized as a precursor protein that is cleaved by furin or other Ca2+-dependent serine proteinase into E2 and a small glycoprotein called E3. Located between sequences encoding E2 and E1 is a sequence encoding a protein called 6K. E3 and 6K are signal sequences which serve to translocate the E2 and E1 glycoproteins, respectively, into the membrane. In the Sindbis virus genome, the coding region for Sindbis envelope proteins includes sequence encoding E3, E2, 6K, and E1. As used herein, "envelope" of an arbovirus virus includes at least E2, and may also include E1, 6K, and E3. An exemplary sequence of envelope glycoproteins of Sindbis virus, strain HR, is presented as SEQ ID NO:17. In certain particular alternative embodiments, an E3/E2 glycoprotein, wherein the E3 sequence corresponds to residues 1-65 of SEQ ID NO:20, or a variant thereof and wherein residues 62-65 are RSKR (SEQ ID NO: 27), may be incorporated into a pseudotyped viral envelope. Sequences of envelope glycoproteins for other arboviruses can be found in publically available databases, such as GenBank. For example, sequences encoding Dengue virus glycoproteins can be found in Accession GQ252677.1 (among others in GenBank) and in the virus variation database at NCBI (GenBank accessions and virus variation database are incorporated by reference for envelope glycoprotein sequences) and an exemplary sequence encoding Venezuelan equine encephalitis virus envelope glycoproteins in Accession NP_040824.1 (incorporated by reference for sequences of envelope glycoproteins).

Although the cellular receptor(s) on dendritic cells for alphaviruses, and Sindbis virus in particular, have not been definitively identified to date, one receptor appears to be DC-SIGN (see, e.g., Klimstra et al., J. Virol. 77:12022, 2003). The use of the terms "attachment," "binding," "targeting" and the like are used interchangeably and are not meant to indicate a mechanism of the interaction between Sindbis virus envelope glycoprotein and a cellular component. DC-SIGN (Dendritic Cell Specific ICAM-3 (Intracellular Adhesion Molecules 3)-Grabbing Nonintegrin; also known as CD209) is a C-type lectin-like receptor capable of rapid binding and endocytosis of materials (see, e.g., Geijtenbeek et al. Annu. Rev. Immunol. 22: 33-54, 2004). E2 appears to target virus to dendritic cells through DC-SIGN. As shown herein, cells expressing DC-SIGN are transduced by viral vector particles pseudotyped with Sindbis virus E2 better (at least 2-fold, at least 3-fold, at least 4-fold, at least 5-fold, at least 6-fold, at least 7-fold, at least 8-fold, at least 9-fold, or at least 10-fold better) than isogenic cells that do not express DC-SIGN. The mechanism of how E2 glycoprotein facilitates viral infection appears to involve DC-SIGN, possibly through direct binding to DC-SIGN or causing a change in conformation or some other mechanism. Regardless of the actual mechanism, the targeting by E2 is preferential for cells expressing DC-SIGN, namely dendritic cells.

Sindbis virus also appears to bind to cells via heparan sulfate (see, e g , Klimstra et al., J. Virol. 72: 7357, 1998; Burmes et al., J. Virol. 72: 7349, 1998). Because heparan sulfate and other cell surface glycosaminoglycans are found on the surface of most cell types, it is desirable to reduce interaction between heparan sulfate and Sindbis envelope glycoproteins. This can be accomplished by diminishing the binding of Sindbis virus envelope to heparan sulfate or increasing the binding, e.g., increasing avidity, of Sindbis virus envelope to dendritic cells or both. As a result, nonspecific binding to other molecules, which may be expressed by other cell types and which may occur even if the envelope is specific for DC-SIGN, is reduced, and the improved specificity may serve to avoid undesired side effects, such as side effects that may reduce the desired immune response, or side effects associated with off-target transduction of other cell types. Alternatively or in addition to the advantages of relatively specific transduction of cells expressing DC-SIGN, viral particles pseudo-typed with Sindbis virus envelope E2 glycoprotein may offer other advantages over viral particles pseudo-typed with glycoproteins such as VSV-G. Examples of such advantages include reduced complement-mediated lysis and/or reduced neuronal cell targeting, both of which are believed to associate with administration of VSV-G pseudo-typed viral particles.

In various exemplifications, the lentiviral vector particles specifically bind to cells expressing DC-SIGN and have reduced or abrogated binding to heparan sulfate. That is, a Sindbis virus envelope E2 glycoprotein may be modified to preferentially direct the virus to dendritic cells that express DC-SIGN relative to other cell types. Based on information obtained from structural studies and molecular modeling among other studies, variant sequences of envelope proteins, especially E2 and E1 glycoproteins, are designed and generated such that the glycoproteins maintain their functions as envelope proteins, but have the desired binding specificity, avidity, or level of binding. Candidate variant sequences may be created for each glycoprotein and assayed using the methods described below, or other methods known in the art, to identify envelope glycoproteins with the most desirable characteristics.

Certain variant sequences of Sindbis E2 have at least one amino acid alteration at residue 160 as compared to SEQ ID NO:1. Residue 160 is deleted or changed to an amino acid other than glutamic acid. An alteration is most commonly a substitution of at least one amino acid, but alternatively can be an addition or deletion of one or more amino acids. Preferably, any additional amino acids are few in number and do not comprise an antigenic epitope (e.g., hemagglutinin tag sequence), which may compromise safety. When there are two or more alterations, they can both be of the same type (e.g., substitution) or differing types (e.g., a substitution and a deletion). Multiple alterations can be scattered or located contiguously in the protein sequence.

By way of example, variant sequences comprise at least one amino acid alteration in the region of about residue 50 to about residue 180 of SEQ ID NO:1. Within this region are amino acids that are involved with binding to heparan sulfate. By reducing the net positive charge of E2, electrostatic interaction with heparan sulfate can be reduced, resulting in decreased binding to heparan sulfate. Candidate positively charged amino acids in this region include lysines at residues 63, 70, 76, 84, 97, 104, 129, 131, 133, 139, 148, 149, 159 and arginine at residues 65, 92, 128, 137, 157, 170, 172 (see, e.g., Bear et al., Virology 347: 183-190, 2006) (see SEQ ID NO:1). At least several of these amino acids are directly implicated in E2 binding to heparan sulfate. Net positive charge can be reduced by deletion of lysine or arginine or substitution of lysine or arginine with a neutral or negatively charged amino acid. For example, one or more of these lysines and arginines may be replaced with glutamic or aspartic acid. Certain embodiments have at least one substitution of lysine 70, 76 or 159. Exemplary amino acid sequences of the E2 glycoprotein are set forth in SEQ ID NOS:3-16. In cases where E2 is expressed as a polyprotein with E3, the lysine located adjacent to the natural E3/E2 cleavage site is maintained—that is, the recognition sequence and cleavage site is unaltered. Alternatively, the native endopeptidase cleavage site sequence is replaced with a recognition sequence for a different endopeptidase.

Certain variants of E2 are also modified in a way that positively impacts binding to dendritic cells. Alteration of the glutamic acid found at residue 160 in the reference HR sequence can improve binding to dendritic cells (see, e.g., Gardner et al., J. Virol. 74, 11849, 2000). Alterations, such as a deletion of residue 160 or substitution of residue 160 are found in certain variants. In particular variants, a non-charged amino acid is substituted for Glu, in other variants, a non-acidic amino acid is substituted for Glu. Typically, Glu160 is replaced with one of the small or aliphatic amino acids, including glycine, alanine, valine, leucine or isoleucine.

Other variants comprise two or more amino acid alterations. Typically in these variants one of the alterations is Glu160 and the remaining alteration(s) are changes of one or more of the lysines and arginines in the region spanning residue about 50 to about 180 of SEQ ID NO:1. Certain of the variants comprise an alteration of Glu160 to a non-acidic residue or deletion and one or more alterations of lysine 70, lysine 76, or lysine 159 with a non-basic amino acid. Some specific variants comprise a Glu160 to Gly, Lys 70 to Glu, and Lys 159 to Glu; a Glu 160 to Gly, Lys 70, 76 and 159 to Glu; a deletion of Glu 160 and Lys 70 and 159 to Glu; and a deletion of Glu 160 and Lys 70, 76, and 159 to Glu. (See, e.g., SEQ ID NOS:3-16.)

In certain embodiments, E2 protein is first expressed as a polyprotein in fusion with at least E3 or in fusion with a leader sequence. Regardless of whether the leader sequence is E3 or another sequence, E2 in the viral envelope should be free of the E3 or other leader sequence. In other words, E2 is preferably not an E3/E2 fusion protein (e.g., the E3/E2 fusion protein called SVGmu). In certain embodiments, E2 is expressed as part of E3-E2-6K-E1 polyprotein. Sindbis virus naturally expresses E2 as part of a polyprotein and the junction regions for E3/E2, E2/6K, and 6K/E1 have sequences recognized and cleaved by endopeptidases. Normally, the E3/E2 junction is cleaved by furin or a furin-like serine endopeptidase between residues 65 and 66. Furin has specificity for paired arginine residues that are separated by two amino acids. To maintain E3/E2 cleavage by furin, residues 62-66 (RSKRS; SEQ ID NO: 26) should maintain the two arginine residues with two amino acid separation and the serine residue. Alternatively, a different cleavage sequence can be used in place of the E3/E2 furin cleavage sequence or any of the other cleavage sequences. Recognition and cleavage sites can be incorporated for endopeptidases, including, without limitation, aspartic endopeptidases (e.g., cathepsin D, chymosin, HIV protease), cysteine endopeptidases (bromelains, papain, calpain), metalloendopeptidases, (e.g., collagenase, thermolysin), serine endopeptidases (e.g., chymotrypsin, factor IXa, factor X, thrombin, trypsin), streptokinases. The recognition and cleavage site sequences for these enzymes are well known.

Amino acids in E2, other than those already mentioned, may also be altered. Generally, a variant E2 sequence will have at least 80% sequence amino acid identity to the reference E2 sequence, or it may have at least 82%, at least 85%, at least 87%, at least 90%, at least 92%, at least 95%, or at least 98% sequence identity. The variant glycoprotein should exhibit biological function, such as the ability to facilitate infection of dendritic cells by a viral particle having an envelope comprising E2. Experiments have identified regions of envelope glycoproteins that appear to have an important role in various aspects of viral assembly, attachment to cell surface, and infection. When making variants, the following information can be used as guidelines. The cytoplasmic tail of E2—approximately residues 408 to 415—is important for virus assembly (see, e.g., West et al. J. Virol. 80: 4458-4468, 2006; incorporated in its entirety). Other regions are involved in forming secondary structure (approximately residues 33-53), and involved in transport and protein stability (approximately residues 86-119) (see, e.g., Navaratmarajah et al., J. Virol. 363:124-147, 2007; incorporated in its entirety). The variant may retain hydrophobic character of a region that spans the membrane, approximately residues 370-380. The variant may retain one or both N-linked glycosylation sites residues NIT (residues 196-198) and NFT (residues 318-320) and may retain one or more of the sites that are palmitoylated (C-396, C416 and C417) (see, e.g., Strauss et al., Microbiol. Rev. 58, 491-562, 1994; pp. 499-509 incorporated herein by reference in its entirety). On the other hand, many regions of E2 may be altered without deleterious event. For example, insertions of transposons at many different locations in E2 still resulted in viable virus (see, e.g., Navaratmarajah, supra).

In certain embodiments, a tag peptide may be incorporated into E3, 6K, or E1 proteins. For some purposes, a tag may be incorporated into E2, but a tag is not desirable for use in a product for administration to human patients. A tag peptide, which is a short sequence (e.g., 5-30 amino acids), can be used to facilitate detection of envelope expression and its presence in viral particles. For detection purposes, a tag sequence will typically be detectable by antibodies or chemicals. Another use for a tag is to facilitate purification of viral particles. A substrate containing a binding partner for the tag can be used to absorb virus. Elution of the virus can be accomplished by treatment with a moiety that displaces the tag from the binding partner or when the tag sequence is in linkage with a cleavable sequence, treatment with the appropriate endopeptidase will conveniently allow release of virus. (See, for example, QiaGEN® catalog, Factor Xa Protease System). Removal of the tag peptide is generally desirable for safety purposes of the virus particles use in animal subjects. If the tag is not removed, an immune response to the tag may occur.

Suitable tags include, without limitation, FLAG (DYKDDDDK) (SEQ ID NO:35) (U.S. Pat. No. 4,703,004, incorporated in its entirety), for which antibodies are commercially available, chitin binding protein, maltose binding protein, glutathione-S-transferase, poly(His) (U.S. Pat. No. 4,569,794, incorporated in its entirety), thioredoxin, HA (hemagglutinin)-tag, among others. Poly(His) can be adsorbed onto affinity media containing bound metal ions, such as, nickel or cobalt, and eluted with a low pH medium The vector particles may be evaluated to determine the specificity of the envelope glycoprotein incorporated into the virus that targets dendritic cells. For example, a mixed population of bone marrow cells can be obtained from a subject and cultured in vitro. Alternatively, isogenic cells lines that express or do not express DC-SIGN can be obtained and used. The recombinant virus can be administered to the mixed population of bone marrow cells or isogenic cell lines, and expression of a reporter gene incorporated into the virus can be assayed in the cultured cells. Certain embodiments may employ a limiting dilution analysis, in which the mixed population of cells is split into separate parts, which are then separately incubated with decreasing amounts of virus (e.g., 2-fold, 5-fold, 10-fold less virus in each part). In some embodiments, at least about 50%, or at least about 60%, 70%, 80% or 90%, or at least about 95% of infected cells in the mixed cell population are dendritic cells that express DC-SIGN. In certain embodiments, the ratio of infected dendritic cells to infected non-dendritic cells (or non DC-SIGN expressing cells) is at least about 2:1, at least about 3:1, at least about 4:1, at least about 5:1, at least about 6:1, at least about 7:1, at least about 8:1, at least about 9:1, at least about 10:1, at least about 20:1, at least about 30:1, at least about 40:1, at least about 50:1, at least about 100:1, at least about 200:1, at least about 500:1, at least about 1000:1, at least about 5000:1, at least about 10,000:1, or more. For limiting dilution, greater selectivity is typically seen at higher dilutions (i.e., lower amounts) of input virus.

Activity of pseudotyped viral particles can be determined by any of a variety of techniques. For example, a preferred method to measure infectivity efficiency (IU, infectious units) is by administering viral particles to cells and measuring expression of a product encoded in the vector genome. Any product that can be assayed may be used. One convenient type of product is a fluorescent protein, such as green fluorescent protein (GFP). Other products that can be used include proteins expressed on a cell surface (e.g., detection by antibody binding), enzymes, and the like. If the product is an antigen and cells are dendritic cells, infectivity / activity can be assessed by determining an immune response. Furthermore, it is possible to ascertain side effects in a mammal The ability to specifically target dendritic cells can also be tested directly, for example, in cell culture as described below.

Vector particles, which include the viral particles described herein can also be prepared and tested for their selectivity and/or their ability to facilitate penetration of the target cell membrane. Viral particles that have an envelope with unmodified glycoproteins can be used as controls for comparison. Briefly, cells expressing a receptor for an envelope glycoprotein are infected by the virus using a standard infection assay. After a specified time, for example 48 hours post-infection, cells can be collected and the percentage of cells infected by the virus can be determined by flow cytometry, for example. Selectivity can be scored by calculating the percentage of cells infected by virus. Similarly, the effect of a variant envelope glycoprotein on viral titer can be quantified by dividing the percentage of cells infected by virus comprising a variant envelope by the percentage of cells infected by virus comprising the corresponding wild type (unmodified) envelope glycoprotein. A particularly suitable variant will have the best combination of selectivity and infectious titer. Once a variant is selected, viral concentration assays may be performed to confirm that these viruses can be concentrated without compromising activity. Viral supernatants are collected and concentrated by ultracentrifugation. The titers of viruses can be determined by limited dilution of viral stock solution and infection of cells expressing the receptor for the envelope glycoprotein, measuring the expression of a product expressed by the viruses as described above.

The entry of a lentiviral vector particle into a target cell is another type of evaluation of activity. BlaM-Vpr (beta-lactamase Vpr) fusion protein has been used to evaluate HIV-1 viral penetration; a fusion of BlaM and a Sindbis virus envelope glycoprotein, such as E1 or an E2/E1 fusion protein can be used to assess the efficacy of an envelope protein in facilitating fusion and penetration into a target cell. Viral particles may be prepared, for example, by transient transfection of packaging cells with one or more vectors comprising the viral elements, BlaM-Vpr, and the variant envelope of interest (and an affinity molecule if appropriate). The resulting viruses can be used to infect cells expressing a molecule the targeting molecule (or affinity molecule) specifically binds in the absence or presence of the free inhibitor of binding (such as an antibody). Cells can then be washed with CO2-independent medium and loaded with CCF2 dye (Aurora Biosciences, San Diego, Calif.). After incubation at room temperature to allow completion of the cleavage reaction, the cells can be fixed by paraformaldehyde and analyzed by flow cytometry and microscopy. The presence of blue cells indicates the penetration of viruses into the cytoplasm; fewer blue cells would be expected when blocking antibody is added (see, e.g., Cavrois et al., Nat. Biotechnol. 20:1151-54, 2002).

To investigate whether penetration is dependent upon a low pH, and to identify envelope glycoproteins with the desired pH dependence, NH4Cl or other compound that alters pH can be added at the infection step (NH4Cl will neutralize the acidic compartments of endosomes). In the case of NH4Cl, the disappearance of blue cells will indicate that penetration of viruses is low pH-dependent. In addition, to confirm that the activity is pH-dependent, lysosomotropic agents, such as ammonium chloride, chloroquine, concanamycin, bafilomycin Al, monensin, nigericin, etc., may be added into the incubation buffer. These agents elevate the pH within the endosomal compartments (see, e.g., Drose et al., J. Exp. Biol. 200, 1-8, 1997). The inhibitory effect of these agents will reveal the role of pH for viral fusion and entry. The different entry kinetics between viruses displaying different fusogenic molecules may be compared and the most suitable selected for a particular application.

PCR-based entry assays can be utilized to monitor reverse transcription and measure kinetics of viral DNA synthesis as an indication of the kinetics of viral entry. For example, viral particles comprising a particular envelope protein molecule are incubated with target cells, such as 293T cells, DCs, or any other cells that have been engineered to express, or which naturally express, the appropriate binding partner (receptor) for the envelope protein molecule. Either immediately, or after a time increment (to allow infection to occur), unbound viruses are removed and aliquots of the cells are analyzed for viral nucleic acids. DNA is extracted from these aliquots and subjected to amplification analysis, generally in a semi-quantitative assay, primed with LTR-specific primers. The appearance of LTR-specific DNA products indicates the success of viral entry.

Following viral infection with the viral vector particle, the immunogen is expressed by the target dendritic cells. If contacted ex vivo, the target dendritic cells are then transferred back to the patient, for example by injection, where they interact with immune cells that are capable of generating an immune response against the desired antigen. In preferred embodiments, the recombinant virus is injected into the patient where it transduces the targeted dendritic cells in situ. The dendritic cells then express the particular antigen associated with a disease or disorder to be treated, and the patient is able to mount an effective immune response against the disease or disorder.

The viral vector genome may contain a polynucleotide sequence encoding more than one immunogen, and upon transduction of a target dendritic cell, generates immune responses to each immunogen delivered to the cell. In some embodiments, the immunogens are related to a single disease or disorder. In other embodiments, the immunogens are related to multiple diseases or disorders.

In some of the vector particles, DC maturation factors that activate and/or stimulate maturation of the DCs are delivered in conjunction with the immunogen-encoding sequence of interest. In certain alternative embodiments, the DCs are activated by delivery of DC maturation factors prior to, simultaneously with, or after delivery of the vector particles. DC maturation factors may be provided separately from administration of the vector particles.

As described herein, one or more immune modulation or DC maturation factors can be encoded by one or more sequences that are contained in the vector particle and expressed after the particle enters or infects a dendritic cell. The sequences encoding immune modulation factors can also be provided in a separate vector that is co-transfected with the vector particle encoding one or more immunogens in a packaging cell line.

The methods described herein may be used for adoptive immunotherapy in a subject. As described above, an immunogen against which an immune response is desired is identified. A polynucleotide encoding the desired immunogen(s) is obtained and packaged into a vector particle. Target dendritic cells are obtained from the patient and transduced with the vector particle containing a polynucleotide that encodes the desired immunogen. The dendritic cells are then transferred back into the patient.

The vector particles (e.g., the viral vector particles described herein) may be injected in vivo, where the particles infect DCs and deliver the immunogen-encoding nucleotide sequence of interest. The amount of viral particles is at least $3\times10^6$ infectious units (IU), and can be at least $1\times10^7$ IU, at least $3\times10^7$ IU, at least $1\times10^8$ IU, at least $3\times10^8$ IU, at least $1\times10^9$ IU, or at least $3\times10^9$ IU. At selected intervals, DCs from the recipient's lymphoid organs may be used to measure expression, for example, by observing marker expression, such as GFP or luciferase if co-expressed by a polynucleotide sequence present in the recombinant expression vector included in the vector particle. Nucleic acid monitoring techniques and measurements of reverse transcriptase (RT) activity can also be used to analyze the biodistribution of vector particles when the vector particle is a lentiviral vector particle. T cells from peripheral blood mononuclear cells, lymph nodes, spleens, or malignant or target pathogen-infected tissue of vector particle (including lentiviral vector particle) treated recipients may be measured from the magnitude and durability of response to antigen stimulation. Tissue cells other than DCs, such as epithelial cells and lymphoid cells, may be analyzed for the specificity of in vivo gene delivery.

Immune Response

As described herein, methods are provided for inducing an immune response to an immunogen. Cells of the immune system that are involved in an immune response are referred to, generally, as immune cells and include a lymphocyte and a non-lymphoid cell such as accessory cell. Lymphocytes are cells that specifically recognize and respond to foreign antigens, and accessory cells are those that are not specific for certain antigens but are involved in the cognitive and activation phases of immune responses. For example, mononuclear phagocytes (macrophages), other leukocytes (e.g., granulocytes, including neutrophils, eosinophils, basophils), and dendritic cells function as accessory cells in the induction of an immune response. The activation of lymphocytes by a foreign antigen leads to induction or elicitation of numerous effector mechanisms that function to eliminate the antigen. Accessory cells such as mononuclear phagocytes that affect or are involved with the effector mechanisms are also called effector cells.

Major classes of lymphocytes include B lymphocytes (B cells), T lymphocytes (T cells), and natural killer (NK) cells, which are large granular lymphocytes. B cells are capable of producing antibodies. T lymphocytes are further subdivided into helper T cells (CD4+ (also referred to herein and in the art as CD4)) and cytolytic or cytotoxic T cells (CD8+ (also referred to herein and in the art as CD8)). Helper cells secrete cytokines that promote proliferation and differentiation of the T cells and other cells, including B cells and macrophages, and recruit and activate inflammatory leukocytes. Another subgroup of T cells, called regulatory T cells or suppressor T cells actively suppress activation of the immune system and prevent pathological self-reactivity, that is, autoimmune disease.

The methods described herein for inducing an immune response are useful for inducing a cell-mediated immune response involving various types of T cells (i.e., T lymphocytes). In a cell mediated response, the various types of T lymphocytes act to eliminate an antigen by a number of mechanisms. For example, helper T cells that are capable of recognizing specific antigens may respond by releasing soluble mediators such as cytokines to recruit additional cells of the immune system to participate in an immune response. Also, cytotoxic T cells are capable of specifically recognizing an antigen and may respond by binding to and destroying or damaging an antigen-bearing cell or particle. The methods described herein for inducing an immune response may also induce a humoral response, also called a B cell response herein and in the art. A humoral response includes production of antibodies that specifically bind to an antigen (or immunogen). Antibodies are produced by differentiated B lymphocytes known as plasma cells.

Whether an immune response is induced and the type of immune response induced in a host or subject may be determined by any number of well-known immunological methods described herein and with which those having ordinary skill in the art will be familiar. As described herein, methods and techniques for determining the presence and level of an immune response include, for example, fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence, immunoassays, (such as enzyme-linked immunosorbant assays (ELISA), radioimmunoassay, immunoblotting, immunohistochemistry, and the like), surface plasmon resonance, cell-based assays such as those that use reporter genes, and functional assays (e.g., assays that measure immune function and immunoresponsiveness).

Such assays include, but need not be limited to, in vivo or in vitro determination of the presence and level of soluble antibodies, soluble mediators such as cytokines (e.g., IFN-γ, IL-2, IL-4, IL-10, IL-12, IL-6, IL-23, TNF-α, and TGF-β), lymphokines, chemokines, hormones, growth factors, and the like, as well as other soluble small peptide, carbohydrate, nucleotide and/or lipid mediators Immunoassays also include determining cellular activation state changes by analyzing altered functional or structural properties of cells of the immune system, for example, cell proliferation, altered motility, induction of specialized activities such as specific gene expression or cytolytic behavior; cell maturation, such as maturation of dendritic cells in response to a stimulus; alteration in relationship between a Th 1 response and a Th2 response; cellular differentiation by cells of the immune system, including altered surface antigen expression profiles or the onset of apoptosis (programmed cell death). Procedures for performing these and similar assays are may be found, for example, in Lefkovits (Immunology Methods Manual: The Comprehensive Sourcebook of Techniques, 1998). See also Current Protocols in Immunology; Weir, Handbook of Experimental Immunology, Blackwell Scientific, Boston, Mass. (1986); Mishell and Shigii (eds.) Selected Methods in Cellular Immunology, Freeman Publishing, San Francisco, Calif. (1979); Green and Reed, Science 281:1309 (1998) and references cited therein).

Determining the presence and/or level of antibodies that specifically bind to an immunogen and the respective designated antigen of interest may be determined using any one of several immunoassays routinely practiced in the art, including but not limited to, ELISAs, immunoprecipitation, immunoblotting, countercurrent immunoelectrophoresis, radioimmunoassays, dot blot assays, inhibition or competition assays, and the like (see, e.g., U.S. Pat. Nos. 4,376,110 and 4,486,530; Harlow et al., Antibodies: A Laboratory Manual, Cold Spring Harbor Laboratory (1988)) Immunoassays may also be performed to determine the class and isotype of an antibody that specifically binds to an immunogen. Antibodies (polyclonal and/or monoclonal or antigen-binding fragments thereof), which specifically bind to an immunogen and which may be used as controls in immunoassays detecting an antibody-specific immune response in an immunized subject, may generally be prepared by any of a variety of techniques known to persons having ordinary skill in the art. See, e.g., Harlow et al., Antibodies: A Laboratory Manual, Cold Spring Harbor Laboratory (1988); Peterson, ILAR J. 46:314-19 (2005); (Kohler et al., Nature, 256:495-97 (1976); Kohler et al., Eur. J. Immunol. 6:511-19 (1975); Coligan et al. (eds.), Current Protocols in Immunology, 1:2.5.1-2.6.7 (John Wiley & Sons 1991); U.S. Pat. Nos. 4,902,614, 4,543,439, and 4,411,993; Monoclonal Antibodies, Hybridomas: A New Dimension in Biological Analyses, Plenum Press, Kennett et al. (eds.) (1980); Antibodies: A Laboratory Manual, Harlow and Lane (eds.), Cold Spring Harbor Laboratory Press (1988); see also, e.g., Brand et al., Planta Med. 70:986-92 (2004); Pasqualini et al., Proc. Natl. Acad. Sci. USA 101:257-59 (2004). The immunogen, or immunogenic fragments thereof, or a cell or particle bearing the immunogen or immunogenic fragment thereof may be used for immunizing an animal for production of either polyclonal antibodies or monoclonal antibodies.

Levels of cytokines may be determined according to methods described herein and practiced in the art, including for example, ELISA, ELISPOT, intracellular cytokine staining, and flow cytometry and combinations thereof (e.g., intracellular cytokine staining and flow cytometry) Immune cell proliferation and clonal expansion resulting from an antigen-specific elicitation or stimulation of an immune response may be determined by isolating lymphocytes, such as spleen cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-, IL-12, IL-2, and TNF-β, and Type 2 cytokines, such as IL-4, IL-5, IL-9, IL-10, and IL-13.

The level of a CTL immune response and the level of a memory CD4 T cell response may be determined by any one of numerous immunological methods described herein and routinely practiced in the art. The level of a CTL immune response may be determined prior to administration of any one of the compositions, vectors, or vector particles described herein and then used for comparison with the level of CTL immune response at an appropriate time point after one or more administrations of the compositions, vectors, or vector particles that provide memory CD4 T cell help. Cytotoxicity assays for determining CTL activity may be performed using any one of several techniques and methods routinely practiced in the art (see, e.g., Henkart et al., "Cytotoxic T-Lymphocytes" in Fundamental Immunology, Paul (ed.) (2003 Lippincott Williams & Wilkins, Philadelphia, Pa.), pages 1127-50, and references cited therein).

As used herein, a binding partner or an antibody is said to be "immunospecific," "specific for" or to "specifically bind" an immunogen of interest if the antibody reacts at a detectable level with the immunogen or immunogenic fragment thereof, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to about $10^8$ $M^{-1}$. Affinity of an antibody for its cognate antigen is also commonly expressed as a dissociation constant $K_D$, and an antibody specifically binds to the immunogen of interest if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M.

Affinities of binding partners or antibodies can be readily determined using conventional techniques, for example, those described by Scatchard et al. (Ann. N.Y. Acad. Sci. USA 51:660 (1949)) and by surface plasmon resonance (SPR; BIAcore™, Biosensor, Piscataway, N.J.). For surface plasmon resonance, target molecules are immobilized on a solid phase and exposed to a binding partner (or ligand) in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., Cancer Res. 53:2560-2565 (1993)).

A biological sample may be obtained from the subject for determining the presence and level of an immune response to an immunogen and/or the respective designated antigen in the subject who has received any one or more of the immunogenic compositions described herein, such as an immunogenic composition comprising an immunogen and an immunogenic composition comprising a recombinant expression vector comprising a nucleotide sequence encoding the immunogen or who has received both immunogenic compositions, including one or more compositions comprising an adjuvant according to the methods described herein. A "biological sample" as used herein may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from the subject or a biological source. Biological samples may also be obtained from the subject prior to receiving any immunogenic composition, which biological sample is useful as a control for establishing baseline (i.e., pre-immunization) data.

With respect to all immunoassays and methods described herein for determining an immune response, a person skilled in the art will also readily appreciate and understand which controls are appropriately included when practicing these methods. Concentrations of reaction components, types of buffers, temperature, and time periods sufficient to permit interaction of the reaction components can be determined and/or adjusted according to methods described herein and with which persons skilled in the art are familiar Methods of Inducing an Immune Response Methods are provided herein that comprise administering at least two different immunogenic compositions for inducing an adaptive, antigen-specific immune response against one or more antigens. Dual immunization of a subject with the immunogenic compositions as described herein results in induction of a humoral immune response and a cellular immune response (including a CD4 T cell response and a CD8 T cell response). The two immunogenic compositions may be administered concurrently or sequentially in either order. Accordingly, provided herein are methods for inducing a humoral immune response and a cellular response, which comprises a CD4 T cell response and a CD8 T cell response (and which may include a cytotoxic T cell response), wherein each of the immune responses is specific for an immunogen(s) and thereby specific for the respective designated antigen(s). These methods comprise administering an immunogenic composition that comprises at least one immunogen, (which is isolated and/or recombinantly produced), and administering a second immunogenic composition that comprises a recombinant expression vector that encodes and directs expression of the immunogen.

In one embodiment, methods are provided for inducing an immune response specific for one or more designated antigens in a subject by administering an immunogenic composition that comprises at least one immunogen capable of eliciting a specific immune response against a designated antigen (which, for convenience, may be called herein a first designated antigen). The methods further comprise concurrently administering or sequentially administering (i.e., prior to or subsequent to) another (i.e., second, different/heterologous) immunogenic composition that comprises a recombinant expression vector comprising a nucleotide sequence that encodes the immunogen. The recombinant expression vector further comprises at least one regulatory sequence operatively linked to the nucleotide sequence that encodes the immunogen, and, thus, the recombinant expression vector is capable of directing expression of the immunogen.

In certain embodiments, the recombinant expression vector administered according to these methods for inducing an immune response is incorporated into a vector particle (e.g., a virus vector particle or a cell particle). The recombinant expression vector or vector particle comprising the vector is constructed in a manner that enables the particle to be introduced into (i.e., delivered to) a target cell. In certain embodiments, the target cell is an antigen-presenting cell. In more specific embodiments, the target cell is a professional antigen-presenting cell such as a dendritic cell. The immunogen (or a fragment thereof) is then expressed in the target cell, and the immunogen or a fragment thereof is presented on the surface of the antigen-presenting cell and induces an immune response specific for the immunogen and thereby for the respective designated antigen.

The immunogenic composition that comprises at least one immunogen (first immunogenic composition) may further comprise at least one adjuvant that is pharmaceutically or physiologically suitable for administering to the subject in need thereof to whom the immunogenic compositions are administered. The immunogenic composition that comprises a recombinant expression vector (second immunogenic composition) may also further comprise an adjuvant. If both the first composition and the second composition comprise an adjuvant, the adjuvants may be the same or different Immunogens, the respective designated antigens, adjuvants, and recombinant expression vectors and vector particles are discussed in detail herein.

In another embodiment, the immunogenic composition comprising the at least one immunogen (which may further comprise an adjuvant) is first administered followed by administration of the immunogenic composition that comprises the recombinant expression vector concurrently with administration of the immunogenic composition comprising the at least one immunogen (which may further comprise an adjuvant). In other words, the immunogenic composition comprising the at least one immunogen (which may further comprise an adjuvant) is the first or priming immunization and the immunogenic composition that comprises the recombinant expression vector and the second dose of the immunogenic composition comprising the at least one immunogen (which may further comprise an adjuvant) both are administered concurrently as boosting compositions.

In other embodiments, methods are provided for inducing an immune response, wherein the immunogenic composition that comprises at least one immunogen further comprises at least one additional immunogen (or at least a second immunogen). In other embodiments of the methods described herein, the recombinant expression vector that encodes the immunogen and that is included in the second immunogenic composition also encodes and directs expression of at least one additional immunogen. In still another embodiment, the immunogenic composition that comprises at least one immunogen further comprises at least one additional immunogen and the recombinant expression vector included in the other (or second) immunogenic composition encodes and directs expression of at least one additional immunogen. The immunogen included in each of the first and second immunogenic compositions may be the same or different. In particular embodiments, the at least one additional immunogen included in the first composition and encoded by the recombinant expression vector included in the second immunogenic composition are the same. As discussed in detail herein, when more than one immunogen is included in the immunogenic composition or encoded by the recombinant expression vector, each immunogen may induce a specific immune response for the same or different designated antigens.

Accordingly, in one specific embodiment, methods are provided wherein the immunogenic composition that comprises at least one immunogen (and which may further comprise an adjuvant) further comprises at least one additional immunogen (i.e., at least two, at least three, at least four, at least five, at least six or more immunogens which may be restated as two, three, four, five, six or more immunogens)). In certain embodiments, the immunogenic composition that comprises at least two immunogens (e.g., two, three, four, five, six or more immunogens) forms a multivalent immunogenic composition. In instances when the two or more immunogens are combined with an adjuvant, the immunogenic composition may comprise each immunogen formulated separately with an adjuvant and then the adjuvanated immunogens are combined to form the immunogenic composition that is administered to the subject. Alternatively, the two or more immunogens may be combined with an adjuvant and formulated together to form the immunogenic composition. In certain specific embodiments, one or more of each additional immunogen (e.g., the second, third, fourth, fifth, sixth immunogen, etc.) may induce an immune response to the same designated antigen as the first immunogen. In other specific embodiments, each additional immunogen (e.g., second, third, fourth, fifth immunogen, etc.) may induce an immune response specific for a different designated antigen (e.g., a second, third, fourth, fifth, sixth etc. designated antigen), respectively.

As described above, in certain embodiments, methods are provided wherein the recombinant expression vector in an immunogenic composition may be multicistronic and comprise a nucleotide sequence that encodes at least one additional immunogen (i.e., at least two, at least three, at least four, at least five, at least six, or more immunogens which may be restated as two, three, four, five, six or more immunogens)). The recombinant expression vector is constructed to include all appropriate regulatory sequences in frame with the respective nucleotide sequences encoding each immunogen such that each immunogen is expressed in the cell into which the recombinant expression vector is introduced. In certain specific embodiments, one or more of each additional immunogen (e.g., the second, third, fourth, fifth, sixth immunogen, etc.) may induce an immune response to the same designated antigen as the first immunogen. In other specific embodiments, each of the additional immunogens (e.g., the second, third, fourth, fifth, sixth immunogen, etc.) may induce an immune response specific for a different designated antigen (e.g., the second, third, fourth, fifth, sixth designated antigen etc.), respectively.

In other particular embodiments, methods for inducing an immune response are provided wherein the first immunogenic composition comprises at least one isolated/recombinant immunogen (for convenience, called a first immunogen) and may further comprise at least one additional isolated/recombinant immunogen. In other embodiments, the methods comprise administering a second immunogenic composition comprising a recombinant expression vector that encodes the first immunogen and encodes at least one additional immunogen. In a specific embodiment, the first immunogenic composition comprises at least two isolated/recombinant immunogens and the second immunogenic composition comprises a recombinant expression vector that contains a nucleotide sequence that encodes the the at least two immunogens.

When two or more immunogens are included in the immunogenic composition comprising isolated/recombinant immunogens and/or are encoded by a polynucleotide sequence present in the recombinant expression vector, each immunogen may comprise amino acid sequences that include two different immunogenic regions or epitopes of a designated antigen of interest. At least one immunogen may comprise at least one B cell epitope or may comprise a T cell epitope or may comprise amino acid sequences that include both a B cell epitope and a T cell epitope. A second, different immunogen may comprise comprise amino acid sequences that correspond to different B cell and/or T cell epitopes. When two or more immunogens are included in an immunogenic composition (or encoded by a recombinant expression vector), at least one immunogen comprises at least one T cell epitopic region. In more specific embodiments, at least one T cell epitopic region is capable of inducing a CD8 T cell specific immune response to the immunogen and the respective designated antigen.

In certain embodiments, when induction of an immune response specific for two or more immunogens is desired, at least one immunogen is capable of inducing an immune response that comprises at least a specific humoral and/or CD4 T cell response and at least one additional immunogen is capable of inducing an immune response that comprises at least a specific CD8 T cell immune response. Accordingly, provided herein in one embodiment is a method comprising administering to a subject in need thereof (a) an immunogenic composition (which may be called a first immunogenic composition) that comprises a first isolated/recombinant immunogen (which composition may further comprise an adjuvant) and (b) a second immunogenic composition that comprises a recombinant expression vector that encodes and directs expression of the first immunogen and a second immunogen, wherein at least the second immunogen is capable of inducing a specific CD8 T cell response. In certain embodiments, each of the at least two immunogens has the capability to induce an immune response to the same designated antigen. Alternatively, each of the at least two immunogens has the capability to induce an immune response specific for a different designated antigen (for convenience, also called the first and second designated antigens, etc. respectively).

In specific embodiments of the methods described herein, the two different immunogenic compositions are sequentially administered to the subject in need thereof. In one specific embodiment, the method comprises administering the immunogenic composition comprising the at least one isolated/recombinant immunogen (which may further comprise an adjuvant) prior to administration of the immunogenic composition that comprises the recombinant expression vector. Stated in another way, in certain embodiments, the method comprises administering an immunogenic composition comprising the recombinant expression vector subsequent to (i.e., after) administering the immunogenic composition comprising the isolated/recombinant immunogen (which composition may further comprise an adjuvant).

In other embodiments, the immunogenic composition comprising the recombinant expression vector is administered prior to the immunogenic composition comprising the isolated/recombinant immunogen (which composition may further comprise an adjuvant). Stated in another way, in certain embodiments, the method comprises administering the immunogenic composition comprising the at least one immunogen (which may further comprise an adjuvant) subsequent to (i.e., after) administering the immunogenic composition comprising the recombinant expression vector.

Inducing an immune response using the dual immunization methods and immunogenic compositions described herein may be accomplished by employing a variety of different immunization regimens. An exemplary, nonexhaustive list of immunization regimens is presented in FIG. 6. These and additional embodiments of the methods for inducing an adaptive, antigen-specific immune response are described in greater detail below and herein.

In specific embodiments, methods comprise administering the immunogenic composition comprising the isolated/recombinant immunogen (for ease of reference called a first immunogenic composition) and/or the immunogenic composition comprising the recombinant expression vector (for ease of reference called a second immunogenic composition) more than once to the subject. In particular embodiments, the immunogenic composition comprising the immunogen (which may further comprise an adjuvant) is administered at least two, at least three, at least four, at least five, or more times (e.g., twice (two times), three times, four times, five times, or more) to the subject. Stated another way, multiple doses (i.e., 2, 3, 4, 5, 6, or more doses) of the first immunogenic composition are administered to the subject. When the first immunogenic composition is administered multiple times (i.e., twice (two times), three times, four times, five times, or more), each administration of the first immunogenic composition may be sequential and each and all administrations of the first composition are prior to administration of the second composition. In other particular embodiments, the second composition is administered after one dose of the first composition and prior to a subsequent dose of the first composition. By way of example, when the first composition is administered two times to the subject, the second composition may be administered subsequent to the first administration (i.e., first dose) of the first immunogenic composition and prior to administration of the second administration (i.e., second dose) of the immunogenic composition. In another specific embodiment, such as when the first immunogenic composition is administered three times (i.e., three doses are administered), the second composition may be administered after the first dose and prior to the second dose; after the second dose and prior to the third dose; or after all three doses of the first immunogenic composition. In yet another specific embodiment, such as when the first immunogenic composition is administered four times (i.e., four doses are administered), the second composition may be administered after the first dose and prior to the second dose; after the second dose and prior to the third dose; after the third dose and prior to the fourth dose; or after all four doses of the first immunogenic composition. A person skilled in the art can readily appreciate that when five or more doses of the first immunogenic composition are administered, the second composition may be administered subsequent to any one of the multiple doses of the first immunogenic composition or subsequent to administration of all doses of the first immunogenic composition. In alternative embodiments, the second immunogenic composition is administered once and is administered prior to all administrations of the first immunogenic composition.

In still another embodiment, when the first immunogenic composition is administered multiple times (i.e., two or more times), one dose of the first immunogenic composition may be administered concurrently with administration of the second immunogenic composition. By way of example, when the dosing regimen comprises administering two doses of the first immunogenic composition, a first dose may be administered prior to concurrent administration of the second immunogenic composition and the second dose of the first immunogenic composition. By way of additional example, when the dosing regimen comprises administering three or more doses of the first immunogenic composition, at least one of the three doses is administered concurrently with administration of the second immunogenic composition and the additional doses of the first immunogenic composition may be administered prior to concurrent administration of both compositions, subsequent to concurrent administration of both compositions, or one or more doses may be administered prior to concurrent administration of both compositions and the remaining doses of the first immunogenic composition may be administered subsequent to concurrent administration of both compositions depending on the total number of doses of the first immunogenic composition intended to be administered according to the particular dosing regimen.

In certain particular embodiments, administration of the first immunogenic composition is administered two times and the second immunogenic composition is administered (a)

subsequent to the first administration of the first immunogenic composition and prior to the second administration of the first immunogenic composition; (b) subsequent to the second administration of the first immunogenic composition; (c) prior to the first administration of the first immunogenic composition; or (d) concurrently with the first or the second administration of the first immunogenic composition. In another particular embodiment, the first immunogenic composition is administered three times and the second immunogenic composition is administered (a) subsequent to the first administration of the first immunogenic composition and prior to the second administration of the first immunogenic composition; (b) subsequent to the second administration of the first immunogenic composition and prior to the third administration of the first composition; (c) subsequent to the third administration of the first immunogenic composition; (d) prior to the first administration of the first immunogenic composition; or (e) concurrently with the first, the second, or the third administration of the first immunogenic composition. In still another particular embodiment, the first immunogenic composition is administered four times and the second immunogenic composition is administered (a) subsequent to the first administration of the first immunogenic composition and prior to the second administration of the first immunogenic composition; (b) subsequent to the second administration of the first immunogenic composition and prior to the third administration of the first composition; (c) subsequent to the third administration of the first immunogenic composition and prior to the fourth administration of the first composition; (d) subsequent to the fourth administration of the first immunogenic composition; (e) prior to the first administration of the first immunogenic composition; or (f) concurrently with the first, the second, the third, or the fourth administration of the first immunogenic composition.

In still other specific embodiments, methods are provided wherein the second composition (i.e., the immunogenic composition comprising the recombinant expression vector encoding at least one immunogen) is administered two times and the first immunogenic composition (i.e., the immunogenic composition comprising the at least one isolated/recombinant immunogen and which may further comprise an adjuvant) is administered once, two times, three times, four times, five times, or more. Each of the two administrations (i.e., two doses) of the second composition and each administration of the first immunogenic composition (i.e., the first, second, third, fourth, or fifth dosing) may be administered sequentially in any order. In other particular embodiments, at least one of the doses of the second immunogenic composition is administered concurrently with a dose of the first immunogenic composition.

As described herein, in other embodiments, the immunogenic composition comprising the isolated/recombinant immunogen (which composition may further comprise an adjuvant) and the immunogenic composition comprising a recombinant expression vector that comprises a nucleotide sequence encoding the immunogen may be administered concurrently at least once. In one such embodiment, methods are provided herein that comprise administering (1) an immunogenic composition comprising the immunogen (which composition may further comprise an adjuvant) and sequentially administering, in either order, (2) a second dose of the immunogenic composition comprising the immunogen concurrently with an immunogenic composition comprising a recombinant expression vector encoding the immunogen. In one particular embodiment, the immunogenic composition comprising the immunogen is administered prior to administering concurrently the immunogenic composition comprising the recombinant expression vector and the immunogenic composition comprising the immunogen (i.e., a second dose of the immunogenic composition comprising the immunogen). In another specific embodiment, the immunogenic composition comprising the immunogen is administered subsequent to concurrent administration of the immunogenic composition comprising a recombinant expression vector with the immunogenic composition comprising the immunogen. In still more particular embodiments, each dose of the immunogenic composition comprising a recombinant/isolated immunogen (i.e., first immunogenic composition) is administered concurrently with a dose of the immunogenic composition comprising the recombinant expression vector encoding the immunogen (i.e., second immunogenic composition). More specifically, methods are provided herein wherein a first dose of the first immunogenic composition is administered concurrently with a first dose of the second immunogenic composition (also called the priming immunization), followed by concurrent administration of a second dose of the first immunogen and a second dose of the second immunogenic composition (also called the boosting immunization). In certain embodiments, the subject may be immunized a third time by concurrent administration of the first and second immunogenic compositions. The time interval between the priming immunization and the boosting immunization(s) is discussed in greater detail herein and is selected on the basis of results from pre-clinical and/or clinical studies.

With respect to the methods described herein that include sequential administration of the immunogenic compositions, the time interval between doses can be readily determined by a person skilled in the art practicing clinical trials. The dosing regimen for human subjects may also be informed by results from pre-clinical studies and knowledge in the art. In certain embodiments, time interval between administration of doses of the immunogenic compositions may be at least one, two, three, four, five, six, or seven days or one, two, three, four, five, six, seven, or eight weeks, or may be at least one, two, three, four, five, six, seven, eight, nine, ten, or eleven months, or at least one, two, three, or four years. By way of illustration, when the immunogenic composition comprising a recombinant expression vector (for ease of discussion, called the second immunogenic composition) is administered subsequent to at least one dose of the immunogenic composition comprising the immunogen (for ease of discussion, called the first immunogenic composition), the second immunogenic composition is administered subsequent to administration of the at least one dose of the first immunogenic composition at any one of the time intervals described herein or that may be determined by appropriate preclinical and clinical studies. In certain embodiments, the subject may be immunized a third, fourth, or fifth time with one or more of the immunogenic compositions. The time interval between a third immunization and the second immunization may be the same or different than the time interval between administrations of the first immunogenic composition and the second immunogenic composition or the time interval may be different. The time intervals as described herein between administrations of the same or different immunogenic compositions pertain to any of the administration regimens described herein (including, for example, the regimens illustrated in FIG. 6).

The immune response induced by administering the immunogenic compositions described herein according to the methods described above comprises an adaptive immune response that includes a humoral response and a cellular response (which comprises a CD4 immune response and a CD8 immune response) specific for each immunogen present in each immunogenic composition and thereby specific for the designated antigen respective to each immunogen. When the immunogenic composition comprising the isolated/recombinant immunogen (which composition may further comprise an adjuvant) and the immunogenic composition comprising a recombinant expression vector that comprises a nucleotide sequence encoding the immunogen are administered sequentially, at least the composition or compositions administered first (which may also be called the priming composition) are capable of inducing an immune response that comprises a CD4 T cell response specific for the immunogen and the respective designated antigen. The immune response induced by the priming composition may also comprise an antibody response specific for the immunogen and the respective designated antigen. The immunogenic composition(s) administered second (which may also be called a boosting composition) induces an immune response that comprises a CD8 T cell response specific for the immunogen and the designated antigen. Administration of the boosting composition may also induce or boost the antigen-specific antibody response and/or CD4 T cell specific immune response. In certain specific embodiments and as described herein, administration of an immunogenic composition comprising a recombinant expression vector that comprises a nucleotide sequence encoding an immunogen is capable of inducing an immune response that at least comprises inducing a CD8 T cell immune response specific for the immunogen and the respective designated antigen.

The immune response induced by the first administration (i.e., the first dosing) of an immunogenic composition described herein may comprise a humoral immune response and a CD4 T cell immune response, each specific for the immunogen included in the immunogenic composition. The first dosing may comprise administering an immunogenic composition comprising the isolated/recombinant immunogen (which may further comprise an adjuvant) or an immunogenic composition comprising the recombinant expression vector that encodes and directs expression of the immunogen, or the first dosing may comprise concurrent administration of each of the aforementioned immunogenic compositions. A second immunization (i.e., boosting immunization) includes administration of one or more of these immunogenic compositions and is capable of inducing an immune response that comprises a specific CD8 T cell immune response.

In particular embodiments, the immunogenic composition (also called a first immunogenic composition) that comprises the at least one isolated/recombinant immunogen (and which may further comprise an adjuvant) is capable of inducing an immune response that comprises a CD4 T cell response specific for the immunogen and thereby specific for the respective designated antigen, and which immune response may also comprise inducing a humoral response (i.e., specific antibody response or antigen-specific antibody response) to the immunogen. The other immunogenic composition (or second immunogenic composition) comprising the recombinant expression vector that comprises a nucleotide sequence encoding the immunogen is capable of at least inducing a CD8 T cell response specific for the immunogen and thus capable of inducing a CD8 T cell response specific for the designated antigen.

Accordingly, methods are provided for inducing a cytotoxic T cell response (CTL) comprising administering to the subject in need thereof, an immunogenic composition comprising at least one isolated/recombinant immunogen (which composition may further comprise an adjuvant) and sequentially and/or concurrently administering an immunogenic composition comprising a recombinant expression vector that comprises a nucleotide sequence encoding the immunogen. These methods may be performed according to any of the herein described steps of administration of the two immunogenic compositions, including the multiple dosing regimens. The CTL response is specific for a cell or particle that bears or presents the immunogen and/or respective designated antigen. In certain particular embodiments, and by way of example, when the immunogen is a tumor-associated antigen, the CTL response is specific for a tumor cell that expresses the immunogen and/or designated antigen. The immunogen and/or designated antigen may be present on the tumor cell surface and therefore accessible to cytotoxic T cells. The methods and compositions described in detail herein are therefore useful for reducing the likelihood of occurrence or recurrence of a tumor comprising a plurality of tumor cells that bear or express the tumor-associated antigen.

In other particular embodiments, the immunogen and designated antigen may be from an infectious disease microorganism, such as a virus, bacterium, parasite, or fungus, and the CTL immune response is specific for the virus, bacterium, parasite, or fungus, respectively, that expresses or bears the immunogen and/or designated antigen. The methods described herein are therefore useful for preventing or treating an infection caused by the respective infectious disease organism.

Also as described herein, in certain embodiments, these methods for inducing a CTL response may comprise administering a recombinant expression vector that is multicistronic and comprises a nucleotide sequence that encodes at least one additional immunogen (i.e., at least two, at least three, at least four, at least five, at least six, or more immunogens which may be restated as two, three, four, five, six or more immunogens)). In certain specific embodiments, upon expression of each of the additional immunogens (e.g., the second, third, fourth, fifth, sixth immunogen, etc.), each may induce an immune response to the same designated antigen as the first immunogen. In other specific embodiments, each of the additional immunogens (e.g., the second, third, fourth, fifth, sixth immunogen, etc.) may induce an immune response specific for a different designated antigen (e.g., the second, third, fourth, fifth, sixth etc.), respectively. In other certain embodiments, the immunogenic composition that comprises the at least one isolated/recombinant immunogen may comprise at least two isolated/recombinant immunogens (e.g., two, three, four, five, six or more immunogens) to form a multivalent immunogenic composition. In instances when the two or more immunogens are combined with an adjuvant, the immunogenic composition may comprise each immunogen formulated separately with an adjuvant and then the adjuvanated immunogens are combined to form the immunogenic composition that is administered to the subject. Alternatively, the two or more immunogens may be combined with an adjuvant and formulated together to form the immunogenic composition. In certain specific embodiments, each additional immunogen (e.g., the second, third, fourth, fifth, sixth immunogen, etc.) may induce an immune response to the same designated antigen as the first immunogen. In other specific embodiments, each additional immunogen (e.g., second, third, fourth, fifth immunogen, etc.) may induce an immune response specific for a different designated antigen (e.g., a second, third, fourth, fifth, sixth etc.), respectively.

In more specific embodiments for practicing the methods and uses described herein, an adjuvant, for example, a non-toxic lipid A-related adjuvant, may be formulated with the immunogen. In other specific embodiments, an adjuvant, such as a non-toxic lipid A-related adjuvant, may be administered in combination with an immunogenic composition comprising a recombinant expression vector that comprises a nucleotide sequence encoding the immunogen. In even more specific embodiments, the non-toxic lipid A-related adjuvant is GLA. In still more specific embodiments, GLA is formulated with SE to form a stable oil-in water emulsion (GLA/SE) for use in the methods and compositions described herein.

When an adjuvant is included in an immunogenic composition comprising the at least one isolated/recombinant immunogen, the adjuvant and immunogen are typically combined (i.e., formulated together, mixed) prior to administration to the subject. In alternative embodiments, the immunogenic composition comprising the at least one immunogen and the adjuvant may be administered separately but concurrently to the subject. When the immunogenic composition comprising the immunogen and the adjuvant are administered separately and concurrently, each of the immunogenic composition and the adjuvant may be administered at the same site via the same route or may be administered at the same site via different routes, or may be administered at different sites on the subject by the same or different administration routes. In certain embodiments, the adjuvant is a non-toxic lipid A-related adjuvant, such as GLA/SE.

When an adjuvant is included in an immunogenic composition comprising the recombinant expression vector, the adjuvant may be combined with (i.e., formulated together, mixed with) the recombinant expression vector (or vector particle comprising the recombinant expression vector) to form the immunogenic composition. In other embodiments, the immunogenic composition comprising the recombinant expression vector (or vector particle comprising the recombinant expression vector) are separate compositions, which may be administered at the same site via the same route or may be administered at the same site via different routes, or may be administered at different sites on the subject by the same or different administration routes. In certain embodiments, the adjuvant is a non-toxic lipid A-related adjuvant, such as GLA/SE.

In another specific embodiment, the immunization methods described herein for inducing a specific immune response comprise administering to the subject in need thereof an immunogenic composition comprising the adjuvant GLA/SE and an immunogen capable of inducing an immune response specific for a designated antigen. As described herein, GLA targets TLR4. TLR4 is unique among the TLR family in that downstream signaling occurs via both the MyD88- and TRIF-dependent pathways. Collectively, these pathways stimulate DC maturation, antigen processing/presentation, T cell priming, and the production of cytokines (e.g., IL-12, IFNα/β, and TNFα) (see, e.g., Iwasaki et al., Nat. Immunol. 5:987 (2004)).

In certain embodiments as described herein, the recombinant expression vector is incorporated into a vector particle, and methods described herein comprise administering an immunogenic composition that comprises the vector particle comprising a recombinant expression vector that encodes and directs expression of the immunogen. In more specific embodiments, the vector particle is a virus vector particle, such as a lentiviral vector particle. As described herein, the lentiviral vector particle may be DC-NILV, a self-inactivating, non-integrating lentivector that uses a modified Sindbis virus envelope glycoprotein to selectively enter dendritic cells (DCs). Upon vector entry into the DC, antigenic peptides generated via the active transcription and translation of the immunogen encoded by the vector are introduced into the MHC class I presentation pathway. Without wishing to be bound by any particular theory, use of DC-NILV generates robust CD8 T cell responses.

In one embodiment, the immunogenic composition comprising the recombinant expression vector or a vector particle comprising the recombinant expression vector is administered directly to the subject. In other specific embodiments, the target cell(s) may be isolated from a subject to whom the immunogenic composition will be administered, and the vector particle introduced into the target cells ex vivo. Then the targeted cells comprising the vector particle are introduced into the subject.

In even more specific embodiments, dual immunization methods comprise administering an immunogenic composition that comprises a recombinant/isolated immunogen(s) of interest is combined with the adjuvant GLA/SE. The methods further comprise administering a second immunogenic composition that comprises DC-NILV that encodes and expresses the immunogen(s). Exemplary but nonexhaustive immunization regimens for using these immunogenic compositions are shown in Table 1 below.

TABLE 1

Immunization Regimens

| Prime | $1^{st}$ Boost | $2^{nd}$ Boost |
| --- | --- | --- |
| Immunogen(s) + GLA/SE | DC-NILV* | None |
| immunogen(s) + GLA/SE | DC-NILV | immunogen(s) + GLA/SE |
| immunogen(s) + GLA/SE | immunogen(s) + GLA/SE | DC-NILV |
| immunogen(s) + GLA/SE | immunogen(s) + GLA/SE and DC-NILV | None |
| immunogen(s) + GLA/SE and DC-NILV | None | None |
| immunogen(s) + GLA/SE and DC-NILV | immunogen(s) + GLA/SE and DC-NILV | None |
| DC-NILV | immunogen(s) + GLA/SE | None |
| DC-NILV | immunogen(s) + GLA/SE | DC-NILV |

*DC-NILV comprises a polynucleotide that encodes the immunogen(s).

The methods described herein are useful for inducing an immune response specific for any one of the immunogens and its respective designated antigen. As described in detail herein, a designated antigen of interest may be a tumor-associated antigen or an antigen from an infectious microorganism (e.g., a virus, bacterium, fungus, or a parasite). In certain particular embodiments, the methods described herein are useful for inducing an immune response specific for a tumor-associated antigen, including but not limited to a renal cell carcinoma antigen, a prostate cancer antigen, a mesothelioma antigen, a pancreatic cancer antigen, a melanoma antigen, a breast cancer antigen, a lung cancer antigen, and an ovarian cancer antigen. In more particular embodiments, the designated antigen of interest is a prostate cancer antigen, for example, prostatic acid phosphatase, prostate specific antigen, NKX3.1, or prostate specific membrane antigen.

In another specific embodiment, compositions and methods are provided for immunizing a subject against a virus, such as HIV, CMV, a hepatitis virus, EBV, RSV, VSV, influenza, or HSV-2 or any other infectious virus described herein or in the art. Accordingly, the methods described herein may be used for inducing an immune response specific for a viral antigen. In more specific embodiments, the designated antigen of interest is an HSV-2 protein such as gD and UL19.

The dual immunization methods provided herein may be used for inducing a cytotoxic T lymphocyte (CTL) response against a cell, a particle, or a microorganism bearing or expressing at least one designated antigen of interest. In particular embodiments, methods are provided herein for inducing a CTL response against a tumor cell that expresses at least one designated antigen of interest. In particular embodiments, the designated antigen (or a portion or portions thereof) is present on the outer cell surface of the tumor cell and exposed to the extracellular environment. The methods described herein are useful for reducing the likelihood of occurrence or recurrence (i.e., reducing the likelihood of occurrence or recurrence in a statistically, clinically, or biologically significant manner) of a tumor (which comprises a plurality of tumor cells) that bear, express, or secrete the tumor-associated antigen that is the designated antigen of interest.

In other particular embodiments, the methods described herein induce a CTL response against a microorganism, such as a virus, parasite, bacterium, or fungus cell. The designated antigen may be a microbial antigen that is typically secreted by the microorganism or may be a microbial antigen that is present on the cell surface of the microorganism and thereby has one or more immunogenic regions exposed and available for recognition by, and interaction with, molecules and cells of the subject's immune system. Accordingly, the methods described herein that comprise dual immunization of the subject are useful for treating and/or preventing (i.e., reducing the likelihood of occurrence of in a statistically, clinically, or biologically significant manner) a microbial infection, which would become exacerbated or would occur in the absence of administration of the immunogenic compositions described hereinto the subject.

As understood by a person skilled in the medical art, the terms, "treat" and "treatment," refer to medical management of a disease, disorder, or condition of a subject (i.e., patient, host, who may be a human or non-human animal) (see, e.g., Stedman's Medical Dictionary). In general, an appropriate dose and treatment regimen provide the immunogen and optionally an adjuvant as detailed herein in an amount sufficient to provide therapeutic and/or prophylactic benefit. Therapeutic and/or prophylactic benefit resulting from therapeutic treatment and/or prophylactic or preventative methods include, for example an improved clinical outcome, wherein the object is to prevent or slow or retard (lessen) an undesired physiological change or disorder, or to prevent or slow or retard (lessen) the expansion or severity of such disease or disorder. Beneficial or desired clinical results from treating a subject include, but are not limited to, abatement, lessening, or alleviation of symptoms that result from or are associated the disease or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of the methods and compositions described herein include those who already have the disease or disorder as well as subjects prone to have or at risk of developing the disease or disorder. Subjects in need of prophylactic treatment include subjects in whom the disease, condition, or disorder is to be prevented (i.e., decreasing the likelihood of occurrence or recurrence of the disease or disorder). The clinical benefit provided by the compositions (and preparations comprising the compositions) and methods described herein can be evaluated by design and execution of in vitro assays, preclinical studies, and clinical studies in subjects to whom administration of the compositions is intended to benefit. The design and execution of the appropriate preclinical studies and clinical studies can be readily performed by persons skilled in the relevant art(s).

The isolated/recombinant immunogens, recombinant expression vectors and/or vector particles may be administered to a subject in a pharmaceutically or physiologically acceptable or suitable excipient or carrier. Pharmaceutically acceptable excipients are biologically compatible vehicles, e.g., physiological saline, which are described in greater detail herein, that are suitable for administration to a human or other non-human subject including a non-human mammalian subject.

With respect to administration of a recombinant expression vector, a therapeutically effective amount provides an amount of the polynucleotide which is capable of producing a medically desirable result (i.e., a sufficient amount of the immunogen is expressed to induce or enhance the immune response specific for the immunogen (humoral and/or cell-mediated response, including a cytotoxic T cell response) in a statistically, biologically, and/or significant manner) in a treated human or non-human animal As is well known in the medical arts, the dosage for any one patient depends upon many factors, including the patient's size, body surface area, age, the particular compound to be administered, sex, time and route of administration, general health, and other drugs being administered concurrently. Doses will vary, but a preferred dose for administration of a vector particle comprising a recombinant expression vector is sufficient to provide approximately $10^6$ to $10^{12}$ copies of the vector polynucleotide molecule.

Pharmaceutical compositions, including the immunogenic and adjuvant compositions described herein, may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's disease, the particular form of the active ingredient, and the method of administration. In general, an appropriate dose and treatment regimen provides the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

In general, the amount of an immunogen, including fusion polypeptides as described herein, present in a dose, or produced in situ by an encoding polynucleotide present in a dose, ranges from about 0.01 µg to about 1000 µg per kg of host. The use of the minimum dosage that is sufficient to provide effective therapy is usually preferred. Patients may generally be monitored for therapeutic or prophylactic effectiveness using assays suitable for the condition being treated or prevented, which assays will be familiar to those having ordinary skill in the art and which are described herein. When administered in a liquid form, suitable dose sizes will vary with the size of the patient, but will typically range from about 1 ml to about 500 ml (comprising from about 0.01 μg to about 1000 μg per kg) for a 10-60 kg subject. Optimal doses may generally be determined using experimental models and/or clinical trials. The optimal dose may depend upon the body mass, body area, weight, or blood volume of the subject. As described herein, the appropriate dose may also depend upon the patient's (e.g., human) condition, that is, stage of the disease, general health status, as well as age, gender, and weight, and other factors familiar to a person skilled in the medical art.

Pharmaceutical compositions may be formulated for any appropriate manner of administration, including, for example, topical, oral, enteral, nasal (i.e., intranasal), inhalation, intrathecal, rectal, vaginal, intraocular, subconjunctival, sublingual, intradermal, intranodal, intratumoral, transdermal, or parenteral administration, including subcutaneous, percutaneous, intravenous, intramuscular, intrasternal, intracavernous, intrameatal or intraurethral injection or infusion. Methods of administration are described in greater detail herein.

For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

An immunogenic composition comprising a recombinant/isolated immunogen and an immunogenic composition comprising the recombinant vector construct or the vector particle may be formulated for delivery by any route that provides an effective dose of the immunogen. Such administrations methods include oral administration or delivery by injection and may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

For pharmaceutical compositions comprising a nucleic acid molecule such as the recombinant expression vectors described herein, the nucleic acid molecule may be present within any of a variety of delivery systems known to those of ordinary skill in the art, including nucleic acid, and bacterial, viral and mammalian expression systems such as, for example, vector particles and recombinant expression constructs as provided herein. Techniques for incorporating a polynucleotide (e.g., DNA) into such expression systems are well known to those of ordinary skill in the art. In other certain embodiments, the recombinant expression vector, which is typically DNA, may also be "naked," as described, for example, in Ulmer et al., Science 259:1745-49 (1993) and reviewed by Cohen, Science 259:1691-92 (1993). The uptake of naked DNA may be increased by coating the DNA onto biodegradable beads, which are efficiently transported into the cells.

Nucleic acid molecules may be delivered into a cell according to any one of several methods described in the art (see, e.g., Akhtar et al., Trends Cell Bio. 2:139 (1992); Delivery Strategies for Antisense Oligonucleotide Therapeutics, ed. Akhtar, 1995, Maurer et al., Mol. Membr. Biol. 16:129-40 (1999); Hofland and Huang, Handb. Exp. Pharmacol. 137: 165-92 (1999); Lee et al., ACS Symp. Ser. 752:184-92 (2000); U.S. Pat. No. 6,395,713; International Patent Application Publication No. WO 94/02595); Selbo et al., Int. J. Cancer 87:853-59 (2000); Selbo et al., Tumour Biol. 23:103-12 (2002); U.S. Patent Application Publication Nos. 2001/0007666, and 2003/077829). Such delivery methods known to persons having skill in the art, include, but are not restricted to, encapsulation in liposomes, by iontophoresis, or by incorporation into other vehicles, such as biodegradable polymers; hydrogels; cyclodextrins (see, e.g., Gonzalez et al., Bioconjug. Chem. 10:1068-74 (1999); Wang et al., International Application Publication Nos. WO 03/47518 and WO 03/46185); poly(lactic-co-glycolic)acid (PLGA) and PLCA microspheres (also useful for delivery of peptides and polypeptides and other substances) (see, e.g., U.S. Pat. No. 6,447,796; U.S. Patent Application Publication No. 2002/130430); biodegradable nanocapsules; and bioadhesive microspheres, or by proteinaceous vectors (International Application Publication No. WO 00/53722). In another embodiment, the nucleic acid molecules can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives (see also, e.g., U.S. Patent Application Publication No. 2003/0077829).

In particular embodiments of the methods described herein, the subject is a human or non-human animal A subject in need of the treatments described herein may exhibit symptoms or sequelae of a disease, disorder, or condition described herein or may be at risk of developing the disease, disorder, or condition. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

The compositions provided herein can be in various forms, e.g., in solid, liquid, powder, aqueous, or lyophilized form. Examples of suitable pharmaceutical excipients and carriers for administering a vector particle, including a viral vector particle and a bacterial vector particle, immunogenic compositions, and recombinant expression vectors are known in the art. Such excipients, carriers, and/or additives can be formulated by conventional methods and can be administered to the subject at a suitable dose. Stabilizing agents such as lipids, nuclease inhibitors, polymers, and chelating agents that may be included in the compositions described herein can assist preservation of the compositions and components of the compositions from degradation within the body.

The vector particles, including a viral vector particle and a bacterial vector particle, immunogenic compositions, adjuvant compositions, and recombinant expression vectors provided herein can be packaged as kits. Kits can optionally include one or more components such as instructions for use, devices, and additional reagents, and components, such as tubes, containers and syringes for practice of the methods.

Exemplary kits can optionally include instructions for use, a device or reagents for detecting a vector particle, the recombination expression vector, or the immunogen in a subject, and a device for administering the composition or compositions to a subject.

Kits comprising polynucleotides encoding an immunogen are also contemplated herein. Such a kit may also include at least one plasmid that encodes virus packaging components and a vector encoding Sindbis virus E2 glycoprotein variant. Some kits will contain at least one plasmid encoding virus packaging components, a vector encoding Sindbis virus E2 glycoprotein variant, and a vector encoding at least one DC maturation factor.

Kits comprising a viral vector encoding a sequence of interest (typically encoding an antigen or immunogen) and optionally, a polynucleotide sequence encoding a DC maturation factor are also contemplated herein. In some kits, the kit includes at least one plasmid encoding virus packaging components and a vector encoding Sindbis virus E2 glycoprotein variant.

A kit may also contain instructions. Instructions typically describe methods for administration, including methods for determining the proper state of the subject, the proper dosage amount, and the proper administration method, for administering the composition. Instructions can also include guidance for monitoring the subject over the duration of the treatment time.

Kits provided herein also can include devices for administration of each of the immunogenic compositions described herein and/or for administration of an adjuvant composition to a subject. Any of a variety of devices known in the art for administering medications, immunogenic compositions, and vaccines can be included in the kits provided herein. Exemplary devices include, but are not limited to, a hypodermic needle, an intravenous needle, a catheter, a needle-less injection device, an inhaler, and a liquid dispenser, such as an eyedropper. Typically, the device for administering a composition is compatible with the active components of the kit. For example, a needle-less injection device, such as a high pressure injection device can be included in kits with vector particles, polynucleotides, and polypeptides not damaged by high pressure injection, but is typically not included in kits that include vector particles, polynucleotides, and polypeptides that may be damaged by high pressure injection.

Exemplary Embodiments

In some embodiments of the disclosure, multiple immunogenic compositions are administered to a subject in need thereof. The following parameters are varied according to various aspects: the number of doses of the immunogenic compositions, the routes of administration of the immunogenic compositions, the sites on the subject for administration of the immunogenic compositions, the concentration or amount of active ingredient or ingredients in the immunogenic compositions, and the number of immunogens and/or adjuvants in the immunogenic compositions.

In addition to any of the foregoing embodiments described in the detailed description, embodiments are contemplated including any of the following or any combinations thereof:

1. A method for inducing an immune response in a subject, the method comprising
  (a) administering to the subject a first dose of a first immunogenic composition comprising
    (1) a first polypeptide comprising any of (i) a first designated antigen, (ii) an immunogenic fragment thereof, or (iii) a variant thereof capable of inducing an immune response specific for the first designated antigen, and
    (2) a TLR4 agonist adjuvant or a non-toxic lipid A-related adjuvant; and
  (b) administering to the subject a first dose of a second immunogenic composition comprising a vector particle that preferentially delivers a recombinant expression vector to an antigen-presenting cell, wherein said recombinant expression vector comprises a nucleotide sequence that encodes a second polypeptide comprising any of (i) the first designated antigen, (ii) an immunogenic fragment thereof, or (iii) a variant thereof capable of inducing an immune response specific for the first designated antigen;
  each in amounts effective to induce or enhance an immune response specific for the first designated antigen.

In embodiment 1, the first polypeptide can be the same as, or different from, the second polypeptide.

2. Embodiment 1 wherein any of the immunogenic fragments retains the ability to induce an immune response specific for the first designated antigen, and comprises, e.g., at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 48 or 50 contiguous amino acids of the antigen.

3. Embodiment 1 wherein any of the immunogenic variants can, e.g., retain at least 90% amino acid identity over at least 10 contiguous amino acids of the antigen, or at least 85% amino acid identity over at least 15 contiguous amino acids of the antigen. Other examples include at least 70%, 75%, 80%, 85%, 90%, 91%, 92%, 93%, 94%, 95%, 96%, 97%. 98%, or 99% identity over at least 50 contiguous amino acids of the antigen, or over at least 100 contiguous amino acids of the antigen.

4. Embodiment 1 wherein the first polypeptide is a small immunogenic fragment of the antigen, of about 50 amino acids or less in length, and the second polypeptide is full-length antigen or a larger fragment thereof, of about 50 amino acids or more in length, optionally having at least 80%, 85%, 90% or 95% identity to the full length antigen.

In embodiment 1, the second immunogenic composition can be administered subsequent to, prior to, or concurrently with, administration of the first immunogenic composition.

5. Any of the preceding embodiments wherein the second immunogenic composition comprising the vector particle is administered subsequent to administration of the first immunogenic composition comprising the polypeptide immunogen.

6. Any of the preceding embodiments further comprising, subsequent to administration of the first doses of the first and second immunogenic compositions, any of (a) administration of a third immunogenic composition, or (b) administration of a second dose of the first immunogenic composition, or (c) administration of a second dose of the second immunogenic composition.

7. Any of the preceding embodiments wherein (a) the interval between the first and second administrations, and/or (b) the interval between the second and third administrations is 2-4 weeks, up to 1, 2, 3, 4, 5, 6, 7, 8, 9, 10, 11, 12, 13, 14, 15, 16, 17, 18, 19, 20, 21, 22, 23, 24, 25, 26, 26, or 28 days, or up to 1, 2,3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks, or up to 1, 2,3, 4, 5, 6, 7, 8, 9, or 10 years following the previous immunization.

8. Any of the preceding embodiments wherein (a) two doses; (b) three doses; (c) four doses; or (d) five doses of the first immunogenic composition are administered. Any combination of any of the foregoing administrations is contemplated, e.g., wherein (a) each dose of the first immunogenic composition is administered prior to administration of the second immunogenic composition; (b) at least one dose of the first immunogenic composition is administered subsequent to administration of the second immunogenic composition; (c) at least one dose of the first immunogenic composition is administered concurrently with administration of the second immunogenic composition; (d) at least one dose of the first immunogenic composition is administered prior to administration of the second immunogenic composition and each of any remaining doses of the first immunogenic composition is administered subsequent to administration of the second immunogenic composition; or (e) each dose of the first composition is administered concurrently with the second composition.

Administration of a regimen comprising (a) first, an immunogenic composition comprising a polypeptide and (b) second, an immunogenic composition comprising viral vector particle, resulted in a superior immune response comprising a strong antigen-specific CD4+ T cell response, strong antibody response, and a strong antigen-specific CD8+ T cell response. Following this regimen with (c) third, an immunogenic composition comprising a polypeptide, resulted in even superior results. Both the primary response (i.e., the response observed after the prime) and secondary response (i.e., the response observed after the boost) can be measured in terms of maximum response (e.g., peak height) and subsequent memory response (e.g., where the x axis is time, and y axis is % number of CD4 or CD8 T cells over the total number of cells). By way of example, according to the present disclosure, the secondary response (i.e., the response observed after administering the boost) is greater than the prime response in at least one of maximum response or memory response, where "greater than" means at least or up to 10% or 20% or 30% or 40% or 50% greater than the corresponding response obtained after the prime (the primary response). By way of example, the second immunization enhances CD8 and CD4 response, by at least 25%.

9. Any of the preceding embodiments wherein the first immunogenic composition further comprises another immunogen, said immunogen being a polypeptide comprising any of (i) a second designated antigen, (ii) an immunogenic fragment thereof, or (iii) a variant thereof capable of inducing an immune response specific for the second designated antigen.

10. Any of the preceding embodiments wherein the recombinant expression vector (of the second immunogenic composition) further comprises another nucleotide sequence that encodes another immunogen, said immunogen being a polypeptide comprising any of (i) a second designated antigen, (ii) an immunogenic fragment thereof, or (iii) a variant thereof capable of inducing an immune response specific for the second designated antigen.

11. In any of the preceding embodiments, the first and second designated antigen can be the same or different. In these embodiments, an immune response is generated against both the first and second designated antigens, comprising a strong antigen-specific CD4+ T cell response, strong antibody response, and a strong antigen-specific CD8+ T cell response. As further examples, immunogenic compositions comprising polypeptide and viral vector for inducing an immune response for a third designated antigen, or fourth or fifth, can be administered.

12. Any of the preceding embodiments wherein the antigen (first, second, third, fourth and/or fifth) is (a) a tumor-associated antigen or (b) from an infectious microorganism selected from a virus, a bacterium, a fungus, and a parasite. In various examples, the tumor-associated antigen is a renal cell carcinoma antigen, a prostate cancer antigen, a mesothelioma antigen, a pancreatic cancer antigen, a melanoma antigen, a breast cancer antigen, a lung cancer antigen, or an ovarian cancer antigen; optionally the prostate cancer antigen is prostatic acid phosphatase, prostate specific antigen, NKX3.1, or prostate specific membrane antigen. In various examples, the antigen is a virus antigen, optionally from Herpes Simplex Virus-2 (HSV-2). The antigen may be any of the antigens described herein.

13. The first and second designated antigens, for example, may be different antigens from the same tumor or same virus or other microorganism. Alternatively the first and second designated antigens may be from different cancers, or from different viruses or microorganisms.

14. Any of the preceding embodiments wherein the polypeptide of the first immunogenic composition may be included at a range from about 0.01 μg to about 1000 μg per kg body weight of the subject. In various embodiments, the immunogen is present at a range from about 0.1 μg to about 100 μg per kg body weight of the subject.

15. Any of the preceding embodiments, wherein the amounts administered are effective to induce a cytotoxic T lymphocyte response against a cell bearing the antigen, e.g. against a tumor cell or against a microorganism. In any of the preceding embodiments, the amounts administered are effective to reduce the likelihood of occurrence or recurrence of a tumor comprising the tumor-associated antigen. In any of the preceding embodiments, the amounts administered are effective to reduce the likelihood of occurrence or severity of a disease caused by the microorganism. Such methods can prevent or treat an infection caused by the infectious microorganism.

16. Any of the preceding embodiments wherein the TLR4 agonist adjuvant or non-toxic lipid A-related adjuvant, is a monophosphoryl lipid A, or 3 De-O-acylated monophosphoryl lipid A (MPL), or a lipid A mimetic, or GLA of formula I as described in its entirety above, or GLA of formula (Ia):

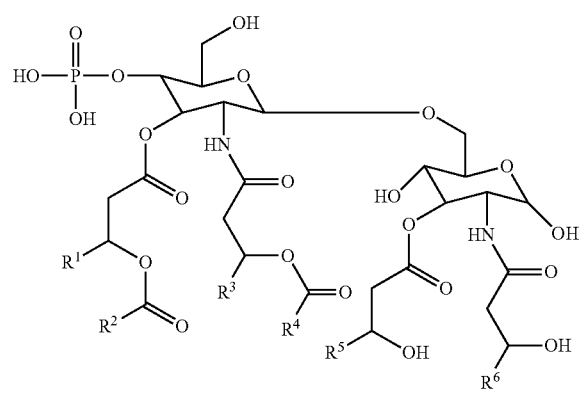

or a pharmaceutically acceptable salt thereof, where: R1, R3, R5 and R6 are C11-C20 alkyl; and R2 and R4 are C12-C20 alkyl; in a more specific embodiment, the GLA has the formula (Ia) set forth above wherein R1, R3, R5 and R6 are C11-14 alkyl; and R2 and R4 are C12-15 alkyl; in a further more specific embodiment, the GLA has the formula (Ia) set forth above wherein R1, R3, R5 and R6 are C11 alkyl; and R2 and R4 are C13 alkyl;

or the GLA has a structure selected from the following chemical formula (Ib):

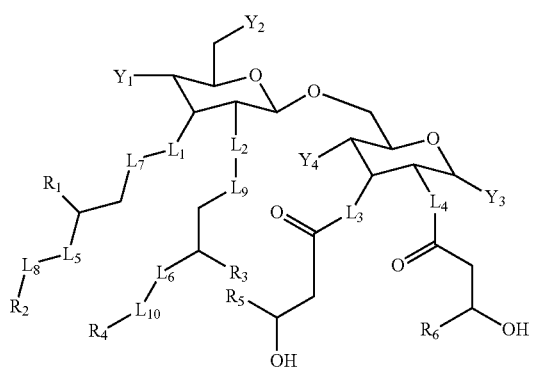

or a pharmaceutically acceptable salt thereof, wherein: L1, L2, L3, L4, L5 and L6 are the same or different and are independently selected from O, NH, and (CH2); L7, L8, L9 and L10 are the same or different, and at any occurrence may be either absent or C(=O); Y1 is an acid functional group; Y2 and Y3 are the same or different and are each independently selected from OH, SH, and an acid functional group; Y4 is OH or SH; R1, R3, R5 and R6 are the same or different and are each independently selected from the group of C8-C13 alkyl; and R2 and R4 are the same or different and are each independently selected from the group of C6-C11 alkyl.

17. Any of the preceding embodiments wherein another adjuvant (in addition to the TLR4 agonist adjuvant or non-toxic lipid A-related adjuvant of the first immunogenic composition) is included in any of the immunogenic compositions.

18. Any of the preceding embodiments wherein the adjuvant, preferably GLA, is formulated in a stable oil-in-water emulsion. In examples of embodiments, the GLA is present in an amount of 0.1-10 µg/injection, or in an amount of 0.2-5 µg/injection, or in an amount of 0.5-2.5 µg/injection, where an injection is given to a person of at least 50 Kg body mass.

19. Any of the preceding embodiments wherein the vector particle that preferentially delivers a recombinant expression vector to an antigen-presenting cell is a cell, virus vector particle, or virus-like particle.

20. Any of the preceding embodiments wherein the antigen-presenting cell is a dendritic cell, preferably a dendritic cell expressing DC-SIGN.

21. Any of the preceding embodiments wherein the vector particle comprises preferably a lentiviral vector genome, or alternatively a poxvirus vector genome, vaccinia virus vector genome, adenovirus vector genome, adenovirus-associated virus vector genome, herpes virus vector genome, and an alpha virus vector genome.

22. Any of the preceding embodiments wherein the vector particle is a lentiviral vector particle that comprises the lentiviral vector genome; a poxvirus vector particle that comprises the poxvirus vector genome; a vaccinia virus vector particle that comprises the vaccinia virus vector genome; an adenovirus vector particle that comprises the adenovirus vector genome; an adenovirus-associated virus vector particle that comprises the adenovirus-associated virus vector genome; a herpes virus vector particle that comprises the herpes virus vector genome; or an alpha virus vector particle that comprises the alpha virus vector genome.

23. Any of the preceding embodiments wherein the vector particle comprises an envelope protein that preferentially delivers the vector particle to a dendritic cell expressing DC-SIGN, optionally an envelope that is a variant of an Arbovirus envelope, or an alphavirus envelope, or a Sindbis virus envelope.

24. Any of the preceding embodiments wherein the vector particle is a lentivirus vector particle comprising a lentiviral genome and comprising (pseudotyped with) a glycoprotein from an arbovirus that preferentially delivers the vector particle to a dendritic cell expressing DC-SIGN, preferably a glycoprotein from an alphavirus, optionally a Sindbis virus, and optionally a Sindbis virus E2 glycoprotein comprising a mutation at position 160. Alternatively, the vector particle comprises an alphavirus genome and an alphavirus glycoprotein that preferentially delivers the vector particle to a dendritic cell expressing DC-SIGN.

25. Any of the preceding embodiments wherein the lentiviral vector particle comprises an envelope comprising a Sindbis virus E2 glycoprotein variant having at least 70%, 75%, 80%, 85%, 90%, or 95% amino acid identity to the amino acid sequence of native Sindbis E2, and (a) comprising at least one mutation wherein the amino acid at residue 160 is either absent or an amino acid other than glutamic acid, and (b) wherein the E2 glycoprotein is not a moiety of a fusion protein that comprises Sindbis virus E3 protein.

26. In any of the preceding embodiments wherein the vector particle preferentially delivers the recombinant expression vector to dendritic cells, optionally the vector particle preferentially infects dendritic cells, e.g. the ratio of infected dendritic cells to infected non-dendritic cells (or non DC-SIGN expressing cells) is at least about 2:1, at least about 3:1, at least about 4:1, at least about 5:1, at least about 6:1, at least about 7:1, at least about 8:1, at least about 9:1, at least about 10:1, at least about 20:1, at least about 30:1, at least about 40:1, at least about 50:1, at least about 100:1, at least about 200:1, at least about 500:1, at least about 1000:1, at least about 5000:1, at least about 10,000:1, or more.

27. Any of the preceding embodiments wherein the two compositions are administered at different sites, optionally by different routes of administration. For example, route of administration can be parenteral, enteral, oral, intramuscular, intradermal, subcutaneous, intratumoral, intranodal, intranasal, transdermal, inhalation, mucosal, or topical.

28. Any of the preceding embodiments wherein the second immunogenic composition comprising the vector particle is administered subcutaneously or intradermally.

29. Any of the preceding embodiments lwherein the composition comprising the adjuvant is administered subcutaneously or intramuscularly, or orally.

In related aspects of the embodiments, disclosed herein are kits comprising the first and immunogenic compositions as described in any of the preceding embodiments, and optionally comprising any of the features described above.

In further related aspects of the embodiments, disclosed herein are a first immunogenic composition for use in (or for use in preparation of a medicament for use in) any of the preceding methods, said first immunogenic composition comprising
(1) a first polypeptide comprising any of (i) a first designated antigen, (ii) an immunogenic fragment thereof, or (iii) a variant thereof capable of inducing an immune response specific for the first designated antigen, and
(2) a TLR4 agonist adjuvant or a non-toxic lipid A-related adjuvant, each of the polypeptide and adjuvant in amounts effective to induce or enhance an immune response specific for the first designated antigen.

In yet further related aspects of the embodiments, also disclosed herein are a second immunogenic composition for use in (or for use in preparation of a medicament for use in)

any of the preceding methods, said second immunogenic composition comprising a vector particle that preferentially delivers a recombinant expression vector to an antigen-presenting cell, wherein said recombinant expression vector comprises a nucleotide sequence that encodes a second polypeptide comprising any of (i) the first designated antigen, (ii) an immunogenic fragment thereof, or (iii) a variant thereof capable of inducing an immune response specific for the first designated antigen, said vector particle in an amount effective to induce or enhance an immune response specific for the first designated antigen.

Other embodiments and uses will be apparent to one skilled in the art in light of the present disclosures. The following examples are provided merely as illustrative of various embodiments and shall not be construed to limit the invention in any way.

EXAMPLES

Example 1

Immune Response to an Immunogen

Administration of an Immunogen and an Adjuvant

This Example describes the immune response induced by an immunogen combined with an adjuvant that is an agonist of Toll-like Receptor 4 (TLR4).

Materials: GLA is synthesized by Avanti Polar Lipids (Alabaster, Ala.) and formulated in SE by the Infectious Disease Research Institute (Seattle, Wash.) (see also, e.g., U.S. Patent Application Nos. 2008/0131466 and 2010/0310602). HSV-2 recombinant UL19 protein is expressed in a Baculovirus expression system (Paragon Bioservices, Baltimore, Md.). An exemplary, full-length UL19 polypeptide sequence is provided in SEQ ID NO:36 (see, e.g., GenBank Acc. No. NP_044488.1). The amino acid sequences of peptides comprising UL19 epitopes used in these examples refer to the positions of amino acids in this full-length UL19 polypeptide.

Animal Care: Mice are housed in a dedicated animal space in an Animal Research Facility within Immunde Design Research Institute (IDRI). The facility complies with USDA regulations and has Animal Welfare Assurance from the Office of Laboratory Animal Welfare (OLAW). IDRI is certified by the Association for Assessment of Laboratory Animal Care (AALAC) and has an active Institutional Animal Care and Use Committee (IACUC), which includes a consulting veternarian. All animal protocols are reviewed and approved by the IDRI IACUC. Euthanasia of animals is performed when needed by controlled administration of inhalation carbon dioxide and/or cervical dislocation. These methods are consistent with the recommendations of the Panel on Euthanasia of the American Veterinary Medical Association.

Groups of five mice were immunized intramuscularly via a prime/boost immunization regimen; mice were initially immunized at day 0 (priming immunization) and then boosted at day 21 (d0 prime/d21 boost) with 5 µg of recombinant HSV-2 UL19 protein in combination with 5 µg of glucopyranosyl Lipid A (GLA) formulated in a stable oil-in water emulsion (GLA-SE), stable oil-in water emulsion (SE) alone, or PBS. The animals were sacrificed and spleen cells were isolated from the animals four days after the boosting immunization. Splenic CD4 T cell responses were measured after ex vivo re-stimulation with UL19 peptide epitope one (amino acids 997-1011, sequence NYFSSIRQPVVQHAR (SEQ ID NO:37)) or epitope 2 (amino acids 1185-1199, sequence CEFIATPVATDINYF (SEQ ID NO:38) by determining the level of IFN-γ, TNF-α, and IL-2 by intracellular cytokine staining (ICS) followed by fluorescence activated cell sorting (FACS). The results are presented in FIG. 1. Percent cytokine positive CD4 T cells are depicted for each group.

Antibody titers were determined by Enzyme Linked Immunosorbent Assay (ELISA). Blood samples were obtained from mice and sera were prepared. Serial dilutions of samples were added to 96 well immunoassay plates coated with recombinant UL19 protein. The presence of specific anti-UL19 antibodies were detected with murine class specific and isotype-specific antibodies (anti-IgG, -IgG1, -IgG2a, and -IgG2b) conjugated with horseradish peroxidase (HRP). Bound HRP-conjugates were detected by standard peroxidase assay using SureBlue® TMB microwell substrate (KPL, Kirkegard & Perry Laboratories, Gaithersburg, Md.). Reactions were quanitified by reading plates at 450 nm using a SpectraMax® Plus plate reader (Molecular Devices, Inc., Sunnyvale, Calif.). Mice immunized with recombinant UL19 protein combined with GLA-SE also generated a greatly increased specific antibody response than mice immunized with recombinant HSV-2 UL19 protein alone (in PBS).

Example 2

Immune Response to an Immunogen Combined with an Adjuvant and when Expressed by a Viral Recombinant Expression Vector This Example describes the immune response induced when mice are immunized with an immunogen combined with an adjuvant or immunized with a vector particle comprising a recombinant expression vector that encodes and expresses the immunogen.

A lentiviral vector (DC-NILV) is a self-inactivating, integration-defective lentivector that uses a modified Sindbis virus envelope glycoprotein to selectively enter DCs (see, e.g., International Patent Application Publication No. WO 2011/011584). Briefly, the vector was made redundantly integration incompetent through the combination of a mutant Integrase (pol$^{D64V}$), rendering it non-functional (Apolonia et al., *Mol. Ther.* 15:1947 (2007)), and a vector backbone deleted of the U3 region of the LTR (up to att) and the 3' LTR poly-purine tract (PPT). Thus in addition to a disabled Integrase, the composition of the vector backbone prevents transcription of the full-length vector genome (self-inactivating mutation) resulting in single-LTR reverse transcribed episomal dsDNA circles in the infected dendritic cells, which are not a template for chromosomal integration (Bayer et al., *Mol. Ther.* 16:1968 (2008); Kantor et al., *Proc. Natl. Acad. Sci. USA* 106:18786-791 (2009); Epub 2009 Oct. 20; Ma et al., *Mol. Ther.* 10:139 (2004)). Seventy-five percent of the parental HIV genome has been removed from DC-NILV, including all of the regulatory and accessory proteins except for Rev.

Groups of five mice were immunized either with GLA-SE-adjuvanted rUL19 protein intramuscularly or with a lentiviral vector (DC-NILV) (Immune Design Corporation, Seattle, Wash.) encoding the HSV-2 polypeptide, UL19 subcutaneously. Recombinant UL19 protein is expressed in a Baculovirus expression system (Paragon Bioservices, Baltimore, Md.). Antibody titers were determined, and splenic UL19-specific CD4 and CD8 T cells were analyzed for the production of IFN-γ and TNF-α by ICS (see experimental details in Example 1). Splenic CD4 T cell responses were measured after ex vivo re-stimulation with the UL19 peptide epitope 2 (amino acids 1185-1199, (SEQ ID NO:38) (see Example 1)). Splenic CD8 T cell responses were measured after ex vivo re-stimulation with a combination of UL19 CD8 peptide epitope 1 (amino acids 1017-1031, sequence ENALTYAL-MAGYFKM (SEQ ID NO:39) and UL19 CD8 peptide epitope 2 (amino acids 1045-1059, sequence HPGFGFTV-VRQDRFV (SEQ ID NO:40)). The data are presented in FIG. 2 (left side).

Figure 2:
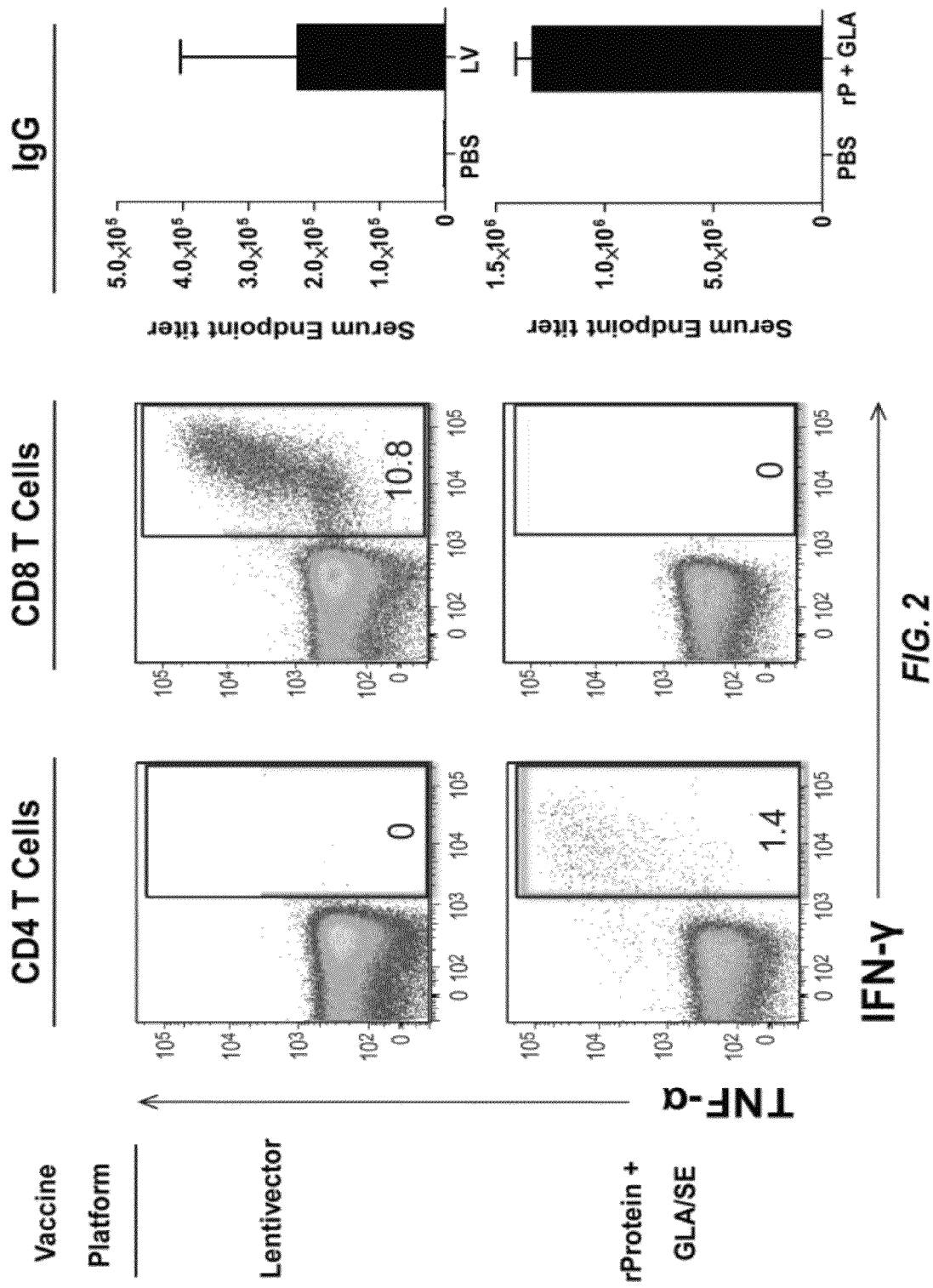
FIG. 2 illustrates the immune response to HSV-2 UL19 protein. Groups of five mice were immunized either with GLA-SE-adjuvanated rUL19 protein (rProtein+GLA/SE) or with a lentiviral vector (DC-NILV) (Immune Design Corporation, Seattle, Wash.) encoding the HSV-2 polypeptide, UL19 (Lentivector). Antibody titers were determined (right), and splenic UL19-specific CD4 and CD8 T cells were analyzed for the production of IFN-γ and TNF-α by ICS (left). The numbers in the boxed area indicate the percent CD4 or CD8 cells that are IFN-γ$^+$ and TNF-α$^+$.

Antibody serum endpoint titers were determined by Enzyme Linked Immunosorbent Assay (ELISA) as described in Example 1. Blood samples were obtained from mice just prior to sacrifice. Specific antibody titers (IgG) were determined. Data are shown in FIG. 2 (right side).

Example 3

Immune Response to an Immunogen (Ovalbumin) Administration of Two Immunogenic Compositions This Example describes the immune response induced when mice are first immunized with a vector particle comprising a recombinant expression vector that encodes and expresses the immunogen and then subsequently immunized with the immunogen combined with an adjuvant.

Figure 3:
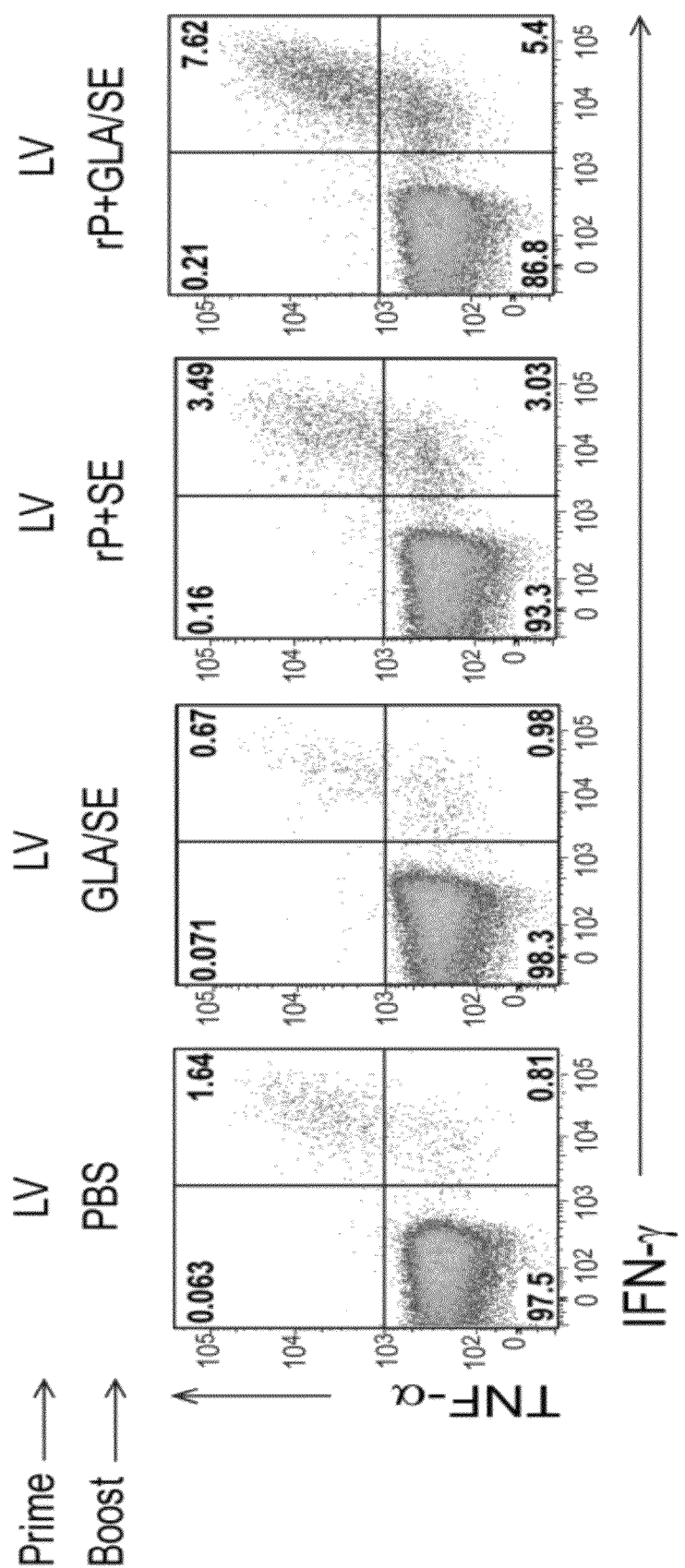
FIG. 3 depicts the immune response induced in mice first immunized with DC-NILV encoding ovalbumin (LV) and then boosted with PBS, GLA/SE alone, recombinant ovalbumin combined with SE (rP+SE), or GLA-SE-adjuvanated ovalbumin (rP+GLA/SE). Spleen cells were isolated from the animals four days after the boosting immunization. Splenic ovalbumin-specific CD8 T cells were analyzed for the production of IFN-γ and TNF-α by ICS. The numbers in each quadrant represent the percent CD8 cells that are IFN-γ$^+$ and TNF-α$^+$.

Groups of mice were immunized subcutaneously with DC-NILV encoding ovalbumin and then boosted with PBS, GLA/SE alone, recombinant ovalbumin combined with SE (rP+SE), or GLA-SE-adjuvanated ovalbumin (rP+GLA/SE) intramuscularly. Spleen cells were isolated from the animals four days after the boosting immunization. Splenic ovalbumin-specific CD8 T cells were analyzed for the production of IFN-γ and TNF-α by ICS. The data are presented in FIG. 3.

Example 4

Immune Response to an Immunogen (HSV-2 UL119) Administration of Two Immunogenic Compositions This Example describes the immune response induced when mice are immunized with an immunogenic composition comprising a vector particle containing a recombinant expression vector that encodes and expresses the immunogen, immunized with an immunogenic composition comprising the immunogen combined with an adjuvant, or immunized sequentially with each immunogenic composition.

Figure 4A:
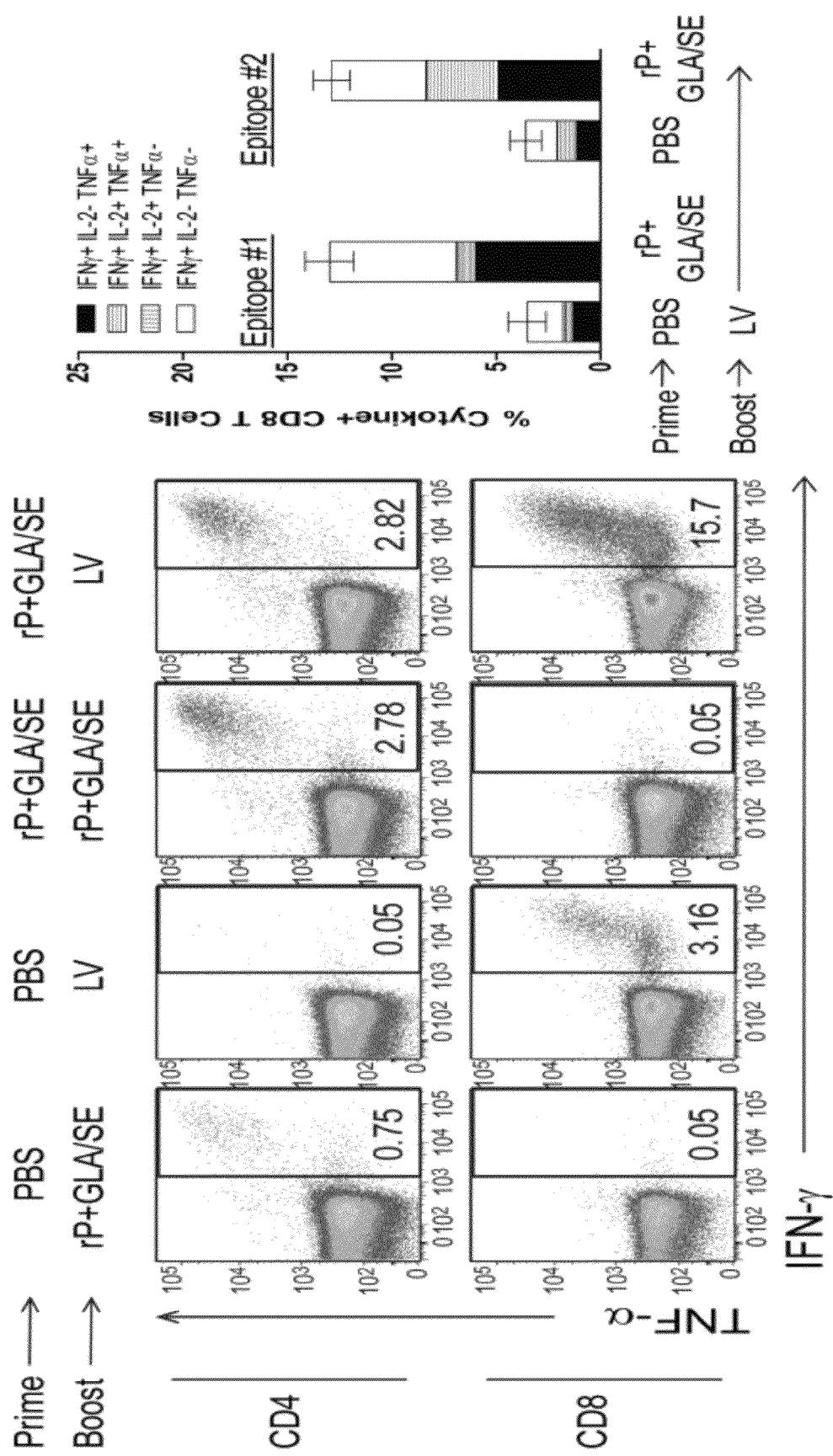
FIGS. 4A and 4B illustrate the immune response of animals immunized with recombinant HSV-2 UL19 protein formulated with GLA-SE and immunized with DC-NILV encoding UL19. Groups of five C57BL/6 mice were immunized with GLA-SE-adjuvanated rUL19 protein (rP+GLA/SE) or PBS and boosted with GLA-SE-adjuvanated rUL19 protein or DC-NILV containing a polynucleotide that encoded UL19 (LV). Spleen cells were isolated from the animals ten days after the boosting immunization. After ex vivo stimulation with single 15-mer peptides containing either a CD4 or CD8 UL19 epitope, splenic UL19-specific CD4 and CD8 T cells were analyzed for the production of IFN-γ, TNF-α, and IL-2 by ICS.

Mice were immunized with rUL19 protein+GLA-SE intramuscularly and with DC-NILV encoding the HSV-2 polypeptide, UL19 subcutaneously. Groups of five C57BL/6 mice were immunized with GLA-SE-adjuvanated rUL19 protein or PBS and boosted with GLA-SE-adjuvanated rUL19 protein or DC-NILV containing a polynucleotide that encoded UL19. Spleen cells were isolated from the animals ten days after the boosting immunization. After ex vivo stimulation with single 15-mer peptides containing either a CD4 or CD8 UL19 epitope, splenic UL19-specific CD4 and CD8 T cells were analyzed for the production of IFN-γ, TNF-α, and IL-2 by ICS. The dot plots are shown in FIG. 4A for one representative mouse per group. The numeric values indicated on the right side of each dot plot represent the % CD4 or CD8 T cells that are IFN-γ+ and TNF-α+.

FIG. 4A (right side) illustrates the percent cytokine positive CD8 T cells stimulated by each of two different CD8 UL19 epitopes (UL19 CD8 peptide epitope 1 (amino acids 1017-1031, (SEQ ID NO:39) and UL19 CD8 peptide epitope 2 (amino acids 1045-1059, (SEQ ID NO:40) (see Example 2)). These data were obtained from splenic CD8 cells from animals in the group immunized first with GLA-SE-adjuvanated rUL19 protein (priming composition) and then with DC-NILV encoding UL19 (boosting composition).

Figure 4B:
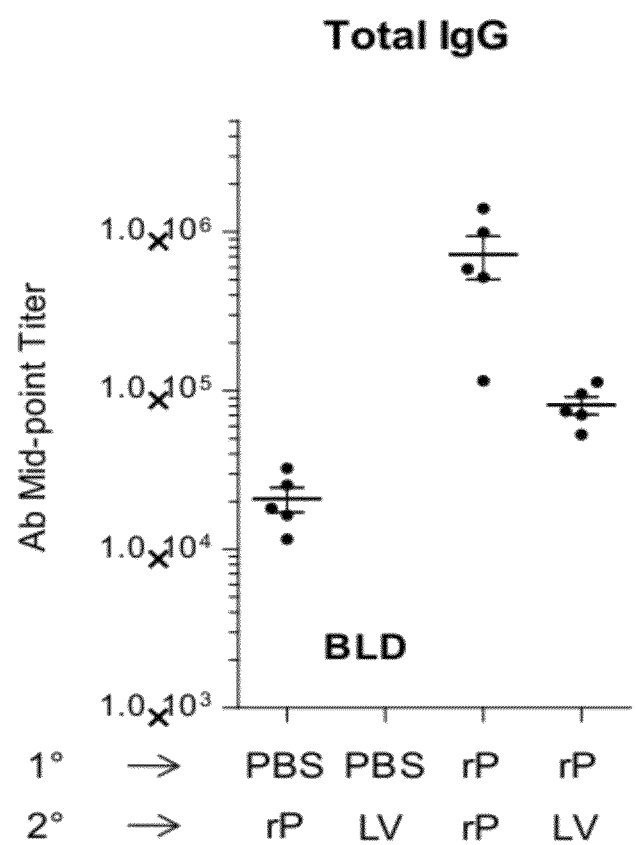

Antibody mid-point titers were determined by Enzyme Linked Immunosorbent Assay (ELISA). Blood samples were obtained from mice 10 days following the last immunization, and sera were prepared. Serial dilutions of samples were added to 96 well immunoassay plates coated with recombinant UL19 protein. The presence of specific anti-UL19 antibodies were detected with murine class specific and isoytpe-specific antibodies (anti-IgG, -IgG1, -IgG2a, and -IgG2b) conjugated with horseradish peroxidase (HRP). Bound HRP-conjugates were detected by standard peroxidase assay using SureBlue® TMB microwell substrate (KPL, Kirkegard & Perry Laboratories, Gaithersburg, Md.). Reactions were quanitified by reading plates at 450 nm using a SpectraMax® Plus plate reader (Molecular Devices, Inc., Sunnyvale, Calif.). Antibody titers measured at midpoint for each animal are presented in FIG. 4B.

Unexpectedly and desirably, the CD8 T cell response generated by a single DC-NILV immunization was increased ~5 fold in mice that had been primed with rUL19+GLA-SE when compared to un-primed controls. The lentivector did not prime TH1 CD4 T cells as a monoagent, however when it was delivered as a boost to a protein/GLA prime, surprisingly it was equally as effective at boosting (as recombinant protein GLA boost) the TH1 CD4 T cell response.

Example 5

Immune Response to an Immunogen (HSV-2 UL19) Administration of Two Immunogenic Compositions This Example describes the immune response induced when mice are immunized concurrently with an immunogenic composition comprising the immunogen combined with an adjuvant and with an immunogenic composition comprising a vector particle containing a recombinant expression vector that encodes and expresses the immunogen.

Figure 5A:
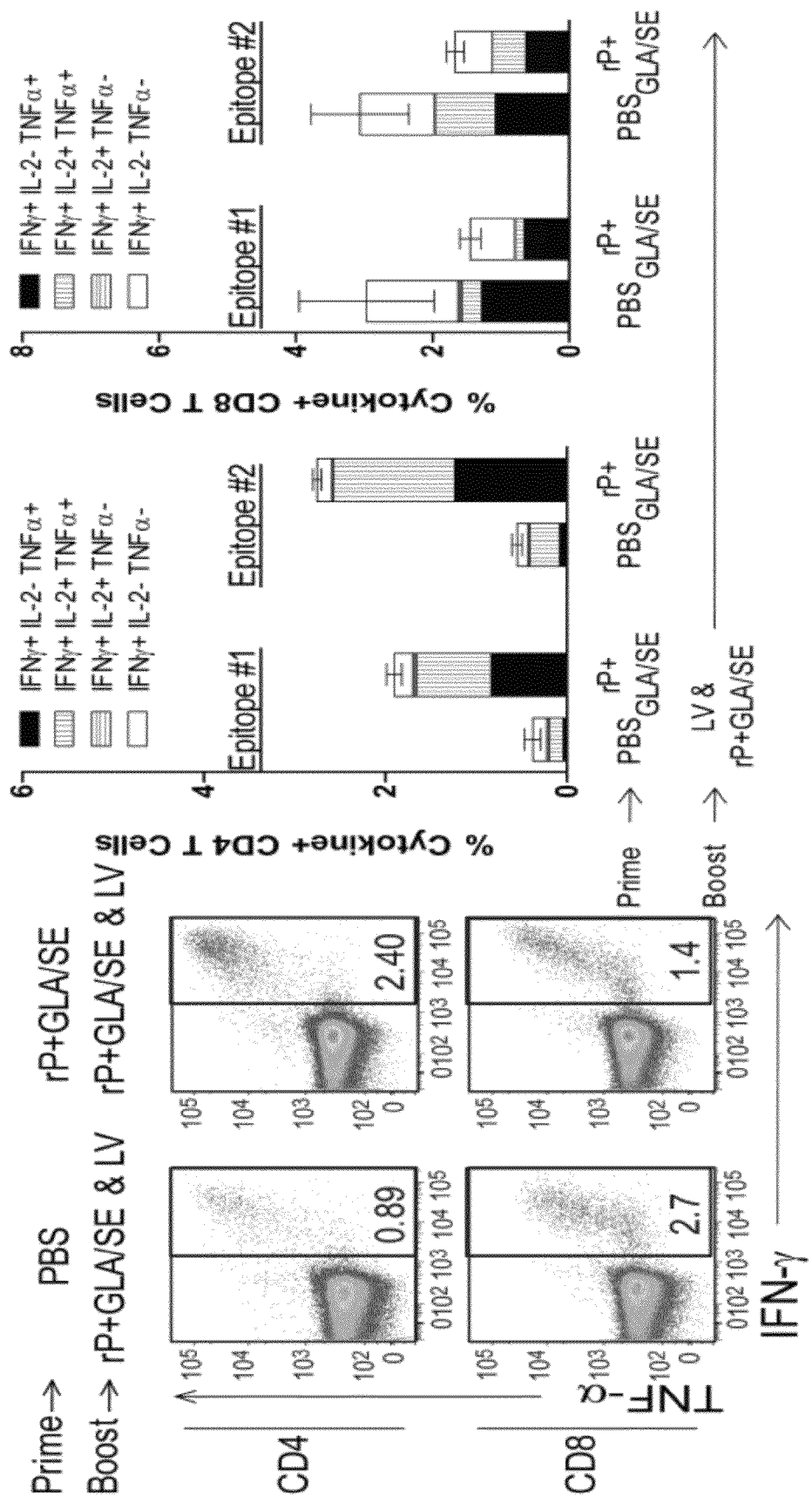
FIGS. 5A and 5B depict the immune response in animals immunized with recombinant protein formulated with the adjuvant, GLA/SE and then boosted with the adjuvanated recombinant protein and a lentiviral vector encoding the protein. Groups of five C57BL/6 mice were immunized with GLA-SE-adjuvanated rUL19 protein (rP+GLA/SE) or PBS and boosted with GLA-SE-adjuvanated rUL19 protein (rP+GLA/SE) and DC-NILV containing a polynucleotide that encoded UL19 (LV). Spleen cells were isolated from the animals ten days after the boosting immunization. After ex vivo stimulation with single 15-mer peptides containing either a CD4 or CD8 UL19 epitope, splenic UL19-specific CD4 and CD8 T cells were analyzed for the production of IFN-γ, TNF-α, and IL-2 by ICS.
Figure 5B:
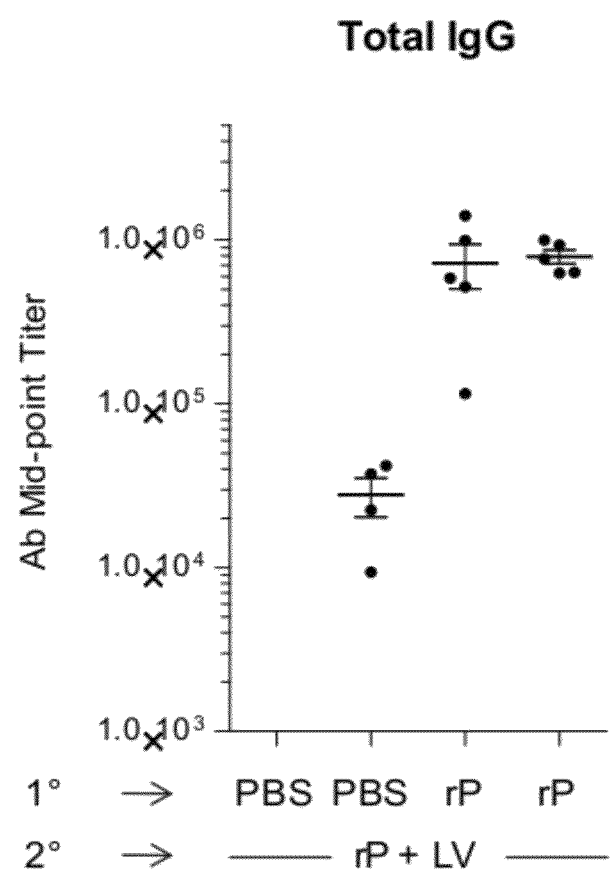

Groups of five C57BL/6 mice were immunized with GLA-SE-adjuvanated rUL19 protein or PBS intramuscularly and boosted with GLA-SE-adjuvanated rUL19 protein intramuscularly and DC-NILV containing a polynucleotide that encoded UL19 subcutaneously. Spleen cells were isolated from the animals ten days after the boosting immunization. After ex vivo stimulation with single 15-mer peptides containing either a CD4 or CD8 UL19 epitope, splenic UL19-specific CD4 and CD8 T cells were analyzed for the production of IFN-γ, TNF-α, and IL-2 by ICS. The data are presented in FIG. 5. The data suggest that simultaneous delivery of rP+GLA/SE and lentivirus-based vaccines effectively generated both CD4 and CD8 antigen-specific T cells in both the presence and absence of a pre-existing antigen-specific CD4 T cell pool. FIG. 5A (right side) illustrates the percent cytokine positive CD4 T cells stimulated by each of two different CD4 UL19 epitopes (CD4 peptide epitope 1 and CD4 peptide epitope 2; see Example 1) and the percent cytokine positive CD8 T cells stimulated by each of two different CD8 UL19 epitopes (CD8 peptide epitope 1 and CD8 peptide epitope 2; see Examples 2 and 4).

Sera were obtained from animals in each group five days post-boost and ten days post boost, and specific IgG antibodies were detected. Antibody mid-point titers were determined as described in Example 4. Specific IgG antibody titers at these midpoints for each animal are presented in FIG. 5B.

Example 6

Immune Response Induced by Administration of an Immunogenic Composition Comprising a First Immunogen and Adjuvant and Administration of a Vector Particle Comprising a Recombinant Expression Vector for Expression of the First Immunogen and a Second Immunogen DC-NILV vector construction: The DC-NILV vector is prepared as described in Example 1. The HSV-2 proteins, gD and UL19, are encoded in a multicistronic vector, wherein the two antigens are separated by a self-cleaving 2A peptide (see, e.g., Szymczak et al., Nat. Biotechnol. 22:589 (2004); Trichas et al., BMC. Biol. 6:40 (2008); Yang et al., Gene Ther. 15:1411 (2008)). The recombinant expression vector is constructed to express both of gD and UL19 according to molecular biology methods and techniques routinely practiced in the art. For lentiviral vector construction, see also International Patent Application Publication No. WO 2011/011584.

HSV-2 recombinant proteins, UL19 and gD, are each expressed in a Baculovirus expression system (Paragon Bioservices, Baltimore, Md.) Immunogenic compositions are prepared that comprise gD formulated with GLA/SE, UL19 formulated with GLA/SE, and gD and UL19 formulated together with GLA/SE.

Groups of five mice are immunized as indicated in Table 1 below. The first boost is administered 28 days after the priming immunization. Groups of mice that receive a second boost are immunized 28 days after the first boost.

TABLE 2

| Immunization Regimens | | |
|---|---|---|
| Prime | 1st Boost | 2nd Boost |
| rP + GLA/SE | DC-NILV | None |
| rP + GLA/SE | DC-NILV | rP + GLA/SE |
| rP + GLA/SE | rP + GLA/SE | DC-NILV |
| rP + GLA/SE | rP + GLA/SE and DC-NILV | None |
| rP + GLA/SE and DC-NILV | None | None |
| rP + GLA/SE and DC-NILV | rP + GLA/SE and DC-NILV | None |
| DC-NILV | rP + GLA/SE | None |
| DC-NILV | rP + GLA/SE | DC-NILV |

The immune response (antibody, CD4 T cell, and CD8 T cell) is analyzed on day 4 post-last immunization except for mice that receive only one immunization when the immune response is analyzed on day 12. Blood samples are taken from each mouse and spleens are removed from the animals. Total cell numbers will be determined via the Guava EasyCyte™ Plus (Millipore, Billerica, Mass.). The overall frequency of CD8 and CD4 T cells and their memory phenotype (central v. effector) within each sample is determined by flow cytometry. ICS is also performed for analyzing antigen-specific T cell responses and determining the presence of IFN-γ, IL-2, and TNF-α producing T cells after ex vivo stimulation of splenocytes with 15-mer peptides containing known T cell epitopes, essentially as described (Liu et al., Nature 457(7225):87 (2009); Seder et al., Nat. Rev. Immunol. 8:247 (2008)). Specific antibody response to gD is determined by ELISA.

Protection Studies: Groups of ten mice are immunized initially (priming immunization) (at day 0) and boosted 28 days later (day 28). Certain groups of mice receive a second boost 28 days after the first boost (day 56). The immunogenic compositions for each of the priming, first, and second immunizations is determined by results obtained from the previous study. Four days after the second boost (day 60) mice are challenged with at least 50×LD50 of HSV-2. Blood is collected from each animal on each day of the immunizations (i.e., day 0, day 28, and day 56). Vaginal swabs are taken at 1, 3, and 5 days after challenge. At day 14 after challenge, vaginal swabs are taken from surviving animals, and then blood and spleens are collected from the animals. The endpoints include survival and reduction in viral titer (determined by real-time HSV-2 DNA PCR, sensitive to 1-10 copies). Antigen specific antibody response, CD4 T cell response, and CD8 T cell responses specific for gD and UL19 are determined as described above.

Example 7

Prime/Boost Regimens Induce a Robust Functional CD8 T Cell Responses to SIV-GAG

This Example describes the immune response induced when mice are first immunized (primed) with a vector particle comprising a recombinant expression vector that encodes and expresses the immunogen and then subsequently immunized (boosted) with the recombinant expression vector that encodes and expresses the immunogen.

Groups of C57BL/6 mice (4 per group) were immunized once over a 25-fold dose range with DC-NILV encoding SIV-Gag subcutaneously with a prime or prime/boost (d0/d28) immunization regimen. Splenic SIV-Gag-specific CD8 T cells were analyzed 12 days following prime or 5 days following boost for epitope-specific functional responses, as measured by production of IFN-γ, TNF-α, and IL-2 via intracellular cytokine staining (ICS) assays after ex vivo stimulation with known CD8 T cell minimal epitope peptides AL11 (amino acids 312-322 of SIV GAG; AAVKNWMTQTL; SEQ ID NO: 43) or KV9 (amino acids 76-84 of SIV GAG; =KSLYNTVCV; SEQ ID NO: 44)

Figure 7:
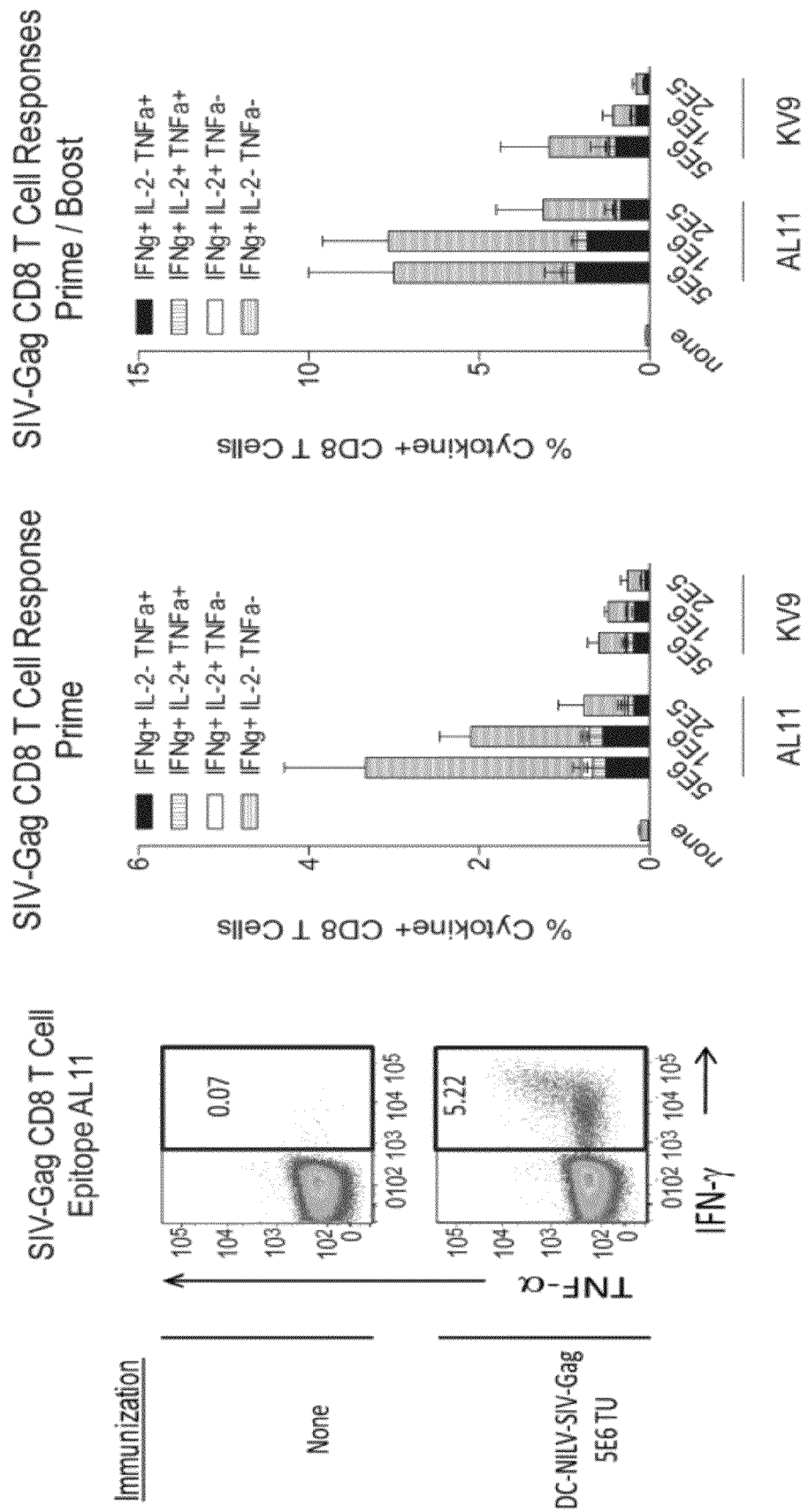
FIG. 7 demonstrates that DC-NILV generates robust Gag-specific CD8 T cell responses.

The data are presented in FIG. 7 and demonstrate that prime and prime/boost regimens where both immunizations are viral vectors both generate dose-dependent robust functional Gag-specific CD8 T cell responses to both the dominant AL11 epitope and the subdominant KV9 epitope. The prime/boost regimen further increased the observed responses to both epitopes by at least about 2-fold.

Example 8

Adminstration of an Immunogen and Adjuvant Induces TH1 CD4 T Cell Responses

This Example describes the immune response induced by an SIV immunogen combined with an adjuvant (GLA).

C57BL/6 mice (4 per group) were immunized intramuscularly via a prime/boost immunization regimen (d0 prime/d21 boost) with 5 µg of recombinant SIV-Gag protein+5 µg of GLA-SE, SE alone, or PBS. Splenic CD4 T cell responses were measured on day 5 post-boost by ICS for IFN-γ, TNF-α, and IL-2 after ex vivo re-stimulation with SIV-Gag CD4 T cell epitope containing peptide DD13 (amino acids 299-311 of SIV-GAG; DRFYKSLRAEQTD; SEQ ID NO: 45)

Figure 8:
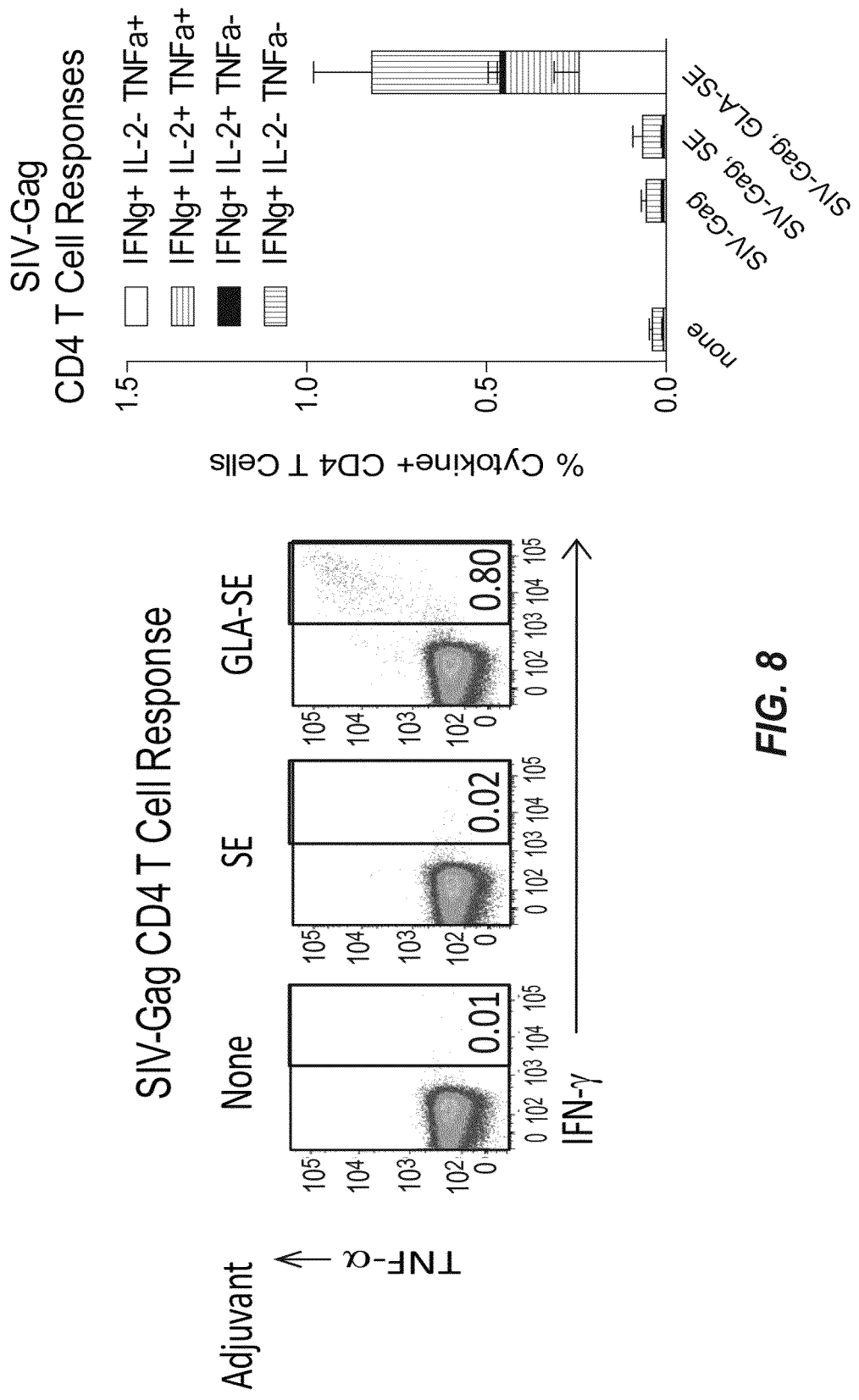
FIG. 8 demonstrates that GLA is required for a robust Th1 CD4 T cell after immunization with SIV-Gag recombinant protein.

The results are shown in FIG. 8 and demonstrate that a GLA type adjuvant is required for a robust Th1 CD4 T cell response after immunization with SIV-Gag recombinant protein.

Example 9

Comparison of Same-Vehicle Multiple-Dose Vaccinations to Heterologous Multiple-Dose Vaccination Regimens, and Order of Prime/Boost Vaccinations This Example describes the immune response induced by heterologous, prime, boost, boost vaccinations with SIV-Gag recombinant Protein+GLA-SE and DC-NILV expressing SIV-Gag.

Figure 9:
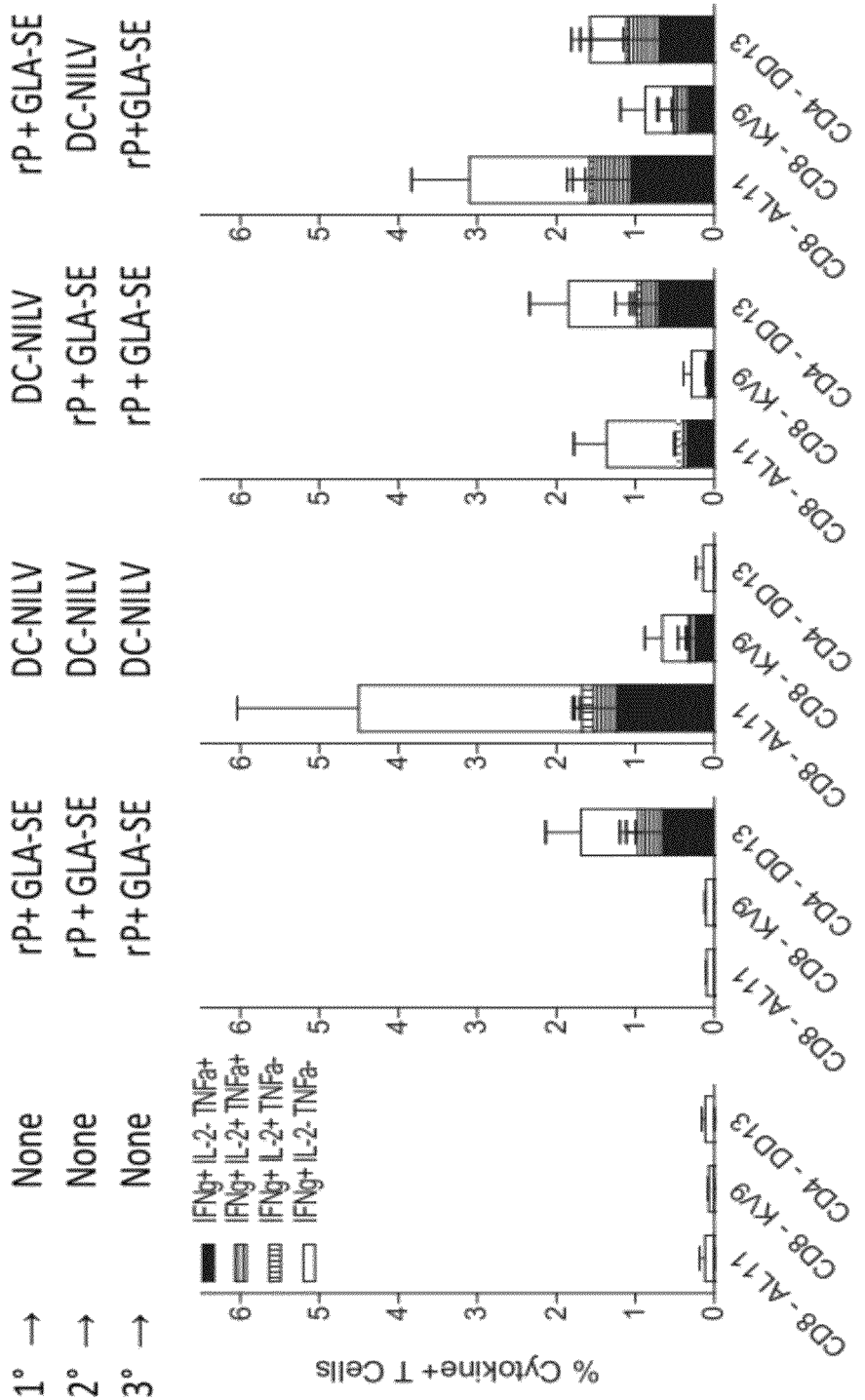
FIG. 9 demonstrates that heterologous, prime, boost, boost vaccinations with SIV-Gag recombinant Protein+GLA-SE and DC-NILV expressing SIV-Gag generate both CD8 and CD4 antigen-specific T cell responses.

C57BL/6 mice (4 per group) were immunized with rSIV-Gag+GLA-SE intramuscularly and/or DC-NILV encoding SIV-Gag subcutaneously in the immunization regimen as indicated. Antigen-specific CD4 and CD8 T cells were analyzed 25 days post boost using CD8 T cell minimal epitope peptides AL11, KV9 or CD4 (DD13) and analyzed for the production of IFN-γ, TNF-α, and IL-2 by ICS. The results are shown in FIG. 9 and demonstrate that heterologous, prime/boost/boost vaccinations with SIV-Gag recombinant Protein+GLA-SE and DC-NILV expressing SIV-Gag generate both CD8 and CD4 antigen-specific T cell responses.

The data show that three immunizations with recombinant protein together with GLA type adjuvant resulted in a very robust CD4 T cell response, but not a robust CD8 T cell response. Similarly, three immunizations with lentivector resulted in a very robust CD8 T cell response that was dramatically skewed towards the dominant AL11 epitope, without a robust CD4 T cell response. In contrast, heterologous regimens unexpectedly resulted in both strong CD8 and strong CD4 T cell responses. Significant and balanced CD8 T cell responses were observed for both the dominant and subdominant epitopes. It was further unexpected that a regimen where the first (prime) immunization was protein with GLA and a subsequent immunization (boost) was viral vector resulted in superior CD8 T cell responses compared to a regimen where the prime was viral vector, and a boost was protein. Notably, priming with protein and boosting with viral vector resulted in a significantly greater increase in the CD8 T cell response to the subdominant epitope KV9. This was unexpected because it is difficult to alter the intrinsic immunodominance hierarchies elicited by vaccination. Responses against subdominant epitopes can be important for diversity of immune response and can result in superior efficacy of a vaccine across a population.

Example 10

A Second Boost Increases Both CD8 and TH1 CD4 T Cell Responses Generated by Heterologous Vaccination This Example describes the immune response induced by a heterologous vaccination boosted with rSIV-Gag and GLA-SE.

Figure 10:
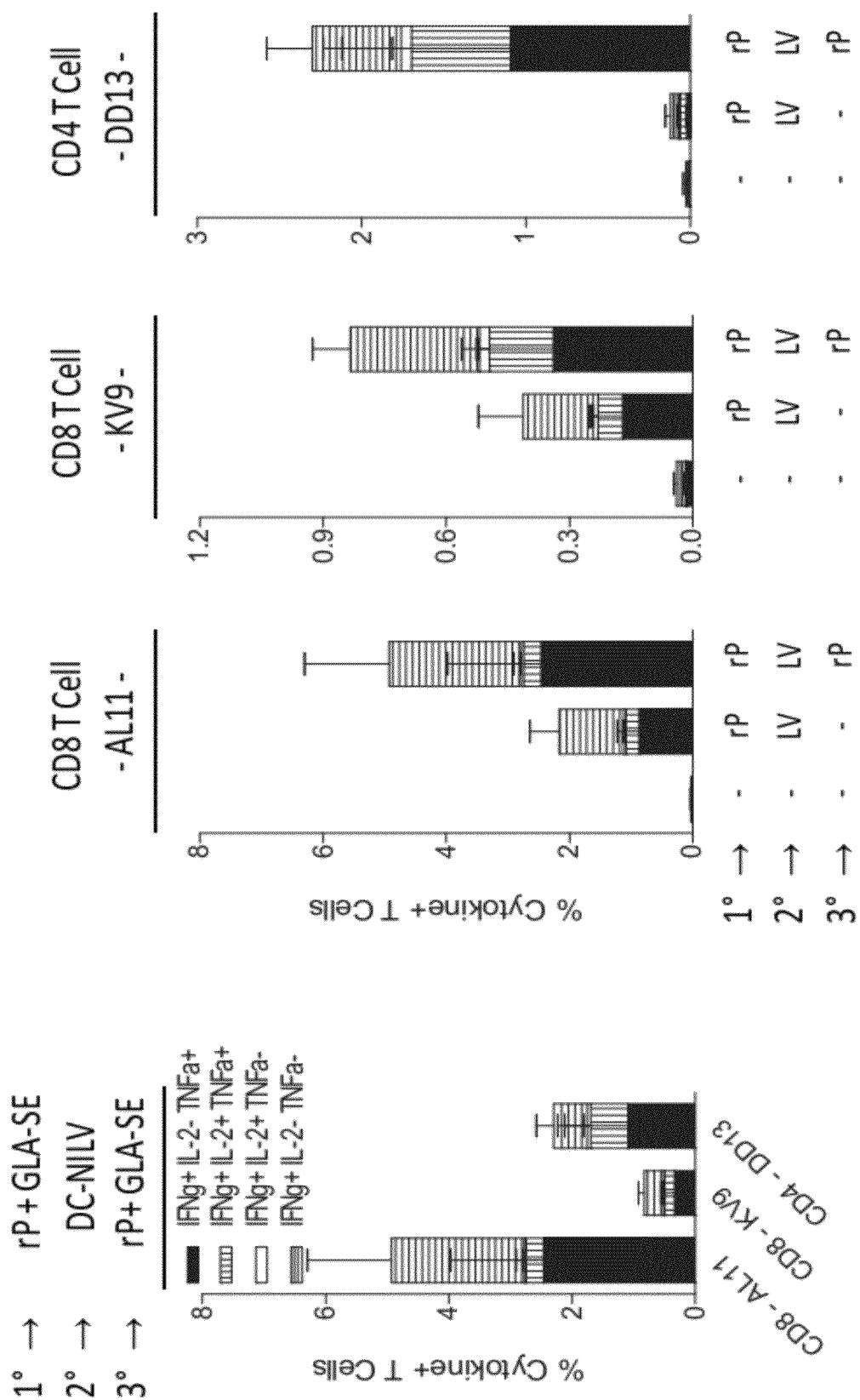
FIG. 10 demonstrates that CD8 and TH1 CD4 T cell responses generated by heterologous vaccination can be boosted with rSIV-Gag+GLA-SE.

C57BL/6 mice (4 per group) were immunized with rSIV-Gag+GLA-SE intramuscularly and boosted with DC-NILV encoding SIV-Gag subcutaneously in the immunization regimen as indicated in FIG. 10. Immunizations were separated by 21 days. Antigen-specific CD4 and CD8 T cells were analyzed 25 days post boost using CD8 (AL11 or KV9 or CD4 (DD13) T cell epitope peptides and analyzed for the production of IFN-γ, TNF-α, and IL-2 by ICS.

The results are shown in FIG. 10 and demonstrate that both CD8 and TH1 CD4 T cell responses generated by heterologous vaccination can be enhanced by a third immunization (second boost) with protein and a GLA type adjuvant. Three-dose vaccination regimens produced further increases in both CD8 and CD4 antigen-specific T cell responses compared to the respective responses after two-dose vaccinations.

Example 11

CD8 T Cell Responses Generated by DC-NILV can be Boosted with Synthetic Long Peptides with Adjuvant This Example describes the immune response induced by DC-NILV encoding SIV-Gag boosted with a synthetic long peptide (SLP) and GLA-SE.

Figure 11:
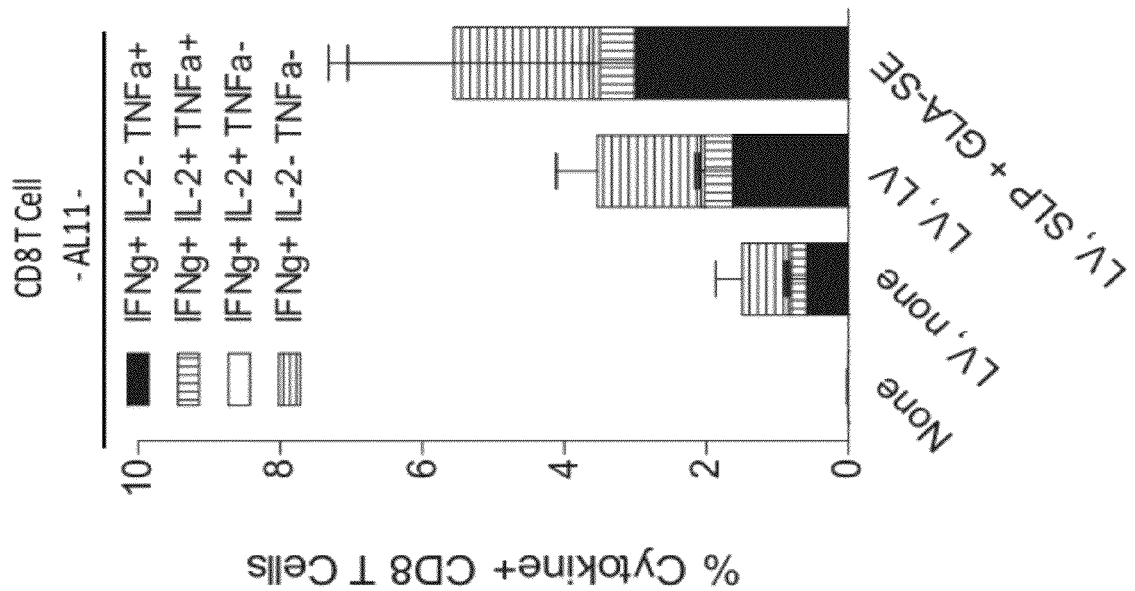
FIG. 11 illustrates demonstrate that CD8 T cell responses generated by DC-NILV can be boosted with synthetic long pepetides plus GLA-SE. Amino acids 289-333 of SIV-Gag are shown (GPKEPFQSYVDRFYKSLRAEQTDAAVKNWMTQTLLIQNANPDCKL; SEQ ID NO: 42)

C57BL/6 mice (4 per group) were immunized via a prime/boost immunization regiment (d0 prime/d21 boost) with DC-NILV encoding SIV-Gag and/or a SLP containing SIV-Gag amino acids 289-333 (SEQ ID NO. 42) (AL11 epitope is indicated in bold font in FIG. 11) plus GLA-SE according to the immunization regimen indicated in FIG. 11. Antigen-specific CD8 T cells were analyzed 25 days post boost using CD8 (AL11) T cell epitope peptides and analyzed for the production of IFN-γ, TNF-α, and IL-2 by ICS.

The results are shown in FIG. 11 and demonstrate that the methods of the invention are functional when different immunogen variants are used in the first and second immunizations, e.g. full length immunogen vs fragment. After a first immunization (priming) with lentivector viral vector carrying a polynucleotide encoding the full length immunogen, a second immunization (boost) with a small 45-amino acid immunogen fragment produced an enhanced CD8 T cell response compared to a boost with the same lentivector.

The various embodiments described above can be combined to provide further embodiments. All U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:
1. A method for priming and boosting a CD8 T cell immune response in a subject, the method comprising (a) administering to the subject at least one dose of a first immunogenic composition comprising (i) a lentiviral vector comprising a nucleotide sequence that encodes a first immunogen or an immunogenic fragment thereof, wherein the lentiviral vector is incorporated into a vector particle, wherein the vector particle comprises a lentiviral vector genome and an alpha virus envelope; and (b) subsequently administering to the subject at least one dose of a second immunogenic composition comprising (i) at least the first immunogen or an immunogenic fragment thereof and (ii) a TRL4 agonist, thereby priming and boosting a CD8 T cell immune response specific for the first immunogen, wherein the TRL4 agonist is a compound of the following structure:

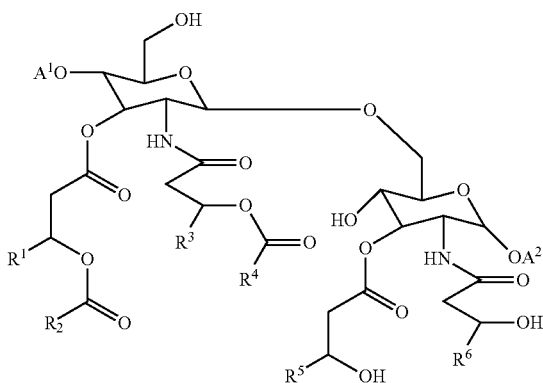

wherein A1 and A2 are independently selected from the group of hydrogen, phosphate, and phosphate salts and R1, R2, R3, R4, R5, and R6 are independently selected from the group of hydrocarbyl having 3 to 23 carbons, represented by C3-C23.

2. The method of claim 1, wherein (i) the first immunogenic composition further comprises a second adjuvant; or (ii) the second composition further comprises an adjuvant; or both (i) and (ii).

3. The method of claim 1, wherein at least two doses of the first immunogenic composition are administered or wherein at least two doses of the second immunogenic composition are administered.

4. The method of claim 1, wherein (a) two doses; (b) three doses; (c) four doses; or (d) five doses of the first immunogenic composition are administered.

5. The method of claim 4, wherein two doses of the first immunogenic composition are administered prior to administration of the second immunogenic composition.

6. The method of claim 1, wherein the immune response induced by the method comprises a CD4 T cell immune response specific for the first immunogen.

7. The method of claim 1, wherein the second immunogenic composition further comprises a second immunogen or an immunogenic fragment thereof, and wherein the lentiviral vector further comprises a nucleotide sequence that encodes the second immunogen or an immunogenic fragment thereof, wherein the method induces an immune response specific for the second immunogen.

8. The method of claim 7 wherein the immune response induced by the method comprises a CD4 T cell response specific for the second immunogen.

9. The method of claim 1, wherein A1 is phosphate or phosphate salt, A2 is hydrogen, R1, R3, R5 and R6 are undecyl, and R2 and R4 are tridecyl.

10. The method of claim 9, wherein the compound is formulated in a stable oil-in-water emulsion.

11. The method of claim 2, wherein the first immunogen is (a) a tumor-associated antigen or (b) from an infectious microorganism selected from a virus, a bacterium, a fungus, and a parasite.

12. The method of claim 11, wherein the first immunogen is a tumor-associated antigen selected from a renal cell carcinoma antigen, a prostate cancer antigen, a mesothelioma antigen, a pancreatic cancer antigen, a melanoma antigen, a breast cancer antigen, a lung cancer antigen, and an ovarian cancer antigen.

13. The method of claim 11, wherein the first immunogen is selected from the group consisting of prostatic acid phosphatase, prostate specific antigen, NKX3.1, prostate specific membrane antigen, PRAME; BAGE; RAGE, Lage (also known as NY ESO 1), SAGE, HAGE, GAGE, Plu-1, HASH-1, HasH-2, Cripto, Criptin, MART-1/Melan-A, gp100, gp75, mda-7, tyrosinase, tyrosinase-related protein, p53, Ras, c-Myc, A-Raf, B -Raf, and C- Raf, MAGE-A1, MAGE-A2, MAGE-A3, MAGE-A4, MAGE-A6, MAGE-A10, MAGE-A12, MART-1, BAGE, DAM-6, -10, GAGE-I, GAGE-2, GAGE-8, GAGE-3, GAGE-4, GAGE-5, GAGE-6, GAGE-7B, NA88-A, MART-I, MC1R, Gp100, PSM, TRP-1, TRP-2, ART-4, CAMEL, CEA, Cyp-B, hTERT, hTRT, iCE, MUC1, MUC2, PRAME, P15, RU1, RU2, SART-1, SART-3, Wilms' tumor antigen (WT1), AFP, μ-catenin/m, Caspase-8/m, CEA, CDK-4/m, ELF2M, GnT-V, G250, HSP70-2M, HST-2, KIAA0205, MUM-I, MUM-2, MUM-3, Myosin/m, SART-2, TRP-2/INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD 1) TACSTD2, Epidermal Growth Factor receptor (EGFR and EGFRvIII), platelet derived growth factor receptor (PDGFR), vascular endothelial growth factor receptor (VEGFR), integrin-linked kinase (ILK), STAT3, STAT5, STAT6, HIF-1, HIF-2, Nuclear Factor-Kappa B (NF-KB), Notch1-4, c-Met, mammalian targets of rapamycin (mTOR), WNT, PMSA, PR-3, MDM2, Mesothelin, renal cell carcinoma—5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGs5, SART3, STn, PAX5, OY-TES 1, sperm protein 17, LCK, HMWMAA, AKAP-4, SSX2, XAGE 1, B7H3, legumain, TIE2, PAGE4, MAD-CT-1, FAP, MAD-CT-2, and fos related antigen 1.

14. The method of claim 11, wherein the first immunogen is from a virus.

15. The method of claim 14, wherein the virus is Herpes Simplex Virus-2 (HSV-2).

16. The method of claim 15, wherein the first immunogen is HSV-2 UL19 polypeptide or HSV-2 gD polypeptide.

17. The method of claim 7, wherein each of the first immunogen and the second immunogen is a tumor-associated antigen.

18. The method of claim 17, wherein each of the first immunogen and the second immunogen is selected from a renal cell carcinoma antigen, a prostate cancer antigen, a mesothelioma antigen, a pancreatic cancer antigen, a melanoma antigen, a breast cancer antigen, a lung cancer antigen, and an ovarian cancer antigen.

19. The method according to claim 18, wherein each of the first immunogen and the second immunogen is selected from the group consisting of a prostate cancer antigen selected from prostatic acid phosphatase, prostate specific antigen, NKX3.1, o~prostate specific membrane antigen, PRAME; BAGE; RAGE, Lage (also known as NY ESO 1), SAGE, HAGE, GAGE, Plu-1, HASH-1, HasH-2, Cripto, Criptin, MART-1/Melan-A, gp100, gp75, mda-7, tyrosinase, tyrosinase-related protein, p53, Ras, c-Myc, A-Raf, B-Raf, and C-Raf, MAGE-A1, MAGE-A2, MAGE-A3, MAGE-A4, MAGE-A6, MAGE-A10, MAGE- A12, MART-1, BAGE, DAM-6, -10, GAGE-I, GAGE-2, GAGE-8, GAGE-3, GAGE-4, GAGE-5, GAGE-6, GAGE-7B, NA88-A, MART-I, MC1R, Gp100, PSM, TRP-1, TRP-2, ART-4, CAMEL, CEA, Cyp-B, hTERT, hTRT, iCE, MUC1, MUC2, PRAME, P15, RU1, RU2, SART-1, SART-3, Wilms' tumor antigen (WT1), AFP, μ-catenin/m, Caspase-8/m, CEA, CDK-4/m, ELF2M, GnT-V, G250, HSP70-2M, HST-2, KIAA0205, MUM-I, MUM-2, MUM-3, Myosin/m, SART-2, TRP-2/INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD 1) TACSTD2, Epidermal Growth Factor receptor (EGFR and EGFRvIII), platelet derived growth factor receptor (PDGFR), vascular endothelial growth factor receptor (VEGFR), integrin-linked kinase (ILK), STAT3, STAT5, STAT6, HIF-1, HIF-2, Nuclear Factor-Kappa B (NF-κB), Notch1-4, c-Met, mammalian targets of rapamycin (mTOR), WNT, PMSA, PR-3, MDM2, Mesothelin, renal cell carcinoma—5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGs5, SART3, STn, PAX5, OY-TES1, sperm protein 17, LCK, HMWMAA, AKAP-4, SSX2, XAGE 1, B7H3, legumain, TIE2, PAGE4, MAD-CT-1, FAP, MAD-CT-2, and fos related antigen 1.

20. The method of claim 7, wherein each of the first immunogen and the second immunogen is an antigen from an infectious microorganism selected from a virus, a bacterium, a fungus, and a parasite.

21. The method of claim 20, wherein the infectious disease organism is a virus.

22. The method of claim 21, wherein the virus is Herpes Simplex Virus-2 (HSV-2).

23. The method of claim 22, wherein at least one of the first immunogen and the second immunogen is HSV-2 UL19 polypeptide and the other of the first immunogen and the second immunogen is HSV-2 gD polypeptide.

24. The method of claim 1, wherein the lentiviral vector particle delivers the nucleotide sequence to an antigen-presenting cell.

25. The method of claim 24, wherein the antigen-presenting cell is a dendritic cell, preferably a dendritic cell expressing DC-SIGN.

26. The method of claim 1, wherein the vector particle comprises an envelope that delivers the lentiviral vector particle to a dendritic cell expressing DC-SIGN.

27. The method of claim 26, wherein the envelope comprises a Sindbis virus E2 glycoprotein comprising an amino acid sequence having at least one amino acid change compared to SEQ ID NO:1, wherein residue 160 of SEQ ID NO:1 is either absent or an amino acid other than glutamic acid, and wherein the E2 glycoprotein is not fused to Sindbis virus E3 protein.

28. The method of claim 27, wherein the E2 glycoprotein binds to dendritic cell-specific intercellular adhesion molecule-3-grabbing non-integrin (DC-SIGN).

29. The method of claim 1, wherein R1, R3, R5 and R6 are C11-C20 alkyl, and R2 and R4 are C12-C20 hydrocarbyl.

30. The method of claim 11 wherein the first immunogen is MAGE3 or Lage (NY ESO 1).

31. The method of claim 1, wherein the first immunogenic composition and the second immunogenic composition are administered concurrently and two doses are administered.

32. The method of claim 1 wherein the first composition further comprises (i) at least the first immunogen or an immunogenic fragment thereof and (ii) the TRL4 agonist, and wherein the second composition further comprises a lentiviral vector comprising a nucleotide sequence that encodes the first immunogen or an immunogenic fragment thereof, wherein the lentiviral vector is incorporated into a vector particle, wherein the vector particle comprises a lentiviral vector genome and an alpha virus envelope.

33. A method for priming and boosting a CD8 T cell immune response in a subject, the method comprising (a) administering to the subject at least one dose of a first immunogenic composition comprising (i) a lentiviral vector comprising a nucleotide sequence that encodes a first immunogen or an immunogenic fragment thereof, wherein the lentiviral vector is incorporated into a vector particle, wherein the vector particle comprises a lentiviral vector genome and an alpha virus envelope, and concurrently administering a second immunogenic composition comprising (i) at least the first immunogen or an immunogenic fragment thereof and (ii) a TRL4 agonist; and (b) subsequently administering the first and second immunogenic compositions of (a), thereby priming and boosting a CD8 T cell immune response specific for the first immunogen, wherein the TRL4 agonist is a compound of the following structure:

wherein A1 and A2 are independently selected from the group of hydrogen, phosphate, and phosphate salts and R1, R2, R3, R4, R5, and R6 are independently selected from the group of hydrocarbyl having 3 to 23 carbons, represented by C3-C23.

* * * * *

UNITED STATES PATENT AND TRADEMARK OFFICE
CERTIFICATE OF CORRECTION

PATENT NO. : 9,044,420 B2
APPLICATION NO. : 13/441502
DATED : June 2, 2015
INVENTOR(S) : Thomas W. Dubensky, Jr. et al.

It is certified that error appears in the above-identified patent and that said Letters Patent is hereby corrected as shown below:

In the claims:

Column 191, Claim number 1, line numbers 13 and 15 should recite:

1. A method for priming and boosting a CD8 T cell immune response in a subject, the method comprising (a) administering to the subject at least one dose of a first immunogenic composition comprising (i) a lentiviral vector comprising a nucleotide sequence that encodes a first immunogen or an immunogenic fragment thereof, wherein the lentiviral vector is incorporated into a vector particle, wherein the vector particle comprises a lentiviral vector genome and an alpha virus envelope; and (b) subsequently administering to the subject at least one dose of a second immunogenic composition comprising (i) at least the first immunogen or an immunogenic fragment thereof and (ii) a TLR4 agonist, thereby priming and boosting a CD8 T cell immune response specific for the first immunogen, wherein the TLR4 agonist is a compound of the following structure:

Column 191, Claim number 2, line number 39 should recite:

2. The method of claim 1, wherein (i) the first immunogenic composition further comprises an adjuvant; or
(ii) the second composition further comprises an adjuvant; or
both (i) and (ii).

Signed and Sealed this
Eighth Day of December, 2015

Michelle K. Lee
*Director of the United States Patent and Trademark Office*